US008889667B2

(12) United States Patent
Salituro et al.

(10) Patent No.: US 8,889,667 B2
(45) Date of Patent: Nov. 18, 2014

(54) THERAPEUTIC COMPOUNDS AND COMPOSITIONS

(75) Inventors: Francesco G. Salituro, Marlborough, MA (US); Jeffrey Saunders, Lincoln, MA (US); Shunqi Yan, Irvine, CA (US)

(73) Assignee: Agios Pharmaceuticals, Inc, Cambridge, MA (US)

( * ) Notice: Subject to any disclaimer, the term of this patent is extended or adjusted under 35 U.S.C. 154(b) by 0 days.

(21) Appl. No.: 13/339,708

(22) Filed: Dec. 29, 2011

(65) Prior Publication Data

US 2012/0172349 A1 Jul. 5, 2012

Related U.S. Application Data

(60) Provisional application No. 61/428,030, filed on Dec. 29, 2010.

(51) Int. Cl.
| | | |
|---|---|---|
| A61K 31/55 | (2006.01) | |
| A61K 31/496 | (2006.01) | |
| C07D 401/00 | (2006.01) | |
| C07D 241/02 | (2006.01) | |
| C07D 241/04 | (2006.01) | |
| C07D 487/08 | (2006.01) | |
| C07D 401/06 | (2006.01) | |

(52) U.S. Cl.
CPC ............ C07D 241/04 (2013.01); C07D 487/08 (2013.01); C07D 401/06 (2013.01)
USPC .................. 514/215; 514/253.06; 514/252.11; 544/363; 544/357

(58) Field of Classification Search
USPC ................................... 514/215; 544/363, 357
See application file for complete search history.

(56) References Cited

U.S. PATENT DOCUMENTS

| | | |
|---|---|---|
| 3,046,122 A | 7/1962 | Siis et al. |
| 3,097,210 A | 7/1963 | Bicking |
| 3,998,828 A | 12/1976 | Wiedermann |
| 4,235,871 A | 11/1980 | Papahadjopoulos et al. |
| 4,315,940 A | 2/1982 | Hitzel et al. |
| 4,474,599 A | 10/1984 | Rogers et al. |
| 4,501,728 A | 2/1985 | Geho et al. |
| 4,593,102 A | 6/1986 | Shanklin, Jr. |
| 4,775,762 A | 10/1988 | Knox et al. |
| 4,837,028 A | 6/1989 | Allen |
| 4,849,424 A | 7/1989 | Ikeda et al. |
| 4,881,965 A | 11/1989 | Yamamoto et al. |
| 4,889,553 A | 12/1989 | Rowson et al. |
| 4,959,094 A | 9/1990 | Wegner et al. |
| 5,019,369 A | 5/1991 | Presant et al. |
| 5,122,530 A | 6/1992 | Tomioka et al. |
| 5,180,732 A | 1/1993 | Tomioka et al. |
| 5,220,028 A | 6/1993 | Iwasawa et al. |
| 5,252,590 A | 10/1993 | Tomioka et al. |
| 5,556,866 A | 9/1996 | Aga et al. |
| 5,834,485 A | 11/1998 | Dyke et al. |
| 5,843,485 A | 12/1998 | Fernandez et al. |
| 5,962,490 A | 10/1999 | Chan et al. |
| 5,965,559 A | 10/1999 | Faull et al. |
| 5,965,569 A | 10/1999 | Camps Garcia et al. |
| 6,020,357 A | 2/2000 | Pinto et al. |
| 6,106,849 A | 8/2000 | Malkan et al. |
| 6,150,356 A | 11/2000 | Lloyd et al. |
| 6,172,005 B1 | 1/2001 | Selby |
| 6,265,588 B1 | 7/2001 | Mullner et al. |
| 6,313,127 B1 | 11/2001 | Waterson et al. |
| 6,511,977 B1 | 1/2003 | Lloyd et al. |
| 6,818,631 B1 | 11/2004 | Nakagawa et al. |
| 7,288,554 B2 | 10/2007 | Finkelstein et al. |
| 7,524,848 B2 | 4/2009 | Powers et al. |
| 7,572,913 B2 | 8/2009 | McKerracher et al. |
| 7,615,553 B2 | 11/2009 | Van Emelen et al. |
| 7,863,444 B2 | 1/2011 | Calderwood et al. |
| 8,058,313 B2 | 11/2011 | Reddy et al. |
| 2003/0082877 A1 | 5/2003 | Ootsuka et al. |
| 2003/0095958 A1 | 5/2003 | Bhisetti et al. |
| 2003/0106381 A1 | 6/2003 | Krouth et al. |
| 2003/0158232 A1 | 8/2003 | Cheng et al. |
| 2003/0187001 A1 | 10/2003 | Calderwood et al. |
| 2003/0207882 A1 * | 11/2003 | Stocker et al. ............. 514/235.8 |
| 2004/0048283 A1 | 3/2004 | Pau et al. |
| 2004/0152648 A1 | 8/2004 | Ullrich et al. |
| 2004/0198979 A1 | 10/2004 | Dhanak et al. |
| 2004/0235755 A1 | 11/2004 | Eigenbrodt et al. |
| 2005/0176675 A1 | 8/2005 | Gorny |

(Continued)

FOREIGN PATENT DOCUMENTS

| | | |
|---|---|---|
| CA | 2235621 A1 | 5/1997 |
| DE | 3813886 A1 | 11/1989 |

(Continued)

OTHER PUBLICATIONS

Adveenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.
Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970, pp. 850-853.
Behun et al., "The Chemistry of Pyrazine and Its Derivatives. IV. The Alkylation and Arylation of Methylpyrazine," J Org. Chern., 26 (9),3379-3382 (1961).
Benesch et al., "The clinicopathological and prognostic relevance of pyruvate kinase M2 and pAkt expression in breast cancer." Anticancer Res.;30(5):1689-94 (2010).
Berger, et. al., "Treatment of Pancreatic Cancer: Challenge of the Facts" World J. Surg., Societe Internationale de Chirurgie, vol. 27, pp. 1075-1083, 2003.

(Continued)

Primary Examiner — Jeffrey H Murray
Assistant Examiner — Oluwafemi Masha
(74) Attorney, Agent, or Firm — Lando & Anastasi LLP

(57) ABSTRACT

Compounds and compositions comprising compounds that modulate pyruvate kinase M2 (PKM2) are described herein. Also described herein are methods of using the compounds that modulate PKM2 in the treatment of cancer.

11 Claims, No Drawings

(56) References Cited

U.S. PATENT DOCUMENTS

| | | |
|---|---|---|
| 2007/0032418 A1 | 2/2007 | Shapiro et al. |
| 2007/0127505 A1 | 6/2007 | Laurila et al. |
| 2007/0280918 A1 | 12/2007 | Schwartz et al. |
| 2008/0004269 A1 | 1/2008 | Xu et al. |
| 2008/0021116 A1 | 1/2008 | Ullrich et al. |
| 2008/0044833 A1 | 2/2008 | Connors |
| 2008/0051414 A1 | 2/2008 | Hurley et al. |
| 2009/0048227 A1 | 2/2009 | Chakravarty et al. |
| 2009/0054453 A1 | 2/2009 | Alcaraz et al. |
| 2009/0163545 A1 | 6/2009 | Goldfarb |
| 2009/0247499 A1 | 10/2009 | Fletcher et al. |
| 2009/0270454 A1 | 10/2009 | Weingarten et al. |
| 2010/0105657 A1 | 4/2010 | Nordvall et al. |
| 2010/0179150 A1 | 7/2010 | Basarab et al. |
| 2010/0331307 A1* | 12/2010 | Salituro et al. ........... 514/210.21 |
| 2011/0046083 A1 | 2/2011 | Cantley et al. |
| 2011/0224252 A1 | 9/2011 | Dumeunier et al. |
| 2011/0312931 A1 | 12/2011 | Cioffi et al. |

FOREIGN PATENT DOCUMENTS

| | | |
|---|---|---|
| DE | 19841985 A1 | 3/2000 |
| EP | 0246749 A2 | 11/1987 |
| EP | 0628551 A1 | 12/1994 |
| EP | 1586558 A2 | 10/2005 |
| FR | 2735127 A1 | 12/1996 |
| GB | 1274436 A | 5/1972 |
| IT | 1176770 B | 8/1987 |
| JP | S61129129 A | 6/1986 |
| JP | 06-025177 | 2/1994 |
| JP | 2002-193710 A | 7/2002 |
| JP | 2007/238458 A | 9/2007 |
| WO | 8501289 A1 | 3/1985 |
| WO | 9211761 A1 | 7/1992 |
| WO | 93/13072 A1 | 7/1993 |
| WO | 9630343 A1 | 10/1996 |
| WO | 97/28129 A1 | 8/1997 |
| WO | 97/28141 A1 | 8/1997 |
| WO | 9744322 A1 | 11/1997 |
| WO | 98/03350 A1 | 1/1998 |
| WO | 99/16751 A1 | 4/1999 |
| WO | 0017202 A1 | 3/2000 |
| WO | 00/53596 A2 | 9/2000 |
| WO | 01/07440 A1 | 2/2001 |
| WO | 0119788 A2 | 3/2001 |
| WO | 0119798 A2 | 3/2001 |
| WO | 0164642 A2 | 9/2001 |
| WO | 0164643 A2 | 9/2001 |
| WO | 02/072077 A2 | 9/2002 |
| WO | 02/095063 A1 | 11/2002 |
| WO | 02100822 A1 | 12/2002 |
| WO | 03022277 A1 | 3/2003 |
| WO | 03037252 A2 | 5/2003 |
| WO | 03/062235 A1 | 7/2003 |
| WO | 03/073999 A2 | 9/2003 |
| WO | 03/076422 A1 | 9/2003 |
| WO | 03093297 A2 | 11/2003 |
| WO | 2004/004730 A2 | 1/2004 |
| WO | 2004014851 A2 | 2/2004 |
| WO | 2004/037251 A1 | 5/2004 |
| WO | 2004/073619 A2 | 9/2004 |
| WO | 2004/074438 A2 | 9/2004 |
| WO | 2004089470 A2 | 10/2004 |
| WO | 2004/110375 A2 | 12/2004 |
| WO | 2005/072642 A1 | 8/2005 |
| WO | 2005/117591 A2 | 12/2005 |
| WO | 2005120474 A2 | 12/2005 |
| WO | 2006/004195 A1 | 1/2006 |
| WO | 2006/016062 A1 | 2/2006 |
| WO | 2006033628 A1 | 3/2006 |
| WO | 2006034341 A2 | 3/2006 |
| WO | 2006-038594 A1 | 4/2006 |
| WO | 2006043950 A1 | 4/2006 |
| WO | 2006052190 A1 | 5/2006 |
| WO | 2006070198 A1 | 7/2006 |
| WO | 2006/122546 A1 | 11/2006 |
| WO | 2006117762 A2 | 11/2006 |
| WO | 2007003934 A2 | 1/2007 |
| WO | 2007023186 A1 | 3/2007 |
| WO | 2007/127505 A2 | 11/2007 |
| WO | 2008/019139 A2 | 2/2008 |
| WO | 2008/026658 A1 | 3/2008 |
| WO | 2008047198 A1 | 4/2008 |
| WO | 2008/050168 A1 | 5/2008 |
| WO | 2008052190 A2 | 5/2008 |
| WO | 2008073670 A2 | 6/2008 |
| WO | 2009012430 A1 | 1/2009 |
| WO | 2009013126 A1 | 1/2009 |
| WO | 2009/025781 A1 | 2/2009 |
| WO | 2010/042867 A2 | 4/2010 |
| WO | 2010/105243 A1 | 9/2010 |
| WO | 2010118063 A2 | 10/2010 |
| WO | 2010/129596 A1 | 11/2010 |
| WO | 2010130638 A1 | 11/2010 |
| WO | 2011002817 A1 | 1/2011 |
| WO | 2011032169 A2 | 3/2011 |
| WO | 2011047432 A1 | 4/2011 |
| WO | 2011/072174 A1 | 6/2011 |
| WO | 2011137089 A1 | 11/2011 |
| WO | 2012/092442 A1 | 7/2012 |

OTHER PUBLICATIONS

Bonuccelli et al., "The reverse Warburg effect: Glycolysis inhibitors prevent the tumor promoting effects of caveolin-1 deficient cancer associated fibroblasts." Cell Cycle.;9(10) (2010).

Boxer, et al., "Evaluation of Substituted N,N?-Diarylsulfonamides as Activators of the Tumor Cell Specific M2 Isoform of Pyruvate Kinase", J Med Chem. Feb. 11, 2010; 53(3): 1048.

Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).

Budinger et al., "Cellular Energy Utilization and Supply During Hypoxia in Embryonic Cardiac Myocytes," Am J Physiol. 270: L44-53 (1996).

Buschow et al., "MHC class II-associated proteins in B-cell exosomes and potential functional implications for exosome biogenesis." Immunol Cell Biol. (2010).

Chabner, et. al., "Chemotherapy and the war on cancer", Nature Rev. Cancer, Nature Publishing Group, vol. 5, pp. 65-72, 2005.

Chan et al., "Synthesis and characterization of poly(amide sulfonamide)s (PASAs)," J Polymer. Sci., 33 (15), 2525-2531 (1995).

Christofk et al., "pyruvate Kinase M2 is a Phosphotyrosine-Binding Protein," Nature 452: 181-186 (2008).

Christofk et al. , "The M2 Splice Isoform of Pyruvate Kinase is Important for Cancer Metabolism and Tumour Growth," Nature 452: 230-233 (2008).

Clement, et. al., "Production of Intracellular Superoxide Mediates Dithiothreitol- Dependent Inhibition of Apoptotic Cell Death" Antioxidants and Redox Signaling, Mary Ann Liebert, vol. 7, issues 3-4, pp. 456-464, 2005.

Cuzick, et. al., "Overview of the main outcomes in breast-cancer prevention trials" The Lancet, The Lancet Publishing Group, vol. 361, pp. 296-300, 2003.

Database Chemcats, Chemical Abstracts Service, Columbus, OH, US "Bionet Screening Compounds" Key Organics Ltd., Camelford, Cornwall (2001).

Dombrauckas, et al., Structural Basis for Tumor Pyruvate Kinasa M2 Allosteric Regulation and Catalysis, Biochemistry, vol. 44, p. 9717-9429 (2005).

Eigenbrodt et al., "Double Role for Pyruvate Kinase Type M2 in the Expansion of Phosphometabolite Pools Found in Tumor Cells," Crit Rev Oncog. 3: 91-115 (1992). (Abstract only).

Engelman et al., "Allelic Dilution Obscures Detection of a Biologically Significant Resistance Mutation in EGFR-Amplified Lung Cancer," J Clin Invest. 116: 2695-2706 (2006).

Eswaran et al., "Crystal Structures and Inhibitor Identification for PTPN5, PTPRR and PTPN7: A Family of Human MAPK-Specific Protein Tyrosine Phosphatases," Biochem J. 395: 483-491 (2006).

(56) References Cited

OTHER PUBLICATIONS

European Patent Office Communication (European Application No. 07836571.5), dated Oct. 18, 2010.
Friedman et al., "Leptin and the regulation of body weight in mammals" Nature. vol. 395, 1996.
Gupta et al., "Dominant negative mutations affect oligomerisation of human pyruvate kinase M2 isozyme and promote cellular growth and polyploidy." J Biol Chem. (2010).
Hitosugi T et al: "Tyrosine Phosphorylation Inhibits PKM2 to Promote the Warburg Effect and Tumor Growth" Science Signaling, American Association for the Advancement of Science, US LNKD-DOI:10.1126/SCISIGNAL.2000431, vol. 2, No. 97, Nov. 17, 2009, pp. RA73-1.
Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.
Hulleman, et al., "Pyruvate kinase M2 and prednisolone resistance in acute lymphoblastic leukemia." Haematologica. Sep. 2009; 94(9): 1322-1324.
Inglese et al., "Quantitative high-throughput screening: A titration-based approach that efficiently identifies biological activities in large chemical libraries," ProC. Natl. Acad. Sci., 103 (31), 11473-11478 (2006).
International Preliminary Report on patentability for International Application No. PCT/US2007/017519, issued Feb. 10, 2009.
International Preliminary Report on Patentability for PCT/US2008/009828, dated Feb. 16, 2010.
International Preliminary Report on Patentability, Application No. PCT/US2009/060237, dated Apr. 12, 2011.
International Search Report & Written Opinion for PCT/US10/030139 dated Dec. 10, 2010.
International Search Report & Written Opinion for PCT/US10/40485 dated Aug. 11, 2010.
International Search Report and the Written Opinion of the International Search Authority (PCT/US07/17519), mailed Jul. 8, 2008.
International Search Report dated Mar. 5, 2012 for related international application No. PCT/US2011/067752.
International Search Report for PC/US10/40486 dated Sep. 1, 2010.
International Search Report for PCT/US2008/009828, dated Dec. 5, 2008.
International Search Report for PCT/US2010/033610 dated Jul. 22, 2010.
International Search Report, Application No. PCT/US2009/060237, dated Jun. 16, 2010.
International Search Report, Application No. PCT/US2011/033852, dated Aug. 3, 2011.
Jiang et al., "Evaluation of thieno[3,2-b]pyrrole[3,2-d]pyridazinones as activators of the tumor cell specific M2 isoform of pyruvate kinase." Bioorg. Med. Chern. Lett., 20 (11), 3387-3393 (2010).
Joshi et al., "Age-related faecal calprotectin, lactoferrin and tumour M2-PK concentrations in healthy volunteers." Ann Clin Biochem. ;47(Pt 3):259-63 (2010).
Jurica et al., "The Allosteric Regulation of Pyruvate Kinase by Fructose-1,6-Bisphosphate," Structure 6: 195-210 (1998).
Kao et al., "A Small-Molecule Inhibitor of the Ribonucleolytic Activity of Human Angiogenin That Possesses Antitumor Activity," Proc. Natl. Acad. Sci. USA, 99(15): 10066-10071 (2002).
Kharalkar et al., "Identification of Novel Allosteric Regulators of Human-Erythrocyte Pyruvate Kinase," Chem Biodivers. 4: 2603-2617 (2007).
Klapars et al., "A General and Efficient Copper Catalyst for the Amidation of Aryl Halides and the N-Arylation of Nitrogen Heterocycles," J. Am. Chem. Soc., 123 (31), 7727-7729 (2001).
Kumar et al., "In vivo factors influencing tumour M2-pyruvate kinase level in human pancreatic cancer cell lines." Tumour Biol.;31(2):69-77 (2010).
Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).
Lee, "Consolidation Effect of Phenylalanine-administration of Antitumor Activity of A 5 Fluorouracil," Med. J. Kagoshima Univ. 37(3-4): 285-308 (1985).
Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.
Li et al., "Quantitative proteome analysis of multidrug resistance in human ovarian cancer cell line." J Cell Biochem.;109(4):625-33 (2010).
Li et al., "Screening and identification of interactive proteins of SH2D4A." Yi Chuan.;32(7):712-8 (2010).
Oeda, "On some 2,5-Dialikl-piperazines," Bull. Chem. Soc., 13, 465-470 (1938).
Park, "Prevention of type 2 diabetes mellitus from the viewpoint of genetics." Diabetes Research and Clinical Practice 2004; 66S: S33-S35.
Paudler et al., "3,7-Disubstituted octahydro-1,5-diazocines. Their conversion into tetrahydro-1,5-diazocines and into ring-contracted products," J. Org. Chern., 32 (8), 2425-2430 (1967).
Pollard et al., "Some Amides of Piperazines," J. Am. Chem. Soc., 75 (2), 491 (1953).
Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.
Remington's, "Structure Activity Relationship and Drug Design," Pharmaceutical Sciences, pp. 420-425p. 420-425, 1980.
Rich, et. al., "Development of novel targeted therapies in the treatment of malignant glioma" Nature Rev. Drug Disc., Nature Publishing Group, vol. 3, pp. 430-446, 2004.
Root et al., "Genome-Scale Loss-of-Function Screening with a Lentiviral RNAi Library," Nat Methods 3: 715-719 (2006).
Ruan et al., "HSP60, a protein downregulated by IGFBP7 in colorectal carcinoma." J Exp Clin Cancer Res.;29:41 (2010).
Sabatine et al., "Metabolomic Identification of Novel Biomarkers of Myocardial Ischemia," Circulation 112: 3868-3875 (2005).
Schneider, et. al., "Tumor M2-pyruvate kinase in the follow-up of inoperable lung cancer patients: a pilot study." Cancer Letters, Elsevier, vol. 193, pp. 91-98, 2003.
Schroth et al., "RingschluBreaktion von Diacetylen mit Diaminen: Eine Ciniache von 2,3-Dihydro-1,4-diazepinen," Zeitschritt Fur Chemie., 6 (4), 143 (1969).
Seibel et al., "Synthesis and evaluation of B-lactams (piperazones) as elastase inhibitors," Bioorg. Med. Chern. Ltrs., 13 (3),387-389 (2003).
Shi, et al., "Silencing of pkm2 increases the efficacy of docetaxel in human lung cancer xenografts in mice." Cancer Science, vol. 101, # 6, 1447-1453, Jun. 2010.
Stewart et al., "Piperazines. I. Derivatives of Piperazine-1-Carboxylic and -1,4-Dicarboxylic Acid,", J. Org. Chern., 18 (1),1478-1483 (1953).
Surh, "Cancer Chemoprevention with Dietary Phytochemicals", Nature Reviews Cancer, Nature Publishing Group, vol. 3, p. 768-780, 2003.
Szoka et al., "Comparative properties and methods of preparation of lipid vesicles (liposomes )," Ann. Rev. Biophys. Bioeng., 9, 467-508 (1980).
Tawaka, et al., Caplus an 1998:794998.
Uozumi et al., "Catalytic asymmetric construction of morpholines and piperazines by palladium-catalyzed tandem allylic substitution reactions," J. Org. Chem., 58 (24),6826-6832 (1993).
Vander Heiden et al., "Growth Factors Can Influence Cell Growth and Survival Through Effects on Glucose Metabolism," Mol Cell Bioi. 21: 5899-5912 (2001).
Vander Heiden et al., "Identification of Small Molecule Inhibitors of Pyruvate Kinase M2," Biochemical Pharmacology. 79(8): 1118-1124 (2010).
Villen et al., "Large-Scale Phosphorylation Analysis of Mouse Liver," Proc Nat! Acad Sci USA 104: 1488-1493 (2007).
Written Opinion of the International Searching Authority for PCT/US2008/009828, dated Dec. 5, 2008.

(56) References Cited

OTHER PUBLICATIONS

Yamada and Noguchi, "Nutrient and Hormonal Regulation of Pyruvate Kinase Gene Expression," Biochem J. 337: 1-11 (1999).
Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47 (20),3784-3786 (2008).
Ge et al. "Anaplasma phagocytophilum inhibits human neutrophil apoptosis via upregulation of bfl-1, maintenance of mitochondrial membrane potential and prevention of caspase 3 activation." Cellular Microbiology, 2005, 7(1 ), 29-38.
International Preliminary Report for related application No. PCT/US2010/059778 dated Jun. 21, 2012.
International Preliminary Report for related application No. PCT/US2011/067752 dated Apr. 11, 2013.
International Search Report dated Apr. 4, 2012 for related Application PCT/US2011/065633.
International Search Report dated May 3, 2012 for related application PCT/US2011/066595.
International Search Report for PCT/US2010/059778 dated Mar. 17, 2011.
STN File CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]N-(4-methoxyphenyl)-4-methyl-".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
Supplemental EP Search Report & Written Opinion for EP 10 79 4667 dated Jan. 15, 2013.
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.
Cecil Textbook of Medicine, edited by Bennet, J.C., and Plum F., 20th edition, vol. 1, 1004-1010, 1996.
Cohen et al., "The development and therapeutic potential of protein kinase inhibitors", Current Opinion in Chemical Biology, 3,459-465, 1999.
Dermer et al., "Another Anniversary for the War on Cancer", Bio/Technology, 1994, 12:320.
Fabbro et al. "Protein kinases as targets for anticancer agents: from inhibitors to useful drugs." Pharmacology & Therapeutics 93, 79-98, 2002.
Freshney et al.,Culture of Animal Cells, A Manual of Basic Technique, Alan R. Liss, Inc., 1983, New York, p. 4.
Golub et al., "Molecular Classification of Cancer: Class Discovery and Class Prediction by Gene Expression Monitoring", Science, 286, 531-537, 1999.
Mass, R. D., "The HER receptor family: a rich target for therapeutic development", Int. J. Radiation Oncology Bio. Phys. vol. 58(3): 932-940, 2004.
Supplementary Search Report for EP10794668 Mailed Oct. 18, 2012.
Crawford et al., Caplus an 2010:1218943.
European Search report for EP Application No. 10 794 667.5 dated Oct. 9, 2013.
Furuya et al., Inactivation of the 3-phosphoglycerate dehydrogenase gene in mice: changes in gene expression and associated regulatory networks resulting from serine deficiency. Funct Integr Genomics (2008) 8:235-249.
International Preliminary Report on Patentability for PCT/US2010/040486 dated Jan. 12, 2012.
International Search Report for Application No. PCT/US12/60099 dated Jan. 8, 2013.
International Search Report for PCT/US2011/065633 dated Jun. 18, 2013.
Komoriya et al. "Design, synthesis, and biological activity of non-basic compounds as factor Xa inhibitors: SAR study of S1 and aryl binding sites" Bioorganic & Medicinal Chemistry 13 (2005) 3927-3954.
Kung et al. "Small Molecule Activation of PKM2 in Cancer Cells Induces Serine Auxotrophy" Chemistry & Biology, 19, 1187-1198, Sep. 21, 2012.
Patel et al. "Synthesis of some new idolinone derivatives containing piperazine moiety" Bulgarian Chemical Communications, 2003 Bol 35 No. 4 pp. 242-244.
Proisy et al. "Rapid Synthesis of 3-Aminoisoquinoline-5-sulfonamides Using the Buchwald-Hartwig Reaction" Synthesis 2009, No. 4, pp. 0561-0566.
Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.
Villoutreix et al., Caplus an 2010:20993.
Web posting, Pyruvate kinase M2 isozyme (PKM2), SciBX 5(42), Published online Oct. 25, 2012, Abstract only.
Ye et al., Pyruvate kinase M2 promotes de novo serine synthesis to sustain mTORC1 activity and cell proliferation, PNAS 109(18), 2012, pp. 6904-6909.

\* cited by examiner

THERAPEUTIC COMPOUNDS AND COMPOSITIONS

CLAIM OF PRIORITY

This application claims priority from U.S. Ser. No. 61/428,030, filed Dec. 29, 2010 which is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Thus, the activation of PKM2 may be effective in the treatment of, e.g., obesity, diabetes, autoimmune conditions, and proliferation-dependent diseases, e.g., benign prostatic hyperplasia (BPH). Current inhibitors of pyruvate kinase are not selective, making it difficult to treat disease related to pyruvate kinase function.

Furthermore, phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 (i.e., activators of PKM2) can also inhibit the growth and proliferation of cancer cells, activated immune cells, and fat cells.

There is a continuing need for novel treatments of diseases such as cancer, diabetes, obesity, autoimmune conditions, proliferation-dependent diseases (e.g., BPH), and other diseases related to the function of pyruvate kinase (e.g., PKM2).

SUMMARY OF INVENTION

Described herein are compounds of Formula I that activate pyruvate kinase M2 (PKM2) and pharmaceutically acceptable salts, solvates, and hydrates thereof:

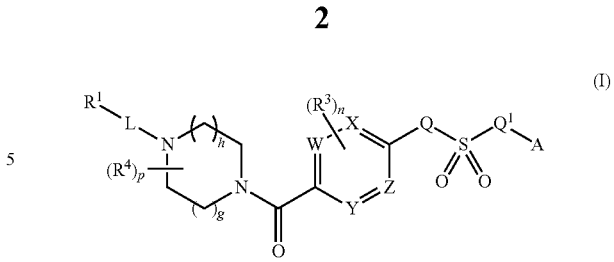

wherein:

W, X, Y and Z are each independently selected from CH or N;

Q and $Q^1$ are independently selected from a bond or $NR^b$;

A is optionally substituted bicyclic aryl or optionally substituted bicyclic heteroaryl;

L is a bond, —C(O)—, —$(CR^cR^c)_m$—, —OC(O)—, —$(CR^cR^c)_m$—OC(O)—, —$(CR^cR^c)_m$—C(O)—, —$NR^bC(S)$—, or —$NR^bC(O)$— (wherein the point of the attachment to $R^1$ is on the left-hand side);

$R^1$ is selected from alkyl, carbocycle, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^4$ is independently selected from halo, haloalkyl, alkyl, hydroxyl, =O, —$OR^a$, and phenyl, or two $R^4$ taken together with the carbon atoms to which they are attached form a carbocycle;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted carbocycle;

each $R^d$ is independently selected from halo, haloalkyl, haloalkoxy, alkyl, alkynyl, nitro, cyano, hydroxyl, —$C(O)R^a$, —$OC(O)R^a$, —$C(O)OR^a$, —$SR^a$, —$NR^aR^b$ and —$OR^a$, or two $R^d$ taken together with the carbon atoms to which they are attached form an optionally substituted heterocyclyl;

n is 0, 1, or 2;

m is 1, 2 or 3;

h is 0, 1, 2;

g is 0, 1 or 2;

the sum of g+h is equal to or greater than 2; and p is 0, 1 or 2; and provided that the compound of formula (I) is not N-[3-[(3,5-dimethoxyphenyl)amino]-2-quinoxalinyl]-4-[(4-methyl-1-piperazinyl)carbonyl]-benzenesulfonamide;

N-[4-[[4-(2-furanylmethyl)-1-piperazinyl]carbonyl]phenyl]-2,3-dihydro-2-oxo-1H-benzimidazole-5-sulfonamide;

2,3-dihydro-2-oxo-N-[4-[[4-(2,2,2-trifluoroethyl)-1-piperazinyl]carbonyl]phenyl]-1H-benzimidazole-5-sulfonamide;

2,3-dihydro-N-[4-[[4-(4-nitrophenyl)-1-piperazinyl]carbonyl]phenyl]-2-oxo-1H-benzimidazole-5-sulfonamide;

N-[4-[[4-(2-ethoxyphenyl)-1-piperazinyl]carbonyl]phenyl]-2,3-dihydro-2-oxo-1H-benzimidazole-5-sulfonamide;

2,3-dihydro-2-oxo-N-[4-[[4-(3-thienylmethyl)-1-piperazinyl]carbonyl]phenyl]-1H-benzimidazole-5-sulfonamide;

N-[4-[[4-(2,3-dimethylphenyl)-1-piperazinyl]carbonyl]phenyl]-2,3-dihydro-2-oxo-1H-benzimidazole-5-sulfonamide;

2,3-dihydro-N-[4-[[4-(2-hydroxyphenyl)-1-piperazinyl]carbonyl]phenyl]-2-oxo-1H-benzimidazole-5-sulfonamide;

4-[4-[[(2,3-dihydro-2-oxo-1H-benzimidazol-5-yl)sulfonyl]amino]benzoyl]-1-piperazinecarboxylic acid ethyl ester;

N-[4-[(4-acetyl-1-piperazinyl)carbonyl]phenyl]-2,3-dihydro-2-oxo-1H-benzimidazole-5-sulfonamide;

N-[4-[[4-(4-fluorophenyl)-1-piperazinyl]carbonyl]phenyl]-2,3-dihydro-2-oxo-1H-benzimidazole-5-sulfonamide;

2,3-dihydro-2-oxo-N-[4-[(4-phenyl-1-piperazinyl)carbonyl]phenyl]-1H-benzimidazole-5-sulfonamide; or 2,3-dihydro-2-oxo-N-[4-[[4-(2-pyridinyl)-1-piperazinyl]carbonyl]phenyl]-1H-benzimidazole-5-sulfonamide.

Also provided are pharmaceutical compositions comprising a compound of Formula I or a pharmaceutically acceptable salt thereof and the use of such compositions in methods of treating diseases and conditions that are related to reduced pyruvate kinase function (e.g., PKM2 function), including, e.g., cancer, diabetes, obesity, autoimmune disorders, and benign prostatic hyperplasia (BPH).

In another embodiments, provided is a method of modulating (e.g., increasing or decreasing) the level of PKM2 activity and/or glycolysis (e.g., modulating the endogenous ability of a cell in the patient to down regulate PKM2) in a patient in need thereof. The method comprises the step of administering an effective amount of a compound described herein to the patient in need thereof, thereby modulating (e.g., increasing or decreasing) the level of PKM2 activity and/or glycolysis in the patient. In certain embodiment, the method includes identifying or selecting a patient who would benefit from activation of PKM2. For example, the patient can be identified on the basis of the level of PKM2 activity in a cell of the patient for treatment of cancer associated with PKM2 function.

In another embodiment, provided is a method of inhibiting cell proliferation in a patient in need thereof. The method comprises the step of administering an effective amount of a compound described herein to the patient in need thereof, thereby inhibiting cell proliferation in the patient.

In another embodiment, the compound described herein is administered at a dosage and frequency sufficient to increase lactate production or oxidative phosphorylation.

DETAILED DESCRIPTION

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DEFINITIONS

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. In certain aspects, the term "alkyl" refers to a monovalent hydrocarbon chain that may be a straight chain or branched chain, containing 1 to 6 carbon atoms. In other aspects, the term "alkyl" refers to a monovalent hydrocarbon chain that may be a straight chain or branched chain, containing 1 to 4 carbon atoms.

The term "haloalkyl" refers to an alkyl in which one or more hydrogen atoms are replaced by halo, and includes alkyl moieties in which all hydrogens have been replaced by halo (e.g., perfluoroalkyl).

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl" refers to a monovalent straight or branched hydrocarbon chain containing 2-4 carbon atoms and having one or more double bonds.

The term "alkynyl" refers to a monovalent straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively.

The term "aralkylamino" refers to a —NH(aralkyl) radical.

The term "alkylaminoalkyl" refers to a (alkyl)NH-alkyl-radical.

The term "dialkylaminoalkyl" refers to a (alkyl)$_2$N-alkyl-radical.

The term "mercapto" refers to an —SH radical.

The term "thioalkoxy" refers to an —S-alkyl radical.

The term "thioaryloxy" refers to an —S-aryl radical.

The term "alkoxy" refers to an —O-alkyl radical.

The term "aryl" refers to a monocyclic, bicyclic, or tricyclic aromatic hydrocarbon ring system. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition. Such bicyclic or tricyclic ring systems may be alternately characterized as being an aryl or a heteroaryl fused to a carbocyclyl or heterocyclyl, particularly in those instances where the ring bound to the rest of the molecule is required to be aromatic.

The terms "heteroarylalkyl" and "heteroaralkyl", as used herein, refers to an alkyl group substituted with a heteroaryl group.

The term "heterocyclylalkyl", as used herein, refers to an alkyl group substituted with a heterocyclyl group.

The term "acyl" refers to an alkylcarbonyl, carbocyclecarbonyl, arylcarbonyl, heterocyclylcarbonyl, or heteroarylcarbonyl substituent, any of which may be further substituted (e.g., by one or more substituents).

All ring systems (i.e., aryl, heteroaryl, carbocyclyl, cycloalkyl, heterocyclyl, etc.) or ring system portions of groups (e.g., the aryl portion of an aralkyl group) are optionally substituted at one or more substitutable carbon atoms with substituents including: halo, —C≡N, $C_1$-$C_4$ alkyl, =O, $C_3$-$C_7$ carbocycle (e.g., cycloalkyl), $C_1$-$C_4$ alkyl, —OH, —O—($C_1$-$C_4$ alkyl), —SH, —S—($C_1$-$C_4$ alkyl), —($C_1$-$C_4$ alkyl)-N($R^{b'}$)($R^{b'}$), —N($R^{b'}$)($R^{b'}$), —O—($C_1$-$C_4$alkyl)-N($R^{b'}$)($R^{b'}$), —($C_1$-$C_4$ alkyl)-O—($C_1$-$C_4$ alkyl)-N($R^{b'}$)($R^{b'}$), —C(O)-O($R^{b'}$), —OC(O)($R^{b'}$), —O—C(O)-O($R^{b'}$), —C(O)—N($R^{b'}$)($R^{b'}$), —N($R^{b'}$)—C(O)$R^{b'}$, —N($R^{b'}$)C(O)N($R^{b'}$)($R^{b'}$), —N($R^{b'}$)—S(O)$_{1-2}R^{b'}$, —S(O)$_{1-2}$N($R^{b'}$)($R^{b'}$), —N($R^{b'}$)S(O)$_{1-2}$N($R^{b'}$)($R^{b'}$), —($C_1$-$C_4$ alkyl)-C(O)—N($R^{b'}$)($R^{b'}$), —O-(heteroaryl), —O-(heterocycle), —O-phenyl, -heteroaryl, -heterocycle, and -phenyl, wherein:
  each $R^{b'}$ is independently selected from hydrogen, —$C_1$-$C_4$ alkyl, carbocycle, carbocyclylalkyl, aryl, aralkyl, heteroaryl, heteroaralkyl, heterocyclyl, or heterocyclylalkyl; or
  two $R^{b'}$ are taken together with the nitrogen atom to which they are bound to form a 4- to 8-membered saturated heterocycle optionally comprising one additional heteroatom selected from N, S, S(=O), S(=O)$_2$, and O,
  any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$; and
  any carbon atom on a phenyl, carbocycle (e.g., cycloalkyl), heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$.

All heterocyclyl ring systems (and any heterocyclyl substituents on any ring system) are optionally substituted on one or more any substitutable nitrogen atom with —$C_1$-$C_4$ alkyl, oxo, fluoro-substituted $C_1$-$C_4$ alkyl, or acyl.

The term "substituted" refers to the replacement of a hydrogen atom by another group.

The term "oxo" refers to an oxygen atom, which forms a carbonyl when attached to carbon, an N-oxide when attached to nitrogen, and a sulfoxide or sulfone when attached to sulfur.

The term "selective" is meant at least 2-fold, 3-fold, 4-fold, 5-fold, 6-fold, or 10-fold greater activation of PKM2 than PKM1.

The term "activator" as used herein means an agent that (measurably) increases the activity of PKM2 or causes PKM2 activity to increase to a level that is greater than PKM2's basal levels of activity. For example, the activator may mimic the effect caused by a natural ligand (e.g., FBP). The activator effect caused by a compound provided herein may be to the same, or to a greater, or to a lesser extent than the activating effect caused by a natural ligand, but the same type of effect is caused. A compound provided herein can be evaluated to determine if it is an activator by measuring either directly or indirectly the activity of the pyruvate kinase when subjected to said compound. The activity of PKM2 can be measured, for example, by monitoring the concentration of a substrate such as ATP or NADH, for example, as described herein.

Compounds

Described herein are compounds and compositions that activate PKM2. Compounds that activate PKM2, can be used to treat disorders such as neoplastic disorders (e.g., cancer) or fat related disorders (e.g., obesity).

In one embodiment, provided is a compound of formula (I) or a pharmaceutically acceptable salt thereof, or a pharmaceutical composition comprising a compound of formula (I) or a pharmaceutically acceptable salt thereof:

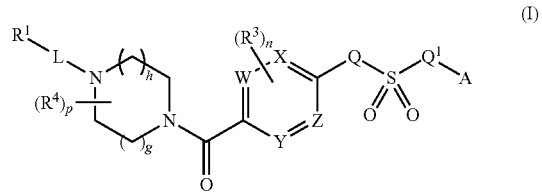

(I)

wherein: W, X, Y and Z are each independently selected from CH or N;

Q and $Q^1$ are independently selected from a bond or $NR^b$;

A is optionally substituted bicyclic aryl or optionally substituted bicyclic heteroaryl;

L is a bond, —C(O)—, —(CR$^c$R$^c$)$_m$—, —OC(O)—, —(CR$^c$R$^c$)$_m$—OC(O)—, —(CR$^c$R$^c$)$_m$—OC(O)—, —NR$^b$C(S)—, or —NR$^b$C(O)— (wherein the point of the attachment to $R^1$ is on the left-hand side);

$R^1$ is selected from alkyl, carbocycle, aryl, heteroaryl, and heterocyclyl; each of which is substituted with 0-5 occurrences of $R^d$;

each $R^3$ is independently selected from halo, haloalkyl, alkyl, hydroxyl and —OR$^a$, or two adjacent $R^3$ taken together with the carbon atoms to which they are attached form an optionally substituted heterocyclyl;

each $R^4$ is independently selected from halo, haloalkyl, alkyl, hydroxyl, =O, —OR$^a$ and phenyl, or two $R^4$ taken together with the carbon atoms to which they are attached form a bridged, fused or spyro-fused carbocycle, an aryl or a heteroaryl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^a R^b$ and —O$R^a$, or two $R^d$ taken together with the carbon atoms to which they are attached form an optionally substituted heterocyclyl;

n is 0, 1, or 2;
m is 1, 2 or 3;
h is 0, 1, 2;
g is 0, 1 or 2;
the sum of g+h is equal to or greater than 2; and
p is 0, 1 or 2; and provided that the compound of formula (I) is not N-[3-[(3,5-dimethoxyphenyl)amino]-2-quinoxalinyl]-4-[(4-methyl-1-piperazinyl)carbonyl]-benzenesulfonamide;

N-[4-[[4-(2-furanylmethyl)-1-piperazinyl]carbonyl]phenyl]-2,3-dihydro-2-oxo-1H-benzimidazole-5-sulfonamide;

2,3-dihydro-2-oxo-N-[4-[[4-(2,2,2-trifluoroethyl)-1-piperazinyl]carbonyl]phenyl]-1H-benzimidazole-5-sulfonamide;

2,3-dihydro-N-[4-[[4-(4-nitrophenyl)-1-piperazinyl]carbonyl]phenyl]-2-oxo-1H-benzimidazole-5-sulfonamide;

N-[4-[[4-(2-ethoxyphenyl)-1-piperazinyl]carbonyl]phenyl]-2,3-dihydro-2-oxo-1H-benzimidazole-5-sulfonamide;

2,3-dihydro-2-oxo-N-[4-[[4-(3-thienylmethyl)-1-piperazinyl]carbonyl]phenyl]-1H-benzimidazole-5-sulfonamide;

N-[4-[[4-(2,3-dimethylphenyl)-1-piperazinyl]carbonyl]phenyl]-2,3-dihydro-2-oxo-1H-benzimidazole-5-sulfonamide;

2,3-dihydro-N-[4-[[4-(2-hydroxyphenyl)-1-piperazinyl]carbonyl]phenyl]-2-oxo-1H-benzimidazole-5-sulfonamide;

4-[4-[[(2,3-dihydro-2-oxo-1H-benzimidazol-5-yl)sulfonyl]amino]benzoyl]-1-piperazinecarboxylic acid ethyl ester;

N-[4-[(4-acetyl-1-piperazinyl)carbonyl]phenyl]-2,3-dihydro-2-oxo-1H-benzimidazole-5-sulfonamide;

N-[4-[[4-(4-fluorophenyl)-1-piperazinyl]carbonyl]phenyl]-2,3-dihydro-2-oxo-1H-benzimidazole-5-sulfonamide;

2,3-dihydro-2-oxo-N-[4-[(4-phenyl-1-piperazinyl)carbonyl]phenyl]-1H-benzimidazole-5-sulfonamide; or 2,3-dihydro-2-oxo-N-[4-[[4-(2-pyridinyl)-1-piperazinyl]carbonyl]phenyl]-1H-benzimidazole-5-sulfonamide.

In certain embodiments of a compound of formula (I) or a pharmaceutically acceptable salt thereof p is 1 or 2. In one aspect of this embodiment, p is 2 and the compound has the formula Ia:

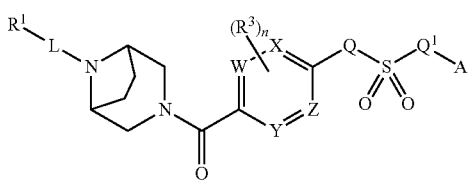

(Ia)

or formula Ib:

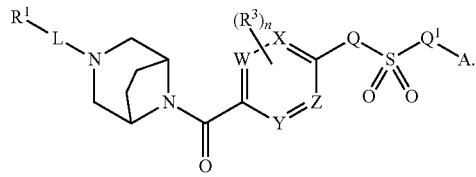

(Ib)

In an alternate aspect of this embodiment, p is 1 or 2; and each $R^4$ is independently selected from (S)-alkyl, (R)-alkyl, (S)-phenyl, and (R)-phenyl. In an even more specific aspect of this embodiment, g is 1, h is 1; p is 1 or 2; and each $R^4$ is independently selected from (S)-methyl, (R)-methyl, (S)-ethyl, (R)-ethyl, (S)-isopropyl, (R)-isopropyl, (S)-phenyl, and (R)-phenyl. In still another alternate aspect, p is 2 and the two $R^4$ taken together with the carbon atoms to which they are attached form a phenyl ring that is fused to the piperazine ring.

In certain embodiments of a compound of formula (I) or a pharmaceutically acceptable salt thereof n is 1 or 2.

In certain embodiments of a compound of formula (I) or a pharmaceutically acceptable salt thereof, A is an optionally substituted bicyclic heteroaryl. In an aspect A is

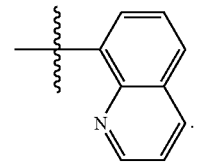 [SMILES: *c1cccc2cccnc12]

In some embodiments, g is 1 or 2; h is 1 or 2; and g+h is 2 or 3. In one aspect of this embodiment g+h=2. In an alternate aspect of this embodiment, g+h=3.

In some embodiments, W, X, Y, Z and the carbons to which they are attached form a phenyl ring.

In some embodiments, W, X, Y, Z and the carbons to which they are attached form a pyridyl ring. In one aspect of this embodiment W, X and Y are CH and Z is N. In an alternate aspect X, Y and Z are CH and W is N.

In some embodiments, W, X, Y, Z and the carbon atoms to which they are attached form a pyrimidyl ring.

In some embodiments, W, X, Y, Z and the carbon atoms to which they are attached form a pyridazinyl ring.

In some embodiments the ring comprising W, X, Y and Z is unsubstituted (i.e., n is 0). In some embodiments, the ring comprising W, X, Y and Z is monosubstituted (i.e., n is 1).

In some embodiments where n is 1, $R^3$ is selected from fluoro, chloro methyl, ethyl, $CF_3$, methoxy, and $OCF_3$.

In some embodiments, Q is $NR^b$ and $Q^1$ is a bond. In some aspects of these embodiments, $R^b$ is methyl. In other aspects of these embodiments, $R^b$ is hydrogen (H).

In some embodiments, L is a bond.

In some embodiments, L is —(C$R^c R^c$)$_m$— and m is 1. In some aspects of these embodiments, each $R^c$ is hydrogen. In other aspects of these embodiments, one $R^c$ is methyl and the other $R^c$ is hydrogen. In some aspects of these embodiments, one $R^c$ is —$CF_3$ and one $R^c$ is hydrogen. In some aspects of these embodiments, both $R^c$ are methyl. In some aspects of these embodiments, two $R^c$ taken together with the carbon to which they are attached form a cyclopropyl, cyclobutyl, cyclopentyl or cyclohexyl.

In some embodiments, L is ethyl or n-propyl.

In some embodiments, L is —C(O)—.

In some embodiments, L is —O—C(O)—.

In some embodiments, L is —(CR$^c$R$^c$)$_m$—C(O)— and m is 1. In some aspects of these embodiments, each R$^c$ is hydrogen. In some aspects of these embodiments, one R$^c$ is methyl and one R$^c$ is hydrogen. In some aspects of these embodiments, both R$^c$ are methyl.

In some embodiments, L is —(CR$^c$R$^c$)$_m$—O—C(O)— and m is 1 or 2. In some aspects of these embodiments, each R$^c$ is hydrogen.

In some embodiments, L is selected from bond, —C(O)—, —OC(O)—, —CH$_2$—OC(O)—, —(CH$_2$)$_2$—OC(O)—, —C(CH$_3$)$_2$—C(O)—, —CH$_2$—, —(CH$_2$)$_2$—, —(CH$_2$)$_3$—, —CH(CH$_3$)—, —CH(CF$_3$)—, —C(CH$_3$)$_2$—, —CHD-, —CD$_2$-,

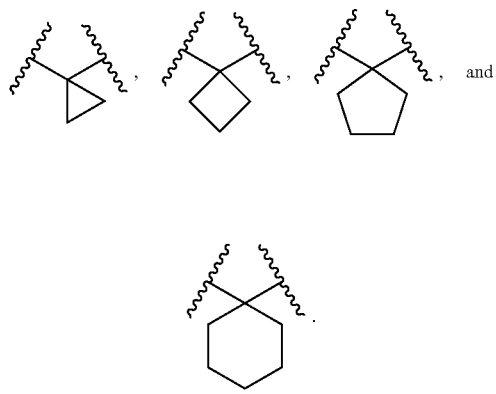, and

In some embodiments, R$^1$ is selected from methyl, ethyl, isopropyl, cyclopropyl, cyclobutyl, cyclopentyl, cyclohexyl, phenyl, pyridin-2-yl, pyridin-3-yl, pyridin-4-yl, 1,2,3-thiadiazol-5-yl, 1,2,3-thiadiazol-4-yl, thiazol-2-yl, thiazol-4-yl, thiazol-5-yl, 1H-imidazol-4-yl, 1H-imidazol-2-yl, 1H-pyrazol-3-yl, 1H-pyrazol-4-yl, 1H-pyrazol-5-yl, pyrazin-2-yl, oxazol-4-yl, isoxazol-5-yl, tetrahydrofuran-2-yl, tetrahydrofuran-3-yl, tetrahydrofuran-4-yl, tetrahydro-2H-pyran-4-yl, tetrahydro-2H-pyran-3-yl, and tetrahydro-2H-pyran-2-yl.

In certain embodiments R$^1$ is substituted with one or more substituents independently selected from fluoro, chloro, methyl, CF$_3$, and methoxy.

In certain embodiments, the compound of Formula I is selected from any one of the compounds set forth in the Examples, Table 1 or Table 2.

TABLE 1

| Cmpd # | Structure |
|---|---|
| 217 | 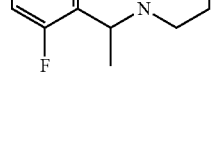 |
| 183 | 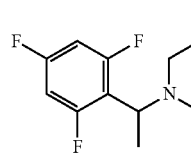 |
| 167 | 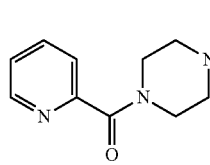 |
| 103 | 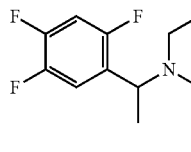 |
| 168 | 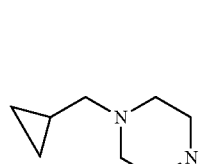 |
| 178 | 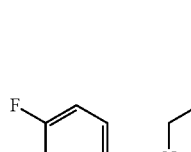 |
| 173 | 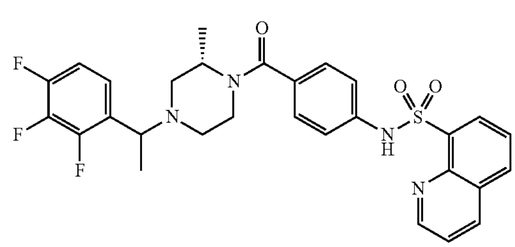 [SMILES: CC(c1ccc(F)c(F)c1F)N1CCN(C(=O)c2ccc(NS(=O)(=O)c3cccc4cccnc34)cc2)[C@@H](C)C1] |

TABLE 1-continued

TABLE 1-continued

| Cmpd # | Structure |
|---|---|
| 181 | 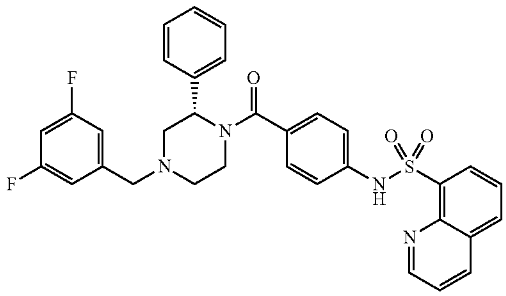 [SMILES: O=C(c1ccc(NS(=O)(=O)c2cccc3cccnc23)cc1)N1CCN(Cc2cc(F)cc(F)c2)C[C@@H]1c1ccccc1] |
| 170 | 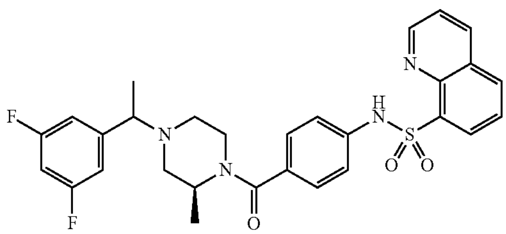 [SMILES: CC(c1cc(F)cc(F)c1)N1CCN(C(=O)c2ccc(NS(=O)(=O)c3cccc4cccnc34)cc2)[C@@H](C)C1] |
| 166 | 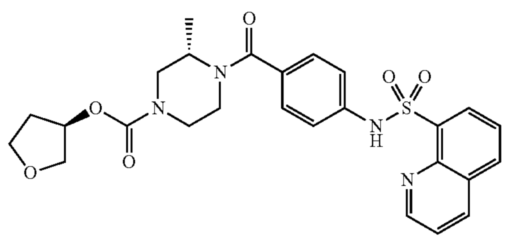 [SMILES: C[C@H]1CN(C(=O)O[C@@H]2CCOC2)CCN1C(=O)c1ccc(NS(=O)(=O)c2cccc3cccnc23)cc1] |
| 209 | 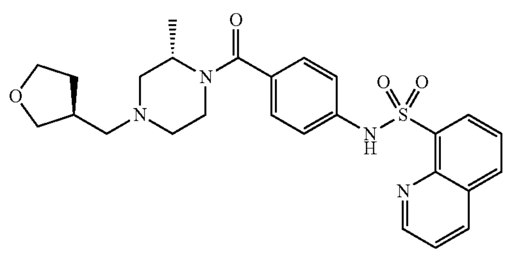 [SMILES: C[C@H]1CN(C[C@@H]2CCOC2)CCN1C(=O)c1ccc(NS(=O)(=O)c2cccc3cccnc23)cc1] |
| 210 | 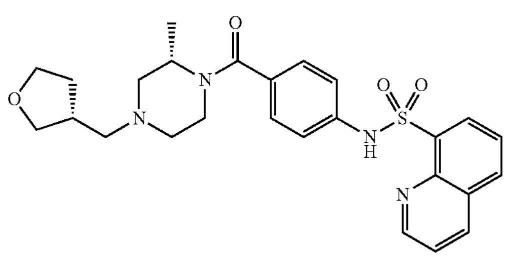 [SMILES: C[C@H]1CN(C[C@H]2CCOC2)CCN1C(=O)c1ccc(NS(=O)(=O)c2cccc3cccnc23)cc1] |
| 182 | 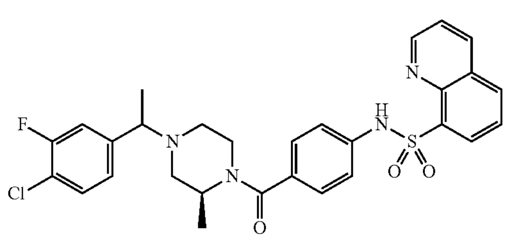 [SMILES: CC(c1ccc(Cl)c(F)c1)N1CCN(C(=O)c2ccc(NS(=O)(=O)c3cccc4cccnc34)cc2)[C@@H](C)C1] |
| 214 | |
| 101 | |
| 177 | |
| 175 | |
| 165 | |
| 102 | |

TABLE 1-continued
| Cmpd # | Structure |
|---|---|
| 171 | 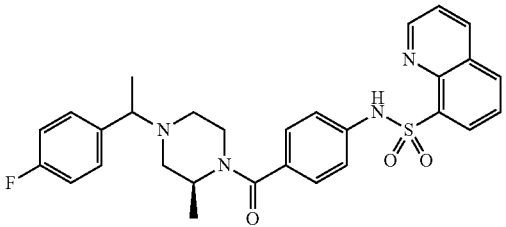 [SMILES: CC(c1ccc(F)cc1)N1CCN(C(=O)c2ccc(NS(=O)(=O)c3cccc4cccnc34)cc2)[C@@H](C)C1] |
| 100 | 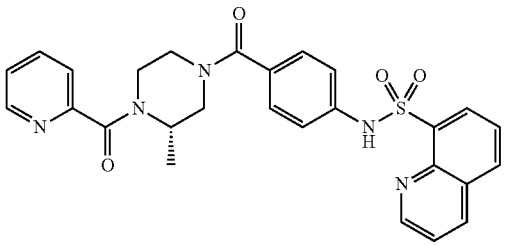 [SMILES: C[C@H]1CN(C(=O)c2ccc(NS(=O)(=O)c3cccc4cccnc34)cc2)CCN1C(=O)c1ccccn1] |
| 180 | 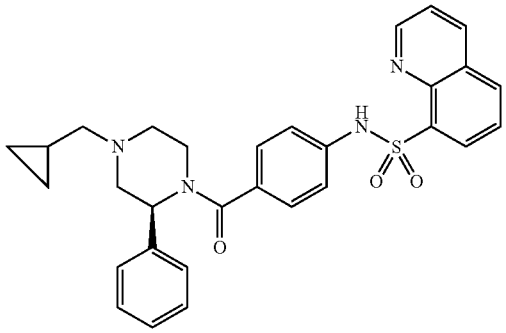 [SMILES: O=C(c1ccc(NS(=O)(=O)c2cccc3cccnc23)cc1)N1CCN(CC2CC2)C[C@@H]1c1ccccc1] |
| 169 | 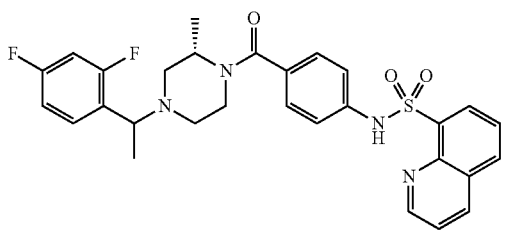 [SMILES: CC(c1ccc(F)cc1F)N1CCN(C(=O)c2ccc(NS(=O)(=O)c3cccc4cccnc34)cc2)[C@@H](C)C1] |
| 172 | 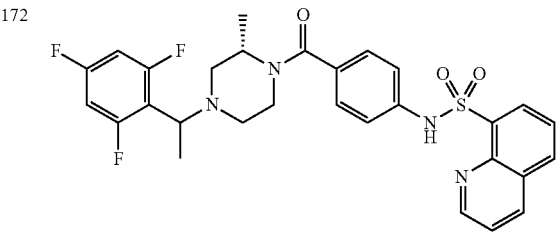 |
| 174 | 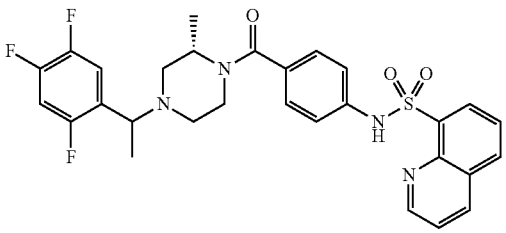 [SMILES: CC(c1cc(F)c(F)cc1F)N1CCN(C(=O)c2ccc(NS(=O)(=O)c3cccc4cccnc34)cc2)[C@@H](C)C1] |
TABLE 1-continued
| Cmpd # | Structure |
|---|---|
| 179 | 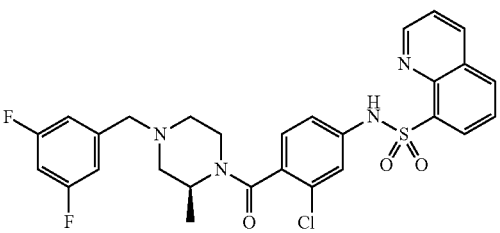 [SMILES: C[C@H]1CN(Cc2cc(F)cc(F)c2)CCN1C(=O)c1ccc(NS(=O)(=O)c2cccc3cccnc23)cc1Cl] |
| 176 | 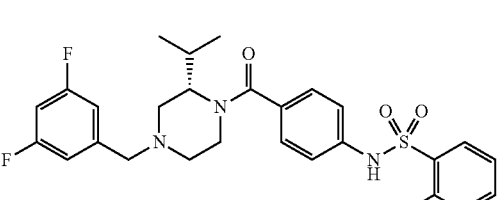 |
TABLE 2
| Cmpd # | Structure |
|---|---|
| 405 | 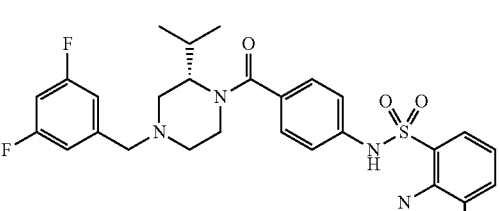 |
| 364 | 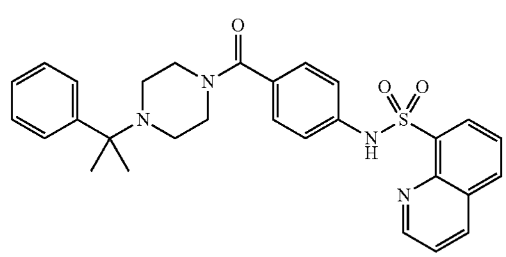 [SMILES: CC(C)(c1ccccc1)N1CCN(C(=O)c2ccc(NS(=O)(=O)c3cccc4cccnc34)cc2)CC1] |
| 372 | 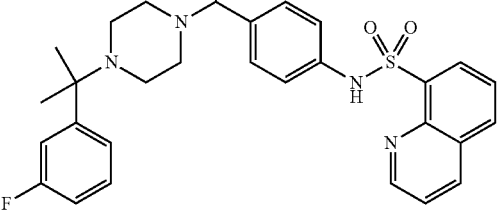 |

TABLE 2-continued

| Cmpd # | Structure |
|---|---|
| 410 | 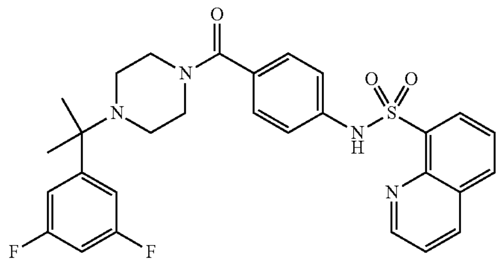 [SMILES: CC(C)(c1cc(F)cc(F)c1)N1CCN(C(=O)c2ccc(NS(=O)(=O)c3cccc4cccnc34)cc2)CC1] |
| 363 | 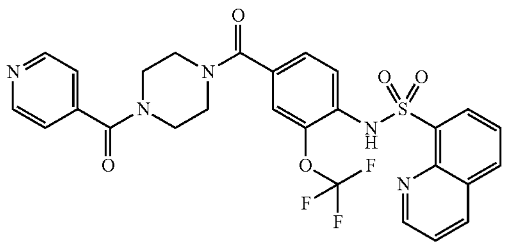 [SMILES: O=C(c1ccncc1)N1CCN(C(=O)c2ccc(NS(=O)(=O)c3cccc4cccnc34)c(OC(F)(F)F)c2)CC1] |
| 454 | 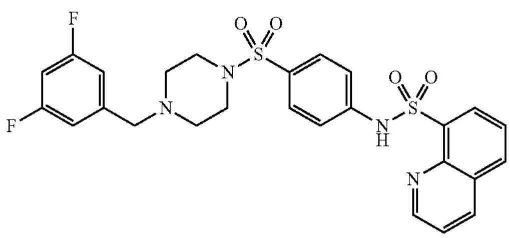 [SMILES: O=S(=O)(Nc1ccc(S(=O)(=O)N2CCN(Cc3cc(F)cc(F)c3)CC2)cc1)c1cccc2cccnc12] |
| 456 | 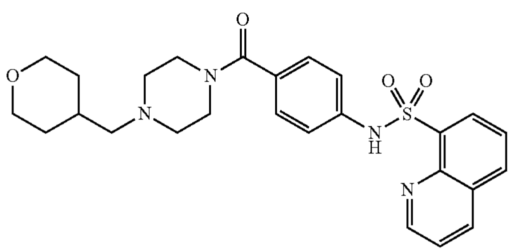 [SMILES: O=C(c1ccc(NS(=O)(=O)c2cccc3cccnc23)cc1)N1CCN(CC2CCOCC2)CC1] |
| 458 | 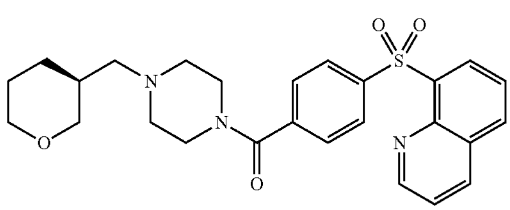 [SMILES: O=C(c1ccc(S(=O)(=O)c2cccc3cccnc23)cc1)N1CCN(C[C@@H]2CCCOC2)CC1] |
| 460 | 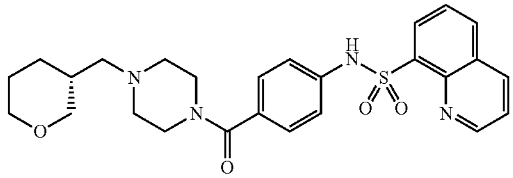 [SMILES: O=C(c1ccc(NS(=O)(=O)c2cccc3cccnc23)cc1)N1CCN(C[C@H]2CCCOC2)CC1] |
| 462 | |
| 383 | |
| 362 | |
| 300 | |
| 360 | |
| 326 | |

TABLE 2-continued

| Cmpd # | Structure |
|---|---|
| 361 | 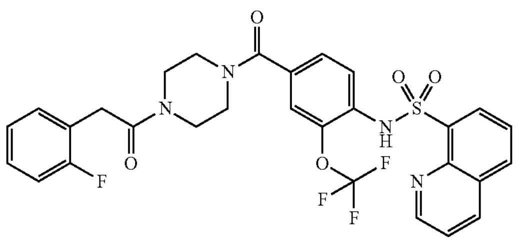 [SMILES: O=C(Cc1ccccc1F)N1CCN(C(=O)c2ccc(NS(=O)(=O)c3cccc4cccnc34)c(OC(F)(F)F)c2)CC1] |
| 455 | 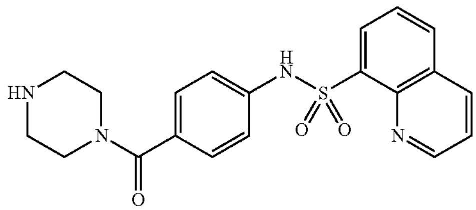 [SMILES: O=C(c1ccc(NS(=O)(=O)c2cccc3cccnc23)cc1)N1CCNCC1] |
| 457 | 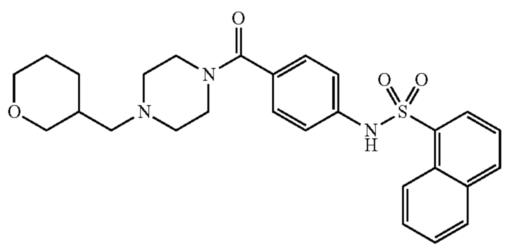 [SMILES: O=C(c1ccc(NS(=O)(=O)c2cccc3ccccc23)cc1)N1CCN(CC2CCCOC2)CC1] |
| 459 | 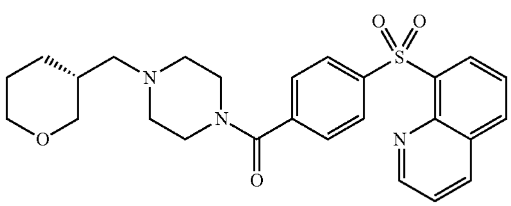 [SMILES: O=C(c1ccc(S(=O)(=O)c2cccc3cccnc23)cc1)N1CCN(C[C@H]2CCCOC2)CC1] |
| 461 | 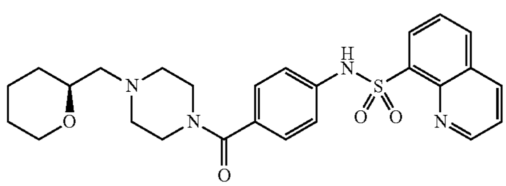 [SMILES: O=C(c1ccc(NS(=O)(=O)c2cccc3cccnc23)cc1)N1CCN(C[C@@H]2CCCCO2)CC1] |

The compounds described herein can be made using a variety of synthetic techniques as set forth in the Examples. As can be appreciated by the skilled artisan, methods of synthesizing additional compounds of the formulae herein will be evident to those of ordinary skill in the art by appropriate modifications of the exemplified schemes. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g. restriction resulting from the presence of a ring or double bond. Accordingly, all cis/trans and E/Z isomers are expressly included.

The compounds provided herein (e.g. of Formula I) may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Methods of Evaluating Compounds

The compounds described herein can be evaluated for ability to activate PKM2 by methods known in the art. Exemplary methods include contacting the compound with a cell-based assay which allows assessment of the ability to modulate (e.g., activate) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate PKM2). The evaluation could also include measuring a change in pyruvate or a determination of an alteration in mitochondrial membrane potential, e.g., as measured by fluorescent potentiometric dyes.

PKM1 and PKM2 for use in the screening/testing method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., E. coli) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening/testing assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 2.

TABLE 2

| Component of Reaction Condition | Amount in Activation Assay |
| --- | --- |
| ADP | 0.1-5.0 mM |
| Phosphoenolpyruvate | 0.1-5.0 mM |
| NADH | 10-1000 µM |
| Lactate dehydrogenase | 0.1-10 units |
| Fructose-1,6-bisphosphate | 0 |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

Compounds useful as PKM2 activators are those demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, compounds can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Other methods for evaluating the present compounds also include an ex vivo assays as described below.

A PKM2 Ex-Vivo Assay.

Described herein is a method to measure the activity of PKM2 activators in living cells and tissue. One of ordinary skill in the art would recognize and understand that this method can be adapted to high throughput format, and can accommodate a variety of cell lines and growth conditions.

In the assay, cells are treated with a compound described herein (i.e., a PKM2 activator). This compound is capable of entering the cell and binding to PKM2, inducing an activated conformation. The excess unbound compound is washed away with PBS, and the cells are lysed by snap-freezing on dry ice, followed by addition of a detergent-containing lysis buffer. The lysate, in which activated PKM2 remains intact, is removed and added to a chemical cocktail including the chemicals necessary to measure pyruvate kinase activity, in an assay that is coupled to the LDHa enzyme. The amount of pyruvate kinase activity that is measured is normalized to the total protein content in the lysate, and related to the concentration of PKM2 activator that was added to the cell. This allows an $AC_{50}$ (concentration at which PKM2 is activated 50%) value to be derived. The total fold-increase in activity over mock-treated cells can also be calculated, and the "maximum level of activation" can be used to distinguish between compounds that fully activate PKM2 and compounds that can only partially activate PKM2.

In the case of measuring PKM2 activity from tissue (for example, in a cell tumor), animals harboring the tissue/tumor of interest are dosed with a compound. After a specified period of time in which exposure has been achieved in the target tissue/tumor of interest, the tissue/tumor is harvested from the animal, snap-frozen, and then lysed and homogenized. The amount of pyruvate kinase activity in this lysate can then be quantitated as described above.

Materials:

Lysis buffer*

20 mM Tris-HCl (pH 7.5)

150 mM NaCl 1 mM $Na_2EDTA$ 1 mM EGTA

1% Triton 2.5 mM sodium pyrophosphate 1 mM beta-glycerophosphate 1 mM $Na_3VO_4$ 1 µg/ml leupeptin 1 mM PMSF**

*This lysis buffer (without PMSF) is available from Cell Signaling Technology as a 10× stock (#9803)

**1 mM PMSF is added fresh from a 100 mM stock solution made up in isopropanol. The stock solution can be stored at 4 degrees indefinitely.

Pyruvate Kinase Assay Master Mix (Same for PKM2 Activator Assay):

TABLE 3

| | |
|---|---|
| KCl | 100 mM |
| Tris (pH 7.5) | 50 mM |
| MgCl$_2$ | 5.0 mM |
| PEP | 0.10 mM |
| NADH | 0.18 mM |
| DTT | 1.00 mM |
| BSA | 0.3 mg/mL |
| LDH | 0.5 units |
| H$_2$O | to 180 uL |
| ADP solution: | |
| ADP | 7.0 mM |
| H$_2$O | to 20 uL |

Procedure:

On the first day (day 1) cells are normally cultured in RPMI-1640 (Lonza #12—115° F.) (with 25 mM Hepes, L-glutamine)/10% FBS. The cells are subsequently trypsinized and plated in RPMI-1640 (Lonza, #12-918F) (no phenol red, supplemented with L-glutamine @300 mg/L (Sigma, #G8540))/10% FBS at the following densities in 96 well plates:

A549: 40 k/well 100 uL final volume of media per well.

On the second day (Day 2), the cells should be 70-90% confluent. The cells are then treated with a compound described herein dissolved in media at final assay concentrations in a 96-well assay block (500 uL) (Costar, #3956). The final DMSO concentration is 0.1% (0.5 µL into 500 uL). Compound dilutions in DMSO are prepared so that the final DMSO concentration is constant at all compound concentrations. The media for the assay is RPMI-1640 (no phenol red, with L-glutamine @300 mg/L).

The media is then aspirated carefully from the cells using a multi-channel aspirator. 100 µL of media w/compounds is added onto cells with a multichannel pipette. Each compound concentration is then assayed in triplicate (a duplicate assay is also sufficient).

The cells are treated for 1-4 hrs (this time is determined empirically compared to DMSO reference treatment). During the cell treatment, PBS (containing calcium and magnesium) and lysis buffer is cooled on ice.

The cells are lysed and the pyruvate kinase activity is assayed. The remaining media is aspirated and the cells are washed 2× with 100 uL ice-cold PBS. The PBS is removed, and the cell plate frozen on dry ice for 5 minutes. The cells are lysed in 50 µL cold lysis buffer. Cells are subsequently kept on ice for 5 minutes, and then agitated on a plate shaker for 5 minutes (repeat 3×). Remove 10 µL for protein quantitation (or use OD$_{280}$ on entire plate).

In a fresh plate, 170 uL of pyruvate kinase assay master mix was added to each well (see end for recipe). 10 uL of cell lysate was then transferred into each well. The assay was initiated upon addition of 20 uL of ADP solution. The rates were then calculated against the initial rates to determine pyruvate kinase specific activity.

The concentration and type of detergent in the lysis buffer can be varied to accommodate the specific physicochemical properties of the specific PKM2 activator. For instance, the interaction between some PKM2 activators and PKM2 can be disrupted by higher detergent concentrations, but preserved when cells are lysed with lower detergent concentrations.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (I-a), (II), in Examples, Table 1 or Table 2).

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a disorder (e.g., a disorder as described herein), a symptom of a disorder, with the purpose to cure, heal, alleviate, relieve, alter, remedy, ameliorate, improve or affect the disorder, or one or more symptoms of the disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "prevent" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a predisposition toward a disorder, with the purpose to prevent the occurrence of at least one symptom of the disorder or to delay onset of at least one symptom of the disorder).

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Without being bound by theory, applicants believe that altered PKM2 levels characterize a subset of all types of cancers, without regard to their cellular nature or location in the body. Thus, the compounds and methods of this invention are useful to treat any type of cancer that is characterized by altered PKM2 levels.

Chemotherapy

In some embodiments, a compound described herein is administered with one or morechemotherapies. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with one or more targeted therapies. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary anbibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with one or more immunotherapies. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with one or more hormonal therapies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g. a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Over-weight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herewith is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds provided herewith include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herewith may also be topically applied to the lower intestinal tract by rectal suppository formulation or in a suitable enema formulation. Topically-transdermal patches are also included.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein activate PKM2. Accordingly, a patient and/or subject can be selected for treatment using a compound described herein by first evaluating the patient and/or subject to determine whether the subject is in need of activation of PKM2, and if the subject is determined to be in need of activation of PKM2, then administering to the subject a compound described herein.

A subject can be evaluated as being in need of activation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

In one embodiment, the methods of treatment of this invention include a first step of identifying or selecting a patient who would benefit from modulation (e.g., activation) of PKM2 by determining the level of PKM2 activity in a patient or more particularly in an organ or cell of the patient (e.g., as opposed to merely being in need of treatment of the disorder itself, e.g., cancer). The level of PKM2 would be compared to a control (e.g., the PKM2 activity of another patient not suffering from the disorder (e.g., cancer) or the PKM2 activity of the same patient taken at an earlier time) to determine if the current level of PKM2 activity warranted treatment with a compound of this invention. In one aspect, a patient who has a level of PKM2 activity below that of a control would be a candidate for treatment with a compound of this invention.

In another embodiment, the methods of treatment of this invention include the subsequent step of monitoring the level of PKM2 activity in a patient or more particularly in an organ or cell of the patient during the course of or following treatment with a compound of this invention to determine the efficacy of the treatment. The level of PKM2 would be compared to a control (e.g., PKM2 activity of the same patient taken just prior to treatment) to determine if the PKM2 activity had been altered by the treatment, thus providing evidence of efficacy of the treatment. In one aspect, an increase in PKM2 activity during the course of or following treatment is indicative that the treatment was effective.

EXAMPLES

In the synthesis examples set forth below, certain compounds have specified stereochemistry at one of more positions. These compounds were prepared using the indicated scheme either using the appropriate chirally pure reagents or were separated from a racemate produced by the indicated scheme using an appropriate chiral separation column, such as a Chiralpak AD-H column (250×4.6 mm) 5 μM column, eluting with 0.05% diethyl amine in hexane/isopropanol (75: 25 v/v) with a flow rate of 2 ml/min with absorbance monitored at 220 nm. The chiral HPLC elution conditions set forth above can be easily modified by those of skill in the art to optimize separation for various chiral compounds of this invention.

Example 1

Preparation of Compounds of Formula Ic

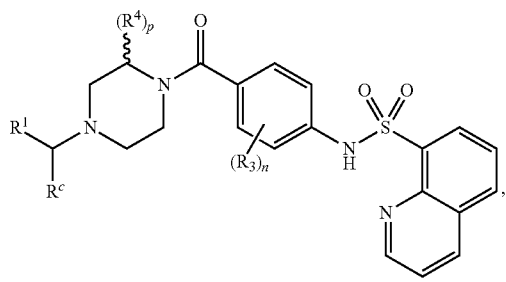

wherein $R^1$ is aryl or cyclopropyl; $R^c$ is methyl or $CF_3$; $R^3$ is alkyl and n is 0 or 1.

Scheme 1

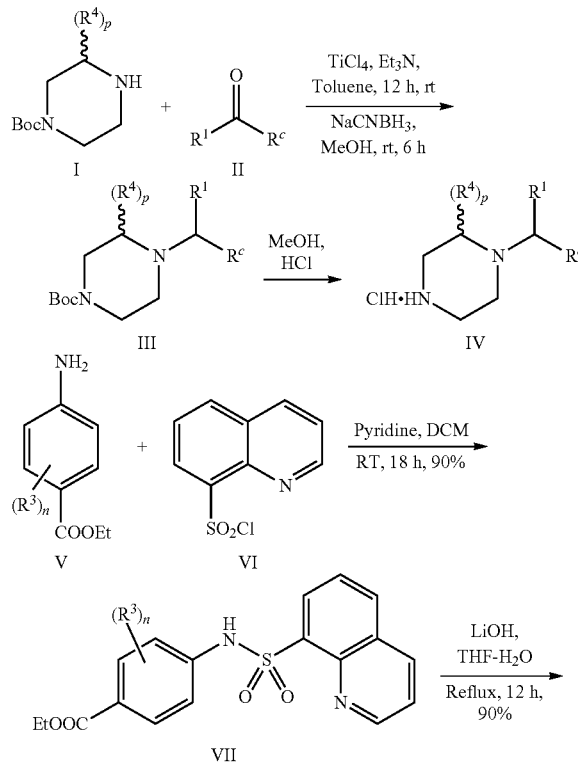

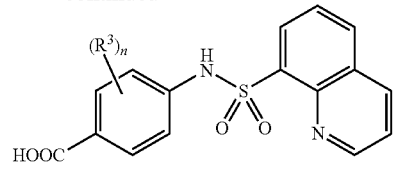

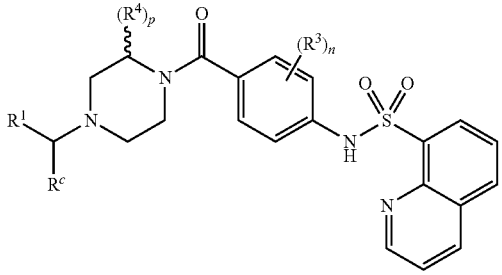

Formula Ic $R^1$ = Aryl, Cyclopropyl
$R^c$ = Me, $CF_3$
$R^4$ = Me, Et, isopropyl
p = 0 or 1

Synthesis of Intermediate IV.

To a stirred solution of aryl ketones II (17 mmol) in 10 ml of dichloromethane were added optionally substituted tert-butyl piperazine-1-carboxylate I (16 mmol), $Et_3N$ (48 mmol) and 1 M $TiCl_4$ (8 mmol) at room temperature, followed by stirring the reaction mixture at room temperature for 18 h. To the reaction mixture was added a solution of $NaBH_3CN$ (48 mmol) in MeOH (5 ml) at room temperature, followed by stirring the reaction mixture at room temperature for 6 h. Ethyl acetate and saturated aqueous $NaHCO_3$ solution were added to the reaction mixture. The insoluble material obtained was filtered off using celite. The ethyl acetate layer was separated, washed with brine, dried over anhydrous $MgSO_4$ and filtered. The filtrate was concentrated in vacuum and the crude compound was taken for the next step without purification. The compound obtained from this step was dissolved in 10 ml of Methanolic HCl and stirred the reaction mixture for 2 h at room temperature. The mixture was concentrated under vacuum to leave intermediate IV as solid. The obtained solid was neutralized with base to get a free base which was used for the next step (45-60% over two steps).

Synthesis of ethyl 4-(quinoline-8-sulfonamido)benzoate (VII)

To a solution of amine V (16 gm, 96.85 mmol) in a mixture (1:1) of DCM and pyridine, sulfonyl chloride VI (27.56 gm, 121.07 mmol) was added at room temperature under $N_2$ atmosphere. The resulting mixture was allowed to stir for 16 hrs. After completion of reaction, the crude mixture was diluted with DCM, washed with water followed by 1N HCl. The organic layer was then dried over $Na_2SO_4$ and concentrated under reduced pressure to afford intermediate VII in 98% yields (34 gm).

Synthesis of 4-(quinoline-8-sulfonamido)benzoic acid (VIII)

To a solution of sulfonamide VII (34 gm, 95.5 mmol) in THF and water (1:1), LiOH (20 gm, 47.66 mmol) was added and the resulting mixture was allowed to stir at 80° C. overnight. After completion of reaction, the crude mixture was washed with EtOAc. The aqueous layer was acidified with citric acid and filtered. Thus obtained solid was washed with Et₂O and azeotroped by toluene, under reduced pressure to afford acid VIII (30 gm, 95.8% yield) which was taken forward for the next step without further purification.

Synthesis of Compounds of Formula I According to Scheme 1.

To a solution of acid VIII (1 mmol) in DMF (2 ml), PyBoP (Benzotriazole-1-yl-oxy-tris-(dimethylamino)-phosphonium hexafluorophosphate) (0.78 gm, 1.5 mmol) was added at 0° C. and allowed to stir for 5 minutes. Then amine IV (1 mmol) was added to the reaction mixture at the same temperature under N₂ atmosphere and stirred overnight at room temperature. After completion of reaction, mixture was diluted with water and extracted with EtOAc. The organic layer was washed with water, dried over Na₂SO₄, and evaporated under reduced pressure. The residue was purified by column chromatography (silica gel, 60-120 mesh; MeOH-DCM, 2:8) to afford product IX in 40-66% yield.

The above procedure was used to produce the following compounds of Formula Ic using the appropriate aryl ketone II and the appropriate optionally substituted tert-butyl piperazine-1-carboxylate I.

(S)—N-(4-(4-(1-phenylethyl)piperazine-1-carbonyl)phenyl)quinoline-8-sulfonamide (Compound 387)

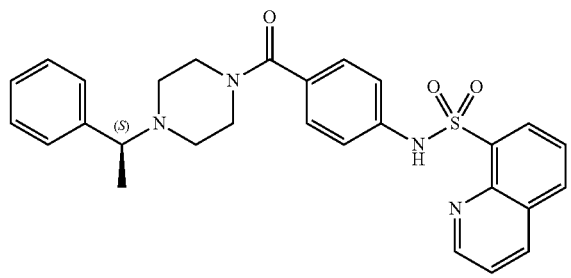

¹H NMR (400 MHz, CDCl₃) δ: 1.3 (d, 3H), 2.2-2.4 (m, 4H), 3.2-3.4 (m, 2H), 3.5 (m, 1H), 3.6-3.8 (m, 2H), 5.3 (s, 1H), 7.0-7.4 (m, 8H), 7.5-7.65 (m, 2H), 8.0 (d, 1H), 8.38 (m, 2H), 8.55 (s, 1H), 9.0 (m, 1H); HPLC Purity: 99.31%; Mass (M+1): 477.40.

N-(4-(4-(1-(3,5-difluorophenyl)ethyl)piperazine-1-carbonyl)phenyl)quinoline-8-sulfonamide (Compound 331)

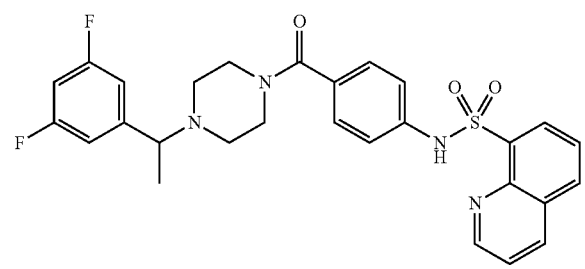 [SMILES: CC(c1cc(F)cc(F)c1)N1CCN(C(=O)c2ccc(NS(=O)(=O)c3cccc4cccnc34)cc2)CC1]

¹H NMR (400 MHz, DMSOd₆) δ: 1.3 (d, 3H), 2.2-2.4 (m, 4H), 3.2-3.5 (m, 2H), 3.6 (m, 1H), 7.0 (m, 4H), 7.2-7.4 (m, 3H), 7.6 (m, 2H), 8.2-8.4 (m, 3H), 9.1 (m, 1H), 10.2 (bs, 1H); HPLC Purity: 91.96%; Mass (M+1): 537.10.

N-(4-(4-(1-(3-chloro-4-fluorophenyl)ethyl)piperazine-1-carbonyl)phenyl)quinoline-8-sulfonamide (Compound 332)

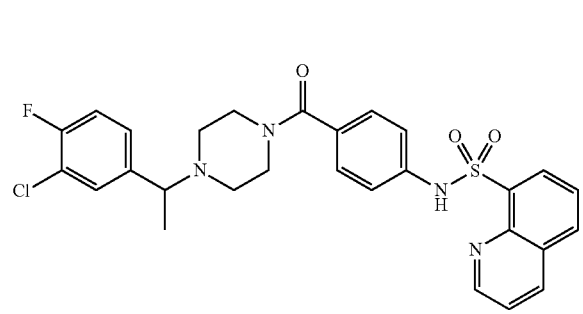 [SMILES: CC(c1ccc(F)c(Cl)c1)N1CCN(C(=O)c2ccc(NS(=O)(=O)c3cccc4cccnc34)cc2)CC1]

¹H NMR (400 MHz, DMSOd₆) δ: 1.2 (d, 3H), 1.3 (m, 1H), 2.2-2.5 (m, 6H), 3.1-3.4 (m, 2H), 7.0 (m, 4H), 7.2-7.4 (m, 3H), 7.8 (m, 2H), 8.2-8.4 (m, 3H), 9.1 (m, 1H), 10.2 (bs, 1H); HPLC Purity: 93.02%; Mass (M+1): 575.10.

N-(4-(4-(1-(2,3,4-trifluorophenyl)ethyl)piperazine-1-carbonyl)phenyl)quinoline-8-sulfonamide (Compound 403)

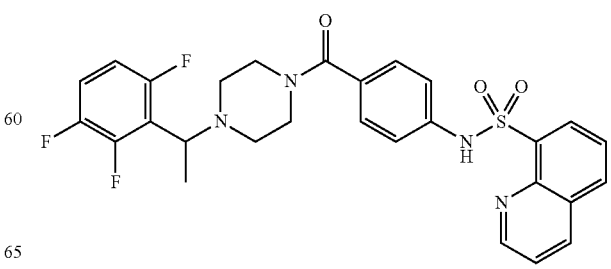

¹H NMR (400 MHz, CDCl₃) δ: 1.2 (d, 3H), 1.4 (m, 1H), 2.2-2.7 (m, 4H), 3.0-3.6 (m, 4H), 7.0-7.25 (m, 6H), 7.55-7.6 (m, 2H), 8.2-8.25 (d, 1H), 8.4 (m, 1H), 8.5-8.55 (d, 1H), 9.1 (m, 1H); HPLC Purity: 99.46%; Mass (M+1): 555.45.

N-(4-(4-(1-(2,3,6-trifluorophenyl)ethyl)piperazine-1-carbonyl)phenyl)quinoline-8-sulfonamide (Compound 404)

¹H NMR (400 MHz, DMSO-d₆) δ: 1.35 (d, 3H), 1.4 (m, 1H), 2.2-2.7 (m, 4H), 3.0-3.6 (m, 4H), 7.0-7.25 (m, 5H), 7.4 (m, 1H), 7.78-7.8 (m, 2), 8.25-8.3 (d, 1H), 8.4 (m, 1H), 8.5-8.55 (d, 1H), 9.1 (m, 1H), 10.4 (s, 1H); HPLC Purity: 98.97%; Mass (M+1): 555.1.

N-(4-(4-(1-(2,6-difluorophenyl)ethyl)piperazine-1-carbonyl)phenyl)quinoline-8-sulfonamide (Compound 357)

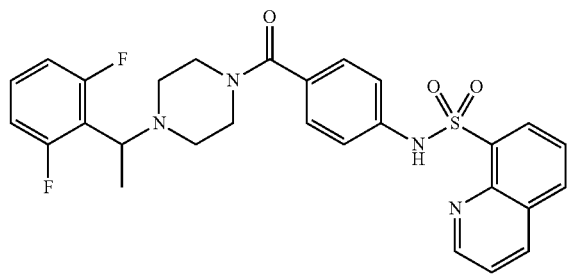 [SMILES: CC(c1c(F)cccc1F)N1CCN(C(=O)c2ccc(NS(=O)(=O)c3cccc4cccnc34)cc2)CC1]

¹H NMR (400 MHz, CDCl₃) δ: 1.3 (s, 3H), 2.2-2.5 (m, 4H), 3.0-3.4 (m, 2H), 3.5-3.8 (m, 2H), 7.0-7.2 (m, 6H), 7.4 (m, 1H), 8.2-8.6 (m, 3H), 8.3 (m, 2H), 8.6 (m, 1H), 9.0 (m, 1H) 10.4 (s, 1H); HPLC Purity: 98.29%; Mass (M+1): 537.20.

N-(4-(4-(1-(pyridin-3-yl)ethyl)piperazine-1-carbonyl)phenyl)quinoline-8-sulfonamide (Compound 370)

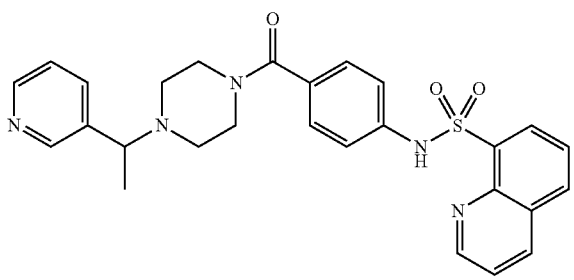 [SMILES: CC(c1cccnc1)N1CCN(C(=O)c2ccc(NS(=O)(=O)c3cccc4cccnc34)cc2)CC1]

¹H NMR (400 MHz, DMSO-d₆) δ: 1.3 (d, 3H), 2.2-2.2.4 (m, 4H), 3.2-3.6 (m, 4H), 3.5 (m, 1H), 7.1 (m, 4H), 7.3 (m, 1H), 7.7 (m, 3H), 8.3-8.5 (m, 5H), 9.0 (m, 1H), 10.0 (s, 1H); HPLC Purity: 98.12%; Mass (M+1): 502.40.

N-(4-(4-(1-(2,4,5-trifluorophenyl)ethyl)piperazine-1-carbonyl)phenyl)quinoline-8-sulfonamide (Compound 395)

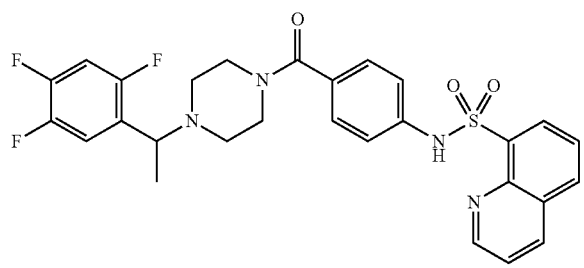 [SMILES: CC(c1cc(F)c(F)cc1F)N1CCN(C(=O)c2ccc(NS(=O)(=O)c3cccc4cccnc34)cc2)CC1]

¹H NMR (400 MHz, DMSO-d₆) δ: 1.4 (d, 3H), 2.2-2.4 (m, 2H), 3.0-3.8 (m, 4H), 3.90 (q, 1H), 7.0-7.2 (m, 6H), 7.6-7.69 (m, 2H), 8.2-8.6 (m, 3H), 9.0 (m, 1H), 10.46 (bs, 1H); HPLC Purity: 96.86%; Mass (M+1): 555.50.

N-(4-(4-(1-(2,3,5-trifluorophenyl)ethyl)piperazine-1-carbonyl)phenyl)quinoline-8-sulfonamide (Compound 396)

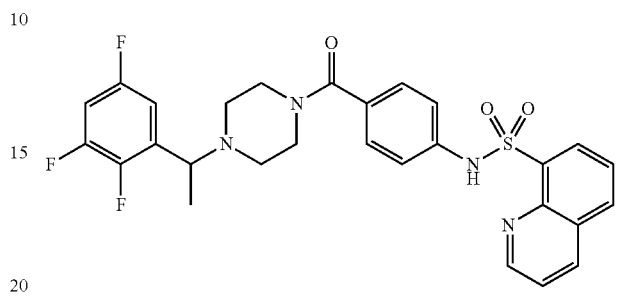

¹H NMR (400 MHz, DMSO-d₆) δ: 1.25 (d, 3H), 2.2-2.4 (m, 4H), 3.1-3.7 (m, 4H), 3.90 (q, 1H), 7.0-7.2 (m, 5H), 7.4 (m, 1H), 7.6-7.69 (m, 2H), 8.2-8.6 (m, 3H), 9.0 (m, 1H), 10.46 (bs, 1H); HPLC Purity: 96.86%; Mass (M+1): 555.50.

N-(4-(4-(1-(2,4,6-trifluorophenyl)ethyl)piperazine-1-carbonyl)phenyl)quinoline-8-sulfonamide (Compound 397)

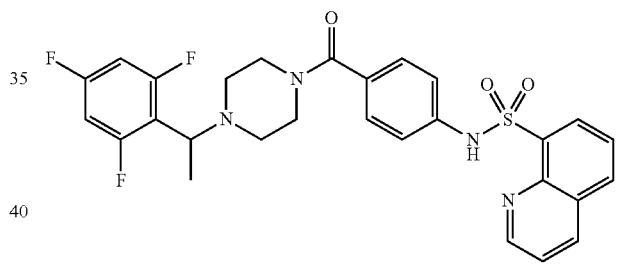

¹H NMR (400 MHz, DMSO-d₆) δ: 1.4 (s, 3H), 2.0-2.4 (m, 4H), 3.0-3.6 (m, 2H), 3.90 (m, 1H), 7.0-7.2 (m, 6H), 7.6-7.69 (m, 2H), 8.2-8.6 (m, 3H), 9.0 (m, 1H), 10.46 (bs, 1H); HPLC Purity: 99.97%; Mass (M+1): 555.50.

N-(4-(4-(1-(3,4,5-trifluorophenyl)ethyl)piperazine-1-carbonyl)phenyl)quinoline-8-sulfonamide (Compound 398)

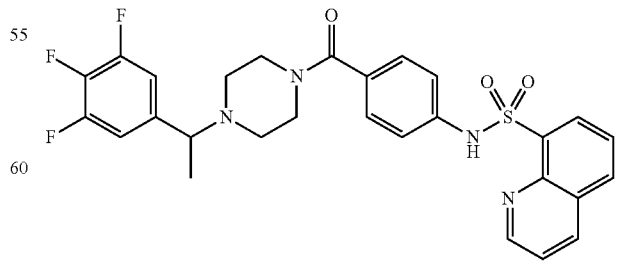

¹H NMR (400 MHz, DMSO-d₆) δ: 1.4 (s, 3H), 2.0-2.4 (m, 4H), 3.0-3.6 (m, 4H), 3.90 (m, 1H), 7.0-7.2 (m, 6H), 7.6-7.69

(m, 2H), 8.2-8.6 (m, 3H), 9.0 (m, 1H), 10.46 (bs, 1H); HPLC Purity: 95.10%; Mass (M+1): 555.45.

N-(4-(4-(1-cyclopropylethyl)piperazine-1-carbonyl)phenyl)quinoline-8-sulfonamide (Compound 442)

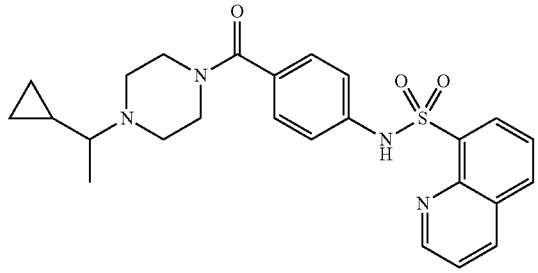 [SMILES: CC(C1CC1)N1CCN(C(=O)c2ccc(NS(=O)(=O)c3cccc4cccnc34)cc2)CC1]

¹H NMR (400 MHz, DMSO-d₆) δ: 1.6 (d, 3H), 2.1-2.2 (m, 2H), 2.21-2.4 (m, 4H), 2.99-3.6 (m, 8H), 7.0-7.2 (m, 4H), 7.6-7.8 (m, 2H), 8.2-8.6 (m, 3H), 9.1-9.2 (m, 1H) 10.41 (bs, 1H); HPLC Purity: 99.49%; Mass (M+1): 465.3.

(R)—N-(4-(4-(1-phenylethyl)piperazine-1-carbonyl)phenyl)quinoline-8-sulfonamide (Compound 388)

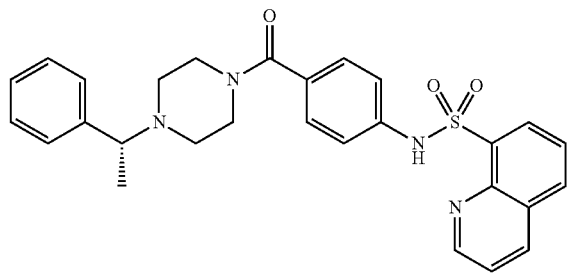 [SMILES: C[C@H](c1ccccc1)N1CCN(C(=O)c2ccc(NS(=O)(=O)c3cccc4cccnc34)cc2)CC1]

¹H NMR (400 MHz, CDCl₃) δ: 1.3 (d, 3H), 2.2-2.4 (m, 4H), 3.2-3.8 (m, 4H), 3.5 (m, 1H), 5.3 (s, 1H), 7.0-7.4 (m, 8H), 7.55-7.65 (m, 2H), 8.0 (d, 1H), 8.38-8.4 (m, 2H), 8.55 (s, 1H), 9.0 (m, 1H); HPLC Purity: 98.51%; Mass (M+1): 501.20.

N-(4-(4-(2,2,2-trifluoro-1-(4-fluorophenyl)ethyl)piperazine-1-carbonyl)phenyl)quinoline-8-sulfonamide (Compound 351)

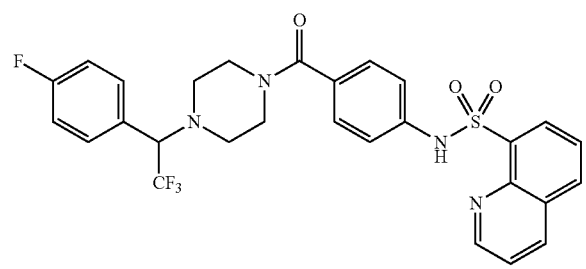 [SMILES: O=C(c1ccc(NS(=O)(=O)c2cccc3cccnc23)cc1)N1CCN(C(c2ccc(F)cc2)C(F)(F)F)CC1]

¹H NMR (400 MHz, CDCl₃) δ: 2.2 (m, 4H), 3.2 (m, 2H), 3.7 (m, 2H), 4.7 (m, 1H), 7.0 (m, 4H), 7.4-7.6 (m, 4H), 7.7 (m, 2H), 8.2-8.4 (m, 3H), 9.0 (m, 1H); HPLC Purity: 97.49%; Mass (M+1): 573.15.

N-(4-(4-(2,2,2-trifluoro-1-phenylethyl)piperazine-1-carbonyl)phenyl)quinoline-8-sulfonamide (Compound 358)

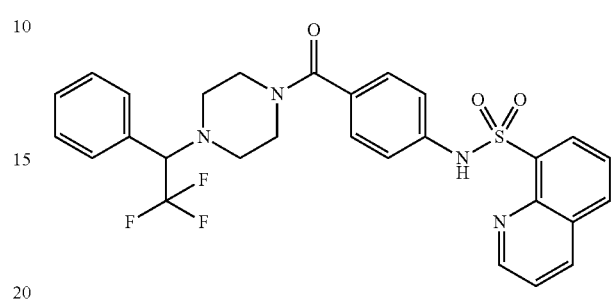

¹H NMR (400 MHz, CDCl₃) δ: 2.2-2.5 (m, 2H), 3.0-3.4 (m, 2H), 3.5-3.8 (m, 4H), 4.6 (m, 1H), 7.0 (m, 4H), 7.4 (m, 5H), 7.9 (m, 2H), 8.2-8.6 (m, 3H), 9.0 (m, 1H) 10.4 (s, 1H); HPLC Purity: 97.65%; Mass (M+1): 555.15.

N-(4-(4-(2,4-dimethoxybenzyl)piperazine-1-carbonyl)-2-(trifluoromethoxy)phenyl)quinoline-8-sulfonamide (Compound 333)

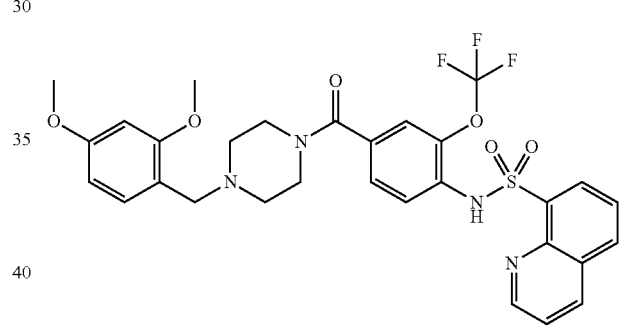

¹H NMR (400 MHz, DMSOd₆) δ: 2.2-2.5 (m, 4H), 3.2-3.6 (m, 4H), 3.8 (m, 6H), 6.5 (m, 2H), 7.2 (m, 3H), 7.5 (m, 1H), 7.8 (m, 2H), 8.3 (m, 2H), 8.6 (m, 1H), 9.0 (m, 1H), 10.0 (bs, 1H); HPLC Purity: 98.57%; Mass (M+1): 631.60.

N-(4-((2R)-4-(1-(4-fluorophenyl)ethyl)-2-methylpiperazine-1-carbonyl)phenyl)quinoline-8-sulfonamide (Compound 133)

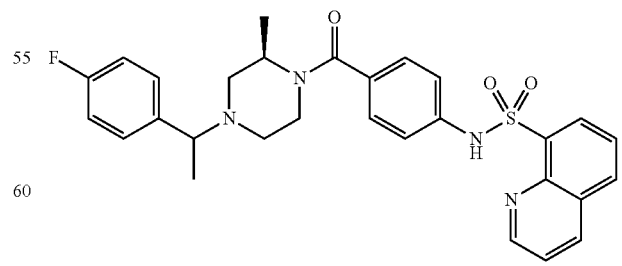

¹H NMR (400 MHz, DMSO-d₆) δ: 0.9 (d, 3H), 1.0-1.12 (m, 1H), 1.13-1.3 (d, 3H), 1.4 (m, 1H), 1.99-2.1 (m, 2H), 2.8-3.6 (m, 4H), 7.0-7.2 (m, 5H), 7.22-7.4 (m, 2H), 7.6-7.8 (d,

2H), 8.25 (d, 1H), 8.4-8.5 (m, 2H), 9.1 (m, 1H), 10.4 (s, 1H); HPLC Purity: 99.93%; Mass (M+1): 533.55.

N-(4-((2R)-4-(1-(3,5-difluorophenyl)ethyl)-2-methylpiperazine-1-carbonyl)phenyl)quinoline-8-sulfonamide (Compound 135)

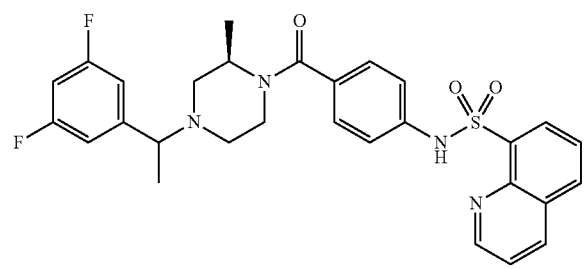 [SMILES: CC(c1cc(F)cc(F)c1)N1CCN(C(=O)c2ccc(NS(=O)(=O)c3cccc4cccnc34)cc2)[C@H](C)C1]

¹H NMR (400 MHz, DMSO-d₆) δ: 1.1-1.21 (d, 6H), 1.82-2.1 (m, 2H), 2.6 (m, 1H), 2.8-3.2 (m, 2H), 3.8-4.0 (m, 3H), 7.0-7.2 (m, 7H), 7.6-7.8 (d, 2H), 8.25 (d, 1H), 8.4-8.5 (m, 2H), 9.1 (m, 1H), 10.4 (s, 1H); HPLC Purity: 99.95%; Mass (M+1): 551.3.

N-(4-((2R)-4-(1-(4-chloro-3-fluorophenyl)ethyl)-2-methylpiperazine-1-carbonyl)phenyl)quinoline-8-sulfonamide (Compound 157)

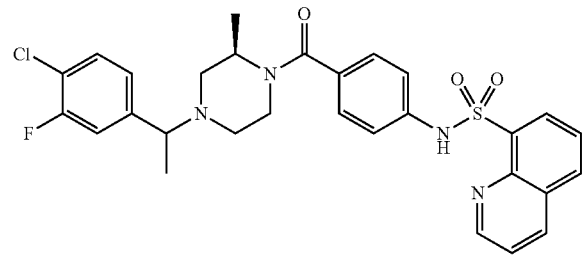 [SMILES: CC(c1ccc(Cl)c(F)c1)N1CCN(C(=O)c2ccc(NS(=O)(=O)c3cccc4cccnc34)cc2)[C@H](C)C1]

¹H NMR (400 MHz, DMSO-d₆) δ: 1.21 (d, 6H), 1.23-1.3 (m, 1H), 1.8-2.1 (m, 3H), 2.6-2.8 (m, 2H), 3.0-3.4 (m, 3H), 7.0-7.2 (m, 4H), 7.4-7.7 (m, 6H), 8.0 (d, 1H), 8.3-8.6 (m, 2H), 9.1 (m, 1H), 10.4 (s, 1H); HPLC Purity: 99.65%; Mass (M+1): 567.3.

N-(4-((2R)-2-methyl-4-(1-(3,4,5-trifluorophenyl)ethyl)piperazine-1-carbonyl)phenyl)quinoline-8-sulfonamide (Compound 158)

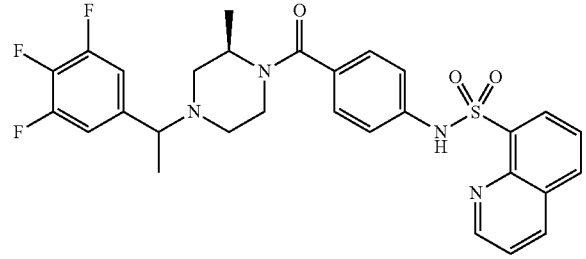 [SMILES: CC(c1cc(F)c(F)c(F)c1)N1CCN(C(=O)c2ccc(NS(=O)(=O)c3cccc4cccnc34)cc2)[C@H](C)C1]

¹H NMR (400 MHz, DMSO-d₆) δ: 1.21 (d, 6H), 1.8-2.1 (m, 2H), 2.4-2.45 (m, 1H), 2.6-2.8 (m, 2H), 2.9-3.25 (m, 2H), 3.5-3.6 (m, 1H), 7.0-7.2 (m, 6H), 7.4-7.7 (m, 2H), 8.0 (d, 1H), 8.3-8.6 (m, 2H), 9.1 (m, 1H), 10.4 (s, 1H); HPLC Purity: 99.18%; Mass (M+1): 569.5.

N-(4-((2R)-4-(1-(2,6-difluorophenyl)ethyl)-2-methylpiperazine-1-carbonyl)phenyl)quinoline-8-sulfonamide (Compound 159)

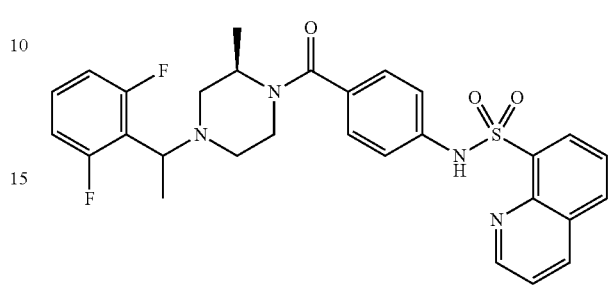

¹H NMR (400 MHz, DMSO-d₆) δ: 1.1 (d, 3H), 1.24 (d, 3H), 1.8-2.0 (m, 2H), 2.6-2.8 (m, 1H), 3.4-3.6 (m, 3H), 3.8-4.0 (m, 2H), 7.0-7.2 (m, 5H), 7.4-7.7 (m, 4H), 8.0 (d, 1H), 8.3-8.6 (m, 2H), 9.1 (m, 1H), 10.4 (s, 1H); HPLC Purity: 99.18%; Mass (M+1): 569.5.

N-(4-((2R)-4-(1-(2,4-difluorophenyl)ethyl)-2-methylpiperazine-1-carbonyl)phenyl)quinoline-8-sulfonamide (Compound 160)

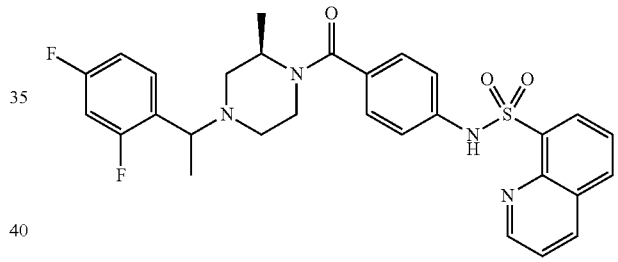

¹H NMR (400 MHz, DMSO-d₆) δ: 1.1 (d, 3H), 1.15 (d, 3H), 1.8-2.0 (m, 2H), 2.6-3.0 (m, 4H), 3.4-3.6 (m, 2H), 7.0-7.4 (m, 5H), 7.41-7.7 (m, 3H), 8.0 (d, 1H), 8.3-8.6 (m, 2H), 9.1 (m, 1H), 10.4 (s, 1H); HPLC Purity: 99.18%; Mass (M+1): 551.3

N-(4-((2S)-4-(1-(3,5-difluorophenyl)ethyl)-2-ethylpiperazine-1-carbonyl)phenyl)quinoline-8-sulfonamide (Compound 161)

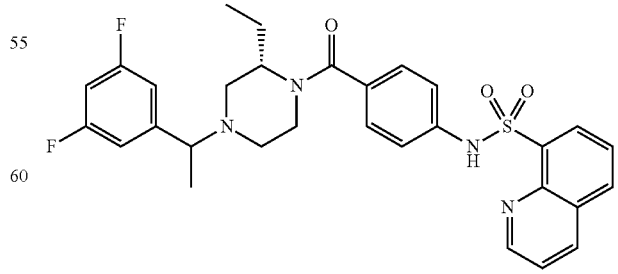

¹H NMR (400 MHz, DMSO-d₆) δ: 0.8 (t, 3H), 1.19 (d, 3H), 1.2 (m, 1H), 1.6-1.8 (m, 2H), 2.0-2.4 (m, 2H), 2.8-3.7 (m,

5H), 7.0-7.4 (m, 7H), 7.6-7.7 (m, 2H), 8.0 (d, 1H), 8.3-8.6 (m, 2H), 9.1 (m, 1H), 10.4 (s, 1H); HPLC Purity: 97.51%; Mass (M+1): 565.3

N-(4-((2S)-2-ethyl-4-(1-(3,4,5-trifluorophenyl)ethyl)piperazine-1-carbonyl)phenyl)quinoline-8-sulfonamide (Compound 162)

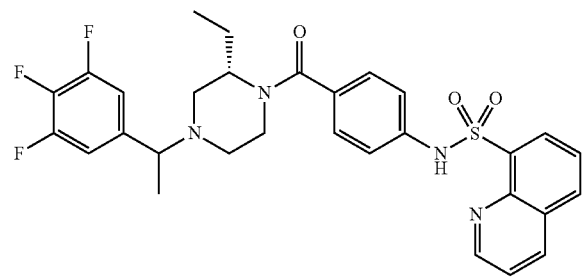 [SMILES: CC[C@H]1CN(C(C)c2cc(F)c(F)c(F)c2)CCN1C(=O)c1ccc(NS(=O)(=O)c2cccc3cccnc23)cc1]

$^1$H NMR (400 MHz, DMSO-d$_6$) δ: 0.8 (t, 3H), 1.19 (d, 3H), 1.6-1.8 (m, 2H), 2.0-2.4 (m, 2H), 2.8-3.2 (m, 2H), 3.8-4.0 (m, 4H), 7.0-7.4 (m, 6H), 7.6-7.7 (m, 2H), 8.0 (d, 1H), 8.3-8.6 (m, 2H), 9.1 (m, 1H), 10.4 (s, 1H); HPLC Purity: 99.86%; Mass (M+1): 583.3

Example 2

Preparation of Compounds of Formula Id

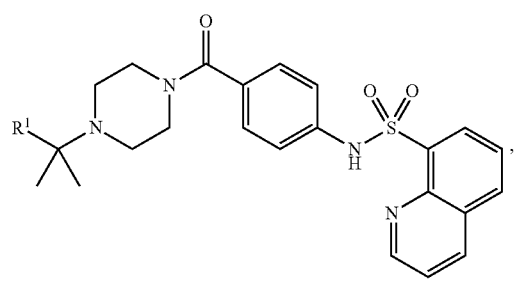
(Id)

wherein R$^1$ is cyclopropyl or aryl.

Scheme 2

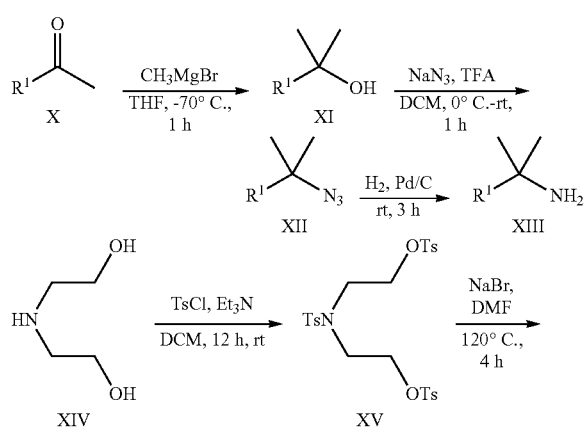

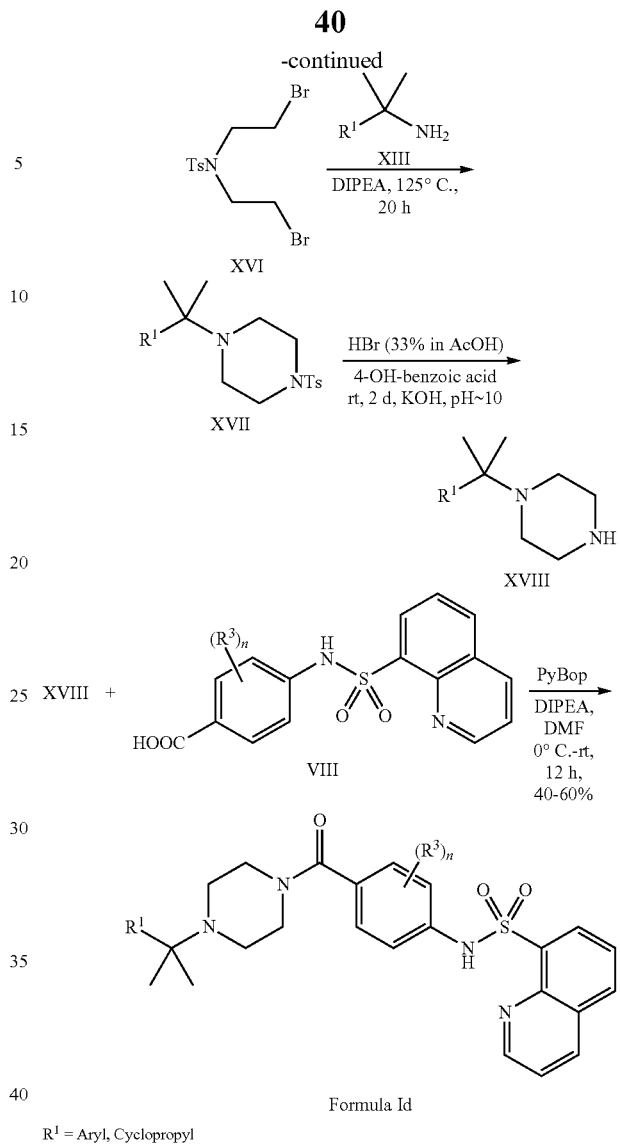

Formula Id
R$^1$ = Aryl, Cyclopropyl

Synthesis of Intermediate XI.

A solution of Aryl/Cycloalkyl methyl ketone X (1.6 mmol) in dry THF (10 ml) was cooled to −70° C. in N$_2$ atmosphere. Methylmagnesium bromide (8 mmol) in THF was added slowly at −70° C. and the reaction mixture stirred for 1 h under N$_2$ atmosphere. The reaction mixture was quenched with saturated NH$_4$Cl and diluted with Ethyl acetate (20 ml) and Brine (20 ml). The organic layer was washed with water, dried over Na$_2$SO$_4$, and evaporated under reduced pressure. The residue was purified by column chromatography (silica gel, 60-120 mesh; EA-Hexane, 2:8) to afford product XI as an oil in 60-72% yield.

Synthesis of Intermediate XII.

To a solution of Gemdimethyl alcohol XI (1.1 mmol) in dry DCM (10 ml) was added sodium azide (3.5 mmol) at room temperature under N$_2$ atmosphere. The reaction mixture was cooled to 0° C. and was added a solution of TFA (3 mmol) in DCM (1 ml). The reaction bath was allowed to warm up to room temperature and stirred further for 1 h at room temperature. The white precipitate formed was filtered and concentrated the solvent to get the desired azide which was used for the next step without purification (Yield 50-55%).

Synthesis of Intermediate XIII.

To a stirred solution of azide (1 mmol) in MeOH (5 ml) under $H_2$ atmosphere, was added 10% Pd/C (0.1 mmol) at room temperature. The reaction mixture stirred further for 3 h at room temperature and filtered through celite. The filtrate concentrated under reduced pressure to leave the amine which was used for the next step without purification (Yield 60%).

Synthesis of Intermediate XV.

Tosyl Chloride (22 g, 0.114 moles, 3 eq) was dissolved in DCM (40 ml) at 0° C. with stirring. To this solution was added a solution of diethanol amine XIV (4 g, 0.038 moles, 1 eq) and triethylamine (17 ml, 0.114 moles, 3 eq) in DCM (20 ml) at 0° C. Stirring was continued for overnight at room temperature after the addition was completed. The precipitate generated from the reaction was filtered and the solutions was washed with water, dilute HCl, saturated $NaHCO_3$ and brine in turn, and dried ($Na_2SO_4$). The organic phase was concentrated under reduced pressure and purified by column chromatography (silica gel, 60-120 mess, 20% ethyl acetate in hexane) to give the intermediate XV as a white solid (9.8 g, 46%). $^1$H NMR (400 MHz, $CDCl_3$) 2.38 (s, 3H), 2.43 (s, 6H), 3.32-3.36 (m, 4H), 4.05-4.16 (m, 4H), 7.21-7.38 (m, 6H), 7.61-7.81 (m, 6H).

Synthesis of Intermediate XVI.

To a solution of Tritosylate XV (1 g, 0.00176 moles, 1 eq) in 6 ml of DMF was added NaBr (0.93 g, 0.009 moles, 5 eq). The resulting suspension was stirred in an oil bath at 120° C. for 4 h. After cooling to room temperature, the reaction mixture was concentrated to about 2 ml. The viscous milky product was poured into rapidly stirred mixture of ice-water (30 ml) and extracted with ethyl acetate (30 ml). The organic phase was dried ($Na_2SO_4$) and concentrated under reduced pressure. The crude product was purified by column chromatography (silica gel, 60-120 mess, 10% ethyl acetate in hexane) to leave the product XVI as a pale yellow liquid (0.34 g, 51%) $^1$H NMR (400 MHz, $CDCl_3$) 2.41 (s, 3H), 3.44 (s, 8H), 7.38 (d, 4H), 7.76 (d, 4H)

Synthesis of Intermediate XVII.

A mixture of dibromide XVI (0.150 g, 0.000389 moles, 1.1 eq) and amine XIII (0.000354 moles, 1 eq) and N,N-diisopropylethyl amine (0.15 ml) under nitrogen atmosphere was heated at 125° C. for 20 h. The reaction was allowed to cool to room temperature. The reaction mixture is extracted with water (10 ml), ethyl acetate (20 ml) and the organic phase was dried ($Na_2SO_4$) and concentrated under reduced pressure. The crude product was purified with column chromatography (silica gel, 60-120 mess, 20% ethyl acetate in hexane) to leave the product XVII as a pale yellow liquid (yield 55-60%)

Synthesis of Intermediate XVIII.

To a mixture of compound N-tosylpiperazine derivative XVII (0.000398 moles, 1 eq) and 4-hydroxybenzoic acid (0.164 g, 0.00119 moles, 3 eq) was added hydrogen bromide solution (33 wt % in acetic acid, 1.8 ml) at room temperature. The reaction mixture was stirred under nitrogen atmosphere for 2 days at room temperature. Water (10 ml) was slowly added to the reaction mixture and the reaction mixture was continuously stirred for 2 h. A white precipitate was formed which was removed by filtration. The filter cake was washed with water (2×10 ml). The combined acidic aqueous washes were washed with toluene (20 ml). The aqueous phase was then cooled to 0° C. and basified with KOH pellets portion wise until pH>10, and extracted with toluene (20 ml) and ethyl acetate (2×20 ml). The combined organic phases were washed with brine, dried ($Na_2SO_4$), and concentrated under pressure to give the product XVIII as a pale yellow liquid which is used for the next step (Yield 90%)

Synthesis of Compounds of Formula Id.

To a solution of acid VIII (1 mmol) in DMF (2 ml), PyBoP (Benzotriazole-1-yl-oxy-tris-(dimethylamino)-phosphonium hexafluorophosphate) (1.5 mmol) was added at 0° C. and allowed to stir for 5 minutes. Then Gem dimethyl piperizine XVIII (1 mmol) was added to the reaction mixture at the same temperature under $N_2$ atmosphere and stirred overnight at room temperature. After completion of reaction, mixture was diluted with water and extracted with EtOAc. The organic layer was washed with water, dried over $Na_2SO_4$, and evaporated under reduced pressure. The residue was purified by column chromatography (silica gel, 60-120 mesh; MeOH-DCM, 2:8) to afford product XIX in 35-55% yield.

The above procedure was used to produce the following compounds of Formula Id using the appropriate methyl ketone X and acid VIII intermediates.

N-(4-(4-(2-(2-fluorophenyl)propan-2-yl)piperazine-1-carbonyl)phenyl)quinoline-8-sulfonamide (Compound 409)

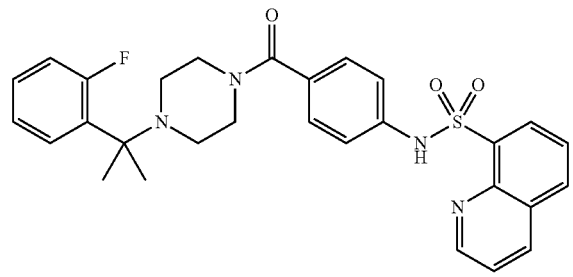 [SMILES: CC(C)(c1ccccc1F)N1CCN(C(=O)c2ccc(NS(=O)(=O)c3cccc4cccnc34)cc2)CC1]

$^1$H NMR (400 MHz, DMSO-$d_6$) δ: 1.22 (s, 6H), 2.2-2.4 (m, 4H), 2.99-3.2 (m, 2H), 3.4-3.6 (m, 2H), 7.0-7.2 (m, 5H), 7.22-7.4 (m, 3H), 7.6-7.8 (d, 2H), 8.25 (d, 1H), 8.4-8.5 (m, 2H), 9.1 (m, 1H), 10.4 (s, 1H); HPLC Purity: 96.19%; Mass (M+1): 535.05.

N-(4-(4-(2-phenylpropan-2-yl)piperazine-1-carbonyl)-2-(trifluoromethoxy)phenyl)quinoline-8-sulfonamide (Compound 340)

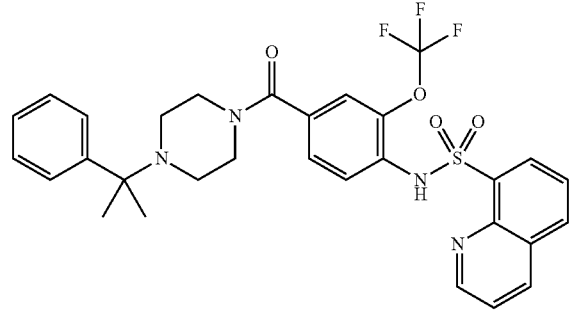 [SMILES: CC(C)(c1ccccc1)N1CCN(C(=O)c2ccc(NS(=O)(=O)c3cccc4cccnc34)c(OC(F)(F)F)c2)CC1]

¹H NMR (400 MHz, DMSOd₆) δ: 1.2 (s, 6H), 2.2-2.4 (m, 4H), 3.1-3.6 (m, 4H), 7.2 (m, 5), 7.5 (m, 3H), 7.7 (m, 2H), 8.3 (m, 2H), 8.6 (m 1H), 9.0 (m, 1H); HPLC Purity: 97.72%; Mass (M+1): 599.4.

N-(3-methoxy-4-(4-(2-phenylpropan-2-yl)piperazine-1-carbonyl)phenyl)quinoline-8-sulfonamide (Compound 355)

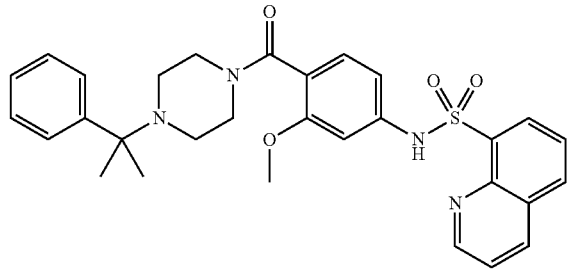 [SMILES: COc1cc(NS(=O)(=O)c2cccc3cccnc23)ccc1C(=O)N1CCN(C(C)(C)c2ccccc2)CC1]

¹H NMR (400 MHz, CDCl₃) δ: 3.4-3.7 (s, 6H), 2.1-2.4 (m, 4H), 3.0 (m, 4H), 4.5 (s, 3H), 6.6-6.9 (m, 3H), 7.1-7.5 (m, 5H), 7.7 (m, 2H), 8.2-8.4 (m, 3H), 9.0 (m, 1H) 10.4 (s, 1H); HPLC Purity: 95.72%; Mass (M+1): 545.3.

N-(2-methoxy-4-(4-(2-phenylpropan-2-yl)piperazine-1-carbonyl)phenyl)quinoline-8-sulfonamide (Compound 356)

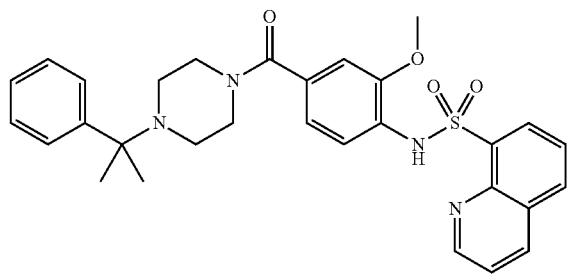 [SMILES: COc1cc(C(=O)N2CCN(C(C)(C)c3ccccc3)CC2)ccc1NS(=O)(=O)c1cccc2cccnc12]

¹H NMR (400 MHz, CDCl₃) δ: 1.3 (s, 6H), 2.2-2.5 (m, 4H), 3.2-3.7 (m, 7H), 6.8-7.1 (m, 2H), 7.0-7.4 (m, 6H), 7.6-7.8 (m, 2H), 8.3 (m, 2H), 8.6 (m, 1H), 9.0 (m, 2H); HPLC Purity: 94.22%; Mass (M+1): 544.66.

N-(4-(4-(2-cyclopropylpropan-2-yl)piperazine-1-carbonyl)phenyl)quinoline-8-sulfonamide (Compound 438)

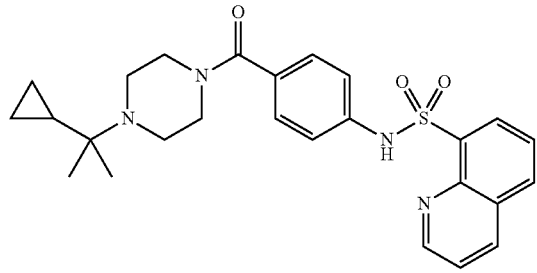 [SMILES: CC(C)(C1CC1)N1CCN(C(=O)c2ccc(NS(=O)(=O)c3cccc4cccnc34)cc2)CC1]

¹H NMR (400 MHz, DMSO-d₆) δ: 0.2-0.37 (m, 4H), 0.8 (s, 6H), 3.0-3.8 (m, 8H), 7.0-7.2 (m, 4H), 7.5-7.8 (m, 2H), 8.0-8.4 (m, 3H), 9.1-9.2 (m, 1H), 10.4 (s, 1H); HPLC Purity: 94.80%; Mass (M+1): 479.4.

N-(4-(4-(2-methyl-2-phenylpropanoyl)piperazine-1-carbonyl)-2-(trifluoromethoxy)phenyl)quinoline-8-sulfonamide (Compound 359)

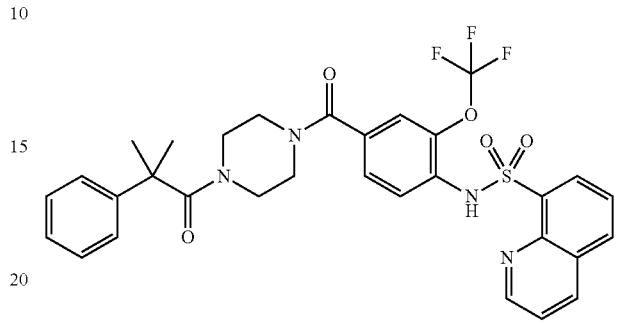

¹H NMR (400 MHz, CDCl₃) δ: 1.2 (m, 6H), 3.0-3.6 (m, 8H), 7.0-7.4 (m, 7H), 7.6 (m, 2H), 7.9 (m, 1H), 8.0-8.4 (m, 3H), 9.0 (m, 1H); HPLC Purity: 99.85%; Mass (M+1): 627.2.

Example 3

Preparation of Compounds of Formula Ie

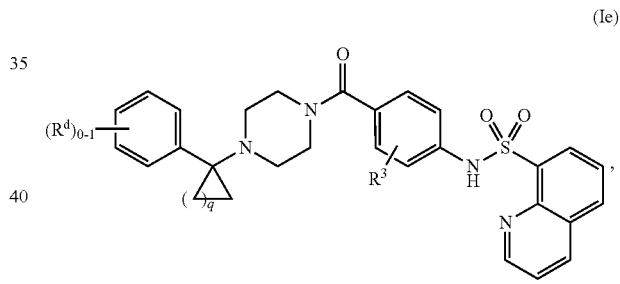

wherein R$^d$, when present, is aryl; R$^3$ is methoxy or OCF$_3$; and q is 1, 2, 3, or 4.

Scheme 3:

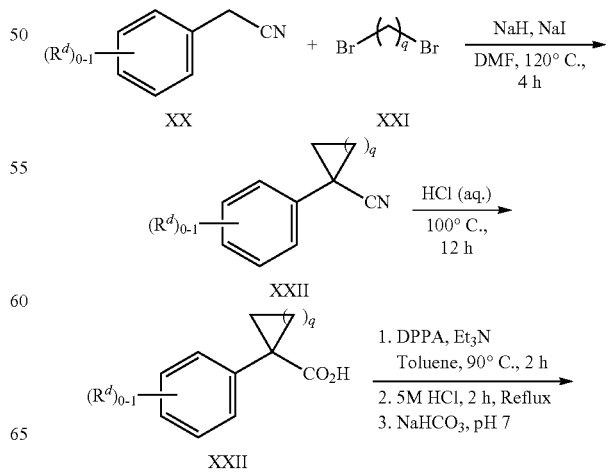

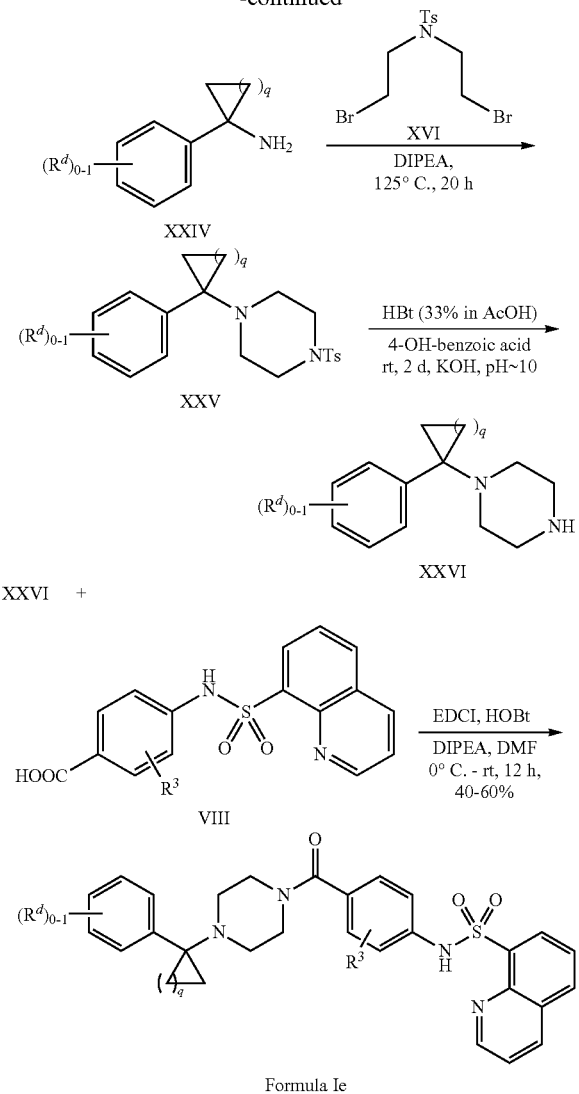

Formula Ie $R^d$ = Aryl (when present)
$R^3$ = 2-OMe, 3-OMe, OCF$_3$
q = 1, 2, 3 or 4

Synthesis of Intermediate XXII.

To a stirred solution NaH (21 mmol) in DMF (10 ml) at 0° C. was added aryl acetonitrile XX (4.2 mmol) in DMF slowly and stirred for 15 minutes at the same temperature. Dibromoalkane (4.2 mmol, n=2, 3, 4, 5) in DMF (5 ml) followed by sodium iodide was added to reaction mixture and was heated to 120° C. for 4 h. After completion of reaction, mixture was diluted with water and extracted with EtOAc. The organic layer was washed with water, dried over Na$_2$SO$_4$, and evaporated under reduced pressure. The residue was purified by column chromatography (silica gel, 60-120 mesh; EA-Hexane, 1:9) to afford product XXII in 75-89% yield.

Synthesis of Intermediate XXIII.

In a sealed tube a stirred solution of Nitrile XXII (3 mmol) in HCl (aqueous, 6 ml) was heated for 24 h at 100° C. After completion of the reaction the reaction mixture was poured into ice water and extracted with ethyl acetate (20 ml). The organic layer was washed with brine, dried over Na$_2$SO$_4$, and evaporated under reduced pressure. The residue was purified by column chromatography (silica gel, 60-120 mesh; EA-Hexane, 1:9) to afford product XXIII as a white solid in 50-65% yield.

Synthesis of Intermediate XXIV.

Diphenylphosphoryl azide (0.85 ml, 0.00386 moles, 1.1 eq) was added to a solution of the acid XXIII (0.00346 moles, 1 eq) and triethylamine (1 ml, 0.00776 moles, 2.2 eq) in Toluene (12 ml) and the mixture was stirred at 90° C. for 2 h. The mixture was cooled, diluted with ethyl acetate (15 ml) and washed with sodium carbonate (2×20 ml). The combined aqueous fractions were washed with brine (40 ml), dried (Na$_2$SO$_4$) and the solvent was evaporated under reduced pressure. The residue was suspended in hydrochloric acid (5M, 2 ml) and the mixture was heated under reflux for 2 h. The mixture was cooled, the solvent was evaporated under reduced pressure and the residue was dried azetropically by evaporating toluene under reduced pressure to give the crude compound as a white solid. The solid was taken in ethyl acetate (20 ml), cooled and saturated solution of NaHCO$_3$ was added to achieve pH~7. The organic phase was dried (Na$_2$SO$_4$), concentrated to leave the compound XXIV as pale yellow liquid.

Synthesis of Intermediate XXV.

A mixture of dibromide XVI (0.150 g, 0.000389 moles, 1.1 eq) and amine XXIV (0.000354 moles, 1 eq) and N,N-diisopropylethyl amine (0.15 ml) under nitrogen atmosphere was heated at 125° C. for 20 h. The reaction was allowed to cool to room temperature. The reaction mixture was extracted with water (10 ml), ethyl acetate (20 ml) and the organic phase was dried (Na$_2$SO$_4$), and concentrated under pressure. The crude product was purified by column chromatography (silica gel, 60-120 mess, 20% ethyl acetate in hexane) to leave the product XXV as a pale yellow liquid (yield 45-55%).

Synthesis of Intermediate XXVI.

To a mixture of compound N-tosylpiperazine derivative XXV (0.000398 moles, 1 eq) and 4-hydroxybenzoic acid (0.164 g, 0.00119 moles, 3 eq) was added hydrogen bromide solution (33 wt % in acetic acid, 1.8 ml) at room temperature. The reaction mixture was stirred under nitrogen atmosphere for 2 days at room temperature. Water (10 ml) was slowly added to the reaction mixture and the reaction mixture was continuously stirred for 2 h. A white precipitate was formed which was removed by filtration. The filter cake was washed with water (2×10 ml). The combined acidic aqueous washes were washed with toluene (20 ml). The aqueous phase was then cooled to 0° C. and basified with KOH pellets portion wise until pH>10, and extracted with toluene (20 ml) and ethyl acetate (2×20 ml). The combined organic phases were washed with brine, dried (Na$_2$SO$_4$), and concentrated under pressure to give the product XXVI as a pale yellow liquid which is used for the next step (Yield 90%).

Synthesis of Compounds of Formula Ie.

To a stirred solution of acid VIII (0.000315 moles, 1 eq) in DMF (5 ml), were added EDCI (0.066 g, 0.000346 moles, 1.1 eq), HOBt (0.047 g, 0.000346 moles, 1.1 eq) and DIPEA (0.13 ml, 0.00078 moles, 2.5 eq) at 0° C. and stirred for 15 minutes. A solution of amine XXVI (0.000315 moles, 1 eq) was then added at 0° C. and then the resulting mixture was allowed to stir at room temperature overnight. After completion of the reaction, water (20 mL) was added and extracted with ethyl acetate (2×30 mL). The combined organic layer was dried over anhydrous Na$_2$SO$_4$ and concentrated under reduced pressure. The crude product was purified by column chromatography (silica gel, 60-120 mess, 70% ethyl acetate in hexane) to give XXVIII in 40-45% yield.

The above procedure was used to produce the following compounds of Formula Ie using the appropriate aryl acetonitrile XX, dibromoalkane XXI, and acid VIII intermediates.

N-(4-(4-(1-phenylcyclopropyl)piperazine-1-carbonyl)phenyl)quinoline-8-sulfonamide (Compound 330)

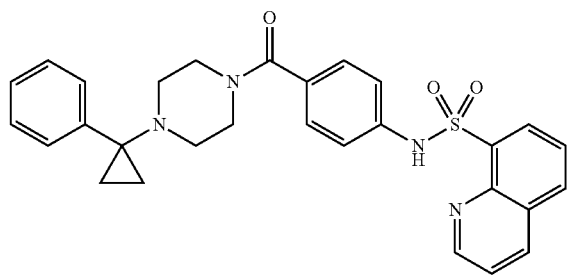 [SMILES: O=C(c1ccc(NS(=O)(=O)c2cccc3cccnc23)cc1)N1CCN(C2(c3ccccc3)CC2)CC1]

$^1$H NMR (400 MHz, CDCl$_3$) δ: 1.6 (m, 4H), 2.5 (m, 4H), 3.2 (m, 2H), 3.6 (m, 2H), 7.0 (m, 3H), 7.2 (m, 6H), 7.6 (m, 2H), 8.0 (m, 1H), 8.3 (m, 2H), 8.5 (s, 1H), 9.1 (m, 1H); HPLC Purity: 97.71%; Mass (M+1): 513.30.

N-(4-(4-(1-(4-fluorophenyl)cyclopropyl)piperazine-1-carbonyl)phenyl)quinoline-8-sulfonamide (Compound 399)

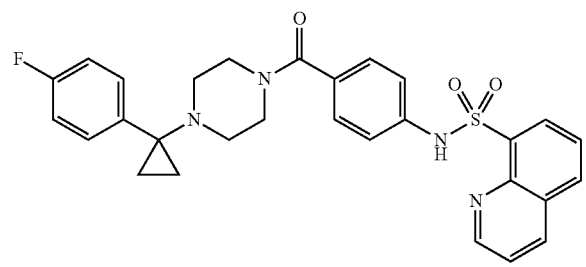 [SMILES: O=C(c1ccc(NS(=O)(=O)c2cccc3cccnc23)cc1)N1CCN(C2(c3ccc(F)cc3)CC2)CC1]

$^1$H NMR (400 MHz, CDCl$_3$) δ: 0.9-1.0 (m, 5H), 2.2-2.7 (m, 4H), 3.15-3.7 (m, 4H), 6.9-7.3 (m, 7H), 7.58-7.61 (m, 2H), 8.0 (d, 1H), 8.2-8.4 (m, 2H), 8.5 (s, 1H), 9.0 (s, 1H); HPLC Purity: 99.60%; Mass (M+1): 531.45.

N-(2-methoxy-4-(4-(1-phenylcyclopropyl)piperazine-1-carbonyl)phenyl)quinoline-8-sulfonamide (Compound 352)

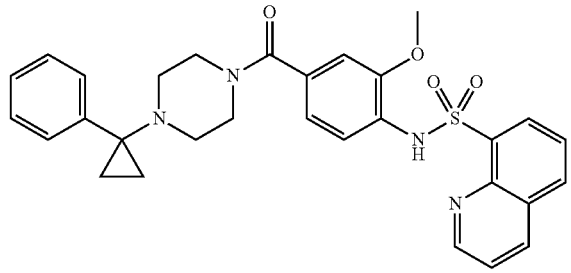 [SMILES: COc1cc(C(=O)N2CCN(C3(c4ccccc4)CC3)CC2)ccc1NS(=O)(=O)c1cccc2cccnc12]

$^1$H NMR (400 MHz, CDCl$_3$) δ: 0.9-1.0 (m, 4H), 2.5 (s, 3H), 3.2-3.7 (m, 8H), 6.5 (m, 2H), 7.2 (m, 6H), 7.7 (m, 3H), 8.0-8.4 (m, 3H), 9.0 (m, 1H); HPLC Purity: 92.0%; Mass (M+1): 543.43.

N-(4-(4-(1-phenylcyclopropyl)piperazine-1-carbonyl)-2-(trifluoromethoxy)phenyl)quinoline-8-sulfonamide (Compound 353)

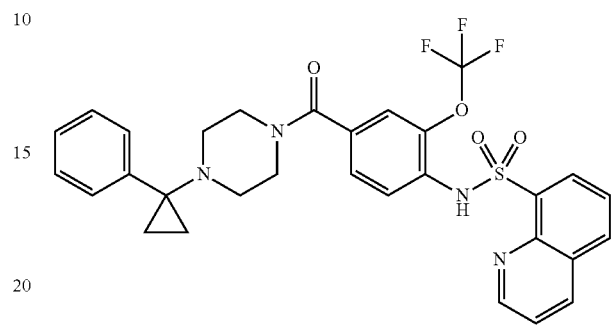

$^1$H NMR (400 MHz, CDCl$_3$) δ: 0.9-1.0 (m, 4H), 2.5 (m, 4H), 3.2-3.7 (m, 5H), 6.8-7.1 (m, 4H), 7.5 (m, 3H), 7.7 (m, 3H), 8.0-8.4 (m, 3H), 9.0 (m, 2H); HPLC Purity: 96.83%; Mass (M+1): 597.34.

N-(3-methoxy-4-(4-(1-phenylcyclopropyl)piperazine-1-carbonyl)phenyl)quinoline-8-sulfonamide (Compound 393)

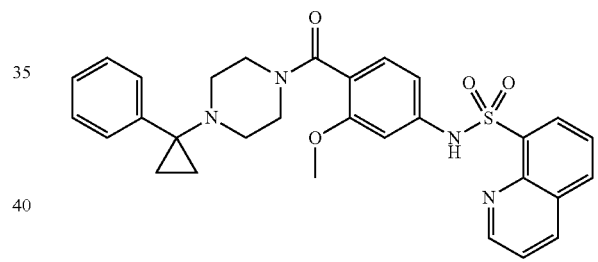

$^1$H NMR (400 MHz, CDCl$_3$) δ: 0.89 (m, 2H), 0.90 (m, 1H), 0.95 (m, 2H), 2.2-2.6 (m, 4H), 2.8-3.0 (m, 2H), 3.4 (s, 3H), 3.45-3.6 (m, 2H), 6.3 (m, 1H), 6.7-6.9 (m, 2H), 7.0-7.2 (m, 4H), 7.55-7.6 (m, 2H), 8.0 (d, 1H), 8.2-8.4 (d, 2H), 8.5 (s, 1H), 9.0 (m, 1H); HPLC Purity: 99.86%; Mass (M+1): 543.4.

N-(4-(4-(1-(4-fluorophenyl)cyclopropyl)piperazine-1-carbonyl)-2-methoxyphenyl)quinoline-8-sulfonamide (Compound 400)

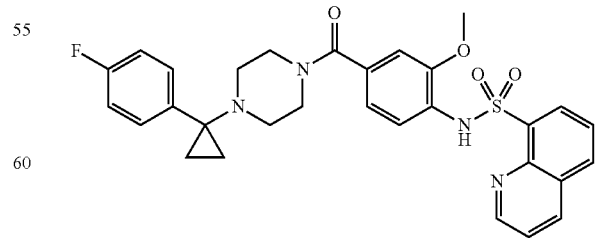

$^1$H NMR (400 MHz, CDCl$_3$) δ: 0.8 (m, 2H), 0.85 (m, 1H), 1.0 (m, 2H), 2.2-2.7 (m, 4H), 3.4 (s, 3H), 3.15-3.7 (m, 4H), 6.6-6.7 (m, 2H), 6.9-7.0 (m, 2H), 7.15-7.2 (m, 4H), 7.55-7.6

(m, 3H), 8.0 (d, 1H), 8.2 (d, 1H), 8.4 (d, 1H), 8.5 (s, 1H), 9.0 (s, 1H); HPLC Purity: 99.93%; Mass (M+1): 561.50.

N-(4-(4-(1-(4-fluorophenyl)cyclopropyl)piperazine-1-carbonyl)-3-methoxyphenyl)quinoline-8-sulfonamide (Compound 401)

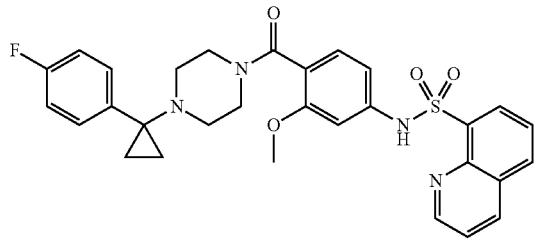 [SMILES: COc1cc(NS(=O)(=O)c2cccc3cccnc23)ccc1C(=O)N1CCN(C2(c3ccc(F)cc3)CC2)CC1]

$^1$H NMR (400 MHz, CDCl$_3$) δ: 0.89-1.0 (m, 4H), 2.2-2.7 (m, 4H), 3.0-3.6 (m, 4H), 3.58 (s, 3H), 6.3 (d, 1H), 6.8-7.2 (m, 6H), 7.55-7.6 (m, 2H), 8.0 (d, 1H), 8.2 (d, 1H), 8.38 (d, 1H), 8.5 (s, 1H), 9.0 (s, 1H); HPLC Purity: 99.68%; Mass (M+1): 561.45.

N-(4-(4-(1-(4-fluorophenyl)cyclopropyl)piperazine-1-carbonyl)-2-(trifluoromethoxy)phenyl)quinoline-8-sulfonamide (Compound 402)

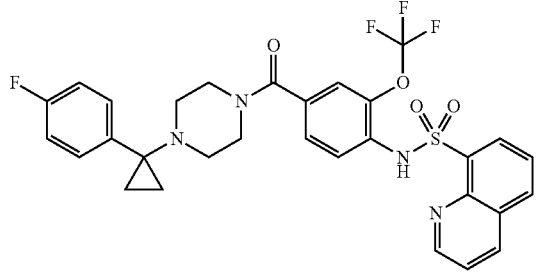 [SMILES: O=C(c1ccc(NS(=O)(=O)c2cccc3cccnc23)c(OC(F)(F)F)c1)N1CCN(C2(c3ccc(F)cc3)CC2)CC1]

$^1$H NMR (400 MHz, CDCl$_3$) δ: 0.79 (m, 2H), 0.8 (m, 2H), 2.2-2.7 (m, 4H), 3.0-3.6 (m, 4H), 6.95-7.25 (m, 5H), 7.55-7.6 (m, 2H), 8.0 (d, 1H), 7.9-7.95 (d, 1H), 8.0-8.1 (d, 1H), 8.38-8.4 (d, 2H), 9.1 (m, 1H); HPLC Purity: 99.75%; Mass (M+1): 615.45.

N-(4-(4-(1-phenylcyclobutyl)piperazine-1-carbonyl)phenyl)quinoline-8-sulfonamide (Compound 408)

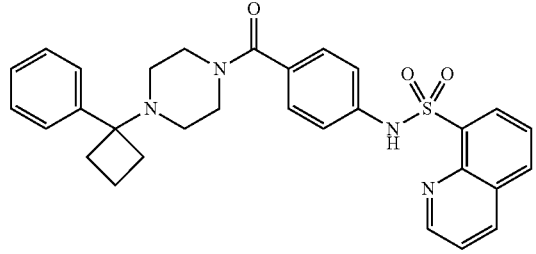 [SMILES: O=C(c1ccc(NS(=O)(=O)c2cccc3cccnc23)cc1)N1CCN(C2(c3ccccc3)CCC2)CC1]

$^1$H NMR (400 MHz, DMSO-d$_6$) δ: 0.92 (m, 1H), 1.22 (m, 2H), 1.8-2.1 (m, 2H), 2.2-2.4 (m, 4H), 2.85-3.2 (m, 1H), 3.4-3.6 (m, 4H), 7.0-7.2 (m, 4H), 7.22-7.4 (m, 5H), 7.6-7.8 (d, 2H), 8.25 (d, 1H), 8.4-8.5 (m, 2H), 9.1 (m, 1H), 10.4 (s, 1H); HPLC Purity: 99.15%; Mass (M+1): 527.55.

N-(4-(4-(1-phenylcyclopentyl)piperazine-1-carbonyl)phenyl)quinoline-8-sulfonamide (Compound 406)

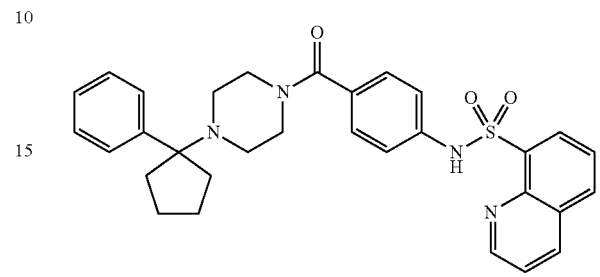

$^1$H NMR (400 MHz, CDCl$_3$) δ: 1.5-2.4 (m, 8H), 1.9-2.4 (m, 4H), 3.0-3.8 (m, 4H), 7.0-7.18 (m, 4H), 7.19-7.3 (m, 4H), 7.5-7.6 (m, 2), 8.0 (d, 1H), 8.2-8.4 (m, 2H), 8.45 (m, 1H), 9.1 (m, 1H); HPLC Purity: 97.95%; Mass (M+1): 541.55.

N-(4-(4-(1-phenylcyclohexyl)piperazine-1-carbonyl)phenyl)quinoline-8-sulfonamide (Compound 407)

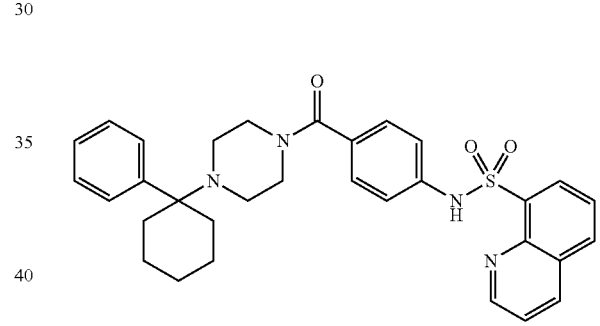

$^1$H NMR (400 MHz, DMSO-d$_6$) δ: 1.15-1.45 (m, 4H), 1.5-1.7 (m, 2H), 2.85-2.2 (m, 8H), 3.0-3.5 (m, 4H), 7.0-7.2 (m, 4H), 7.2-7.4 (m, 5H), 7.6-7.8 (m, 2H), 8.2-8.23 (d, 1H), 8.4-8.5 (m, 2H), 9.1 (m, 1H), 10.4 (s, 1H); HPLC Purity: 96.17%; Mass (M+1): 555.40.

Example 4

Preparation of Compounds of Formula If

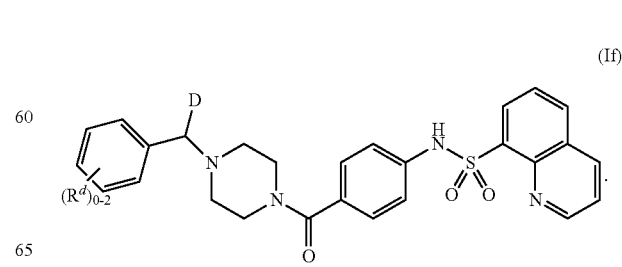

(If)

Scheme 4:

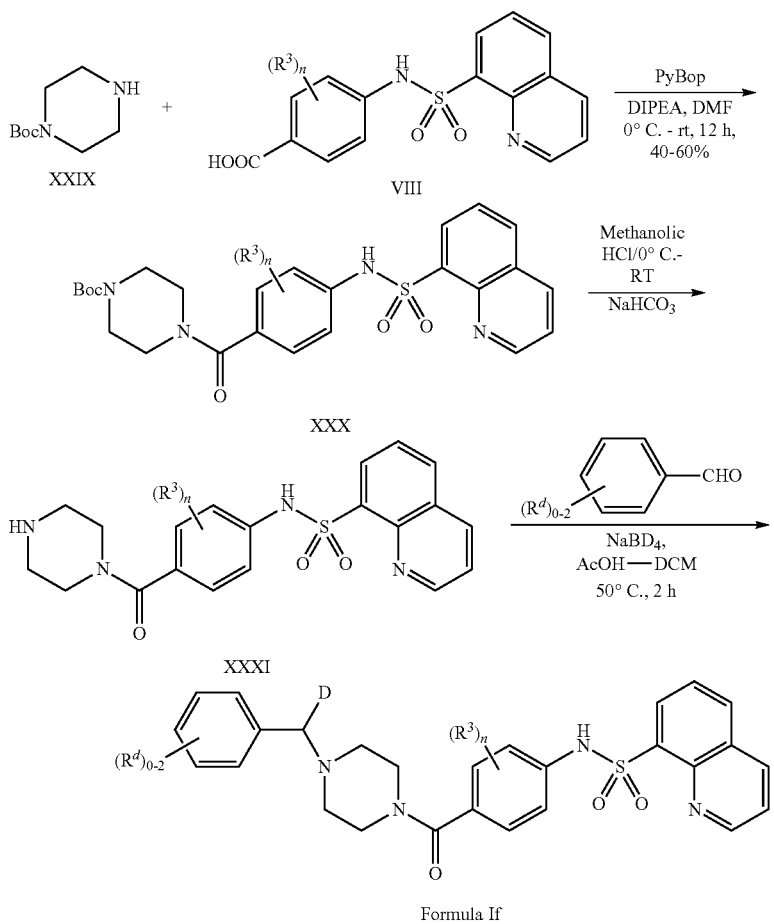

Synthesis of Intermediate XXX.

To a solution of acid VIII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperizine XXIX (6.09 mmol) was added to the reaction mixture at the same temperature under $N_2$ atmosphere and stirred overnight at room temperature. After completion of reaction, mixture was diluted with water and extracted with EtOAc. The organic layer was washed with water, dried over $Na_2SO_4$, and evaporated under reduced pressure. The residue was purified by column chromatography (silica gel, 60-120 mesh; MeOH-DCM, 1:9) to afford product XXVIII in 66% yield.

Synthesis of Intermediate XXXI.

To a solution of MeOH.HCl (10 ml) Boc protected amine XXX (4.03 mmol) was added and the resulting mixture was stirred for 1 hr. After completion of reaction, solvent was removed under reduced pressure, washed with water followed by addition of $NaHCO_3$ and extracted with DCM. The organic layer was dried over $Na_2SO_4$ and evaporated under reduced pressure to afford product XXXI in 94.30% yield.

Synthesis of Compounds of Formula If.

To a solution of amine XXXI (0.25 mmoles) and appropriate aldehyde (0.27 mmol) in DCM, acetic acid (0.2 mL) was added at room temperature and the resulting mixture was allowed to stir for 30 min Then $NaBD_4$ (0.25 mmol) was added to reaction mixture and the resulting mixture was allowed to stir at 50° C. for 2 hr. After completion of reaction, the crude mixture was diluted with DCM washed with water, dried over $Na_2SO_4$ and concentrated under reduced pressure. The residue was purified by column chromatography (silica gel, 60-120 mesh; MeOH-DCM, 2:8) to afford product XXXII in 45-55% yield.

The above procedure was used to produce the following compounds of Formula If using the appropriate aldehyde in the final step.

N-(4-(4-(4-fluorobenzyl)piperazine-1-carbonyl)phenyl)quinoline-8-sulfonamide-(D) (Compound 448)

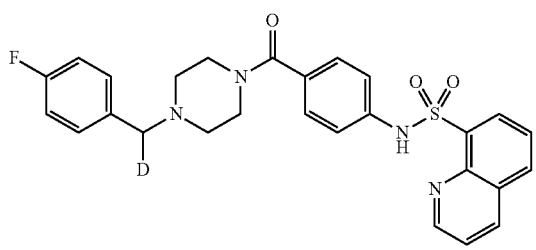 [SMILES: [2H]C(c1ccc(F)cc1)N1CCN(C(=O)c2ccc(NS(=O)(=O)c3cccc4cccnc34)cc2)CC1]

$^1$H NMR (400 MHz, DMSOd$_6$) δ: 2.2-2.4 (m, 4H), 3.1-3.6 (m, 4H), 3.7 (m, 1H), 7.2 (m, 6), 7.3 (m, 2H), 7.7 (m, 2H), 8.3 (m, 3H), 9.0 (m, 1H) 10.2 (bs, 1H); HPLC Purity: 97.28%; Mass (M+1): 506.25

N-(4-(4-(3,5-difluorobenzyl)piperazine-1-carbonyl)phenyl)quinoline-8-sulfonamide-(D) (Compound 450)

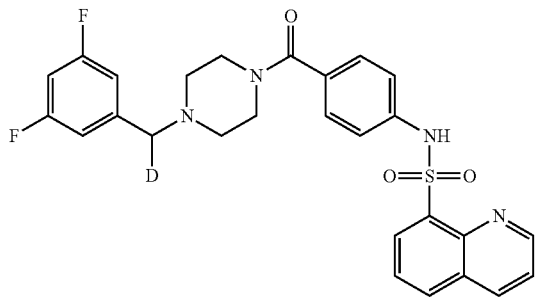 [SMILES: [2H]C(c1cc(F)cc(F)c1)N1CCN(C(=O)c2ccc(NS(=O)(=O)c3cccc4cccnc34)cc2)CC1]

$^1$H NMR (400 MHz, DMSOd$_6$) δ: 2.2-2.4 (m, 4H), 3.1-3.6 (m, 4H), 3.7 (m, 1H), 7.2 (m, 7), 7.8 (m, 2H), 8.3 (m, 3H), 9.0 (m, 1H) 10.2 (bs, 1H); HPLC Purity: 99.50%; Mass (M+1): 524.35

Example 5

Preparation of Compound of Formula Ig

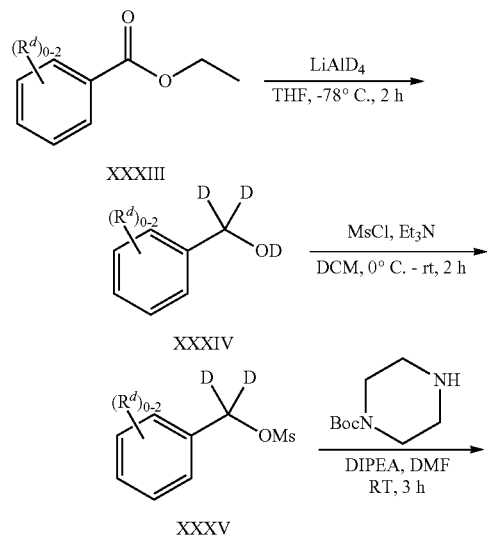

Scheme 5:

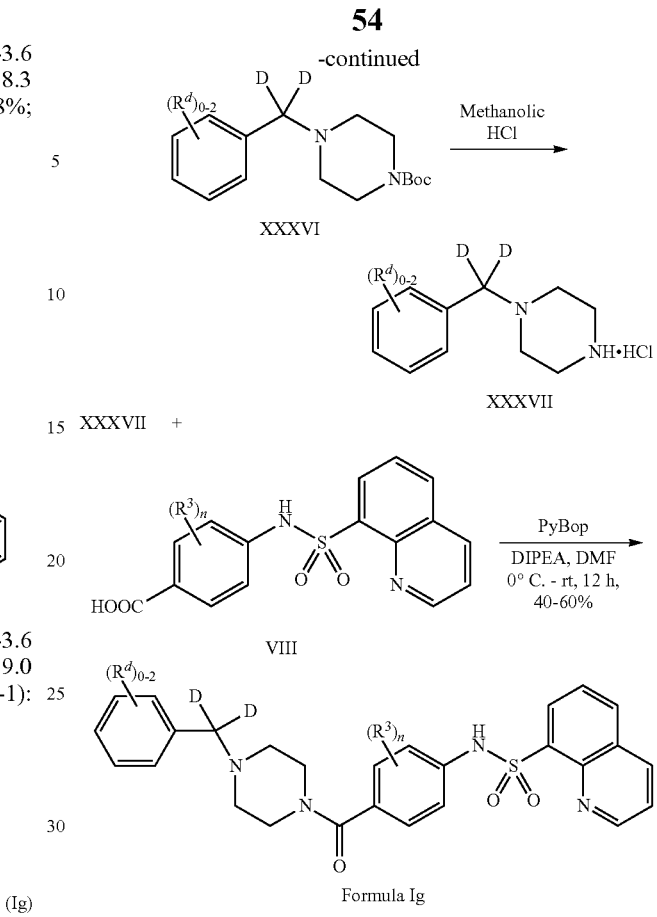

Synthesis of Intermediate XXXIV.

To a stirred solution of optionally substituted ethyl benzoate XXXIII (0.38 g, 0.00204 moles) in dry THF (5 ml) was added LiAlD$_4$ at −78° C. The reaction mixture was stirred further for 2 h at −78° C. and quenched with saturated solution of ammonium chloride. The crude mixture was diluted with ethyl acetate, washed with water, dried over Na$_2$SO$_4$ and concentrated under reduced pressure. The residue was purified by column chromatography (silica gel, 60-120 mesh; EA-Hexane, 2:8) to afford product XXXIV in 60% yield.

Synthesis of Intermediate XXXV.

To a stirred solution of compound XXXIV (0.00204 moles) in dry DCM (10 ml) was added Et$_3$N (0.75 ml, 0.0051 moles) at 0° C. and stirred for 2 h. Mesyl chloride (0.16 ml, 0.00204 moles) was added to the reaction mixture and the mixture was stirred further for 2 h at room temperature. The crude mixture was diluted with DCM and washed with water. The organic layer dried over Na$_2$SO$_4$ and concentrated under reduced pressure. The residue was purified by column chromatography (silica gel, 60-120 mesh; EA-Hexane, 2:8) to afford product XXXV in 75% yield.

Synthesis of Intermediate XXXVI.

To a stirred solution of compound XXXV (0.0013 moles) in dry DMF (10 ml) was added DIPEA (0.7 ml, 0.0039 moles) at room temperature and stirred for 2 h. Boc-piperazine (0.24 gm, 0.0013 moles) was added to the reaction mixture and the mixture was stirred further for 3 h at room temperature. After completion of the reaction, the mixture was quenched with water and diluted with ethyl acetate. The organic layer dried over Na$_2$SO$_4$ and concentrated under reduced pressure. The residue was purified by column chromatography (silica gel, 60-120 mesh; EA-Hexane, 3:7) to afford product XXXVI in 70% yield.

Synthesis of Intermediate XXXVII.

To a solution of MeOH.HCl (10 ml) Boc protected amine XXXVI (4.03 mmol) was added and the resulting mixture was stirred for 1 h. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product XXXVII in 92% yield.

Synthesis of Compounds of Formula Ig.

To a solution of unsubstituted acid VIII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperizine XXXVII (6.09 mmol) was added to the reaction mixture at the same temperature under N$_2$ atmosphere and stirred overnight at room temperature. After completion of reaction, mixture was diluted with water and extracted with EtOAc. The organic layer was washed with water, dried over Na$_2$SO$_4$, and evaporated under reduced pressure. The residue was purified by column chromatography (silica gel, 60-120 mesh; MeOH-DCM, 2:8) to afford product.

The following compound was produced by the above-described method using ethyl-3,5-difluorobenzoate as starting material.

N-(4-(4-(3,5-difluorobenzyl)piperazine-1-carbonyl)phenyl)quinoline-8-sulfonamide-(D2) (Compound 449)

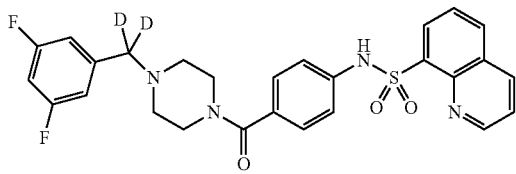 [SMILES: [2H]C([2H])(c1cc(F)cc(F)c1)N1CCN(C(=O)c2ccc(NS(=O)(=O)c3cccc4cccnc34)cc2)CC1]

$^1$H NMR (400 MHz, CDCl$_3$) δ: 2.2-2.6 (m, 4H), 2.4-2.49 (m, 2H), 3.2-3.8 (m, 4H), 6.7-7.0 (m, 3H), 7.0-7.2 (m, 4H), 7.6 (m, 2H), 8.1 (d, 1H), 8.2-8.6 (m, 3H), 9.0 (m, 1H), 10.46 (bs, 1H); HPLC Purity: 98.11%; Mass (M+1): 525.15.

Example 6

Preparation of Compounds of Formula Ih (Ih)

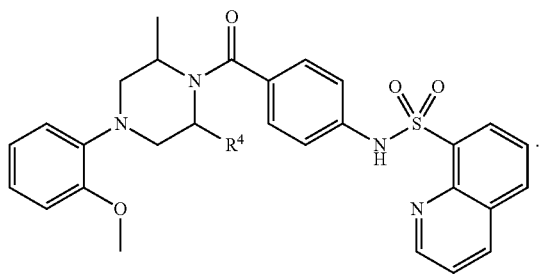

Scheme 6

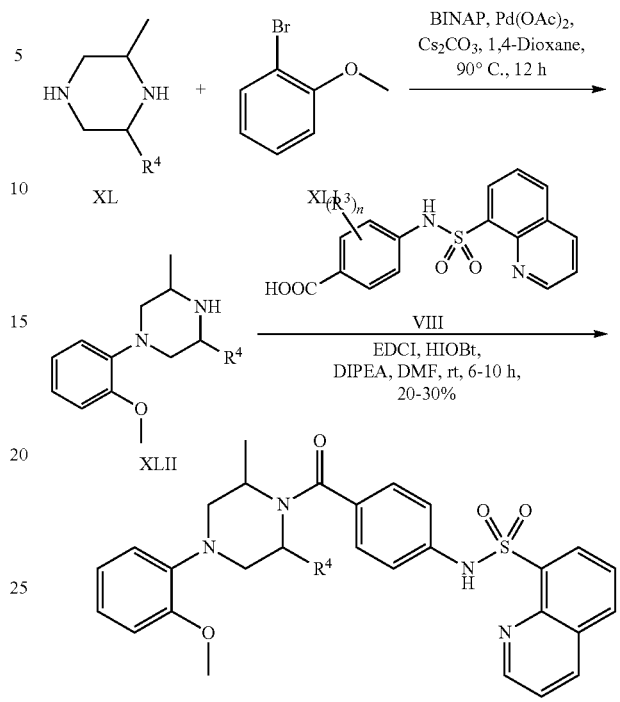

Formula Ih

Synthesis of Intermediate XLII.

Nitrogen was purged through a stirred solution of arylbromide (XLI, 2.15 mmol) in 1,4-dioxane (20 ml) at room temperature for 30 minutes. BINAP (0.134 gm, 0.215 mmol), palladium acetate (0.0096 g, 0.043 mmol) and cesium carbonate (1.40 gm, 4.3 mmol) were added to the reaction mixture and the nitrogen purging was continued for another 20 minutes and finally diamine (XL, 2.15 mmol) was added and stirred at 100° C. overnight under nitrogen atmosphere. After completion of the reaction (monitored by TLC), the reaction mixture was concentrated under vacuum. The residue was dissolved in water, extracted with ethyl acetate (3×50 ml). Combined organic extracts were washed with brine (20 ml), dried over anhydrous sodium sulfate, filtered and concentrated under reduced pressure. The crude product was then purified by column chromatography (60-120 silica gel) using 20% ethyl acetate-hexane to afford compound XLII (40-60%).

Synthesis of Compounds of Formula Ih:

To a stirred solution of the carboxylic acid (VIII, 0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min Amine (XLII 0.61 mmol) was then added at 0° C. and stirred overnight at room temperature. After completion of the reaction (monitored by TLC), the reaction mixture was poured into 1.0 M HCl and extracted with EtOAc. The organic layer was washed with saturated NaHCO$_3$ solution, dried over NaSO$_4$ and filtered. The solvent was removed by rotary evaporation and the product was isolated by chromatography on silica gel (60-120 silica gel, 2% MeOH-DCM) or preparative HPLC to yield product (40-60%) as an off-white solid.

The following compounds were produced by the above-described method using the appropriate amine XL.

N-(4-(4-(2-methoxyphenyl)-2-methylpiperazine-1-carbonyl)phenyl)quinoline-8-sulfonamide (Compound 223)

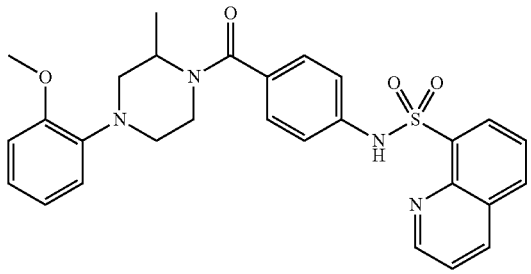 [SMILES: COc1ccccc1N1CCN(C(=O)c2ccc(NS(=O)(=O)c3cccc4cccnc34)cc2)C(C)C1]

$^1$H NMR (400 MHz, DMSOd$_6$) δ: 1.2 (d, 3H), 2.5-2.55 (m, 2H), 2.6-2.69 (m, 1H), 3.0-3.2 (m, 4H), 3.8 (s, 3H), 6.8-7.0 (d, 4H), 7.1-7.2 (m, 4H), 7.6-7.8 (m, 2H), 8.2-8.6 (m, 3H), 9.0 (m, 1H), 10.46 (bs, 1H); HPLC Purity: 99.04%; Mass (M+1): 517.40.

N-(4-((2R,6S)-4-(2-methoxyphenyl)-2,6-dimethylpiperazine-1-carbonyl)phenyl)quinoline-8-sulfonamide (Compound 222)

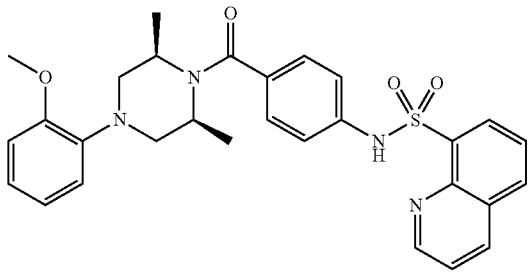 [SMILES: COc1ccccc1N1C[C@@H](C)N(C(=O)c2ccc(NS(=O)(=O)c3cccc4cccnc34)cc2)[C@@H](C)C1]

$^1$H NMR (400 MHz, DMSOd$_6$) δ: 1.2-1.4 (s, 6H), 2.4-2.49 (m, 2H), 2.6-2.69 (m, 2H), 3.0-3.2 (m, 2H), 3.8 (s, 3H), 4.2 (bs, 1H), 6.8-7.0 (d, 4H), 7.1-7.2 (m, 4H), 7.6-7.8 (m, 2H), 8.2-8.6 (m, 3H), 9.0 (m, 1H), 10.46 (bs, 1H); HPLC Purity: 99.74%; Mass (M+1): 531.40.

Example 7

Preparation of Compounds of Formula Ii

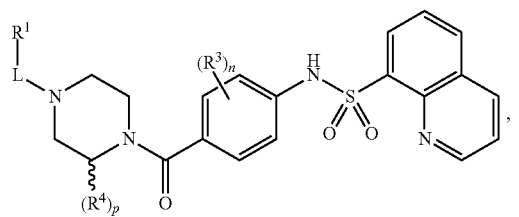

wherein R$^1$ is cycloalkyl, heterocyclyl, aryl, or heteroaryl; R$^3$ is chloro, fluoro, CF$_3$ or OCF$_3$; and R$^4$ is alkyl or phenyl.

Scheme 7

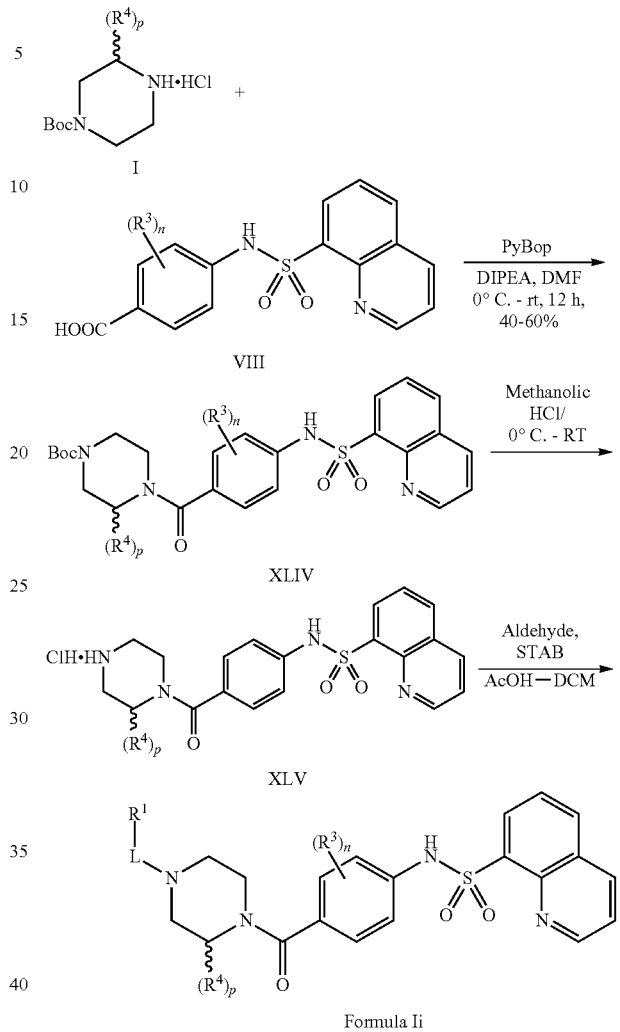

STAB = Sodium tri-acetoxy borohydride
R$^4$ = alkyl, phenyl
R$^3$ = Cl, F, CF$_3$, OCF$_3$
R$^1$ = Cycloalkyl, Heterocyclyl, Aryl, Heteroaryl
L = —(CR$^c$R$^c$)$_m$—
p = 0 or 1

Synthesis of Intermediate XLIV.

To a solution of acid VIII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperazine/substituted piperizine I (1.13 gm, 6.09 mmol) was added to the reaction mixture at the same temperature under N$_2$ atmosphere and stirred overnight at room temperature. After completion of reaction, mixture was diluted with water and extracted with EtOAc. The organic layer was washed with water, dried over Na$_2$SO$_4$, and evaporated under reduced pressure. The residue was purified by column chromatography (silica gel, 60-120 mesh; MeOH-DCM, 2:8) to afford product XLIV in 66% yield.

Synthesis of Intermediate XLV.

To a solution of MeOH.HCl, Boc protected amine XLIV (4.03 mmol) was added and the resulting mixture was stirred for 1 hr. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product XLV (94.30% yield).

Synthesis of Compounds of Formula II.

To a solution of amine XLV (0.25 mmol) and appropriate aldehyde (0.27 mmol) in DCM, acetic acid (0.2 mL) was added at room temperature and the resulting mixture was allowed to stir for 30 minutes. Then sodium triacetoxyborohydride (STAB) (0.26 gm, 1.26 mmol) was added to reaction mixture and the resulting mixture was allowed to stir at 50° C. for 1 h. After completion of reaction, the crude mixture was diluted with DCM washed with water, dried over Na$_2$SO$_4$ and concentrated under reduced pressure. The residue was purified by column chromatography (silica gel, 60-120 mesh; MeOH-DCM, 2:8) to afford product in 32-45% yield.

The following compounds were produced by the above-described method using the appropriate N-Boc protected piperazine I and acid VIII.

N-(4-(4-(4-fluorobenzyl)piperazine-1-carbonyl)phenyl)quinoline-8-sulfonamide (Compound 341)

$^1$H NMR (400 MHz, CDCl$_3$) δ: 2.2-2.6 (m, 4H), 2.8 (s, 2H), 3.2-3.5 (m, 2H), 3.6-3.8 (m, 2H), 6.9-7.3 (m, 9H), 7.6 (m, 2H), 8.0 (m, 1H), 8.3 (m, 2H), 9.0 (m, 1H); HPLC Purity: 98.15%; Mass (M+1): 503.76.

N-(4-(4-41H-pyrazol-3-yl)methyl)piperazine-1-carbonyl)phenyl)quinoline-8-sulfonamide (Compound 384)

$^1$H NMR (400 MHz, DMSO-d$_6$) δ: 2.2-2.4 (m, 2H), 2.65 (s, 2H), 3.2-3.6 (m, 6H), 6.1 (s, 1H), 7.0-7.2 (m, 4H), 7.4 (s, 1H), 7.6-7.8 (m, 3H), 8.3 (d, 1H), 8.4 (d, 1H), 8.5 (d, 1H), 9.0 (m, 1H), 10.4 (s, 1H), 12.6 (s, 1H); HPLC Purity: 96.98%; Mass (M+1): 477.30.

N-(4-(4-(3,5-difluorobenzyl)piperazine-1-carbonyl)phenyl)quinoline-8-sulfonamide (Compound 394)

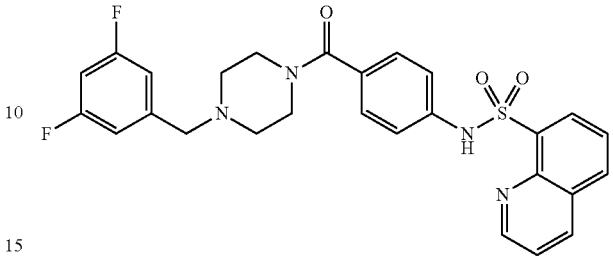

$^1$H NMR (400 MHz, CDCl$_3$) δ: 2.2-2.6 (m, 4H), 2.4-2.49 (m, 2H), 3.2-3.8 (m, 4H), 6.7-7.0 (m, 3H), 7.0-7.2 (m, 4H), 7.6 (m, 2H), 8.1 (d, 1H), 8.2-8.6 (m, 3H), 9.0 (m, 1H), 10.46 (bs, 1H); HPLC Purity: 98.11%; Mass (M+1): 525.15.

N-(4-(4-((1H-pyrazol-4-yl)methyl)piperazine-1-carbonyl)phenyl)quinoline-8-sulfonamide (Compound 385)

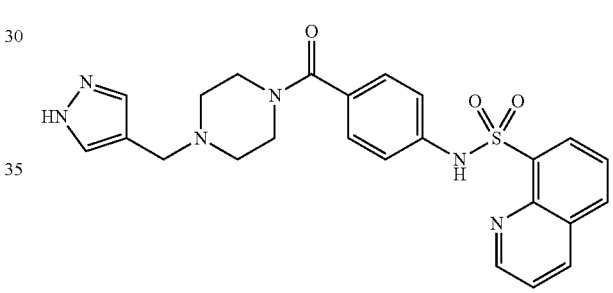

$^1$H NMR (400 MHz, DMSO-d$_6$) δ: 2.2-2.4 (m, 2H), 2.6 (s, 2H), 3.2-3.6 (m, 6H), 6.1 (s, 1H), 7.0-7.2 (m, 4H), 7.4 (s, 1H), 7.6 (s, 1H), 7.7 (m, 2H), 8.3 (d, 1H), 8.4 (d, 1H), 8.5 (d, 1H), 9.0 (m, 1H), 10.4 (s, 1H), 12.7 (s, 1H); HPLC Purity: 99.42%; Mass (M+1): 477.30.

N-(4-(4-((1H-imidazol-4-yl)methyl)piperazine-1-carbonyl)phenyl)quinoline-8-sulfonamide (Compound 386)

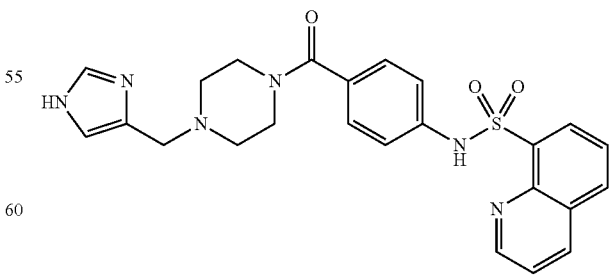

$^1$H NMR (400 MHz, DMSO-d$_6$) δ: 2.2-2.4 (m, 4H), 3.2-3.4 (s, 2H), 3.4-3.6 (m, 3H), 6.1 (s, 1H), 6.9 (s, 1H), 7.0-7.2 (m, 4H), 7.5 (m, 2H), 7.6-7.8 (m, 2H), 8.3 (d, 3H), 8.4 (d, 1H), 8.5

(d, 1H), 9.0 (m, 1H), 10.45 (s, 1H), 12.9 (s, 1H); HPLC Purity: 99.31%; Mass (M+1): 477.40.

N-(3-fluoro-4-(4-(4-fluorobenzyl)piperazine-1-carbonyl)phenyl)quinoline-8-sulfonamide (Compound 420)

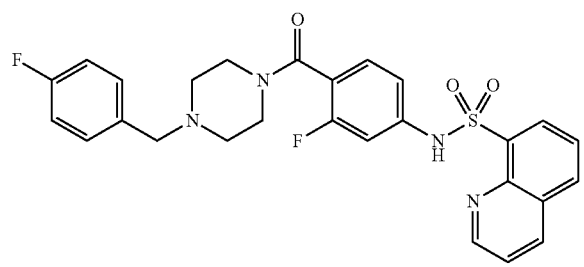 [SMILES: O=C(c1ccc(NS(=O)(=O)c2cccc3cccnc23)cc1F)N1CCN(Cc2ccc(F)cc2)CC1]

¹H NMR (400 MHz, DMSO-d$_6$) δ: 2.2-2.4 (m, 4H), 3.0-3.2 (m, 2H), 3.4 (s, 2H), 3.5-3.6 (m, 2H), 6.9-7.4 (m, 7H), 7.5-7.7 (m, 2H), 8.2-8.4 (m, 3H), 9.1-9.2 (m, 1H), 10.6 (s, 1H); HPLC Purity: 98.69%; Mass (M+1): 523.3.

N-(4-(4-(3,5-difluorobenzyl)piperazine-1-carbonyl)-3-fluorophenyl)quinoline-8-sulfonamide (Compound 421)

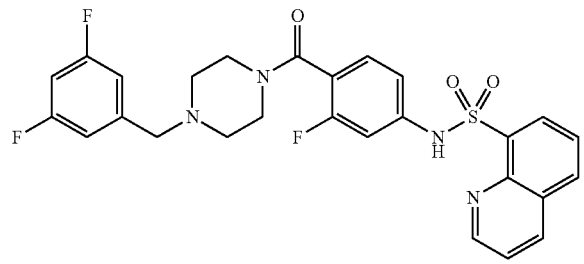 [SMILES: O=C(c1ccc(NS(=O)(=O)c2cccc3cccnc23)cc1F)N1CCN(Cc2cc(F)cc(F)c2)CC1]

¹H NMR (400 MHz, DMSO-d$_6$) δ: 2.2-2.4 (m, 4H), 3.0-3.2 (m, 2H), 3.4 (s, 2H), 3.5-3.6 (m, 2H), 6.9-7.4 (m, 6H), 7.5-7.7 (m, 2H), 8.2-8.4 (m, 3H), 9.1-9.2 (m, 1H), 10.6 (s, 1H); HPLC Purity: 95.95%; Mass (M+1): 541.3.

N-(4-(4-(4-chloro-3-fluorobenzyl)piperazine-1-carbonyl)-3-fluorophenyl)quinoline-8-sulfonamide (Compound 422)

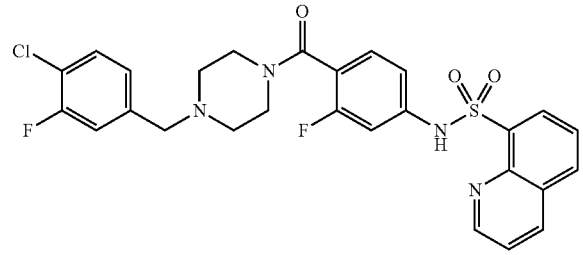 [SMILES: O=C(c1ccc(NS(=O)(=O)c2cccc3cccnc23)cc1F)N1CCN(Cc2ccc(Cl)c(F)c2)CC1]

¹H NMR (400 MHz, DMSO-d$_6$) δ: 2.2-2.4 (m, 4H), 3.0-3.2 (m, 2H), 3.4 (s, 2H), 3.5-3.6 (m, 2H), 6.9-7.4 (m, 6H), 7.5-7.7 (m, 2H), 8.2-8.4 (m, 3H), 9.1-9.2 (m, 1H), 10.6 (s, 1H); HPLC Purity: 92.56%; Mass (M+1): 557.6.

N-(3-fluoro-4-(4-(3,4,5-trifluorobenzyl)piperazine-1-carbonyl)phenyl)quinoline-8-sulfonamide (Compound 423)

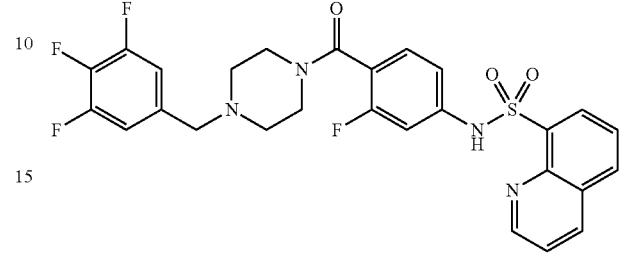

¹H NMR (400 MHz, DMSO-d$_6$) δ: 2.2-2.4 (m, 4H), 3.0-3.2 (m, 2H), 3.4 (s, 2H), 3.5-3.6 (m, 2H), 6.9-7.1 (m, 2H), 7.2-7.4 (m, 3H), 7.5-7.7 (m, 2H), 8.2-8.25 (d, 1H), 8.4-8.6 (m, 2H), 9.1-9.2 (m, 1H), 10.78 (s, 1H); HPLC Purity: 98.93%; Mass (M+1): 559.5.

N-(4-(4-(cyclopropylmethyl)piperazine-1-carbonyl)-3-fluorophenyl)quinoline-8-sulfonamide (Compound 424)

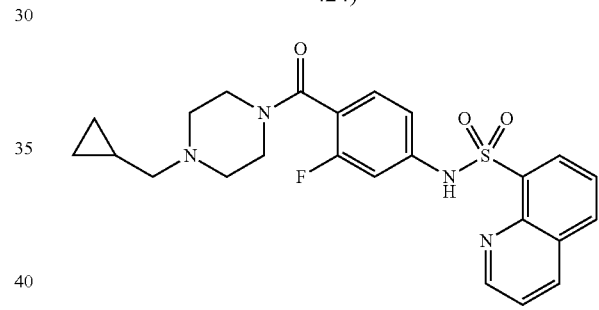

¹H NMR (400 MHz, DMSO-d$_6$) δ: 0.1-0.2 (m, 2H), 0.35-0.45 (m, 2H), 0.8-0.9 (m, 1H), 2.0-2.4 (m, 6H), 3.0-3.2 (m, 2H), 3.4-3.6 (m, 2H), 6.9-7.2 (m, 3H), 7.59-7.7 (m, 2H), 8.2-8.25 (d, 1H), 8.4-8.6 (m, 2H), 9.1-9.2 (m, 1H), 10.78 (s, 1H); HPLC Purity: 98.95%; Mass (M+1): 469.3.

N-(3-fluoro-4-(4-((tetrahydrofuran-3-yl)methyl)piperazine-1-carbonyl)phenyl)quinoline-8-sulfonamide (Compound 425)

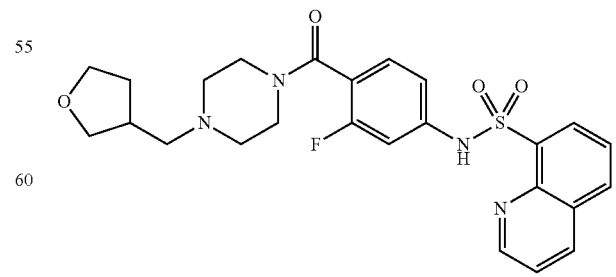

¹H NMR (400 MHz, DMSO-d$_6$) δ: 1.4-1.5 (m, 1H), 1.8-2.0 (m, 1H), 2.0-2.4 (m, 7H), 3.0-3.2 (m, 2H), 3.4-3.6 (m, 7H), 6.9-7.2 (m, 3H), 7.59-7.7 (m, 2H), 8.2-8.25 (d, 1H), 8.4-8.6 (m, 2H), 9.1-9.2 (m, 1H), 10.78 (s, 1H); HPLC Purity: 99.36%; Mass (M+1): 499.3.

N-(3-chloro-4-(4-(3,5-difluorobenzyl)piperazine-1-carbonyl)phenyl)quinoline-8-sulfonamide (Compound 426)

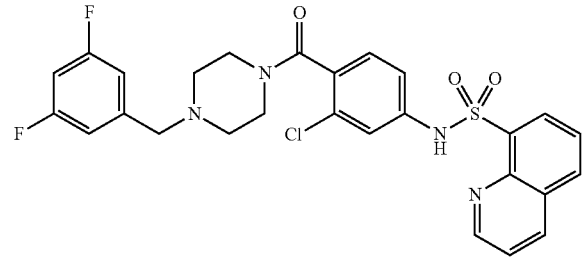 [SMILES: O=C(c1ccc(NS(=O)(=O)c2cccc3cccnc23)cc1Cl)N1CCN(Cc2cc(F)cc(F)c2)CC1]

¹H NMR (400 MHz, DMSO-d₆) δ: 2.2-2.4 (m, 2H), 3.0 (s, 2H), 3.4-3.6 (m, 4H), 7.0-7.2 (m, 6H), 7.59-7.7 (m, 2H), 8.2-8.25 (d, 1H), 8.4-8.6 (m, 3H), 9.1-9.2 (m, 1H), 10.6 (s, 1H); HPLC Purity: 99.12%; Mass (M+1): 557.45.

N-(3-chloro-4-(4-(cyclopropylmethyl)piperazine-1-carbonyl)phenyl)quinoline-8-sulfonamide (Compound 427)

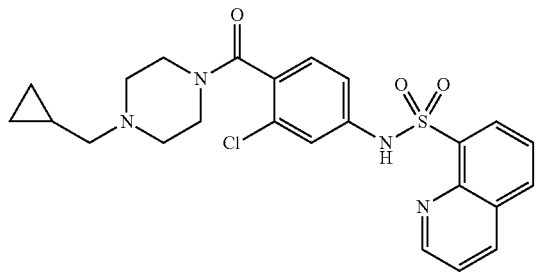 [SMILES: O=C(c1ccc(NS(=O)(=O)c2cccc3cccnc23)cc1Cl)N1CCN(CC2CC2)CC1]

¹H NMR (400 MHz, DMSO-d₆) δ: 0.1-0.2 (m, 2H), 0.3-0.4 (m, 2H), 0.8-0.85 (m, 1H), 2.2-2.4 (m, 6H), 3.0 (s, 2H), 3.5-3.6 (m, 2H), 7.0-7.2 (m, 3H), 7.59-7.7 (m, 2H), 8.2-8.25 (d, 1H), 8.4-8.6 (m, 2H), 9.1-9.2 (m, 1H), 10.6 (s, 1H); HPLC Purity: 99.57%; Mass (M+1): 485.5.

N-(3-chloro-4-(4-(cyclopentylmethyl)piperazine-1-carbonyl)phenyl)quinoline-8-sulfonamide (Compound 428)

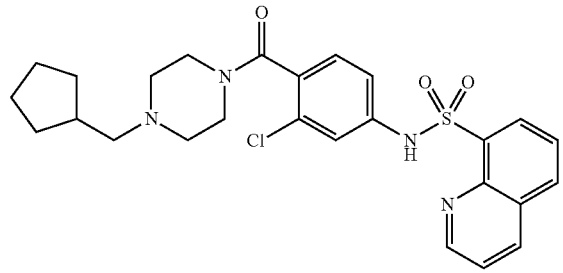 [SMILES: O=C(c1ccc(NS(=O)(=O)c2cccc3cccnc23)cc1Cl)N1CCN(CC2CCCC2)CC1]

¹H NMR (400 MHz, DMSO-d₆) δ: 1.0-1.2 (m, 2H), 1.4-1.6 (m, 6H), 2.2-2.4 (m, 7H), 3.0 (s, 2H), 3.5-3.6 (m, 2H), 7.0-7.2 (m, 3H), 7.59-7.7 (m, 2H), 8.2-8.6 (m, 2H), 9.1-9.2 (m, 1H), 10.6 (s, 1H); HPLC Purity: 99.40%; Mass (M+1): 513.45.

N-(3-chloro-4-(4-((tetrahydrofuran-3-yl)methyl)piperazine-1-carbonyl)phenyl)quinoline-8-sulfonamide (Compound 429)

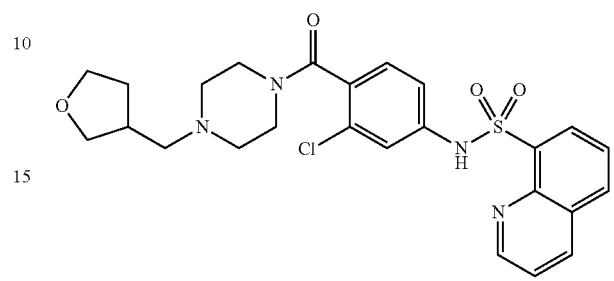

¹H NMR (400 MHz, DMSO-d₆) δ: 1.2-1.5 (m, 1H), 1.8-2.0 (m, 1H), 2.0-2.4 (m, 8H), 3.0 (m, 2H), 3.5-3.8 (m, 5H), 7.0-7.2 (m, 3H), 7.59-7.7 (m, 2H), 8.2-8.6 (m, 3H), 9.1-9.2 (m, 1H), 10.6 (s, 1H); HPLC Purity: 95.96%; Mass (M+1): 515.45.

N-(3-chloro-4-(4-(4-fluorobenzyl)piperazine-1-carbonyl)phenyl)quinoline-8-sulfonamide (Compound 431)

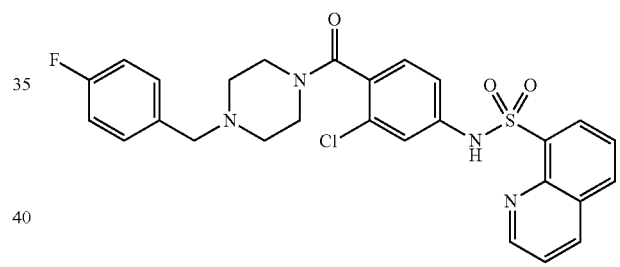

¹H NMR (400 MHz, DMSO-d₆) δ: 2.2-2.4 (m, 4H), 2.9-3.2 (s, 2H), 3.4-3.7 (m, 4H), 7.0-7.2 (m, 5H), 7.3-7.4 (m, 2H), 7.6-7.8 (m, 2H), 8.0-8.6 (m, 3H), 9.1-9.2 (m, 1H), 10.5 (s, 1H); HPLC Purity: 98.11%; Mass (M+1): 539.50.

N-(3-chloro-4-(4-(4-chloro-3-fluorobenzyl)piperazine-1-carbonyl)phenyl)quinoline-8-sulfonamide (Compound 432)

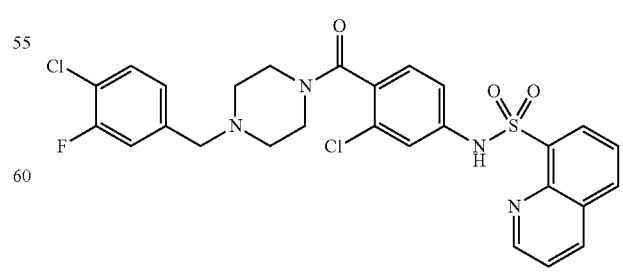

¹H NMR (400 MHz, DMSO-d₆) δ: 2.2-2.4 (m, 4H), 2.9-3.2 (s, 2H), 3.4-3.7 (m, 4H), 7.0-7.2 (m, 5H), 7.3-7.4 (m, 1H), 7.6-7.8 (m, 2H), 8.0-8.6 (m, 3H), 9.1-9.2 (m, 1H), 10.6 (s, 1H); HPLC Purity: 97.27%; Mass (M+1): 573.45.

N-(3-chloro-4-(4-(2,4,5-trifluorobenzyl)piperazine-1-carbonyl)phenyl)quinoline-8-sulfonamide (Compound 433)

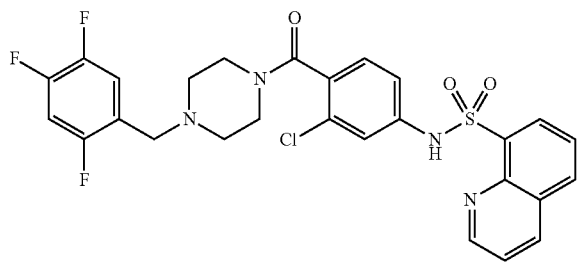 [SMILES: O=C(c1ccc(NS(=O)(=O)c2cccc3cccnc23)cc1Cl)N1CCN(Cc2cc(F)c(F)cc2F)CC1]

$^1$H NMR (400 MHz, DMSO-d$_6$) δ: 2.2-2.4 (m, 4H), 2.9-3.2 (s, 2H), 3.4-3.7 (m, 4H), 7.0-7.2 (m, 3H), 7.3-7.4 (m, 2H), 7.6-7.8 (m, 2H), 8.0-8.6 (m, 3H), 9.1-9.2 (m, 1H), 10.6 (s, 1H); HPLC Purity: 99.17%; Mass (M+1): 575.45.

N-(3-chloro-4-(4-(3,4,5-trifluorobenzyl)piperazine-1-carbonyl)phenyl)quinoline-8-sulfonamide (Compound 434)

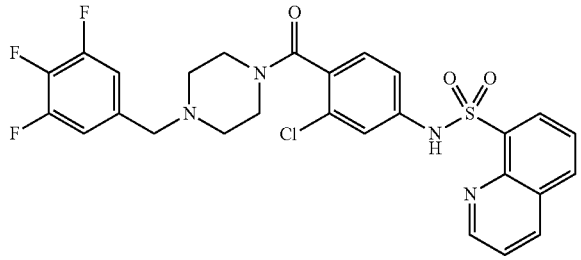

$^1$H NMR (400 MHz, DMSO-d$_6$) δ: 2.2-2.4 (m, 4H), 2.9-3.2 (s, 2H), 3.4-3.7 (m, 4H), 7.0-7.2 (m, 5H), 7.6-7.8 (m, 2H), 8.0-8.6 (m, 3H), 9.1-9.2 (m, 1H), 10.6 (s, 1H); HPLC Purity: 99.55%; Mass (M+1): 575.50.

N-(3-fluoro-4-(4-((tetrahydro-2H-pyran-2-yl)methyl)piperazine-1-carbonyl)phenyl)quinoline-8-sulfonamide (Compound 435)

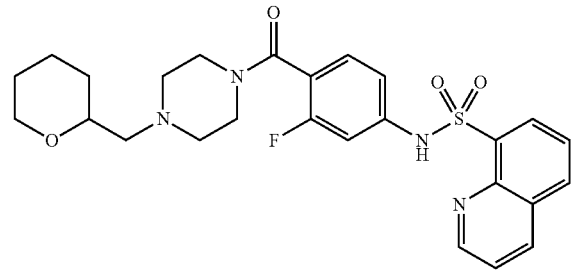 [SMILES: O=C(c1ccc(NS(=O)(=O)c2cccc3cccnc23)cc1F)N1CCN(CC2CCCCO2)CC1]

$^1$H NMR (400 MHz, DMSO-d$_6$) δ: 1.0-1.2 (m, 1H), 1.3-1.56 (m, 5H), 1.6-1.7 (m, 1H), 2.2-2.4 (m, 6H), 2.9-3.4 (m, 3H), 3.7-3.8 (m, 1H), 7.0-7.2 (m, 3H), 7.6-7.8 (m, 2H), 8.0-8.6 (m, 3H), 9.1-9.2 (m, 1H), 10.6 (s, 1H); HPLC Purity: 95.44%; Mass (M+1): 513.3.

N-(3-fluoro-4-(4-((tetrahydro-2H-pyran-4-yl)methyl)piperazine-1-carbonyl)phenyl)quinoline-8-sulfonamide (Compound 436)

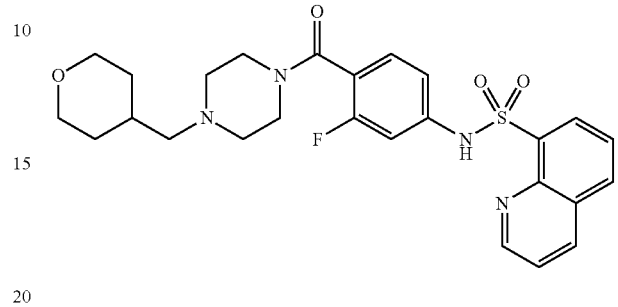

$^1$H NMR (400 MHz, DMSO-d$_6$) δ: 1.0-1.2 (m, 3H), 1.56-1.6 (m, 3H), 2.2-2.6 (m, 5H), 2.99-3.4 (m, 5H), 3.6-3.8 (m, 3H), 7.0-7.2 (m, 3H), 7.6-7.8 (m, 2H), 8.0-8.6 (m, 3H), 9.1-9.2 (m, 1H), 10.4 (s, 1H); HPLC Purity: 93.35%; Mass (M+1): 513.3.

N-(3-fluoro-4-(4-((tetrahydrofuran-2-yl)methyl)piperazine-1-carbonyl)phenyl)quinoline-8-sulfonamide (Compound 437)

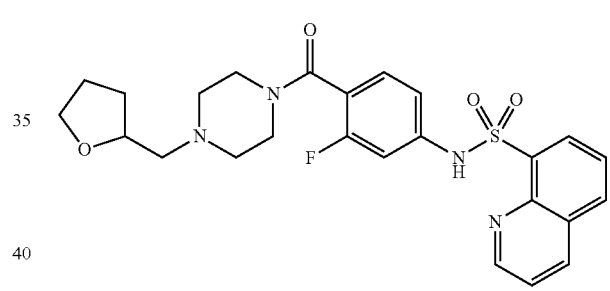

$^1$H NMR (400 MHz, DMSO-d$_6$) δ: 1.4-1.45 (m, 1H), 1.7-2.0 (m, 3H), 2.2-2.6 (m, 6H), 2.99-3.2 (m, 2H), 3.4-4.0 (m, 5H), 7.0-7.2 (m, 3H), 7.6-7.8 (m, 2H), 8.0-8.6 (m, 3H), 9.1-9.2 (m, 1H), 10.4 (s, 1H); HPLC Purity: 97.02%; Mass (M+1): 499.3.

N-(3-chloro-4-(4-((tetrahydro-2H-pyran-2-yl)methyl)piperazine-1-carbonyl)phenyl)quinoline-8-sulfonamide (Compound 439)

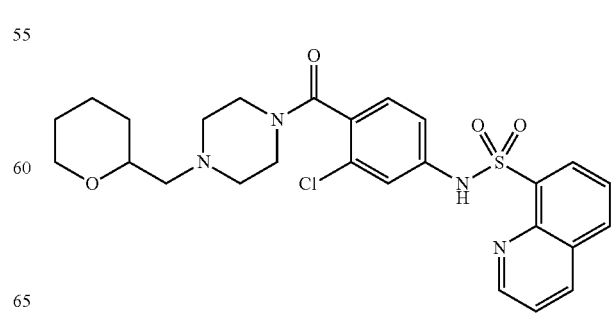

¹H NMR (400 MHz, DMSO-d₆) δ: 1.0-1.8 (m, 6H), 2.1-2.7 (m, 6H), 3.0-3.8 (m, 7H), 7.0-7.2 (m, 3H), 7.6-7.8 (m, 2H), 8.2-8.6 (m, 3H), 9.1-9.2 (m, 1H) 10.6 (s, 1H); HPLC Purity: 95.14%; Mass (M+1): 529.4.

N-(3-chloro-4-(4-((tetrahydro-2H-pyran-4-yl)methyl)piperazine-1-carbonyl)phenyl)quinoline-8-sulfonamide (Compound 440)

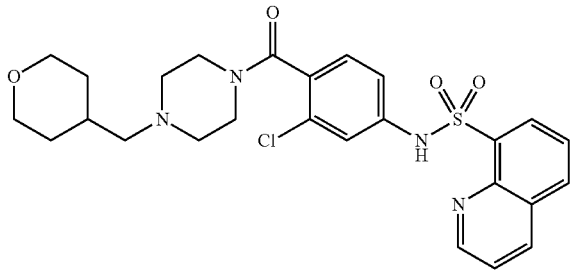 [SMILES: O=C(c1ccc(NS(=O)(=O)c2cccc3cccnc23)cc1Cl)N1CCN(CC2CCOCC2)CC1]

¹H NMR (400 MHz, DMSO-d₆) δ: 1.0-1.8 (m, 4H), 2.1-2.5 (m, 7H), 2.7-3.85 (m, 8H), 7.0-7.2 (m, 3H), 7.6-7.8 (m, 2H), 8.2-8.6 (m, 3H), 9.1-9.2 (m, 1H) 10.6 (bs, 1H); HPLC Purity: 96.39%; Mass (M+1): 529.4.

N-(3-chloro-4-(4-((tetrahydrofuran-2-yl)methyl)piperazine-1-carbonyl)phenyl)quinoline-8-sulfonamide (Compound 441)

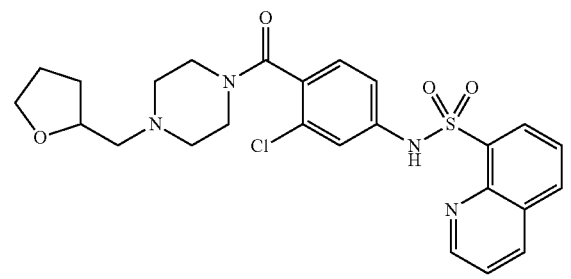

¹H NMR (400 MHz, DMSO-d₆) δ: 1.6-2.0 (m, 4H), 2.1-3.0 (m, 7H), 3.4-4.0 (m, 6H), 7.0-7.2 (m, 3H), 7.6-7.8 (m, 2H), 8.2-8.6 (m, 3H), 9.1-9.2 (m, 1H) 10.6 (bs, 1H); HPLC Purity: 97.11%; Mass (M+1): 515.3.

N-(4-(4-((5-fluoropyridin-3-yl)methyl)piperazine-1-carbonyl)-2-(trifluoromethoxy)phenyl)quinoline-8-sulfonamide (Compound 390)

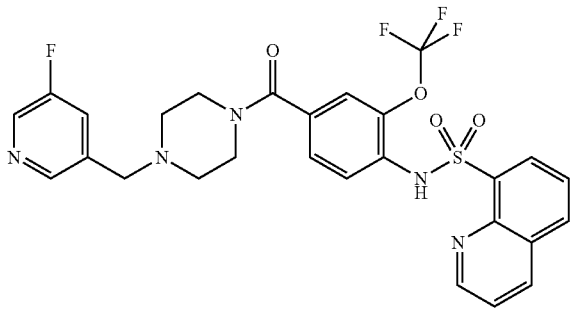 [SMILES: O=C(c1ccc(NS(=O)(=O)c2cccc3cccnc23)c(OC(F)(F)F)c1)N1CCN(Cc2cncc(F)c2)CC1]

¹H NMR (400 MHz, DMSO-d6) δ: 2.3-2.4 (m, 4H), 2.8 (s, 2H), 3.4-3.6 (m, 4H), 7.2-7.4 (m, 2H), 7.5-7.8 (m, 4H), 8.2-8.6 (m, 5H), 9.1 (m, 1H), 10.0 (bs, 1H); HPLC Purity: 97.9%; Mass (M+1): 590.0.

N-(4-(4-(cyclopropylmethyl)piperazine-1-carbonyl)-2-(trifluoromethoxy)phenyl)quinoline-8-sulfonamide (Compound 301)

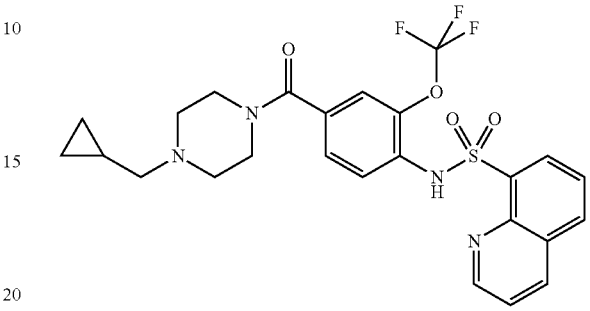

¹H NMR (400 MHz, DMSO-d6) δ: 0.1 (m, 2H), 0.4 (m, 2H), 0.8 (m, 1H), 2.2 (d, 2H), (2.4-2.6 (m, 4H), 3.2-3.6 (m, 3H), 7.3 (d, 2H), 7.5 (d, 1H), 7.8 (m, 2H), 8.3 (m, 2H), 8.6 (m, 1H), 9.1 (m, 1H), 10 (bs, 1H); HPLC Purity: 98.12%; Mass (M+1): 535.0.

N-(4-(4-((tetrahydrofuran-3-yl)methyl)piperazine-1-carbonyl)-2-(trifluoromethoxy)phenyl)quinoline-8-sulfonamide (Compound 302)

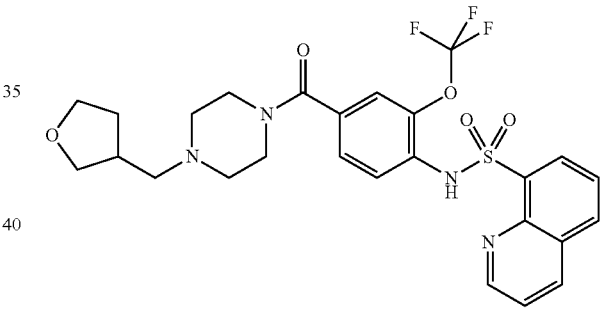

¹H NMR (400 MHz, DMSO-d6) δ: 0.6 (m, 2H), 0.9 (m, 2H), 0.8 (m, 1H), 2.5 (m, 6H), 3.0 (m, 2H), 3.6 (m, 1H), 3.7 (m, 4H), 7.2 (m, 2H), 7.5 (d, 1H), 7.8 (m, 2H), 8.3 (m, 2H), 8.6 (m, 1H), 9.1 (m, 1H), 10 (bs, 1H); HPLC Purity: 97.93%; Mass (M+1): 565.0.

N-(4-(4-phenethylpiperazine-1-carbonyl)-2-(trifluoromethoxy)phenyl)quinoline-8-sulfonamide (Compound 303)

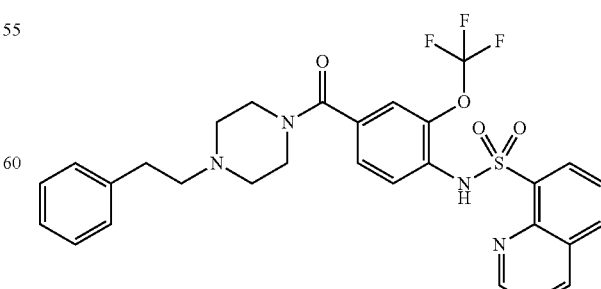

¹H NMR (400 MHz, DMSO-d$_6$) δ: 2.4-2.6 (m, 4H), 2.7 (m, 4H), 3.2 (m, 2H), 3.7 (m, 2H), 7.1-7.4 (m, 7H), 7.6 (s, 1H), 7.8 (m, 2H), 8.3 (m, 2H), 8.6 (m, 1H), 9.1 (m, 1H), 10.0 (bs, 1H); HPLC Purity: 99.67%; Mass (M+1): 585.

N-(4-(4-((3-fluoropyridin-4-yl)methyl)piperazine-1-carbonyl)-2-(trifluoromethoxy)phenyl)quinoline-8-sulfonamide (Compound 304)

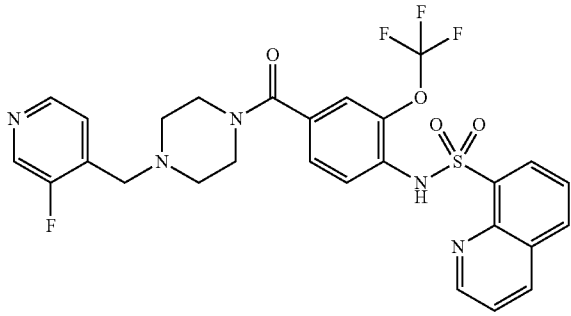 [SMILES: O=C(c1ccc(NS(=O)(=O)c2cccc3cccnc23)c(OC(F)(F)F)c1)N1CCN(Cc2ccncc2F)CC1]

¹H NMR (400 MHz, DMSO-d$_6$) δ: 2.4 (m, 4H), 3.0 (m, 2H), 4.6 (m, 4H), 3.7 (m, 2H), 7.3 (m, 2H), 7.5 (m, 2H), 7.8 (m, 2H), 8.3 (m, 2H), 8.6 (m, 2H), 9.1 (m, 1H), 10.0 (bs, 1H); HPLC Purity: 97.7%; Mass (M+1): 590.

N-(4-(4-((4-methoxypyridin-3-yl)methyl)piperazine-1-carbonyl)-2-(trifluoromethoxy)phenyl)quinoline-8-sulfonamide (Compound 305)

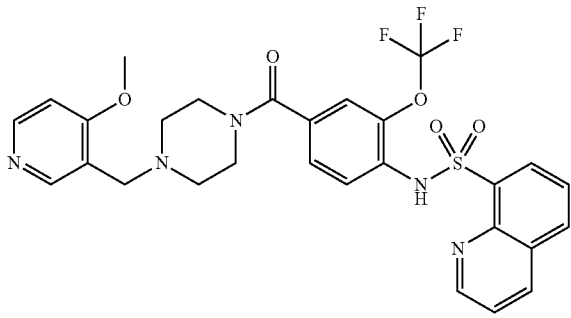 [SMILES: COc1ccncc1CN1CCN(C(=O)c2ccc(NS(=O)(=O)c3cccc4cccnc34)c(OC(F)(F)F)c2)CC1]

¹H NMR (400 MHz, DMSO-d$_6$) δ: 2.4 (m, 4H), 3.4 (m, 6H), 3.8 (s, 3H), 7.0 (m, 1H), 7.3 (m, 2H), 7.5 (m, 1H), 7.7 (m, 2H), 8.3 (m, 4H), 8.6 (m, 1H), 9.1 (m, 1H), 10.0 (bs, 1H); HPLC Purity: 98.7%; Mass (M+1): 602.

N-(4-(4-(2,3-dichlorobenzyl)piperazine-1-carbonyl)-2-(trifluoromethoxy)phenyl)quinoline-8-sulfonamide (Compound 306)

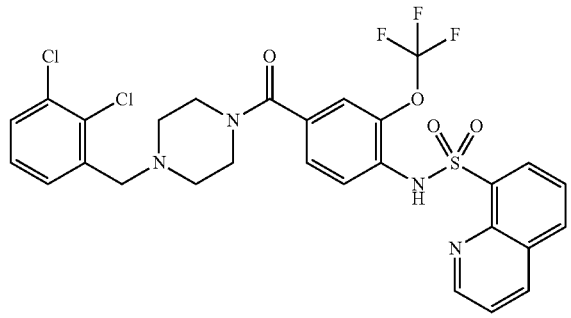 [SMILES: O=C(c1ccc(NS(=O)(=O)c2cccc3cccnc23)c(OC(F)(F)F)c1)N1CCN(Cc2cccc(Cl)c2Cl)CC1]

¹H NMR (400 MHz, DMSO-d$_6$) δ: 2.4 (m, 4H), 3.4 (m, 2H), 3.8 (m, 4H), 7.2-7.4 (m, 6H), 7.8 (m, 2H), 8.3 (m, 2H), 8.6 (m, 1H), 9.1 (m, 1H), 10.0 (bs, 1H); HPLC Purity: 99%; Mass (M+1): 639.

N-(4-(4-((3-chloropyridin-4-yl)methyl)piperazine-1-carbonyl)-2-(trifluoromethoxy)phenyl)quinoline-8-sulfonamide (Compound 307)

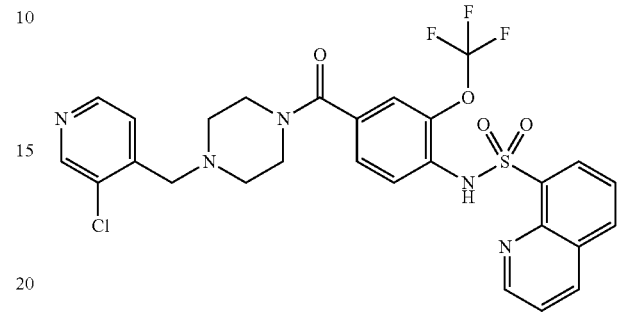

¹H NMR (400 MHz, DMSO-d$_6$) δ: 2.4 (m, 4H), 3.2 (s, 2H), 3.6 (m, 4H), 7.3 (m, 2H), 7.6 (m, 2H), 7.8 (m, 2H), 8.3 (m, 2H), 8.6 (m, 2H), 9.1 (m, 1H), 10.0 (bs, 1H); HPLC Purity: 99.24%; Mass (M+1): 606.

N-(4-(4-(2-fluoro-6-methoxybenzyl)piperazine-1-carbonyl)-2-(trifluoromethoxy)phenyl)quinoline-8-sulfonamide (Compound 308)

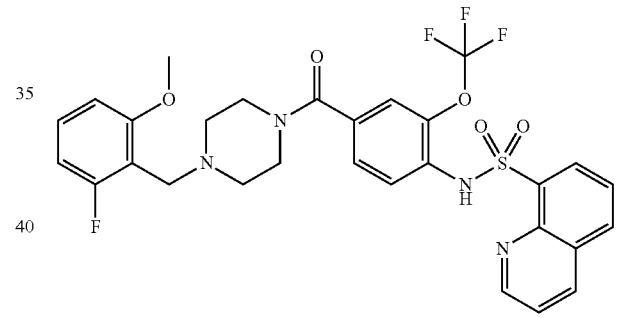

¹H NMR (400 MHz, DMSO-d$_6$) δ: 2.4 (m, 4H), 3.6 (s, 3H), 3.7 (s, 2H), 3.8 (m, 4H), 6.8 (m, 2H), 7.2 (m, 3H), 7.5 (m, 1H), 7.8 (m, 2H), 8.3 (m, 2H), 8.6 (m, 1H), 9.1 (m, 1H), 10.0 (bs, 1H); HPLC Purity: 96.97%; Mass (M+1): 619.

N-(2-(trifluoromethoxy)-4-(4-((3-(trifluoromethyl)pyridin-2-yl)methyl)piperazine-1-carbonyl)phenyl)quinoline-8-sulfonamide (Compound 309)

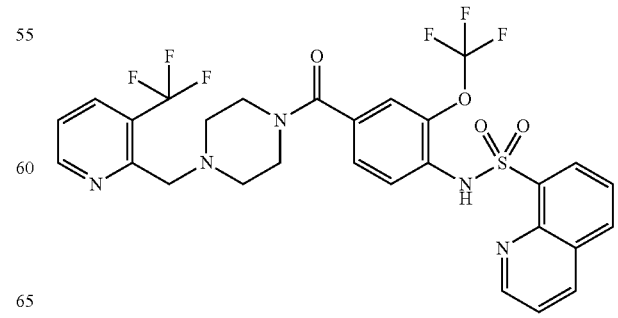

¹H NMR (400 MHz, DMSO-d₆) δ: 2.4 (m, 4H), 3.2 (s, 2H), 3.6-3.8 (m, 4H), 7.2 (m, 2H), 7.5 (m, 2H), 7.8 (m, 2H), 8.3 (m, 2H), 8.6 (m, 1H), 8.8 (m, 1H), 9.1 (m, 1H), 10.0 (bs, 1H); HPLC Purity: 98.32%; Mass (M+1): 640.

N-(4-(4-(4-methoxybenzyl)piperazine-1-carbonyl)-2-(trifluoromethoxy)phenyl)quinoline-8-sulfonamide (Compound 310)

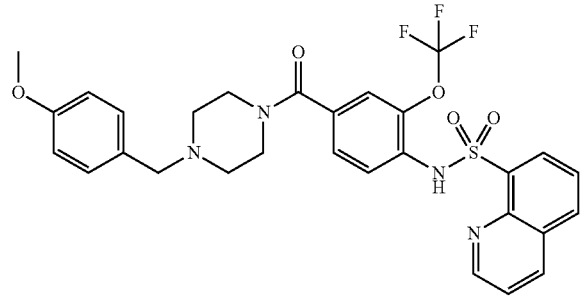 [SMILES: COc1ccc(CN2CCN(C(=O)c3ccc(NS(=O)(=O)c4cccc5cccnc45)c(OC(F)(F)F)c3)CC2)cc1]

¹H NMR (400 MHz, DMSO-d₆) δ: 2.4 (m, 4H), 3.2 (s, 2H), 3.6-3.8 (m, 4H), 7.2 (m, 2H), 7.5 (m, 2H), 7.8 (m, 2H), 8.3 (m, 2H), 8.6 (m, 1H), 8.8 (m, 1H), 9.1 (m, 1H), 10.0 (bs, 1H); HPLC Purity: 97.32%; Mass (M+1): 640.

N-(4-(4-(pyridin-4-ylmethyl)piperazine-1-carbonyl)-2-(trifluoromethyl)phenyl)quinoline-8-sulfonamide (Compound 328)

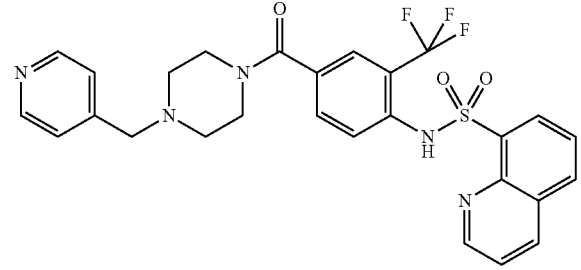 [SMILES: O=C(c1ccc(NS(=O)(=O)c2cccc3cccnc23)c(C(F)(F)F)c1)N1CCN(Cc2ccncc2)CC1]

¹H NMR (400 MHz, CDCl₃) δ: 2.2-2.8 (m, 4H), 2.9 (s, 2H), 3.2-3.7 (m, 4H), 7.2 (m, 1H), 7.6 (m, 4H), 7.9 (m, 1H), 8.1 (m, 1H), 8.3 (m, 2H), 8.6 (m, 3H), 9.1 (m, 1H); HPLC Purity: 99.67%; Mass (M+1): 556.2.

N-(4-(4-((tetrahydrofuran-2-yl)methyl)piperazine-1-carbonyl)-2-(trifluoromethyl)phenyl)quinoline-8-sulfonamide (Compound 329)

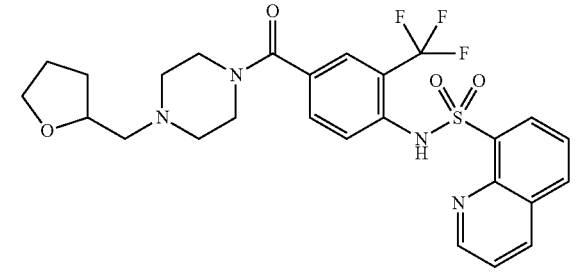 [SMILES: O=C(c1ccc(NS(=O)(=O)c2cccc3cccnc23)c(C(F)(F)F)c1)N1CCN(CC2CCCO2)CC1]

¹H NMR (400 MHz, CDCl₃) δ: 1.5 (m, 1H), 1.8-2.0 (m, 3H), 2.3-2.6 (m, 6H), 3.6 (s, 2H), 3.8 (m, 4H), 4.0 (m, 1H), 7.4 (m, 1H), 7.6 (m, 3H), 7.8 (m, 1H), 8.0 (m, 1H), 8.3 (m, 1H), 8.5 (m, 1H), 9.1 (m, 1H); HPLC Purity: 98.77%; Mass (M+1): 549.2.

N-(2-(trifluoromethoxy)-4-(4-(4-(trifluoromethyl)benzyl)piperazine-1-carbonyl)phenyl)quinoline-8-sulfonamide (Compound 334)

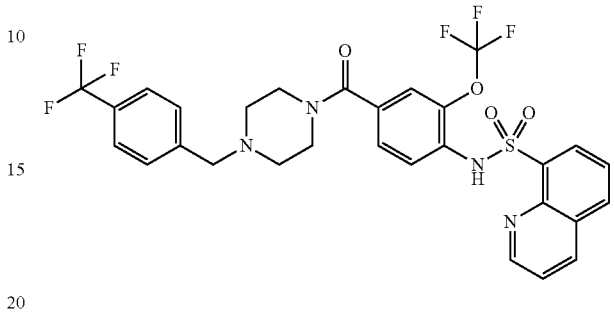

¹H NMR (400 MHz, DMSOd₆) δ: 2.2-2.5 (m, 4H), 2.8 (s, 2H), 3.2-3.6 (m, 2H), 3.8 (m, 2H), 7.2 (m, 2H), 7.5 (m, 3H), 7.8 (m, 4H), 8.3 (m, 2H), 8.6 (m, 1H), 9.0 (m, 1H), 10.0 (bs, 1H); HPLC Purity: 99.88%; Mass (M+1): 639.25.

N-(4-(4-(2-fluorobenzyl)piperazine-1-carbonyl)-2-(trifluoromethoxy)phenyl)quinoline-8-sulfonamide (Compound 335)

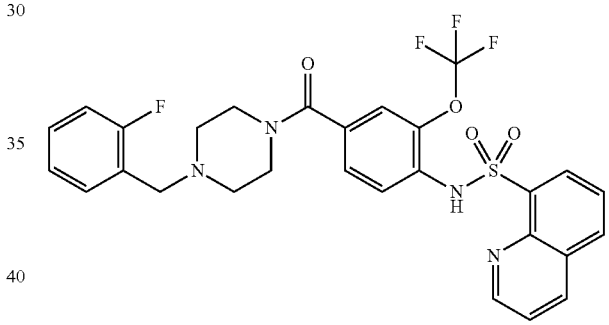

¹H NMR (400 MHz, DMSOd₆) δ: 2.2-2.5 (m, 4H), 2.8 (s, 2H), 3.2-3.6 (m, 2H), 3.8 (m, 2H), 7.2 (m, 6H), 7.5 (m, 1H), 7.8 (m, 2H), 8.3 (m, 2H), 8.6 (m, 1H), 9.0 (m, 1H), 10.0 (bs, 1H); HPLC Purity: 99.63%; Mass (M+1): 589.35.

N-(4-(4-(cyclopentylmethyl)piperazine-1-carbonyl)-2-(trifluoromethoxy)phenyl)quinoline-8-sulfonamide (Compound 336)

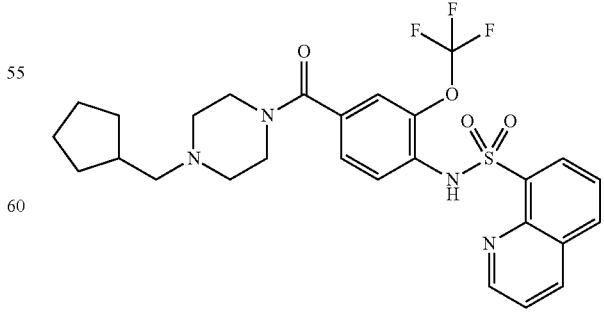

¹H NMR (400 MHz, DMSOd₆) δ: 1.0 (m, 2H), 1.5 (m, 4H), 1.6 (m, 2H), 2.0 (m, 1H), 2.3 (s, 2H), 2.2-2.5 (m, 4H), 3.2-3.6

(m, 4H), 7.2 (m, 2H), 7.5 (m, 1H), 7.7 (m, 2H), 8.3 (m, 2H), 8.6 (m, 1H), 9.0 (m, 1H), 10.0 (bs, 1H); HPLC Purity: 99.92%; Mass (M+1): 563.40.

N-(4-(4-(4-fluorobenzyl)piperazine-1-carbonyl)-2-(trifluoromethoxy)phenyl)quinoline-8-sulfonamide (Compound 337)

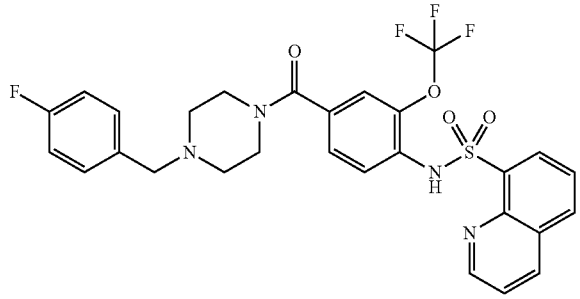 [SMILES: O=C(c1ccc(NS(=O)(=O)c2cccc3cccnc23)c(OC(F)(F)F)c1)N1CCN(Cc2ccc(F)cc2)CC1]

$^1$H NMR (400 MHz, DMSOd$_6$) δ: 2.2-2.5 (m, 4H), 3.1 (s, 2H), 3.2-3.6 (m, 4H), 7.0 (m, 2H), 7.1 (m, 3.0), 7.5 (m, 1H), 7.7 (m, 2H), 8.3 (m, 2H), 8.6 (m, 1H), 9.0 (m, 1H), 10.0 (bs, 1H); HPLC Purity: 97.29%; Mass (M+1): 589.40.

N-(4-(4-(4-chlorobenzyl)piperazine-1-carbonyl)-2-(trifluoromethoxy)phenyl)quinoline-8-sulfonamide (Compound 338)

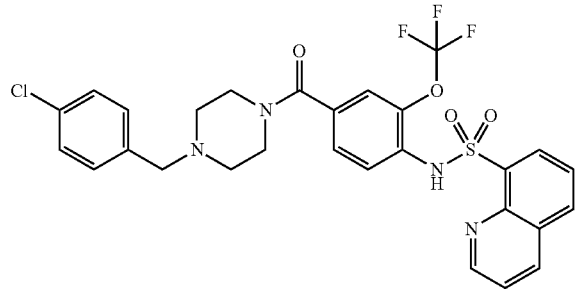 [SMILES: O=C(c1ccc(NS(=O)(=O)c2cccc3cccnc23)c(OC(F)(F)F)c1)N1CCN(Cc2ccc(Cl)cc2)CC1]

$^1$H NMR (400 MHz, DMSOd$_6$) δ: 2.2-2.5 (m, 4H), 3.1 (s, 2H), 3.2-3.6 (m, 4H), 7.3 (m, 5.0), 7.5 (m, 1H), 7.7 (m, 2H), 8.3 (m, 2H), 8.6 (m, 1H), 9.0 (m, 1H), 10.0 (bs, 1H); HPLC Purity: 99.95%; Mass (M+1): 605.35.

N-(4-(4-(4-chloro-2-fluorobenzyl)piperazine-1-carbonyl)-2-(trifluoromethoxy)phenyl)quinoline-8-sulfonamide (Compound 339)

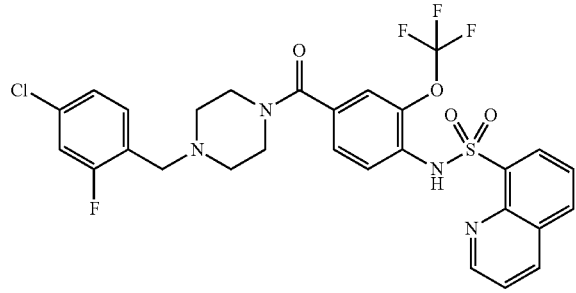 [SMILES: O=C(c1ccc(NS(=O)(=O)c2cccc3cccnc23)c(OC(F)(F)F)c1)N1CCN(Cc2ccc(Cl)cc2F)CC1]

$^1$H NMR (400 MHz, DMSOd$_6$) δ: 2.2-2.5 (m, 4H), 3.1 (s, 2H), 3.2-3.6 (m, 4H), 7.3 (m, 5.0), 7.5 (m, 1H), 7.7 (m, 2H), 8.3 (m, 2H), 8.6 (m, 1H), 9.0 (m, 1H), 10.0 (bs, 1H); HPLC Purity: 99.20%; Mass (M+1): 623.25.

N-(2-(trifluoromethoxy)-4-((4-(trifluoromethyl)pyridin-3-yl)methyl)piperazine-1-arbonyl)phenyl)quinoline-8-sulfonamide (Compound 366)

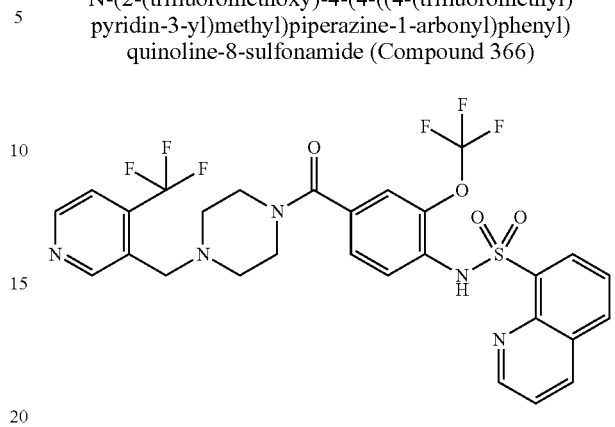

$^1$H NMR (400 MHz, DMSO-d$_6$) δ: 2.2 (s, 4H), 3.2-3.6 (m, 4H), 3.9 (m, 2H), 7.2 (m, 2H), 7.5 (m, 1H), 7.8 (m, 3H), 8.3 (m, 2H), 8.6-9.1 (m, 4H), 10.0 (s, 1H); HPLC Purity: 99.76%; Mass (M+1): 640.40.

N-(4-(4-((5-chloropyridin-3-yl)methyl)piperazine-1-carbonyl)-2-(trifluoromethoxy)phenyl)quinoline-8-sulfonamide (Compound 367)

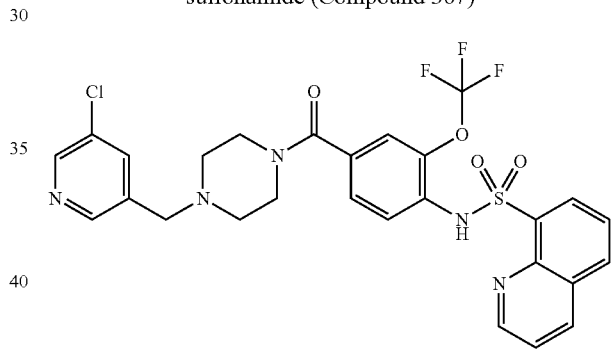

$^1$H NMR (400 MHz, DMSO-d$_6$) δ: 2.2-2.6 (m, 4H), 2.8 (s, 2H), 3.2-3.6 (m, 4H), 7.0-7.8 (m, 6H), 8.3-8.6 (m, 5H), 9.0 (m, 1H), 10.0 (s, 1H); HPLC Purity: 99.85%; Mass (M+1): 606.30.

N-(4-(4-((2-methoxypyridin-3-yl)methyl)piperazine-1-carbonyl)-2-(trifluoromethoxy)phenyl)quinoline-8-sulfonamide (Compound 368)

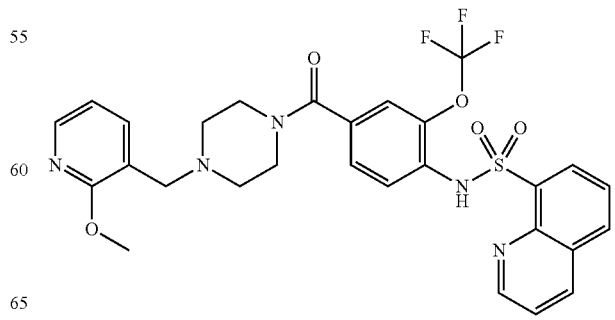

¹H NMR (400 MHz, DMSO-d₆) δ: 2.2-2.6 (m, 4H), 2.8 (s, 2H), 3.2-3.6 (m, 4H), 7.0-7.8 (m, 7H), 8.3-8.6 (m, 4H), 9.0 (m, 1H), 10.0 (s, 1H); HPLC Purity: 99.38%; Mass (M+1): 602.40.

N-(4-(4-(2,4-difluorobenzyl)piperazine-1-carbonyl)-2-(trifluoromethoxy)phenyl)quinoline-8-sulfonamide (Compound 369)

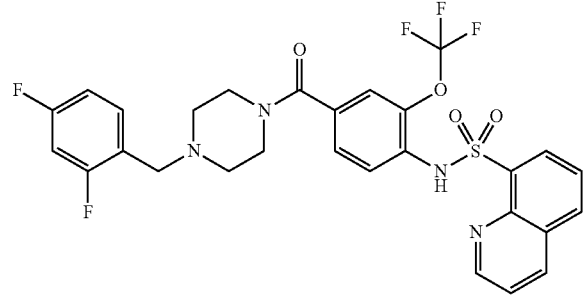 [SMILES: O=C(c1ccc(NS(=O)(=O)c2cccc3cccnc23)c(OC(F)(F)F)c1)N1CCN(Cc2ccc(F)cc2F)CC1]

¹H NMR (400 MHz, DMSO-d₆) δ: 2.2-2.4 (m, 4H), 3.5 (s, 2H), 3.2-3.4 (m, 4H), 7.0 (m, 1H), 7.2-7.3 (m, 3H), 7.4-7.6 (m, 2H), 7.8 (m, 2H), 8.3-8.6 (m, 3H), 9.0 (m, 1H), 10.0 (s, 1H); HPLC Purity: 99.17%; Mass (M+1): 607.30.

N-(4-(4-((3-methoxypyridin-2-yl)methyl)piperazine-1-carbonyl)-2-(trifluoromethoxy)phenyl)quinoline-8-sulfonamide (Compound 373)

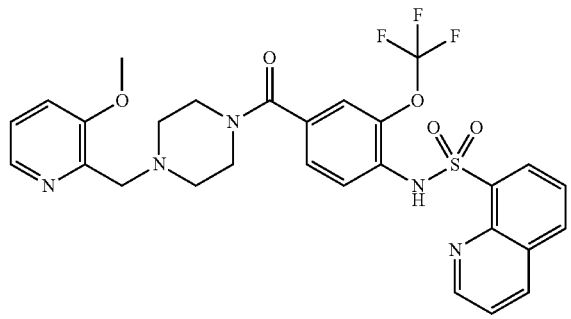 [SMILES: COc1cccnc1CN1CCN(C(=O)c2ccc(NS(=O)(=O)c3cccc4cccnc34)c(OC(F)(F)F)c2)CC1]

¹H NMR (400 MHz, DMSO-d₆) δ: 2.3-2.5 (m, 4H), 3.1-3.45 (s, 2H), 3.5-3.6 (m, 4H), 7.2-7.6 (m, 5H), 7.7 (m, 2H), 8.1 (m, 1H), 8.3 (m, 2H), 8.6 (d, 1H), 9.0 (m, 1H), 9.90 (s, 1H); HPLC Purity: 97.46%; Mass (M+1): 402.30.

N-(4-(4-(2,4-dichlorobenzyl)piperazine-1-carbonyl)-2-(trifluoromethoxy)phenyl)quinoline-8-sulfonamide (Compound 374)

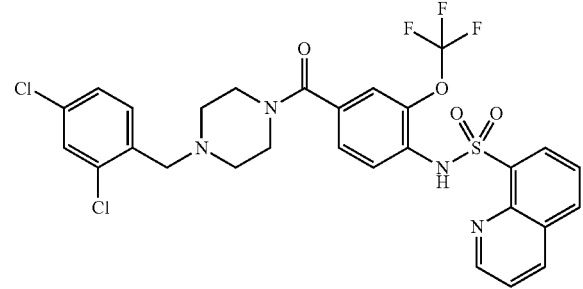 [SMILES: O=C(c1ccc(NS(=O)(=O)c2cccc3cccnc23)c(OC(F)(F)F)c1)N1CCN(Cc2ccc(Cl)cc2Cl)CC1]

¹H NMR (400 MHz, DMSO-d₆) δ: 2.3-2.5 (m, 4H), 3.1-3.40 (m, 4H), 3.5-3.6 (s, 2H), 7.2-7.8 (m, 7H), 8.3 (m, 2H), 8.6 (d, 1H), 9.0 (m, 1H), 9.90 (bs, 1H); HPLC Purity: 99.16%; Mass (M+1): 640.40.

N-(4-(4-(2,3-difluorobenzyl)piperazine-1-carbonyl)-2-(trifluoromethoxy)phenyl)quinoline-8-sulfonamide (Compound 375)

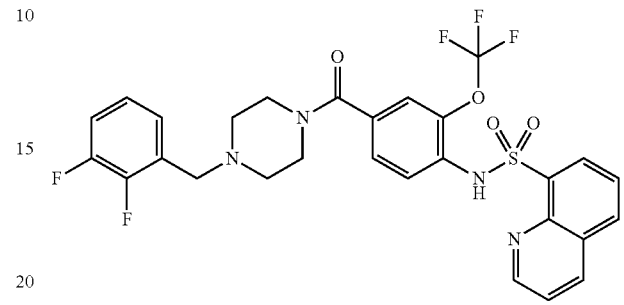

¹H NMR (400 MHz, DMSO-d₆) δ: 2.2-2.5 (m, 2H), 2.8 (s, 2H), 3.1-3.8 (m, 6H), 7.2-7.4 (m, 5H), 7.58 (m, 1H), 7.75 (m, 2H), 8.3 (m, 2H), 8.6 (d, 1H), 9.0 (m, 1H), 9.90 (bs, 1H); HPLC Purity: 98.91%; Mass (M+1): 607.30.

N-(4-(4-(3-chloro-4-fluorobenzyl)piperazine-1-carbonyl)-2-(trifluoromethoxy)phenyl)quinoline-8-sulfonamide (Compound 376)

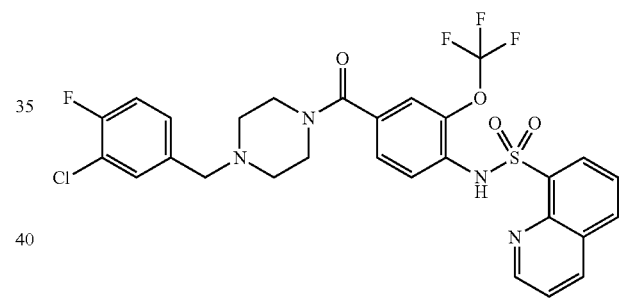

¹H NMR (400 MHz, DMSO-d₆) δ: 2.2-2.5 (m, 4H), 2.69 (s, 2H), 3.2-3.8 (m, 4H), 7.2-7.2 (m, 4H), 7.58 (m, 2H), 7.75 (m, 2H), 8.3 (m, 2H), 8.6 (m, 1H), 9.0 (m, 1H), 9.90 (bs, 1H); HPLC Purity: 95.94%; Mass (M+1): 623.25.

N-(4-(4-(3-fluorobenzyl)piperazine-1-carbonyl)-2-(trifluoromethoxy)phenyl)quinoline-8-sulfonamide (Compound 377)

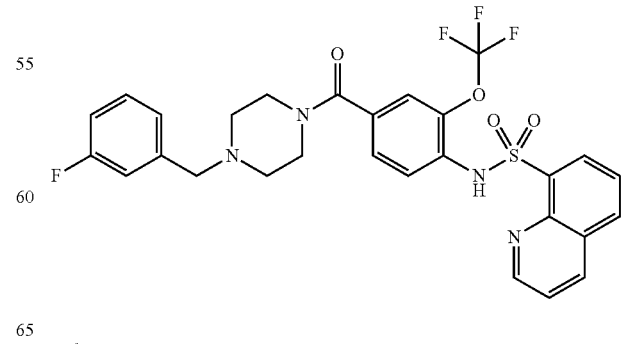

¹H NMR (400 MHz, DMSO-d₆) δ: 2.2-2.5 (m, 4H), 2.7 (s, 2H), 3.2-3.8 (m, 4H), 7.2-7.4 (m, 6H), 7.58 (m, 1H), 7.75 (m,

2H), 8.3 (m, 2H), 8.6 (m, 1H), 9.0 (m, 1H), 9.90 (bs, 1H); HPLC Purity: 98.81%; Mass (M+1): 589.35.

N-(4-(4-(3,4-difluorobenzyl)piperazine-1-carbonyl)-2-(trifluoromethoxy)phenyl)quinoline-8-sulfonamide (Compound 378)

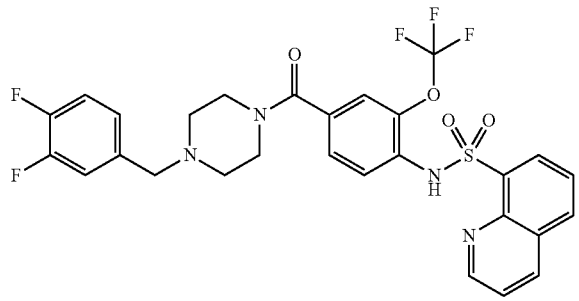 [SMILES: O=C(c1ccc(NS(=O)(=O)c2cccc3cccnc23)c(OC(F)(F)F)c1)N1CCN(Cc2ccc(F)c(F)c2)CC1]

¹H NMR (400 MHz, DMSO-d₆) δ: 2.2-2.5 (m, 4H), 2.8 (s, 2H), 3.2-3.8 (m, 4H), 7.18-7.2 (m, 2H), 7.2-7.4 (m, 3H), 7.58 (m, 1H), 7.75 (m, 2H), 8.3 (m, 2H), 8.6 (m, 1H), 9.0 (m, 1H), 10.0 (bs, 1H); HPLC Purity: 99.27%; Mass (M+1): 607.35.

N-(4-(4-(3-chlorobenzyl)piperazine-1-carbonyl)-2-(trifluoromethoxy)phenyl)quinoline-8-sulfonamide (Compound 379)

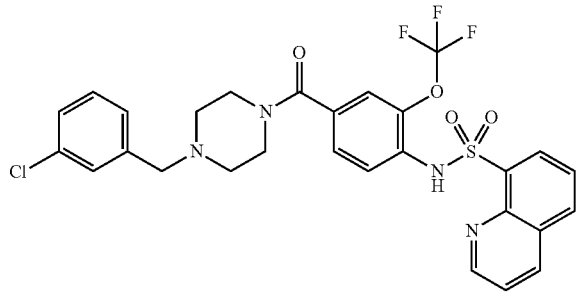 [SMILES: O=C(c1ccc(NS(=O)(=O)c2cccc3cccnc23)c(OC(F)(F)F)c1)N1CCN(Cc2cccc(Cl)c2)CC1]

¹H NMR (400 MHz, DMSO-d₆) δ: 2.2-2.5 (m, 4H), 3.2-3.8 (m, 6H), 7.18-7.4 (m, 6H), 7.58 (m, 1H), 7.75 (m, 2H), 8.3 (m, 2H), 8.6 (m, 1H), 9.0 (m, 1H), 10.0 (bs, 1H); HPLC Purity: 97.70%; Mass (M+1): 607.25

N-(4-(4-((1H-imidazol-2-yl)methyl)piperazine-1-carbonyl)-2-(trifluoromethoxy)phenyl)quinoline-8-sulfonamide (Compound 380)

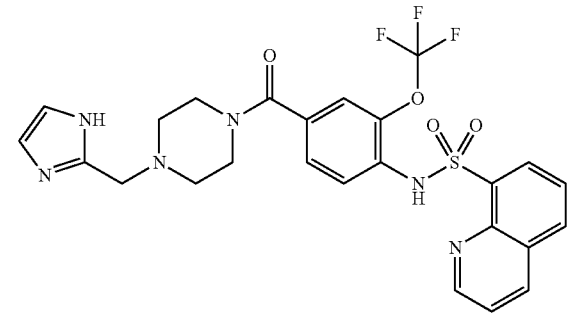 [SMILES: O=C(c1ccc(NS(=O)(=O)c2cccc3cccnc23)c(OC(F)(F)F)c1)N1CCN(Cc2ncc[nH]2)CC1]

¹H NMR (400 MHz, DMSO-d₆) δ: 2.2-2.4 (m, 4H), 2.67 (s, 2H), 3.2-3.6 (m, 4H), 6.9 (s, 1H), 7.2-7.58 (m, 2H), 7.75 (m, 4H), 8.3 (m, 2H), 8.6 (d, 1H), 9.0 (m, 1H); HPLC Purity: 98.55%; Mass (M+1): 561.10.

N-(4-(4-((1H-imidazol-4-yl)methyl)piperazine-1-carbonyl)-2-(trifluoromethoxy)phenyl)quinoline-8-sulfonamide (Compound 381)

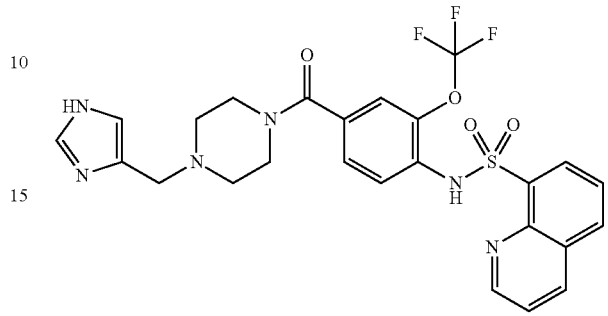

¹H NMR (400 MHz, DMSO-d₆) δ: 2.2-2.4 (m, 2H), 2.8 (s, 2H), 3.2-3.6 (m, 6H), 6.9 (s, 1H), 7.2-7.58 (m, 2H), 7.75 (m, 4H), 8.3 (m, 3H), 9.0 (m, 1H); HPLC Purity: 99.39%; Mass (M+1): 561.10.

N-(4-(4-((1H-pyrazol-5-yl)methyl)piperazine-1-carbonyl)-2-(trifluoromethoxy)phenyl)quinoline-8-sulfonamide (Compound 382)

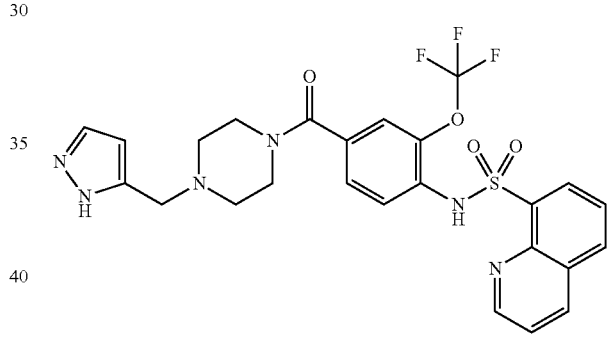

¹H NMR (400 MHz, DMSO-d₆) δ: 2.2-2.4 (m, 2H), 2.6 (s, 2H), 3.2-3.6 (m, 6H), 6.1 (s, 1H), 7.2-7.75 (m, 6H), 8.3 (m, 3H), 8.6 (m, 1H), 9.0 (m, 1H); HPLC Purity: 96.98%; Mass (M+1): 561.10.

N-(4-(4-((1H-pyrazol-5-yl)methyl)piperazine-1-carbonyl)-2-(trifluoromethoxy)phenyl)quinoline-8-sulfonamide (Compound 389)

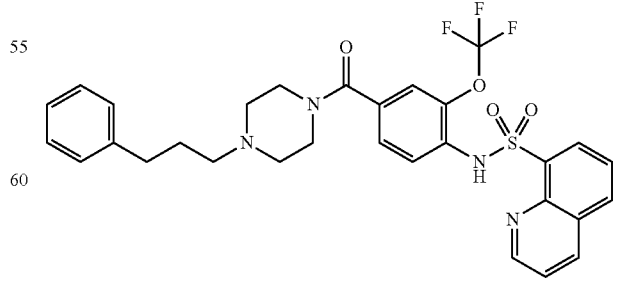

¹H NMR (400 MHz, DMSO-d₆) δ: 1.7 (m, 2H), 2.3 (m, 6H), 2.5 (m, 2H), 3.2-3.8 (m, 2H), 7.1-7.3 (m, 7H), 7.55 (d,

1H), 7.78 (m, 2H), 8.38 (m, 2H), 8.6 (d, 1H), 9.0 (m, 1H), 9.9 (bs, 1H); HPLC Purity: 89.93%; Mass (M+1): 599.35.

N-(4-(4-((5-fluoropyridin-2-yl)methyl)piperazine-1-carbonyl)-2-(trifluoromethoxy)phenyl)quinoline-8-sulfonamide (Compound 390)

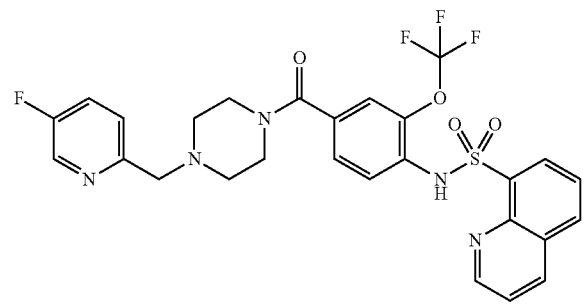 [SMILES: O=C(c1ccc(NS(=O)(=O)c2cccc3cccnc23)c(OC(F)(F)F)c1)N1CCN(Cc2ccc(F)cn2)CC1]

$^1$H NMR (400 MHz, DMSO-$d_6$) δ: 2.2-2.6 (m, 2H), 2.8 (s, 2H), 3.2-3.8 (m, 6H), 7.2-7.3 (m, 2H), 7.55 (m, 2H), 7.78 (m, 3H), 8.38 (m, 2H), 8.6 (d, 2H), 9.0 (m, 1H), 9.9 (bs, 1H); HPLC Purity: 96.54%; Mass (M+1): 590.35.

N-(4-(4-(3,5-dichlorobenzyl)piperazine-1-carbonyl)-2-(trifluoromethoxy)phenyl)quinoline-8-sulfonamide (Compound 391)

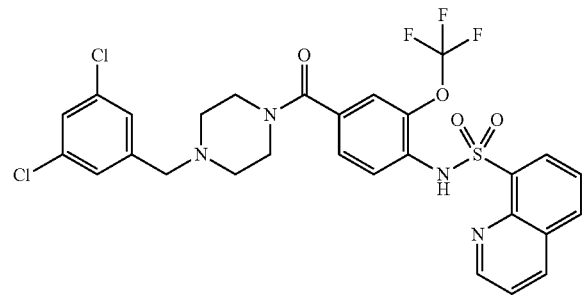 [SMILES: O=C(c1ccc(NS(=O)(=O)c2cccc3cccnc23)c(OC(F)(F)F)c1)N1CCN(Cc2cc(Cl)cc(Cl)c2)CC1]

$^1$H NMR (400 MHz, DMSO-$d_6$) δ: 2.2-2.6 (m, 2H), 2.8 (s, 2H), 3.2-3.8 (m, 6H), 7.2-7.3 (m, 4H), 7.55 (m, 2H), 7.78 (m, 2H), 8.38 (m, 2H), 8.6 (d, 1H), 9.0 (m, 1H); HPLC Purity: 96.54%; Mass (M+1): 639.15.

N-(4-(4-(2,6-dimethoxybenzyl)piperazine-1-carbonyl)-2-(trifluoromethoxy)phenyl)quinoline-8-sulfonamide (Compound 392)

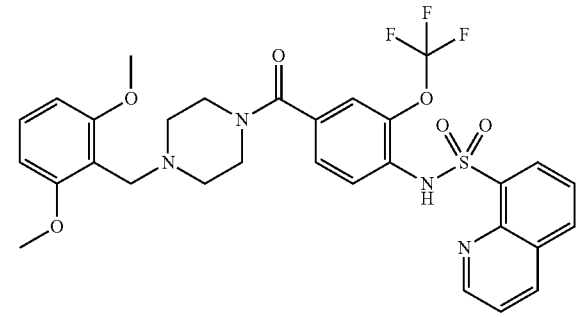 [SMILES: COc1cccc(OC)c1CN1CCN(C(=O)c2ccc(NS(=O)(=O)c3cccc4cccnc34)c(OC(F)(F)F)c2)CC1]

$^1$H NMR (400 MHz, DMSO-$d_6$) δ: 2.2-2.6 (m, 2H), 2.8 (s, 2H), 3.0-3.5 (m, 6H), 3.8 (s, 6H) 6.67 (m, 2H), 7.2-7.3 (m,

3H), 7.55 (m, 1H), 7.78 (m, 2H), 8.38 (m, 2H), 8.6 (d, 1H), 9.0 (m, 1H); HPLC Purity: 99.67%; Mass (M+1): 631.20.

(R)—N-(4-(4-(cyclopropylmethyl)-2-methylpiperazine-1-carbonyl)phenyl)quinoline-8-sulfonamide (Compound 113)

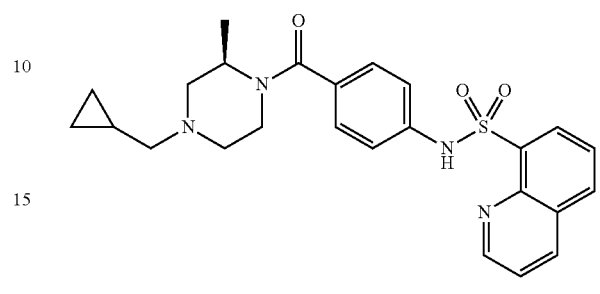

$^1$H NMR (400 MHz, DMSO-$d_6$) δ: 0.12 (m, 2H), 0.4 (m, 2H), 0.9 (m, 1H), 2.0 (s, 2H), 2.1-2.2 (d, 2H), 2.6-3.2 (m, 2H), 4.0 (bs, 1H), 7.0-7.2 (m, 4H), 7.6-7.69 (m, 2H), 8.2-8.6 (m, 3H), 9.0 (m, 1H), 10.46 (bs, 1H); HPLC Purity: 99.84%; Mass (M+1): 465.05.

(R)—N-(4-(4-(cyclopentylmethyl)-2-methylpiperazine-1-carbonyl)phenyl)quinoline-8-sulfonamide (Compound 114)

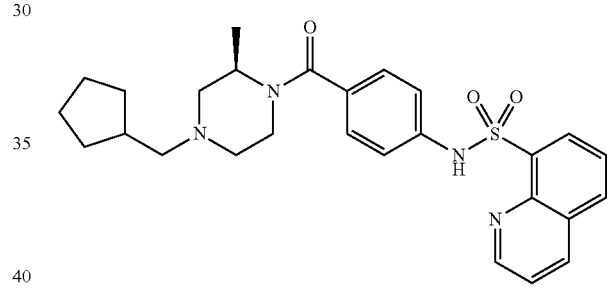

$^1$H NMR (400 MHz, DMSO-$d_6$) δ: 1.2 (m, 5H), 1.4-1.5 (m, 4H), 1.59-1.6 (m, 2H), 1.9 (s, 2H), 2.4 (d, 3H), 2.6-2.8 (m, 2H), 4.0 (bs, 1H), 7.0-7.2 (m, 4H), 7.6-7.69 (m, 2H), 8.2-8.6 (m, 3H), 9.0 (m, 1H), 10.46 (bs, 1H); HPLC Purity: 99.94%; Mass (M+1): 493.10.

N-(4-((2R)-2-methyl-4-((tetrahydrofuran-3-yl)methyl)piperazine-1-carbonyl)phenyl)quinoline-8-sulfonamide (Compound 115)

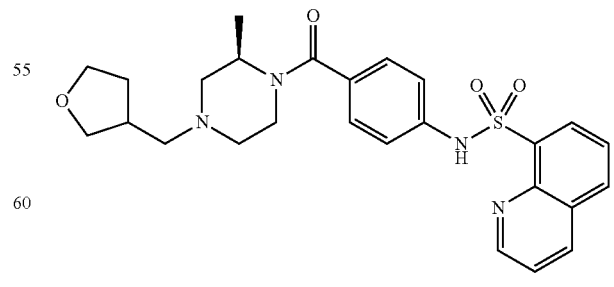

$^1$H NMR (400 MHz, DMSO-$d_6$) δ: 1.19 (m, 4H), 1.45-1.5 (m, 1H), 1.7-2.0 (m, 3H), 2.0-2.2 (m, 2H), 2.35-2.4 (m, 1H), 2.6-2.8 (m, 2H), 3.0 (bs, 1H), 3.59-3.7 (m, 4H), 7.0-7.15 (m,

4H), 7.6-7.69 (m, 2H), 8.2-8.6 (m, 3H), 9.0 (m, 1H), 10.46 (bs, 1H); HPLC Purity: 98.25%; Mass (M+1): 495.10.

(R)—N-(4-(2-methyl-4-(2,3,4-trifluorobenzyl)piperazine-1-carbonyl)phenyl)quinoline-8-sulfonamide (Compound 118)

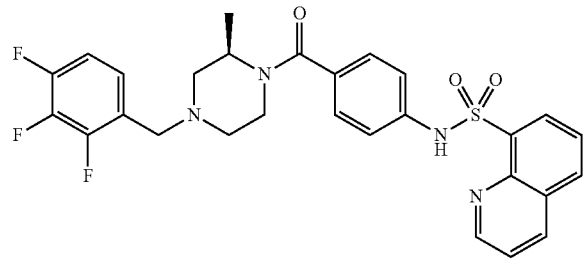

¹H NMR (400 MHz, DMSO-d₆) δ: 1.16 (s, 3H), 1.9-2.1 (m, 2H), 2.5-2.7 (m, 2H), 3.0-3.13 (m, 1H), 3.5 (s, 2H), 4.1 (m, 2H), 7.1-7.4 (m, 6H), 7.7-7.8 (m, 2H), 8.3-8.6 (m, 3H), 9.0 (s, 1H), 10.6-10.7 (bs, 1H); HPLC Purity: 99.83%; Mass (M+1) 555.35.

(R)—N-(4-(4-(3,5-difluorobenzyl)-2-methylpiperazine-1-carbonyl)phenyl)quinoline-8-sulfonamide (Compound 119)

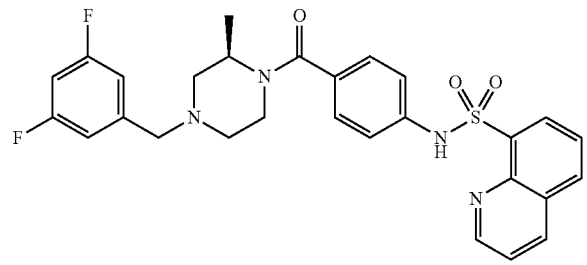

¹H NMR (400 MHz, DMSO-d₆) δ: 1.2 (d, 3H), 1.21 (q, 1H), 1.9-2.1 (m, 2H), 2.5-2.8 (m, 3H), 3.0-3.2 (s, 2H), 3.4-3.6 (m, 2H), 4.0 (bs, 1H), 7.1-7.4 (m, 7H), 7.6-7.8 (m, 2H), 8.3-8.6 (m, 3H), 9.0 (s, 1H), 10.6-10.7 (bs, 1H); HPLC Purity: 99.64%; Mass (M+1): 537.35.

(R)—N-(4-(4-(2,3-dimethoxybenzyl)-2-methylpiperazine-1-carbonyl)phenyl)quinoline-8-sulfonamide (Compound 130)

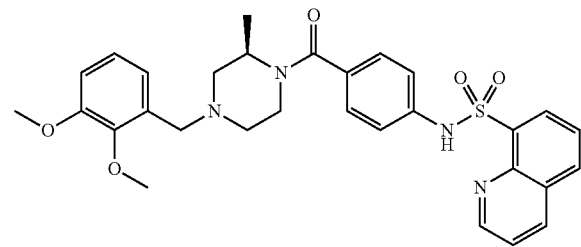 [SMILES: COc1cccc(CN2CCN(C(=O)c3ccc(NS(=O)(=O)c4cccc5cccnc45)cc3)[C@H](C)C2)c1OC]

¹H NMR (400 MHz, DMSO-d₆) δ: 1.18-1.95 (d, 3H), 2.0 (m, 1H), 1.8-2.1 (m, 2H), 2.45-2.8 (s, 2H), 2.99-3.2 (m, 1H), 3.25-3.5 (m, 4H), 3.7 (s, 3H), 3.8 (s, 3H), 6.82-7.19 (m, 7H), 7.6-7.8 (m, 2H), 8.2-8.23 (d, 1H), 8.4-8.5 (m, 2H), 9.1 (m, 1H), 10.4 (s, 1H); HPLC Purity: 98.21%; Mass (M+1): 561.40.

(R)—N-(4-(4-(4-fluorobenzyl)-2-methylpiperazine-1-carbonyl)phenyl)quinoline-8-sulfonamide (Compound 131)

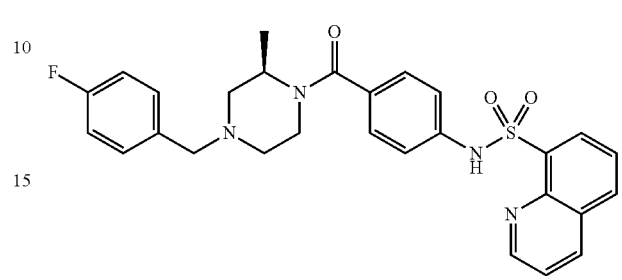

¹H NMR (400 MHz, DMSO-d₆) δ: 1.18-1.95 (d, 3H), 2.0 (m, 1H), 2.1 (s, 2H), 2.45-2.8 (m, 1H), 3.0-3.2 (m, 1H), 3.8-4.0 (m, 4H), 7.0-7.2 (m, 6H), 7.22-7.4 (m, 2H), 7.6-7.8 (d, 2H), 8.25 (d, 1H), 8.4-8.5 (m, 2H), 9.1 (m, 1H), 10.4 (s, 1H); HPLC Purity: 99.51%; Mass (M+1): 519.35.

(R)—N-(4-(2-methyl-4-(2,4,5-trifluorobenzyl)piperazine-1-carbonyl)phenyl)quinoline-8-sulfonamide (Compound 120)

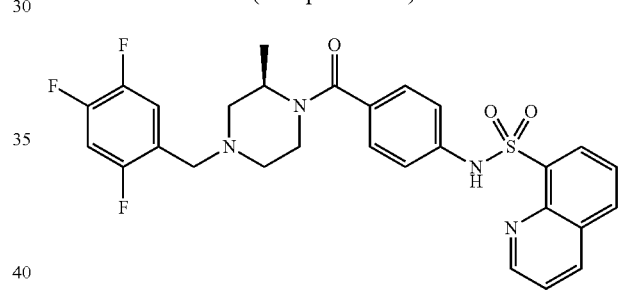

¹H NMR (400 MHz, DMSO-d₆) δ: 1.2 (d, 3H), 1.9-2.15 (m, 2H), 2.6-2.8 (m, 2H), 3.0-3.2 (m, 2H), 3.4 (s, 2H), 4.0 (bs, 1H), 7.4-7.5 (m, 2H), 7.6-7.8 (m, 2H), 8.3-8.6 (m, 3H), 9.0 (s, 1H), 10.4 (bs, 1H); HPLC Purity: 99.97%; Mass (M+1): 555.25.

(R)—N-(4-(4-(4-chloro-3-fluorobenzyl)-2-methylpiperazine-1-carbonyl)phenyl)quinoline-8-sulfonamide (Compound 125)

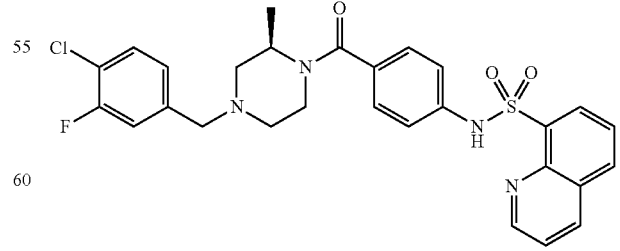

¹H NMR (400 MHz, DMSO-d₆) δ: 1.2 (d, 3H), 1.23 (m, 1H), 1.5 (m, 1H), 1.6-1.7 (m, 2H), 1.89-2.0 (s, 2H), 2.7-3.2 (m, 4H), 3.8-4.85 (m, 6H), 7.0-7.2 (m, 4H), 7.5-7.6 (m, 2H), 7.69-7.8 (m, 2H), 8.0 (d, 1H), 8.2-8.4 (m, 2H), 9.1 (m, 1H), 10.4 (s, 1H); HPLC Purity: 99.96%; Mass (M+1): 553.25.

(R)—N-(4-(2-methyl-4-(2,3,6-trifluorobenzyl)piperazine-1-carbonyl)phenyl)quinoline-8-sulfonamide (Compound 132)

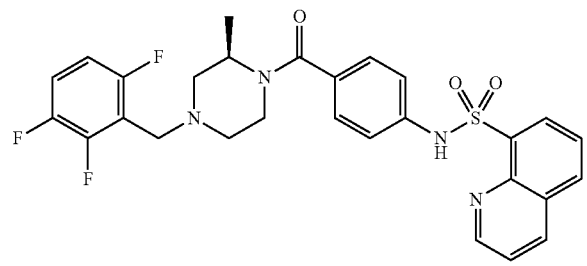 [SMILES: C[C@@H]1CN(Cc2c(F)ccc(F)c2F)CCN1C(=O)c1ccc(NS(=O)(=O)c2cccc3cccnc23)cc1]

$^1$H NMR (400 MHz, DMSO-d$_6$) δ: 1.12 (d, 3H), 1.2 (m, 1H), 1.8-2.1 (m, 2H), 2.45-2.8 (s, 2H), 2.85-3.2 (m, 1H), 3.8-4.0 (m, 3H), 7.0-7.2 (m, 5H), 7.22-7.4 (m, 1H), 7.6-7.8 (d, 2H), 8.25 (d, 1H), 8.4-8.5 (m, 2H), 9.1 (m, 1H), 10.4 (s, 1H); HPLC Purity: 99.18%; Mass (M+1): 555.25.

(S)—N-(4-(2-ethyl-4-(4-fluorobenzyl)piperazine-1-carbonyl)phenyl)quinoline-8-sulfonamide (Compound 134)

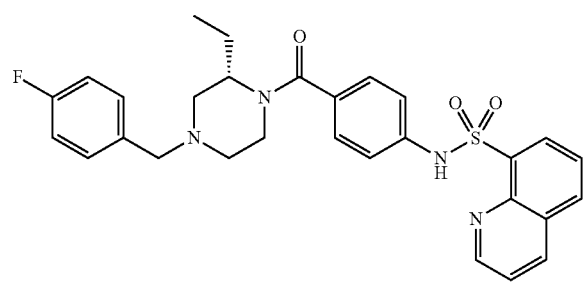 [SMILES: CC[C@H]1CN(Cc2ccc(F)cc2)CCN1C(=O)c1ccc(NS(=O)(=O)c2cccc3cccnc23)cc1]

$^1$H NMR (400 MHz, DMSO-d$_6$) δ: 0.8 (d, 2H), 1.59-2.0 (m, 2H), 2.3-2.5 (s, 2H), 3.2-3.6 (m, 4H), 7.0-7.4 (m, 8H), 7.56-7.8 (m, 2H), 8.0 (d, 1H), 8.2-8.5 (m, 2H), 9.1 (m, 1H) 10.4 (s, 1H); HPLC Purity: 99.88%; Mass (M+1): 533.1.

(S)—N-(4-(4-(3,5-difluorobenzyl)-2-ethylpiperazine-1-carbonyl)phenyl)quinoline-8-sulfonamide (Compound 136)

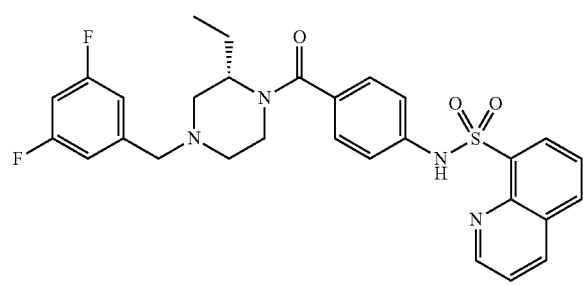 [SMILES: CC[C@H]1CN(Cc2cc(F)cc(F)c2)CCN1C(=O)c1ccc(NS(=O)(=O)c2cccc3cccnc23)cc1]

$^1$H NMR (400 MHz, DMSO-d$_6$) δ: 1.1-1.21 (d, 6H), 1.82-2.1 (m, 2H), 2.6 (m, 1H), 2.8-3.2 (s, 2H), 3.8-4.0 (m, 3H), 7.0-7.2 (m, 7H), 7.6-7.8 (d, 2H), 8.25 (d, 1H), 8.4-8.5 (m, 2H), 9.1 (m, 1H), 10.4 (s, 1H); HPLC Purity: 99.95%; Mass (M+1): 551.3.

(S)—N-(4-(2-methyl-4-(2,3,5-trifluorobenzyl)piperazine-1-carbonyl)phenyl)quinoline-8-sulfonamide (Compound 137)

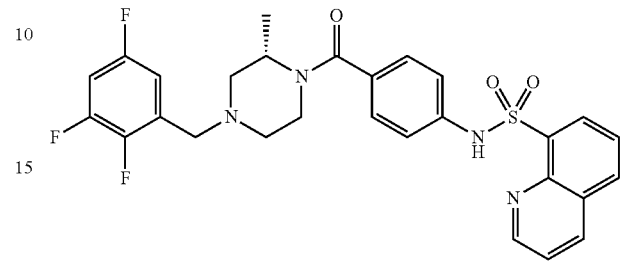

$^1$H NMR (400 MHz, DMSO-d$_6$) δ: 1.21 (d, 3H), 1.23 (m, 1H), 1.82-2.1 (m, 2H), 2.5-2.8 (s, 2H), 3.0-3.2 (m, 2H), 3.4-3.6 (m, 2H), 7.0-7.2 (m, 5H), 7.4-7.45 (m, 1H), 7.6-7.8 (m, 2H), 8.25 (d, 1H), 8.4-8.5 (m, 2H), 9.1 (m, 1H), 10.4 (s, 1H); HPLC Purity: 99.60%; Mass (M+1): 555.3.

(S)—N-(4-(4-(4-chloro-3-fluorobenzyl)-2-methylpiperazine-1-carbonyl)phenyl)quinoline-8-sulfonamide (Compound 138)

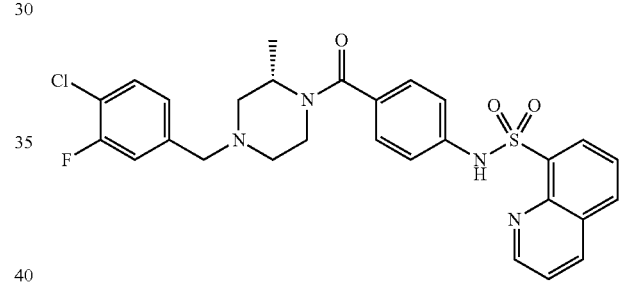

$^1$H NMR (400 MHz, DMSO-d$_6$) δ: 1.96 (d, 3H), 1.23 (m, 1H), 1.82-2.1 (m, 2H), 2.5-2.8 (s, 2H), 3.0-3.2 (m, 2H), 3.4-3.6 (m, 2H), 7.0-7.2 (m, 5H), 7.3 (d, 1H), 7.4-7.45 (m, 1H), 7.6-7.8 (m, 2H), 8.25 (d, 1H), 8.4-8.5 (m, 2H), 9.1 (m, 1H), 10.4 (s, 1H); HPLC Purity: 99.98%; Mass (M+1): 553.3.

N-(4-((2S)-2-methyl-4-((tetrahydrofuran-3-yl)methyl)piperazine-1-carbonyl)phenyl)quinoline-8-sulfonamide (Compound 139)

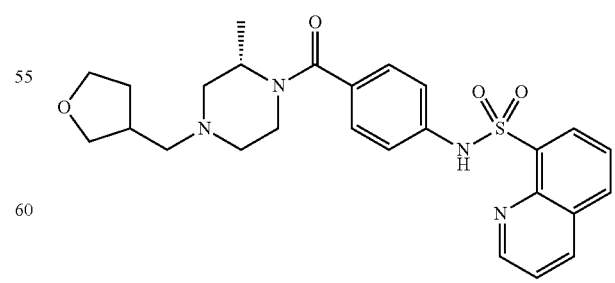

$^1$H NMR (400 MHz, DMSO-d$_6$) δ: 1.96 (d, 3H), 1.23 (m, 1H), 1.5 (m, 1H), 1.8-2.0 (m, 3H), 2.15-2.44 (s, 2H), 2.8-3.1 (m, 4H), 3.6-3.8 (m, 4H), 7.0-7.2 (m, 4H), 7.6-7.8 (m, 2H), 8.25-8.6 (m, 3H), 9.1 (m, 1H), 10.4 (s, 1H); HPLC Purity: 92.25%; Mass (M+1): 495.35.

(S)—N-(4-(4-(cyclopentylmethyl)-2-methylpiperazine-1-carbonyl)phenyl)quinoline-8-sulfonamide (Compound 140)

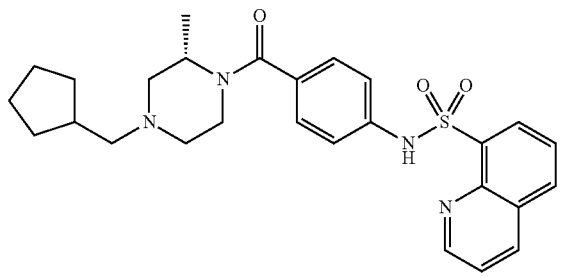 [SMILES: C[C@H]1CN(CC2CCCC2)CCN1C(=O)c1ccc(NS(=O)(=O)c2cccc3cccnc23)cc1]

$^1$H NMR (400 MHz, DMSO-$d_6$) δ: 1.2 (d, 3H), 1.23 (m, 3H), 1.45-1.6 (m, 4H), 1.61-1.8 (m, 3H), 1.86-2.2 (m, 5H), 2.6-3.2 (s, 2H), 7.0-7.2 (m, 4H), 7.6-7.8 (m, 2H), 8.25-8.6 (m, 3H), 9.1 (m, 1H), 10.4 (s, 1H); HPLC Purity: 96.35%; Mass (M+Na): 515.15.

(S)—N-(4-(2-methyl-4-(2,3,6-trifluorobenzyl)piperazine-1-carbonyl)phenyl)quinoline-8-sulfonamide (Compound 141)

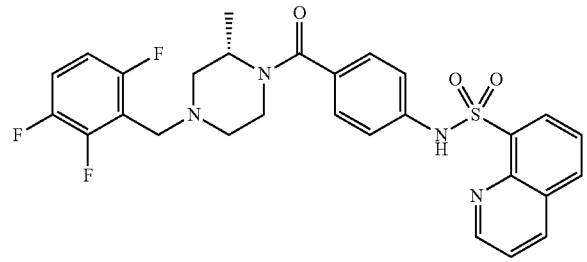

$^1$H NMR (400 MHz, DMSO-$d_6$) δ: 1.15 (d, 3H), 1.23 (m, 1H), 1.86-2.2 (m, 2H), 2.6-3.2 (s, 3H), 7.0-7.2 (m, 5H), 7.4-7.8 (m, 3H), 8.25-8.6 (m, 3H), 9.1 (m, 1H), 10.4 (s, 1H); HPLC Purity: 99.77%; Mass (M+1): 555.05.

(S)—N-(4-(4-(3,5-difluorobenzyl)-2-methylpiperazine-1-carbonyl)phenyl)quinoline-8-sulfonamide (Compound 142)

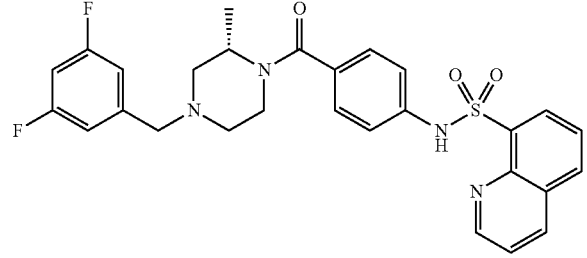 [SMILES: C[C@H]1CN(Cc2cc(F)cc(F)c2)CCN1C(=O)c1ccc(NS(=O)(=O)c2cccc3cccnc23)cc1]

$^1$H NMR (400 MHz, DMSO-$d_6$) δ: 1.2 (d, 3H), 1.86-2.2 (m, 2H), 2.6-3.2 (m, 1H), 3.0-3.2 (s, 2H), 3.3-4.0 (m, 4H), 7.0-7.2 (m, 6H), 7.6-7.8 (m, 2H), 8.25-8.6 (m, 3H), 9.1 (m, 1H), 10.4 (s, 1H); HPLC Purity: 99.80%; Mass (M+1): 537.30.

(S)—N-(4-(4-(2-fluorobenzyl)-2-methylpiperazine-1-carbonyl)phenyl)quinoline-8-sulfonamide (Compound 143)

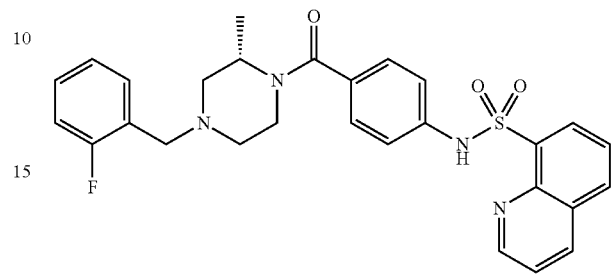

$^1$H NMR (400 MHz, DMSO-$d_6$) δ: 1.2 (d, 3H), 1.23 (m, 1H), 1.86-2.2 (m, 2H), 2.6-3.2 (s, 2H), 3.0-3.2 (m, 2H), 3.3-3.6 (m, 2H), 7.0-7.2 (m, 6H), 7.3-7.4 (m, 2H), 7.6-7.8 (m, 2H), 8.23 (d, 1H), 8.3-8.6 (m, 2H), 9.1 (m, 1H), 10.4 (s, 1H); HPLC Purity: 98.56%; Mass (M+1): 519.10.

(S)—N-(4-(4-(cyclopropylmethyl)-2-methylpiperazine-1-carbonyl)phenyl)quinoline-8-sulfonamide (Compound 144)

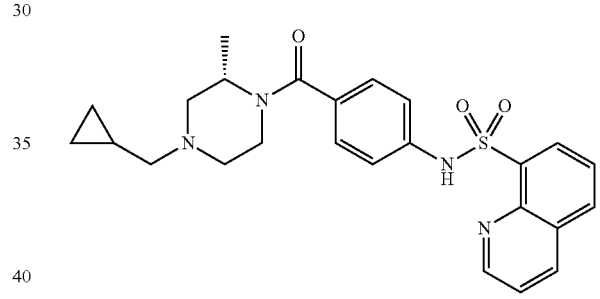

$^1$H NMR (400 MHz, DMSO-$d_6$) δ: 0.12-0.2 (d, 2H), 0.2-0.24 (m, 2H), 0.8-0.86 (m, 1H), 1.1 (d, 3H), 1.23 (m, 1H), 1.8-2.2 (m, 4H), 2.7-3.2 (s, 2H), 3.6-4.0 (m, 2H), 7.0-7.2 (m, 4H), 7.6-7.8 (m, 2H), 8.23 (d, 1H), 8.3-8.6 (m, 2H), 9.1 (m, 1H), 10.4 (s, 1H); HPLC Purity: 96.91%; Mass (M+1): 465.35.

(S)—N-(4-(2-methyl-4-(2,4,5-trifluorobenzyl)piperazine-1-carbonyl)phenyl)quinoline-8-sulfonamide (Compound 145)

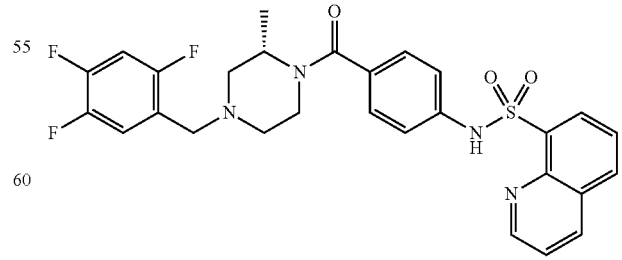

$^1$H NMR (400 MHz, DMSO-$d_6$) δ: 1.1 (d, 3H), 1.23 (m, 1H), 1.8-2.2 (s, 2H), 2.7-3.2 (m, 4H), 3.4-3.6 (m, 2H), 7.0-7.2 (m, 4H), 7.4-7.6 (m, 1H), 7.6-7.8 (m, 2H), 8.23 (d, 1H), 8.3-8.6 (m, 2H), 9.1 (m, 1H), 10.4 (s, 1H); HPLC Purity: 99.12%; Mass (M+1): 465.35.

(S)—N-(4-(4-(2,3-dimethoxybenzyl)-2-methylpiperazine-1-carbonyl)phenyl)quinoline-8-sulfonamide (Compound 146)

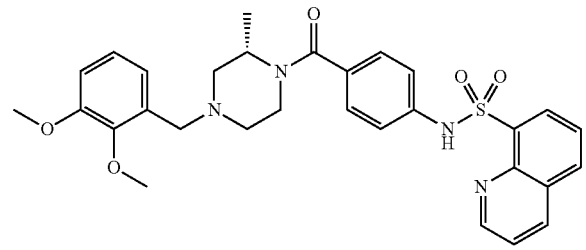 [SMILES: COc1cccc(CN2CCN(C(=O)c3ccc(NS(=O)(=O)c4cccc5cccnc45)cc3)[C@@H](C)C2)c1OC]

$^1$H NMR (400 MHz, DMSO-d$_6$) δ: 1.1 (d, 3H), 1.23 (m, 1H), 1.8-2.2 (s, 2H), 2.6-3.2 (m, 3H), 3.3-3.5 (m, 3H), 3.7 (s, 3H), 3.8 (s, 3H), 7.0-7.2 (m, 7H), 7.6-7.8 (m, 2H), 8.23 (d, 1H), 8.3-8.6 (m, 2H), 9.1 (m, 1H), 10.4 (s, 1H); HPLC Purity: 97.84%; Mass (M+1): 561.40.

N-(4-((2R)-2-methyl-4-((tetrahydrofuran-2-yl)methyl)piperazine-1-carbonyl)phenyl)quinoline-8-sulfonamide (Compound 147)

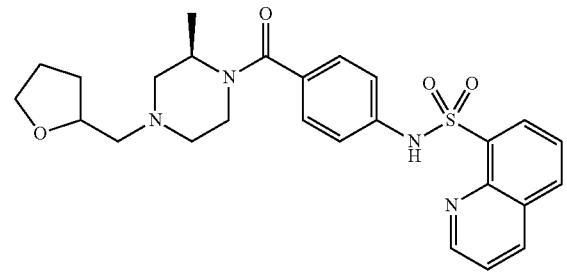

$^1$H NMR (400 MHz, DMSO-d$_6$) δ: 1.1 (d, 3H), 1.5 (m, 1H), 1.76-2.2 (m, 5H), 2.3-2.4 (s, 2H), 2.8-3.2 (m, 4H), 3.6-4.0 (m, 4H), 7.0-7.2 (m, 4H), 7.6-7.8 (m, 2H), 8.23 (d, 1H), 8.3-8.6 (m, 2H), 9.1 (m, 1H), 10.4 (s, 1H); HPLC Purity: 97.78%; Mass (M+1): 495.40.

N-(4-(4-(2-methoxybenzyl)-2-methylpiperazine-1-carbonyl)phenyl)quinoline-8-sulfonamide (Compound 224)

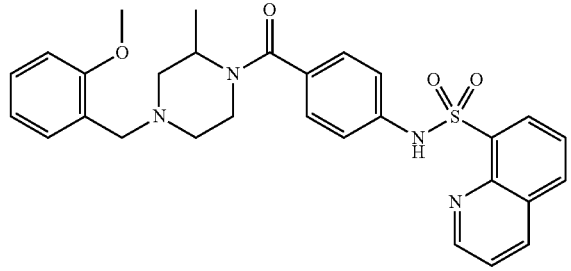 [SMILES: COc1ccccc1CN1CCN(C(=O)c2ccc(NS(=O)(=O)c3cccc4cccnc34)cc2)C(C)C1]

$^1$H NMR (400 MHz, DMSO-d$_6$) δ: 1.1 (d, 3H), 2.5 (m, 1H), 3.0-3.4 (m, 4H), 3.7 (s, 3H), 3.8-4.0 (s, 2H), 6.8-7.2 (m, 8H), 7.6-7.8 (m, 2H), 8.23 (d, 1H), 8.3-8.6 (m, 2H), 9.1 (m, 1H), 10.4 (s, 1H); HPLC Purity: 99.69%; Mass (M+1): 517.35

N-(4-(4-(2-methoxybenzyl)-2-methylpiperazine-1-carbonyl)phenyl)quinoline-8-sulfonamide (Compound 148)

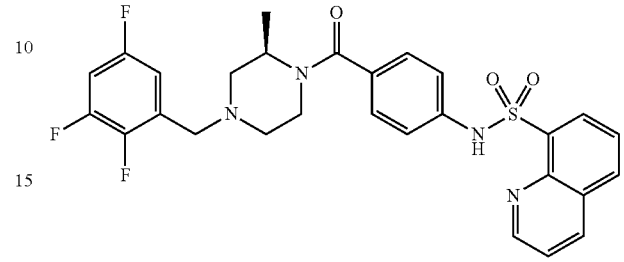

$^1$H NMR (400 MHz, DMSO-d$_6$) δ: 1.1 (d, 3H), 1.8-2.2 (s, 2H), 2.6-3.2 (m, 3H), 3.8-4.0 (m, 4H), 7.0-7.2 (m, 5H), 7.36-7.4 (m, 1H), 7.6-7.8 (m, 2H), 8.23 (d, 1H), 8.3-8.6 (m, 2H), 9.1 (m, 1H), 10.4 (s, 1H); HPLC Purity: 99.69%; Mass (M+1): 555.0.

(R)—N-(4-(2-methyl-4-(3,4,5-trifluorobenzyl)piperazine-1-carbonyl)phenyl)quinoline-8-sulfonamide (Compound 149)

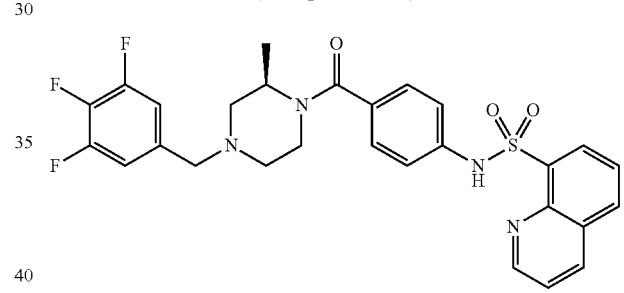

$^1$H NMR (400 MHz, DMSO-d$_6$) δ: 1.2 (d, 3H), 1.8-2.2 (m, 2H), 2.6-2.8 (s, 2H), 3.0-3.2 (m, 1H), 3.6-3.86 (m, 4H), 7.0-7.3 (m, 6H), 7.6-7.8 (m, 2H), 8.23 (d, 1H), 8.3-8.6 (m, 2H), 9.1 (m, 1H), 10.4 (s, 1H); HPLC Purity: 99.97%; Mass (M+1): 554.95.

(R)—N-(4-(4-(2-fluorobenzyl)-2-methylpiperazine-1-carbonyl)phenyl)quinoline-8-sulfonamide (Compound 150)

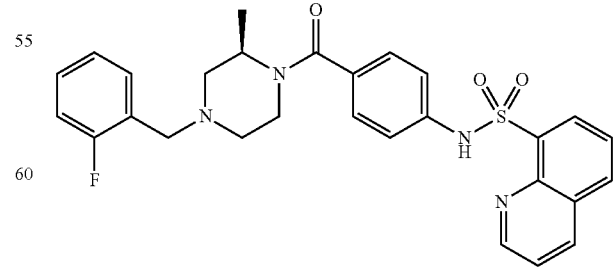

$^1$H NMR (400 MHz, DMSO-d$_6$) δ: 1.2 (d, 3H), 1.8-2.2 (m, 2H), 2.6-2.85 (s, 2H), 3.0-3.2 (m, 1H), 3.8-4.0 (m, 4H), 7.0-

7.5 (m, 8H), 7.7-7.8 (m, 2H), 8.23 (d, 1H), 8.3-8.6 (m, 2H), 9.1 (m, 1H), 10.4 (s, 1H); HPLC Purity: 99.67%; Mass (M+1): 519.05.

(R)—N-(4-(4-(cyclohexylmethyl)-2-methylpiperazine-1-carbonyl)phenyl)quinoline-8-sulfonamide (Compound 151)

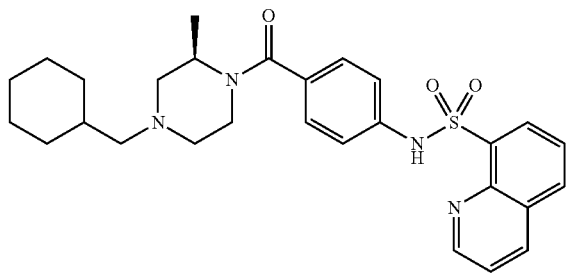 [SMILES: C[C@@H]1CN(CC2CCCCC2)CCN1C(=O)c1ccc(NS(=O)(=O)c2cccc3cccnc23)cc1]

$^1$H NMR (400 MHz, CDCl$_3$) δ: 0.8-0.9 (d, 3H), 1.0-1.4 (m, 8H), 1.5-1.6 (m, 2H), 1.61-1.8 (m, 9H), 2.0-2.1 (4H), 2.6-2.85 (s, 2H), 3.0-3.2 (m, 1H), 4.0-4.1 (m, 1H), 7.0-7.4 (m, 4H), 7.6-7.7 (m, 2H), 8.0 (d, 1H), 8.3-8.6 (m, 2H), 9.1 (m, 1H), 10.4 (s, 1H); HPLC Purity: 99.85%; Mass (M+1): 507.40.

(S)—N-(4-(4-(4-fluorobenzyl)-2-methylpiperazine-1-carbonyl)phenyl)quinoline-8-sulfonamide (Compound 152)

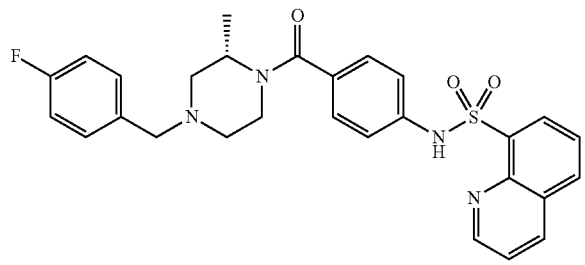 [SMILES: C[C@H]1CN(Cc2ccc(F)cc2)CCN1C(=O)c1ccc(NS(=O)(=O)c2cccc3cccnc23)cc1]

$^1$H NMR (400 MHz, DMSO-d$_6$) δ: 1.2 (d, 3H), 1.21-1.3 (m, 1H), 1.8-2.1 (m, 2H), 2.6-2.85 (s, 2H), 3.0-3.2 (m, 1H), 3.4-3.5 (m, 3H), 7.0-7.4 (m, 8H), 7.6-7.7 (m, 2H), 8.0 (d, 1H), 8.3-8.6 (m, 2H), 9.1 (m, 1H), 10.4 (s, 1H); HPLC Purity: 97.31%; Mass (M+1): 519.35.

(S)—N-(4-(4-(cyclohexylmethyl)-2-methylpiperazine-1-carbonyl)phenyl)quinoline-8-sulfonamide (Compound 153)

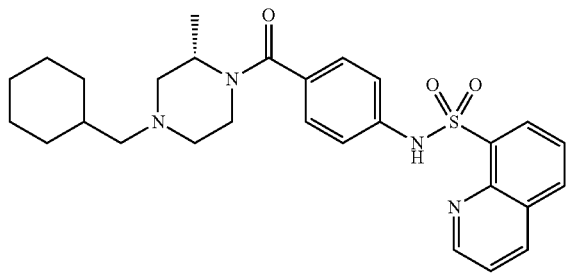 [SMILES: C[C@H]1CN(CC2CCCCC2)CCN1C(=O)c1ccc(NS(=O)(=O)c2cccc3cccnc23)cc1]

$^1$H NMR (400 MHz, DMSO-d$_6$) δ: 0.8-0.9 (m, 2H), 1.21-1.3 (m, 6H), 1.4-1.42 (m, 1H), 1.6-1.8 (m, 6H), 1.96-2.12 (m, 3H), 2.5-2.6 (s, 2H), 3.6-3.8 (m, 2H), 7.0-7.2 (m, 4H), 7.6-7.7 (m, 2H), 8.0 (d, 1H), 8.3-8.6 (m, 2H), 9.1 (m, 1H), 10.4 (s, 1H); HPLC Purity: 99.20%; Mass (M+1): 507.15.

(S)—N-(4-(2-methyl-4-(2,3,4-trifluorobenzyl)piperazine-1-carbonyl)phenyl)quinoline-8-sulfonamide (Compound 154)

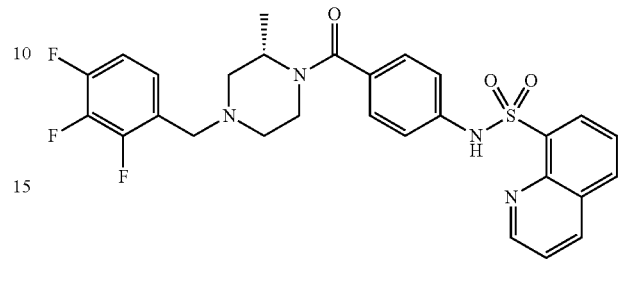

$^1$H NMR (400 MHz, DMSO-d$_6$) δ: 1.21-1.3 (d, 3H), 1.8-2.1 (m, 2H), 2.5-2.8 (s, 2H), 3.0-3.4 (m, 1H), 3.8-4.0 (m, 4H), 7.0-7.2 (m, 6H), 7.6-7.7 (m, 2H), 8.0 (d, 1H), 8.3-8.6 (m, 2H), 9.1 (m, 1H), 10.4 (s, 1H); HPLC Purity: 99.99%; Mass (M+1): 555.35.

(S)—N-(4-(2-methyl-4-(3,4,5-trifluorobenzyl)piperazine-1-carbonyl)phenyl)quinoline-8-sulfonamide (Compound 155)

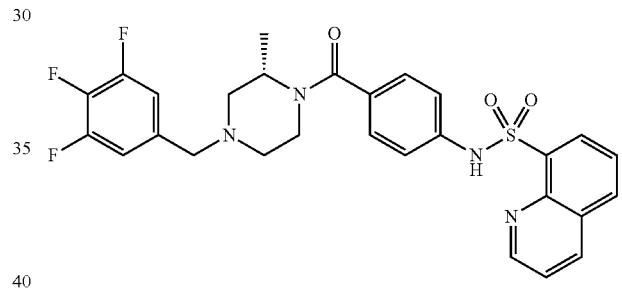

$^1$H NMR (400 MHz, DMSO-d$_6$) δ: 1.21-1.3 (d, 3H), 1.8-2.1 (m, 3H), 2.6-2.8 (s, 2H), 3.0-3.4 (m, 1H), 3.4-3.5 (m, 2H), 3.8-4.0 (m, 1H), 7.0-7.2 (m, 6H), 7.6-7.7 (m, 2H), 8.0 (d, 1H), 8.3-8.6 (m, 2H), 9.1 (m, 1H), 10.4 (s, 1H); HPLC Purity: 99.65%; Mass (M+1): 575.05.

N-(4-((2S)-2-methyl-4-((tetrahydro-2H-pyran-2-yl)methyl)piperazine-1-carbonyl)phenyl)quinoline-8-sulfonamide (Compound 156)

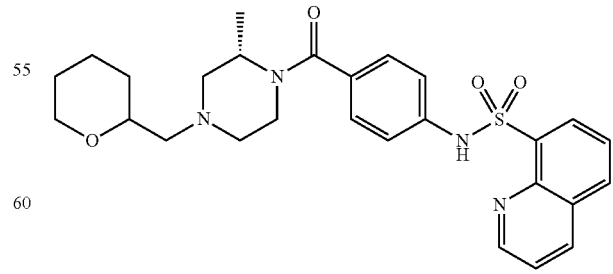

$^1$H NMR (400 MHz, DMSO-d$_6$) δ: 1.21 (d, 3H), 1.23-1.3 (m, 1H), 1.31-1.4 (m, 3H), 1.59-1.6 (m, 2H), 1.8-2.1 (m, 4H), 2.1-2.2 (s, 2H), 2.6-2.8 (m, 2H), 3.0-3.4 (m, 3H), 3.8-4.0 (m,

1H), 7.0-7.2 (m, 4H), 7.6-7.7 (m, 2H), 8.0 (d, 1H), 8.3-8.6 (m, 2H), 9.1 (m, 1H), 10.4 (s, 1H); HPLC Purity: 94.56%; Mass (M+1): 509.05.

N-(4-((2R)-2-methyl-4-((tetrahydro-2H-pyran-2-yl) methyl)piperazine-1-carbonyl)phenyl)quinoline-8-sulfonamide (Compound 163)

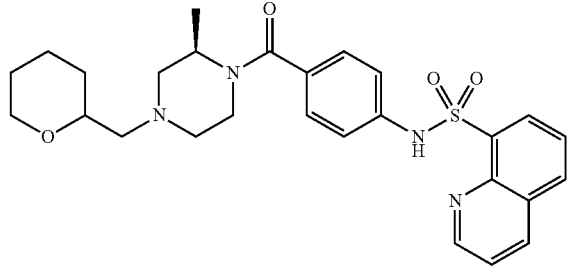 [SMILES: C[C@@H]1CN(CC2CCCCO2)CCN1C(=O)c1ccc(NS(=O)(=O)c2cccc3cccnc23)cc1]

¹H NMR (400 MHz, DMSO-d₆) δ: 1.0-1.4 (m, 7H), 1.56-1.6 (m, 2H), 1.6-1.65 (m, 2H), 2.0-2.4 (s, 2H), 2.6-3.4 (m, 5H), 3.8-3.9 (m, 3H), 7.0-7.4 (m, 4H), 7.6-7.7 (m, 2H), 8.0 (d, 1H), 8.3-8.6 (m, 2H), 9.1 (m, 1H), 10.4 (s, 1H); HPLC Purity: 97.32%; Mass (M+1): 509.15.

(S)—N-(4-(2-methyl-4-(2,4,6-trifluorobenzyl)piperazine-1-carbonyl)phenyl)quinoline-8-sulfonamide (Compound 164)

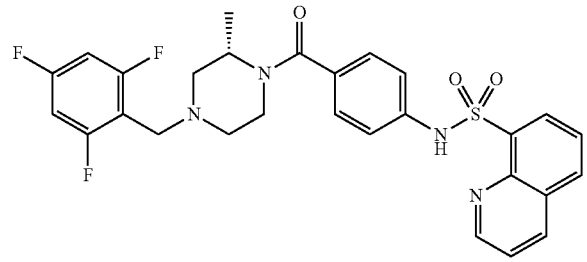 [SMILES: C[C@H]1CN(Cc2c(F)cc(F)cc2F)CCN1C(=O)c1ccc(NS(=O)(=O)c2cccc3cccnc23)cc1]

¹H NMR (400 MHz, DMSO-d₆) δ: 1.2 (d, 3H), 1.8-2.1 (m, 2H), 2.6-2.7 (s, 2H), 2.9-3.2 (m, 1H), 3.6-4.0 (m, 4H), 7.0-7.2 (m, 6H), 7.6-7.7 (m, 2H), 8.0 (d, 1H), 8.3-8.6 (m, 2H), 9.1 (m, 1H), 10.6 (s, 1H); HPLC Purity: 96.52%; Mass (M+1): 544.7.

(S)—N-(3-chloro-4-(4-(4-fluorobenzyl)-2-methylpiperazine-1-carbonyl)phenyl)quinoline-8-sulfonamide (Compound 184)

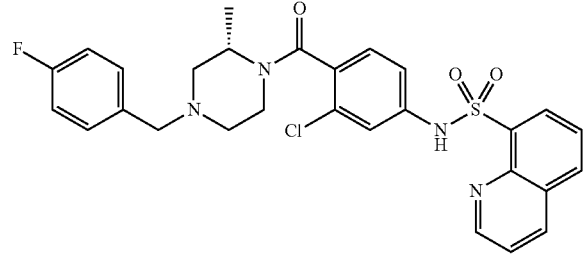 [SMILES: C[C@H]1CN(Cc2ccc(F)cc2)CCN1C(=O)c1ccc(NS(=O)(=O)c2cccc3cccnc23)cc1Cl]

¹H NMR (400 MHz, CDCl₃) δ: 1.0 (d, 3H), 2.0 (m, 1H), 2.8-3.2 (m, 4H), 3.5-3.6 (m, 2H), 4.2 (m, 1H), 7.0-7.4 (m, 6H), 7.6-7.8 (m, 2H), 8.0 (d, 1H), 8.3-8.6 (m, 2H), 9.1 (m, 1H); HPLC Purity: 99.81%; Mass (M+1): 553.2.

(S)—N-(3-chloro-4-(4-(4-chloro-3-fluorobenzyl)-2-methylpiperazine-1-carbonyl)phenyl)quinoline-8-sulfonamide (Compound 185)

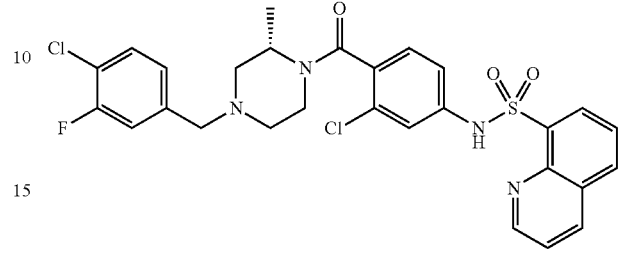

¹H NMR (400 MHz, CDCl₃) δ: 1.0 (d, 3H), 1.99 (m, 1H), 1.8-2.2 (m, 2H), 2.6-3.6 (m, 4H), 4.2 (m, 1H), 4.6 (s, 1H), 7.0-7.6 (m, 6H), 7.61-7.8 (m, 2H), 8.0 (d, 1H), 8.3-8.6 (m, 2H), 9.1 (m, 1H), 10.6 (s, 1H); HPLC Purity: 99.85%; Mass (M+1): 587.1.

(S)—N-(3-chloro-4-(4-(cyclopentylmethyl)-2-methylpiperazine-1-carbonyl)phenyl)quinoline-8-sulfonamide (Compound 186)

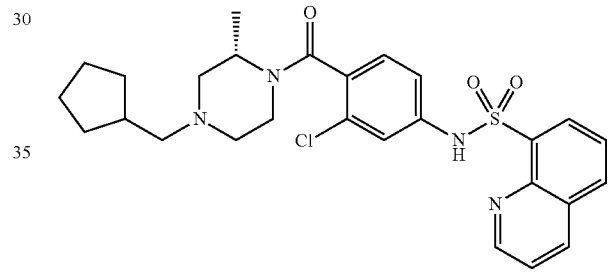

¹H NMR (400 MHz, DMSO-d₆) δ: 0.8 (m, 1H), 1.2-1.4 (m, 7H), 1.5-1.6 (m, 6H), 1.8-2.0 (m, 3H), 2.0-2.2 (m, 2H), 4.2 (m, 1H), 4.6 (m, 1H), 7.0-7.2 (m, 3H), 7.61-7.8 (m, 2H), 8.0 (d, 1H), 8.3-8.6 (m, 2H), 9.1 (m, 1H), 10.6 (s, 1H); HPLC Purity: 99.85%; Mass (M+1): 527.6.

N-(3-chloro-4-((2S)-2-methyl-4-((tetrahydrofuran-3-yl)methyl)piperazine-1-carbonyl)phenyl)quinoline-8-sulfonamide (Compound 187)

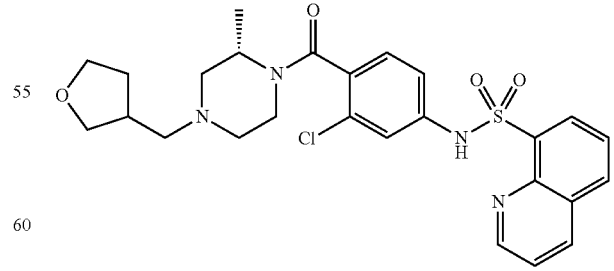

¹H NMR (400 MHz, DMSO-d₆) δ: 0.8 (m, 1H), 1.0-1.4 (m, 4H), 1.5-1.6 (m, 1H), 1.8-2.0 (m, 2H), 2.0-2.4 (m, 3H), 2.8-3.0 (m, 2H), 3.3-3.4 (m, 1H), 3.6-3.7 (m, 3H), 4.2 (m, 1H), 4.6 (m, 1H), 7.0-7.2 (m, 3H), 7.61-7.8 (m, 2H), 8.0 (d, 1H), 8.3-8.6 (m, 2H), 9.1 (m, 1H), 10.6 (s, 1H); HPLC Purity: 94.53%; Mass (M+1): 529.55.

(S)—N-(3-chloro-4-(2-methyl-4-(2,4,6-trifluorobenzyl)piperazine-1-carbonyl)phenyl)quinoline-8-sulfonamide (Compound 188)

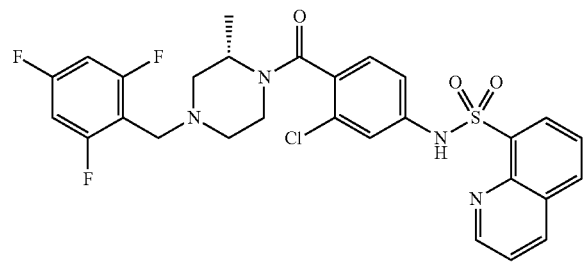 [SMILES: C[C@H]1CN(Cc2c(F)cc(F)cc2F)CCN1C(=O)c1ccc(NS(=O)(=O)c2cccc3cccnc23)cc1Cl]

¹H NMR (400 MHz, DMSO-d$_6$) δ: 0.8 (m, 1H), 1.0-1.3 (m, 4H), 1.8-2.0 (m, 2H), 2.6-2.8 (m, 1H), 3.4 (s, 2H), 4.0-4.1 (m, 1H), 4.55-4.6 (m, 1H), 7.0-7.2 (m, 5H), 7.61-7.8 (m, 2H), 8.0 (d, 1H), 8.3-8.6 (m, 2H), 9.1 (m, 1H), 10.6 (s, 1H); HPLC Purity: 99.17%; Mass (M+1): 589.55.

N-(4-((2R)-2-methyl-4-(1-(2,3,4-trifluorophenyl)ethyl)piperazine-1-carbonyl)phenyl)quinoline-8-sulfonamide (Compound 189)

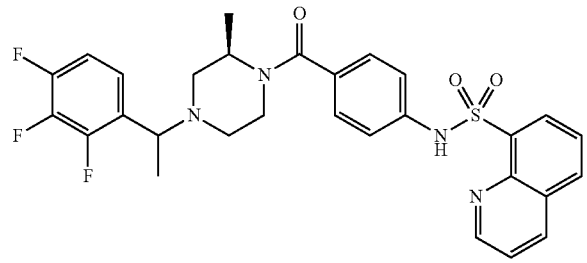 [SMILES: CC(c1ccc(F)c(F)c1F)N1CCN(C(=O)c2ccc(NS(=O)(=O)c3cccc4cccnc34)cc2)[C@H](C)C1]

¹H NMR (400 MHz, DMSO-d$_6$) δ: 1.3 (d, 6H), 1.8-2.0 (m, 2H), 2.6-3.0 (m, 4H), 3.6-3.8 (m, 2H), 7.0-7.4 (m, 6H), 7.61-7.8 (m, 2H), 8.0 (d, 1H), 8.3-8.6 (m, 2H), 9.1 (m, 1H), 10.6 (s, 1H); HPLC Purity: 97.92%; Mass (M+1): 569.3.

N-(4-((2R)-2-methyl-4-(1-(2,3,6-trifluorophenyl)ethyl)piperazine-1-carbonyl)phenyl)quinoline-8-sulfonamide (Compound 190)

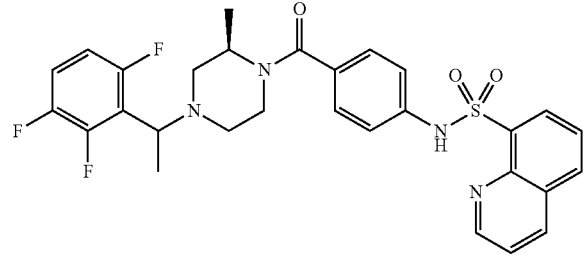 [SMILES: CC(c1c(F)ccc(F)c1F)N1CCN(C(=O)c2ccc(NS(=O)(=O)c3cccc4cccnc34)cc2)[C@H](C)C1]

¹H NMR (400 MHz, DMSO-d6) δ: 1.3 (d, 3H), 1.4 (m, 2H), 1.8-2.0 (m, 2H), 2.6-2.6 (m, 2H), 3.0-3.4 (s, 2H), 4.0 (m, 1H), 7.0-7.2 (m, 5H), 7.3-7.4 (m, 1H), 7.61-7.8 (m, 3H), 8.0 (d, 1H), 8.3-8.6 (m, 2H), 9.1 (m, 1H), 10.6 (s, 1H); HPLC Purity: 99.36%; Mass (M+1): 569.3.

N-(4-((2R)-4-(1-(2-chloro-4-fluorophenyl)ethyl)-2-methylpiperazine-1-carbonyl)phenyl)quinoline-8-sulfonamide (Compound 191)

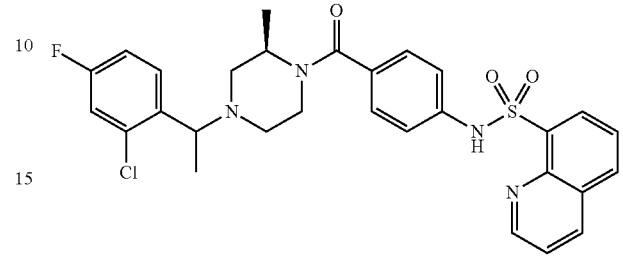

¹H NMR (400 MHz, DMSO-d$_6$) δ: 1.3 (d, 6H), 1.8-2.0 (m, 3H), 2.2-2.4 (m, 1H), 2.8-3.2 (m, 3H), 3.6-4.8 (m, 1H), 7.0-7.6 (m, 6H), 7.61-7.8 (m, 3H), 8.0 (d, 1H), 8.3-8.6 (m, 2H), 9.1 (m, 1H), 10.6 (s, 1H); HPLC Purity: 94.03%; Mass (M+1): 567.5.

N-(4-((2S)-2-methyl-4-(1-(2,3,6-trifluorophenyl)ethyl)piperazine-1-carbonyl)phenyl)quinoline-8-sulfonamide (Compound 192)

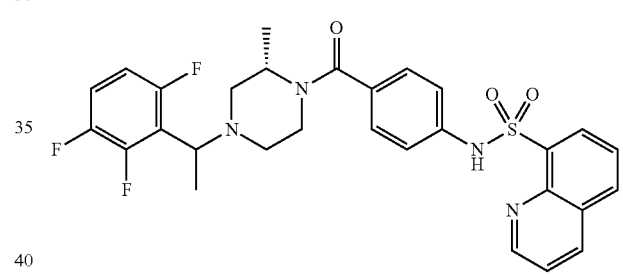

¹H NMR (400 MHz, DMSO-d$_6$) δ: 1.3 (d, 6H), 1.4-1.6 (m, 3H), 1.8-2.2 (m, 2H), 2.8-3.2 (m, 4H), 3.6-4.8 (m, 2H), 7.0-7.5 (m, 6H), 7.61-7.8 (m, 2H), 8.0 (d, 1H), 8.3-8.6 (m, 2H), 9.1 (m, 1H), 10.4 (s, 1H); HPLC Purity: 98.39%; Mass (M+1): 569.55.

(S)—N-(4-(4-(cyclobutylmethyl)-2-methylpiperazine-1-carbonyl)phenyl)quinoline-8-sulfonamide (Compound 207)

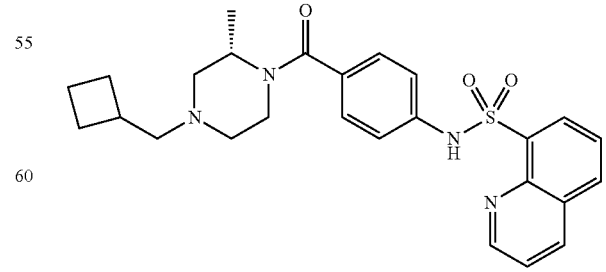

¹H NMR (400 MHz, DMSO-d$_6$) δ: 1.2 (d, 3H), 1.5-1.6 (m, 2H), 1.8-1.85 (m, 3H), 2.0-2.1 (m, 3H), 2.2-2.4 (m, 4H), 2.6-2.99 (m, 4H), 7.0-7.2 (m, 4H), 7.6-7.8 (m, 2H), 8.0-8.6 (m, 3H), 9.1-9.2 (m, 1H), 10.5 (s, 1H); HPLC Purity: 99.03%; Mass (M+1): 479.3.

N-(4-((2S)-2-methyl-4-((tetrahydrofuran-2-yl)methyl)piperazine-1-carbonyl)phenyl)quinoline-8-sulfonamide (Compound 225)

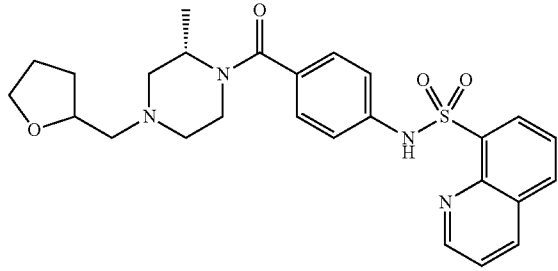 [SMILES: C[C@H]1CN(CC2CCCO2)CCN1C(=O)c1ccc(NS(=O)(=O)c2cccc3cccnc23)cc1]

$^1$H NMR (400 MHz, DMSO-$d_6$) δ: 1.0-1.6 (m, 6H), 1.8-2.4 (m, 6H), 2.6-3.0 (m, 3H), 3.4-3.8 (m, 4H), 7.0-7.2 (m, 4H), 7.5-7.8 (m, 2H), 8.0-8.4 (m, 3H), 9.1-9.2 (m, 1H), 10.4 (s, 1H); HPLC Purity: 99.37%; Mass (M+1): 495.10

N-(4-((2S)-2R-methyl-4-((tetrahydrofuran-2-yl)methyl)piperazine-1-carbonyl)phenyl)quinoline-8-sulfonamide (Compound 211)

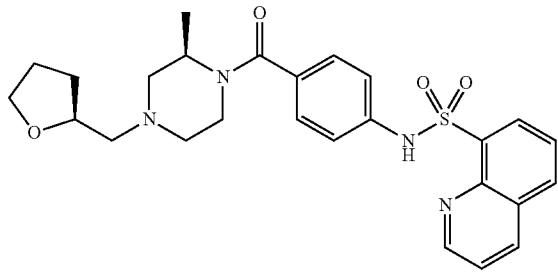 [SMILES: C[C@@H]1CN(C[C@@H]2CCCO2)CCN1C(=O)c1ccc(NS(=O)(=O)c2cccc3cccnc23)cc1]

$^1$H NMR (400 MHz, DMSO-$d_6$) δ: 1.0 (d, 3H), 1.2-1.8 (m, 6H), 2.0-2.4 (m, 3H), 2.6-3.0 (m, 3H), 3.4-4.0 (m, 4H), 7.0-7.2 (m, 4H), 7.5-7.8 (m, 2H), 8.0-8.4 (m, 3H), 9.1-9.2 (m, 1H), 10.4 (s, 1H); HPLC Purity: 96.80%; Mass (M+1): 495.20.

N-(4-((R)-2-methyl-4-(((R)-tetrahydrofuran-2-yl)methyl)piperazine-1-carbonyl)phenyl)quinoline-8-sulfonamide (Compound 212)

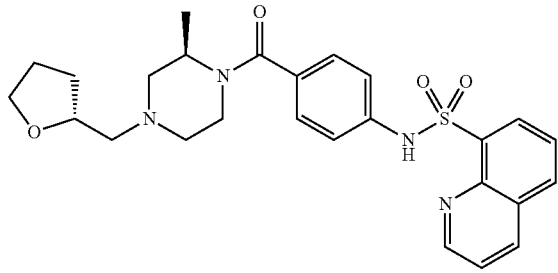 [SMILES: C[C@@H]1CN(C[C@H]2CCCO2)CCN1C(=O)c1ccc(NS(=O)(=O)c2cccc3cccnc23)cc1]

$^1$H NMR (400 MHz, DMSO-$d_6$) δ: 1.0 (d, 3H), 1.2-1.8 (m, 6H), 2.0-2.4 (m, 3H), 2.6-3.0 (m, 3H), 3.4-4.0 (m, 4H), 7.0-7.2 (m, 4H), 7.5-7.8 (m, 2H), 8.0-8.4 (m, 3H), 9.1-9.2 (m, 1H), 10.4 (s, 1H); HPLC Purity: 99.80%; Mass (M+1): 495.20.

(R)— and (S)—N-(4-(4-((tetrahydrofuran-3-yl)methyl)piperazine-1-carbonyl)phenyl)quinoline-8-sulfonamide (Compound 444 and 445)

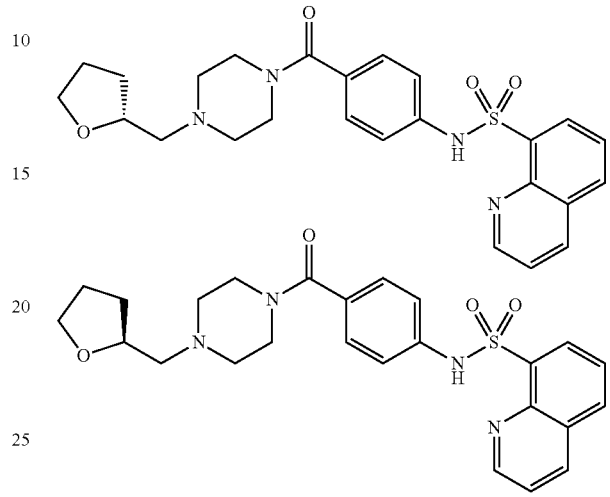

1H-NMR (400 MHz, DMSO-$d_6$) δ: 1.5 (m, 1H), 1.9 (m, 1H), 2.2-2.4 (m, 7H), 3.3 (m, 5H), 3.56-3.8 (m, 3H), 7.0-7.2 (m, 4H), 7.6-7.8 (m, 2H), 8.3 (d, 1H), 8.4 (d, 1H), 8.5 (d, 1H), 9.1-9.2 (m, 1H), 10.4 (s, 1H); HPLC Purity: 99%; $R_T$ 31.15 min and 36.57 min; Mass (M+1): 481.20.

Example 8

Preparation of Compounds of Formula Ij

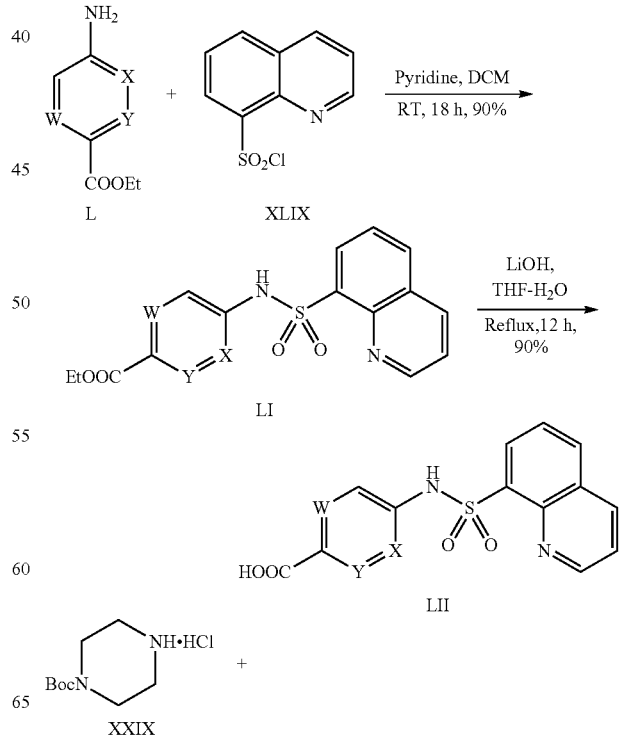

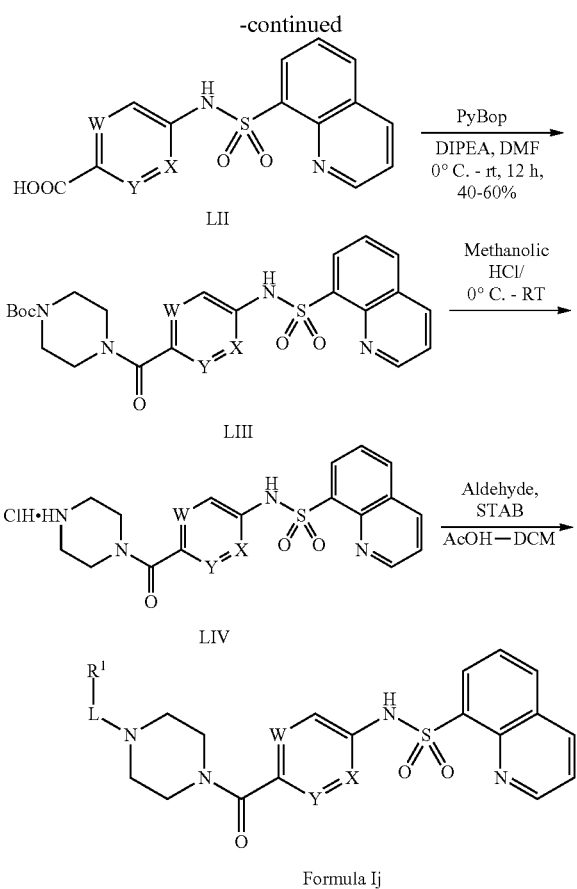

Formula Ij

STAB = Sodium tri-acetoxy borohydride
W, Y, Z = N or CH
L = —(R$^c$R$^c$)$_m$—
R$^1$ = carbocyclyl, aryl, heterocyclyl, heteroaryl Synthesis of Intermediate LI.

To a solution of appropriate amine L (9.6 mmol) in a mixture (1:1) of DCM and pyridine, sulfonyl chloride XLIX (12.1 mmol) was added at room temperature under N$_2$ atmosphere. The resulting mixture was allowed to stir for 16 h. After completion of reaction, the crude mixture was diluted with DCM, washed with water followed by 1N HCl. The organic layer was then dried over Na$_2$SO$_4$ and concentrated under reduced pressure to afford product LI in 78% yield.

Synthesis of Intermediate LII.

To a solution of sulfonamide LI (9.5 mmol) in THF and water (1:1), LiOH (4.7 mmol) was added and the resulting mixture was allowed to stir at 80° C. overnight. After completion of reaction, the crude mixture was washed with EtOAc. The aqueous layer was acidified with citric acid and filtered. Thus obtained solid was washed with Et$_2$O and azeotroped by toluene, under reduced pressure to afford acid LII (75% yield) which was taken forward for the next step without further purification.

Synthesis of Intermediate LIII.

To a solution of acid LII (6.09 mmol) in DMF, PyBoP (Benzotriazole-1-yl-oxy-tris-(dimethylamino)-phosphonium hexafluorophosphate) (4.75 gm, 9.14 mmol) was added at 0° C. and allowed to stir for 5 minutes. Then Boc protected piperazine/substituted piperizine XXIX (1.13 gm, 6.09 mmol) was added to the reaction mixture at the same temperature under N$_2$ atmosphere and stirred overnight at room temperature. After completion of reaction, mixture was diluted with water and extracted with EtOAc. The organic layer was washed with water, dried over Na$_2$SO$_4$, and evaporated under reduced pressure. The residue was purified by column chromatography (silica gel, 60-120 mesh; MeOH-DCM, 1:9) to afford product LIII in 56% yield.

Synthesis of Intermediate LIV.

To a solution of MeOH.HCl, Boc protected amine LIII (4.03 mmol) was added and the resulting mixture was stirred for 1 h. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product LIV (84% yield).

Synthesis of Compounds of Formula Ij.

To a solution of amine LIV (0.25 mmoles) and appropriate aldehyde (0.27 mmol) in DCM, acetic acid (0.2 mL) was added at room temperature and the resulting mixture was allowed to stir for 30 minutes. Then STAB (0.26 gm, 1.26 mmol) was added to reaction mixture and the resulting mixture was allowed to stir at 50° C. for 2 hr. After completion of reaction, the crude mixture was diluted with DCM washed with water, dried over Na$_2$SO$_4$ and concentrated under reduced pressure. The residue was purified by column chromatography (silica gel, 60-120 mesh; MeOH-DCM, 2:8) to afford product in 22-45% yield.

The following compounds were prepared according to the above methods using the appropriate amine L and the appropriate aldehyde.

N-(5-(4-(cyclopropylmethyl)piperazine-1-carbonyl) pyridin-2-yl)quinoline-8-sulfonamide (XIV-1) (Compound 411)

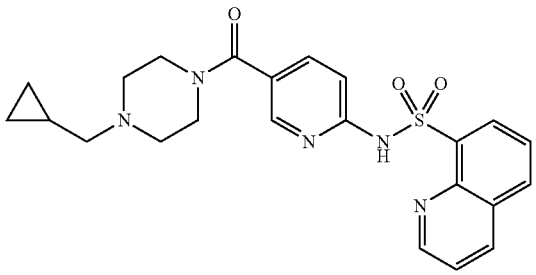 [SMILES: O=C(c1ccc(NS(=O)(=O)c2cccc3cccnc23)nc1)N1CCN(CC2CC2)CC1]

$^1$H NMR (400 MHz, DMSO-d$_6$) δ: 0.1-0.15 (m, 2H), 0.4-0.6 (m, 2H), 08-0.85 (m, 1H), 2.2-2.3 (m, 2H), 2.4-2.8 (m, 4H), 3.6-3.8 (m, 4H), 3.99-4.0 (m, 2H), 7.5-7.7 (m, 4H), 8.3-8.5 (m, 4H), 9.1 (m, 1H); HPLC Purity: 99.67%; Mass (M+1): 452.5.

N-(5-(4-(4-fluorobenzyl)piperazine-1-carbonyl)pyridin-2-yl)quinoline-8-sulfonamide (Compound 412)

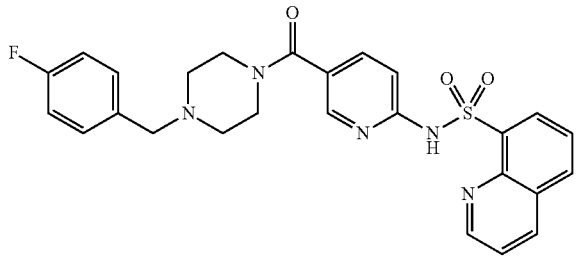 [SMILES: O=C(c1ccc(NS(=O)(=O)c2cccc3cccnc23)nc1)N1CCN(Cc2ccc(F)cc2)CC1]

¹H NMR (400 MHz, DMSO-d₆) δ: 2.3 (s, 2H), 2.35-2.4 (m, 4H), 3.4-3.6 (m, 4H), 7.0-7.4 (m, 4H), 7.6-7.8 (m, 3H), 8.0 (m, 1H), 8.3-8.5 (m, 3H), 8.9-9.0 (m, 1H); HPLC Purity: 99.86%; Mass (M+1): 506.4.

N-(5-(4-(3,5-difluorobenzyl)piperazine-1-carbonyl)pyridin-2-yl)quinoline-8-sulfonamide (Compound 413)

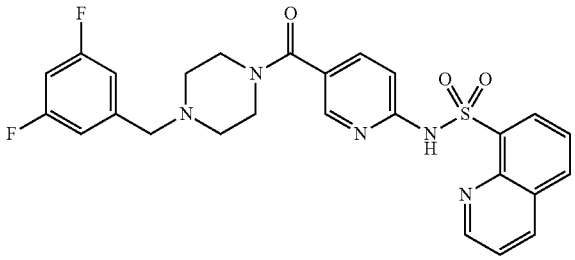 [SMILES: O=C(c1ccc(NS(=O)(=O)c2cccc3cccnc23)nc1)N1CCN(Cc2cc(F)cc(F)c2)CC1]

¹H NMR (400 MHz, CDCl₃) δ: 2.35-2.7 (m, 4H), 3.4-3.59 (m, 4H), 3.6-3.8 (s, 2H), 6.6-7.0 (m, 3H), 7.5-7.7 (m, 4H), 8.3-8.5 (m, 4H), 8.9-9.0 (m, 1H); HPLC Purity: 93.78%; Mass (M+1): 524.5.

N-(6-(4-(3,5-difluorobenzyl)piperazine-1-carbonyl)pyridin-3-yl)quinoline-8-sulfonamide (Compound 414)

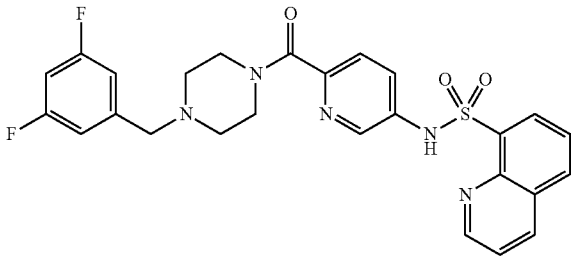 [SMILES: O=C(c1ccc(NS(=O)(=O)c2cccc3cccnc23)cn1)N1CCN(Cc2cc(F)cc(F)c2)CC1]

¹H NMR (400 MHz, CDCl₃) δ: 2.35-2.7 (m, 4H), 3.4-3.59 (m, 4H), 3.6-3.8 (s, 2H), 6.6-7.0 (m, 4H), 7.4-7.8 (m, 3H), 8.0-8.4 (m, 4H), 8.9-9.0 (m, 1H); HPLC Purity: 96.0%; Mass (M+1): 524.3.

N-(6-(4-(cyclopropylmethyl)piperazine-1-carbonyl)pyridin-3-yl)quinoline-8-sulfonamide (Compound 415)

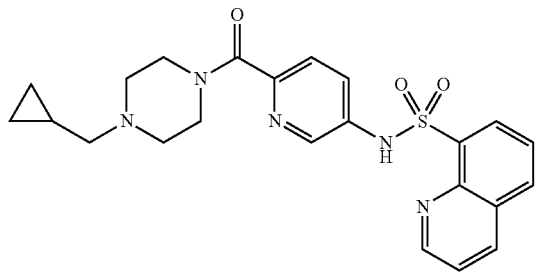

¹H NMR (400 MHz, CDCl₃) δ: 0.9-1.0 (m, 2H), 1.2-1.4 (m, 4H), 1.6-1.8 (m, 3H), 3.4-3.59 (m, 1H), 3.9-4.3 (m, 5H), 7.2-7.75 (m, 9H), 8.2-8.4 (m, 1H); HPLC Purity: 99.35%; Mass (M+1): 452.3.

N-(6-(4-(4-fluorobenzyl)piperazine-1-carbonyl)pyridin-3-yl)quinoline-8-sulfonamide (Compound 416)

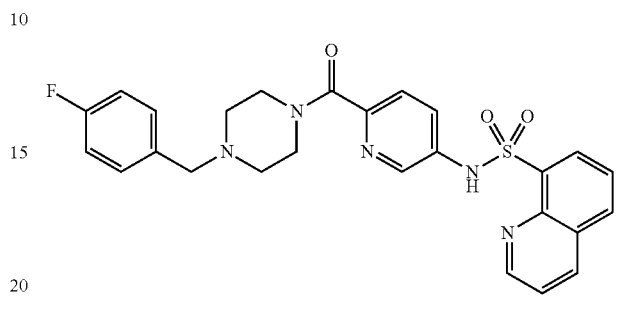

¹H NMR (400 MHz, CDCl₃) δ: 2.2-2.7 (m, 4H), 3.2-3.8 (m, 8H), 7.0-7.5 (m, 4H), 7.56-7.8 (m, 3H), 8.2-8.4 (m, 4H), 8.6-8.8 (m, 1H), 9.1-9.2 (m, 1H); HPLC Purity: 99.85%; Mass (M+1): 506.3.

N-(5-(4-(cyclopropylmethyl)piperazine-1-carbonyl)pyrazin-2-yl)quinoline-8-sulfonamide (Compound 451)

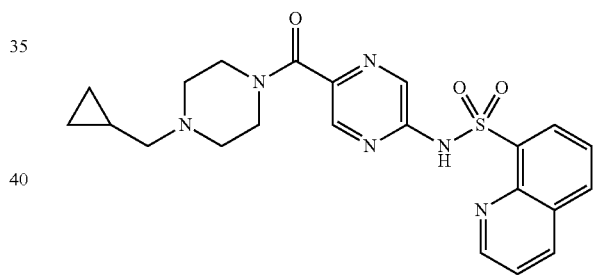

¹H NMR (400 MHz, DMSO-d₆) δ: 0.2 (m, 2H), 0.6 (m, 2H), 0.8-1.0 (m, 1H), 1.2 (s, 2H), 2.5-2.8 (m, 4H), 3.1-3.8 (m, 4H), 7.6-7.8 (m, 2H), 8.2 (m, 1H), 8.2-8.6 (m, 4H), 9.0 (m, 1H); HPLC Purity: 94.0%; Mass (M+1): 453.25.

N-(4-(4-(3,5-difluorobenzoyl)piperazine-1-carbonyl)phenyl)quinoline-8-sulfonamide (Compound 345)

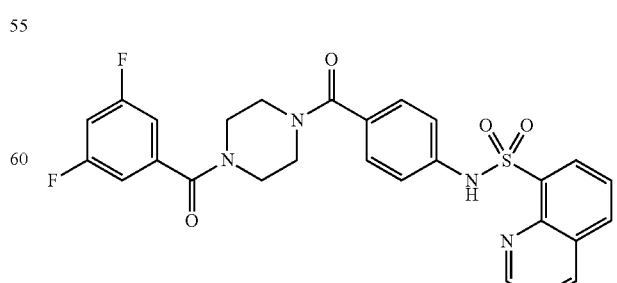

$^1$H NMR (400 MHz, DMSO-d$_6$) δ: 2.5-2.8 (m, 4H), 3.1-3.8 (m, 6H), 7.0-7.2 (m, 4H), 7.6-7.8 (m, 2H), 8.2-8.6 (m, 4H), 9.0 (m, 1H); HPLC Purity: 97.74%; Mass (M+1): 537.40.

N-(5-(4-(4-fluorobenzyl)piperazine-1-carbonyl) pyrazin-2-yl)quinoline-8-sulfonamide (Compound 452)

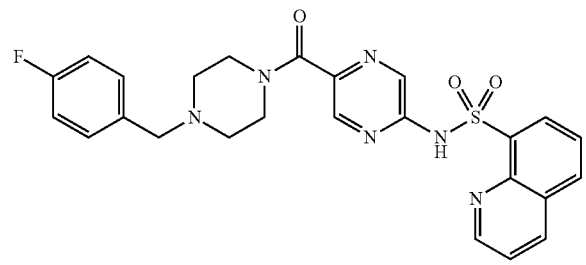 [SMILES: O=C(c1cnc(NS(=O)(=O)c2cccc3cccnc23)cn1)N1CCN(Cc2ccc(F)cc2)CC1]

$^1$H NMR (400 MHz, CDCl$_3$) δ: 2.5-2.8 (m, 6H), 3.1-3.6 (m, 4H), 3.5-3.8 (s, 2H), 7.0-7.2 (m, 3H), 7.6-7.8 (m, 3H), 8.2-8.6 (m, 4H), 8.8-8.85 (m, 1H), 9.0 (m, 1H); HPLC Purity: 92.85%; Mass (M+1): 507.30.

Example 9

Preparation of Compounds of Formula Ik

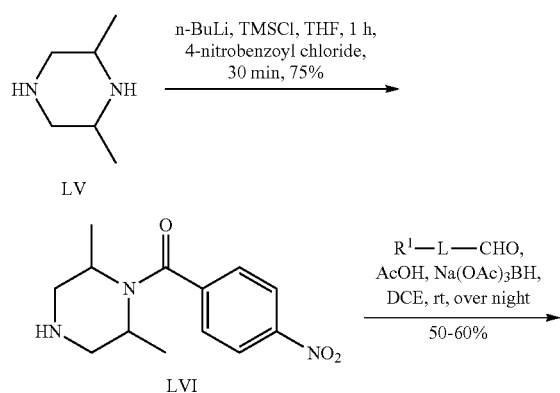

wherein L is —(CR$^c$R$^c$)$_m$—; and R$^1$ is alkyl, carbocyclyl or aryl.

Scheme 9:

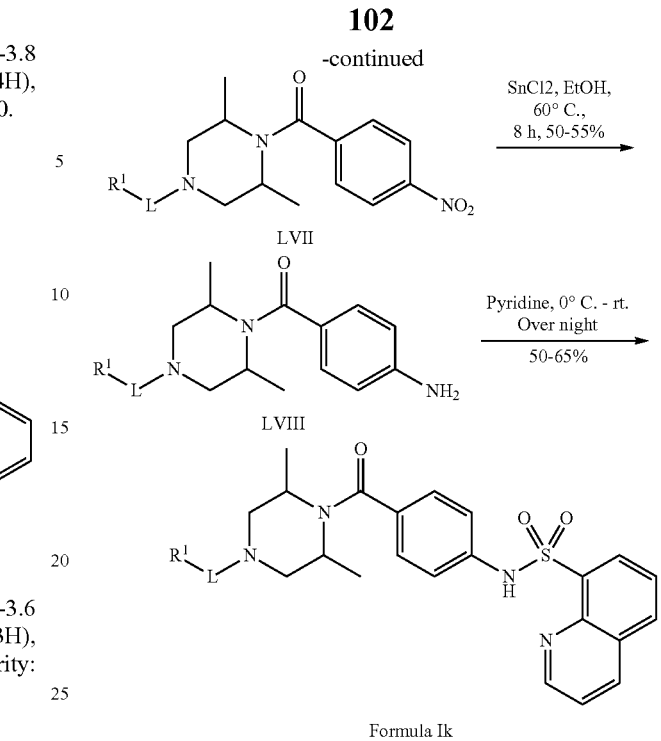

Formula Ik

R$^1$ = aryl, alkyl
L = —(CR$^c$R$^c$)$_m$—

Synthesis of N$^1$-(4-nitrobenzoyl)-2,6-dimethylpiperazine (LVI)

To a stirred solution of 2,6-di-methylpiperazine (LV, 5.0 g, 43.8 mmol) in dry THF (50 mL), maintained at room temperature under an argon atmosphere, was added a solution of 2.5 M n-BuLi in THF (38.54 mL, 96.36 mmol). After the mixture was stirred for 30 min at room temperature, trimethylsilyl chloride (5.5 mL, 43.8 mmol) was added and the reaction mixture stirred for 1 h before the addition of 4-nitrobenzoyl chloride (7.8 gm, 42.05 mmol). After 10 min, the reaction mixture was quenched with MeOH and the solvents were evaporated in vacuo. The residue was purified by silica gel column chromatography to provide product LVI (10.37 gm, 90% yield):

N$^4$-alkylation of N$^1$-(4-nitrobenzoyl)-2,6-dimethylpiperazine (LVII)

To a solution of amine LVI (0.5 gm, 1.9 mmol) and appropriate aldehyde (2.28 mmol) in dichloroethane, acetic acid (0.2 mL) was added at room temperature and the resulting mixture was allowed to stir for 30 minutes. Then sodium triacetoxyborohydride (1.2 gm, 5.7 mmol) was added to the reaction mixture and the resulting mixture was allowed to stir at room temperature over night. After completion of reaction, the crude mixture was concentrated, diluted with DCM washed with water, dried over Na$_2$SO$_4$, concentrated under reduced pressure and purified by column chromatography (silica gel, 60-120 mesh) to afford product LVII in 50-60% yield.

Reduction of N$^4$-alkyl-N$^1$-(4-nitrobenzoyl)-2,6-dimethylpiperazine (LVIII)

To a solution of nitro compound (LVII, 1.10 mmol) in 15 ml of ethanol and ethyl acetate (1:1), SnCl$_2$ (0.418 gm, 2.2 mmol) was added and the mixture was stirred at 60° C. for overnight. The mixture was quenched by the addition of 10 ml of saturated solution of NaHCO$_3$ and extracted with ethyl acetate (2×25 mL). The combined organic layers were washed with brine solution, dried over anhydrous Na$_2$SO$_4$ and concentrated under reduced pressure to afford amine product LVIII in 50-55% yield.

Synthesis of Compounds of Formula Ik.

To a solution of amine (LVIII, 0.55 mmol) in a 5 mL mixture (1:1) of DCM and pyridine, 8-quinoline sulfonyl chloride (0.14 gm, 0.61 mmol) was added at room temperature under N$_2$ atmosphere. The resulting mixture was allowed to stir for overnight. After completion of reaction, the crude mixture was diluted with DCM, washed with water followed by 1N HCl. The organic layer was then dried over Na$_2$SO$_4$, concentrated under reduced pressure to afford product in 50-65% yields.

The following compounds were produced by the above-described method using the appropriate aldehyde.

N-(5-(4-(4-fluorobenzyl)piperazine-1-carbonyl)pyrazin-2-yl)quinoline-8-sulfonamide (Compound 195)

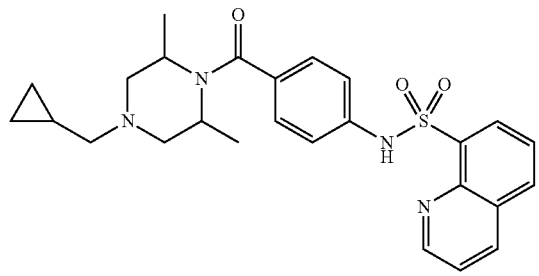 [SMILES: CC1CN(CC2CC2)CC(C)N1C(=O)c1ccc(NS(=O)(=O)c2cccc3cccnc23)cc1]

$^1$H NMR (400 MHz, DMSO-d$_6$) δ: 0.1-0.15 (m, 2H), 0.3-0.4 (m, 2H), 0.8-0.9 (m, 1H), 1.1-1.4 (d, 6H), 1.99-2.3 (m, 4H), 2.4-3.0 (m, 2H), 3.8-4.2 (d, 2H), 7.0-7.2 (m, 4H), 7.61-7.8 (m, 2H), 8.0 (d, 1H), 8.3-8.6 (m, 2H), 9.1 (m, 1H), 10.4 (s, 1H); HPLC Purity: 99.46%; Mass (M+1): 479.50.

N-(4-(2,6-dimethyl-4-((tetrahydrofuran-3-yl)methyl)piperazine-1-carbonyl)phenyl)quinoline-8-sulfonamide (Compound 204)

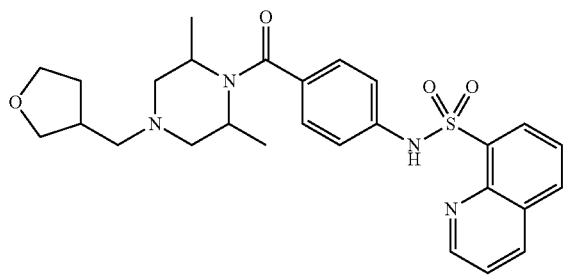 [SMILES: CC1CN(CC2CCOC2)CC(C)N1C(=O)c1ccc(NS(=O)(=O)c2cccc3cccnc23)cc1]

$^1$H NMR (400 MHz, DMSO-d$_6$) δ: 1.0-1.3 (d, 6H), 1.4-1.6 (m, 2H), 1.9-2.67 (m, 8H), 3.6-3.8 (m, 3H), 3.99-4.0 (m, 2H), 7.0-7.27 (m, 4H), 7.6-7.8 (m, 2H), 8.3-8.6 (m, 3H), 9.1 (m, 1H), 10.4 (s, 1H); HPLC Purity: 96.92%; Mass (M+1): 509.5.

N-(4-(4-(cyclohexylmethyl)-2,6-dimethylpiperazine-1-carbonyl)phenyl)quinoline-8-sulfonamide (Compound 198)

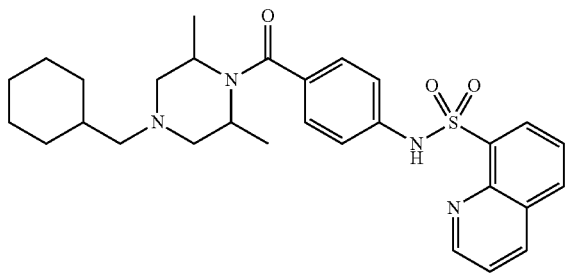 [SMILES: CC1CN(CC2CCCCC2)CC(C)N1C(=O)c1ccc(NS(=O)(=O)c2cccc3cccnc23)cc1]

$^1$H NMR (400 MHz, DMSO-d$_6$) δ: 0.9-1.0 (m, 2H), 1.1-1.4 (m, 11H), 1.45-1.5 (m, 2H), 1.55-1.75 (m, 5H), 1.8-2.1 (m, 4H), 2.2-2.7 (m, 2H), 3.99-4.0 (m, 3H), 7.0-7.2 (m, 4H), 7.55-7.8 (m, 2H), 8.3-8.6 (m, 3H), 9.1 (m, 1H), 10.4 (s, 1H); HPLC Purity: 99.53%; Mass (M+1): 521.60.

N-(4-(4-(4-fluorobenzyl)-2,6-dimethylpiperazine-1-carbonyl)phenyl)quinoline-8-sulfonamide (Compound 196)

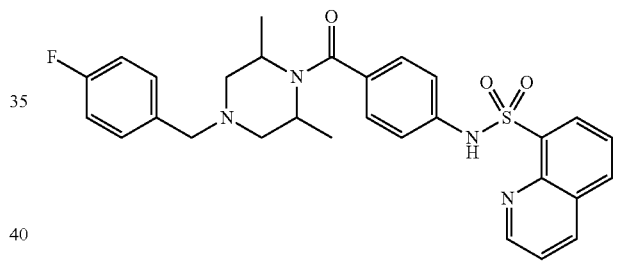

$^1$H NMR (400 MHz, CDCl$_3$) δ: 0.1-0.15 (m, 2H), 1.0-1.4 (d, 6H), 1.99-2.3 (m, 2H), 2.4-2.8 (m, 2H), 3.3-3.6 (s, 2H), 4.19-4.2 (m, 1H), 6.9-7.2 (m, 6H), 7.23-7.4 (m, 2H), 7.55-7.7 (m, 2H), 8.3-8.6 (m, 3H), 9.1 (m, 1H); HPLC Purity: 99.02%; Mass (M+1): 533.55.

N-(4-(4-(3,5-difluorobenzyl)-2,6-dimethylpiperazine-1-carbonyl)phenyl)quinoline-8-sulfonamide (Compound 194)

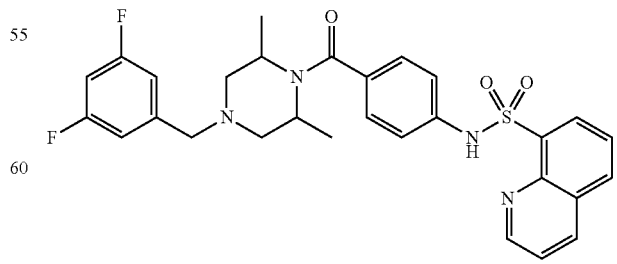

$^1$H NMR (400 MHz, DMSO-d$_6$) δ: 1.2 (d, 6H), 1.3 (m, 2H), 2.0-2.4 (m, 2H), 2.4-2.6 (s, 2H), 3.2-3.6 (s, 2H), 7.0-7.5 (m,

7H), 7.61-7.8 (m, 2H), 8.0 (d, 1H), 8.3-8.6 (m, 2H), 9.1 (m, 1H), 10.4 (s, 1H); HPLC Purity: 98.34%; Mass (M+1): 551.55.

N-(4-(4-(4-chloro-3-fluorobenzyl)-2,6-dimethylpiperazine-1-carbonyl)phenyl)quinoline-8-sulfonamide (Compound 197)

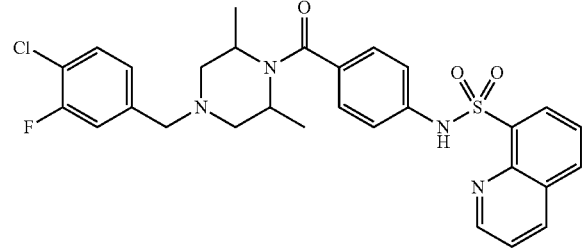 [SMILES: CC1CN(Cc2ccc(Cl)c(F)c2)CC(C)N1C(=O)c1ccc(NS(=O)(=O)c2cccc3cccnc23)cc1]

¹H NMR (400 MHz, DMSO-d₆) δ: 1.0-1.4 (d, 6H), 2.0-2.2 (m, 2H), 2.4-2.6 (m, 2H), 3.5 (s, 2H), 3.9-4.0 (m, 2H), 7.23-7.4 (m, 6H), 7.55-7.8 (m, 3H), 8.3-8.6 (m, 3H), 9.1 (m, 1H), 10.4 (s, 1H); HPLC Purity: 95.27%; Mass (M+1): 567.50.

N-(4-(2,6-dimethyl-4-(2,3,6-trifluorobenzyl)piperazine-1-carbonyl)phenyl)quinoline-8-sulfonamide (Compound 199)

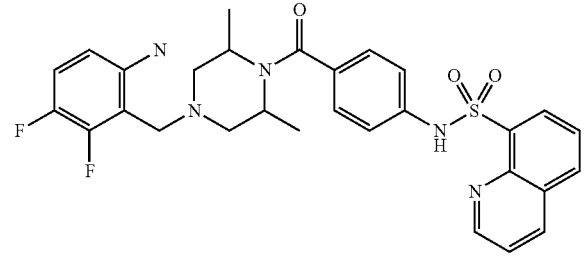 [SMILES: CC1CN(Cc2c(N)ccc(F)c2F)CC(C)N1C(=O)c1ccc(NS(=O)(=O)c2cccc3cccnc23)cc1]

¹H NMR (400 MHz, DMSO-d₆) δ: 1.0-1.2 (d, 6H), 1.1-1.4 (m, 2H), 2.0-2.2 (m, 2H), 2.4-2.6 (m, 2H), 3.6 (s, 2H), 7.0-7.2 (m, 4H), 7.55-7.8 (m, 3H), 8.3-8.6 (m, 3H), 9.1 (m, 1H), 10.4 (s, 1H); HPLC Purity: 99.82%; Mass (M+1): 569.55.

N-(4-(2,6-dimethyl-4-(2,3,5-trifluorobenzyl)piperazine-1-carbonyl)phenyl)quinoline-8-sulfonamide (Compound 200)

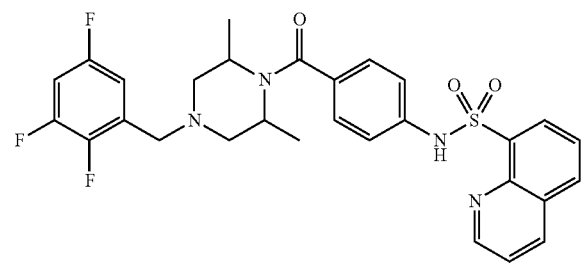 [SMILES: CC1CN(Cc2cc(F)cc(F)c2F)CC(C)N1C(=O)c1ccc(NS(=O)(=O)c2cccc3cccnc23)cc1]

¹H NMR (400 MHz, DMSO-d₆) δ: 1.0-1.2 (d, 6H), 1.25-1.4 (m, 4H), 2.0-2.2 (m, 2H), 2.4-2.6 (m, 2H), 3.6 (s, 2H), 7.0-7.2 (m, 4H), 7.4-7.5 (m, 1H), 7.6-7.8 (m, 2H), 8.3-8.6 (m, 3H), 9.1 (m, 1H), 10.4 (s, 1H); HPLC Purity: 99.92%; Mass (M+1): 569.55.

N-(4-(2,6-dimethyl-4-(3,4,5-trifluorobenzyl)piperazine-1-carbonyl)phenyl)quinoline-8-sulfonamide (Compound 201)

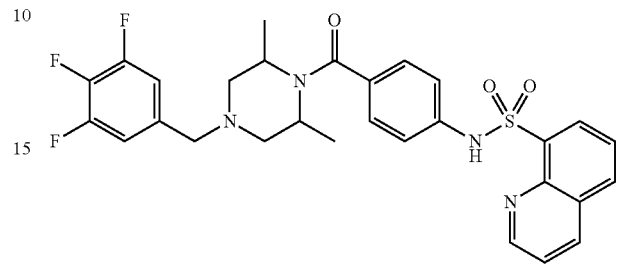

¹H NMR (400 MHz, DMSO-d₆) δ: 1.0-1.2 (d, 6H), 1.3-1.4 (m, 2H), 2.0-2.2 (m, 2H), 2.4-2.6 (m, 1H), 3.6 (s, 2H), 3.99-4.0 (m, 1H), 7.0-7.4 (m, 6H), 7.6-7.8 (m, 2H), 8.3-8.6 (m, 3H), 9.1 (m, 1H), 10.4 (s, 1H); HPLC Purity: 96.13%; Mass (M+1): 569.5.

N-(4-(2,6-dimethyl-4-(2,4,6-trifluorobenzyl)piperazine-1-carbonyl)phenyl)quinoline-8-sulfonamide (Compound 202)

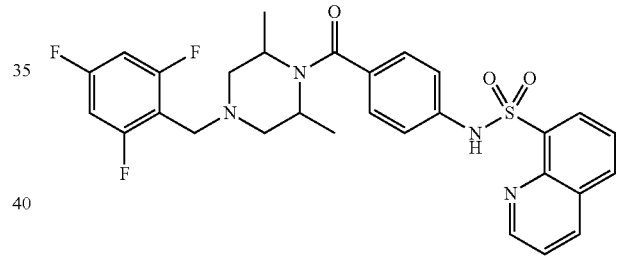

¹H NMR (400 MHz, DMSO-d₆) δ: 1.0-1.2 (d, 6H), 1.3-1.4 (m, 1H), 2.0-2.2 (m, 3H), 3.6 (s, 2H), 3.99-4.0 (m, 2H), 7.0-7.27 (m, 6H), 7.6-7.8 (m, 2H), 8.3-8.6 (m, 3H), 9.1 (m, 1H), 10.4 (s, 1H); HPLC Purity: 96.21%; Mass (M+1): 569.6.

N-(4-(2,6-dimethyl-4-(2,4,5-trifluorobenzyl)piperazine-1-carbonyl)phenyl)quinoline-8-sulfonamide (Compound 203)

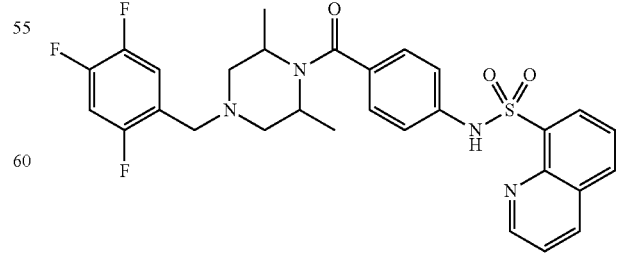

¹H NMR (400 MHz, DMSO-d₆) δ: 1.0-1.4 (d, 6H), 2.0-2.2 (m, 2H), 2.5-2.7 (m, 2H), 3.6 (s, 2H), 3.99-4.0 (m, 2H), 7.0-7.27 (m, 6H), 7.4-7.8 (m, 4H), 8.3-8.6 (m, 3H), 9.1 (m, 1H), 10.4 (s, 1H); HPLC Purity: 98.34%; Mass (M+1): 569.5.

Example 10

Preparation of Compounds of Formula II

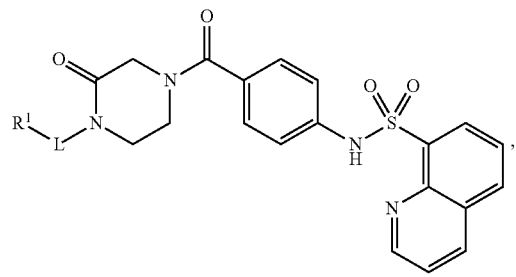

(II)

wherein R¹ is alkyl or aryl; and L is —(CR$^c$R$^c$)$_m$—.

Scheme 10:

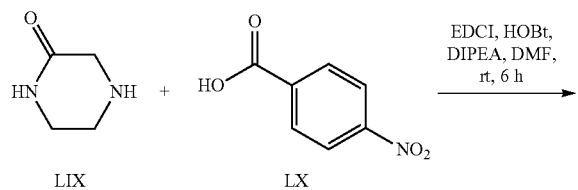

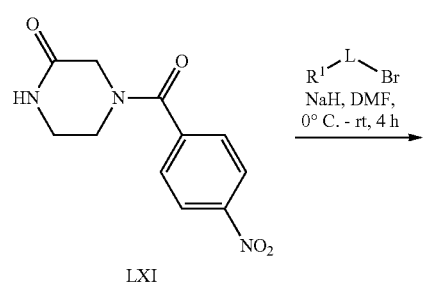

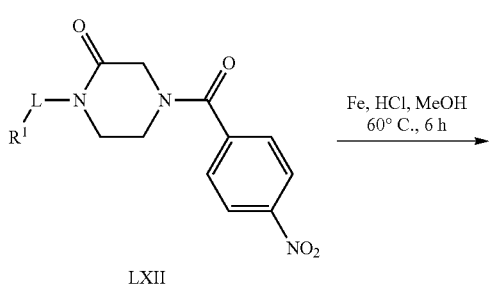

R¹ = Alkyl, Aryl
L = —(CR$^c$R$^c$)$_m$—

Synthesis of 4-(4-nitrobenzoyl)piperazin-2-one (LXI)

EDCI (0.394 gm, 2.05 mmol) and HOBT (0.276 gm, 2.05 mmol) were added to a stirred solution of the 4-nitrobenzoic acid (LX, 0.253 gm, 2.05 mmol) in anhydrous DMF. The temperature of the mixture was reduced to 0° C., at which time DIPEA (1.14 ml, 6.15 mmol) was added under nitrogen atmosphere and the resultant solution (or suspension) was stirred at room temperature for 30 min. 2-piperazinone (LIX, 2.05 mmol) was then added at 0° C. The reaction mixture was then brought to room temperature and stirred for 6 h. After completion of the reaction, the reaction mixture was diluted with water and extracted with ethyl acetate (3×25 ml). The organic layer was washed with water (3×10 ml), dried over anhydrous sodium sulfate, filtered and concentrated over the rotary evaporator to get the crude product. The crude product was purified by column chromatography (60-120 silica gel, ethyl acetate:hexane, 4:6) to afford pure product LXI (0.3 gm, 60%) as an off-white solid.

Synthesis of intermediate LXII. A solution of 4-(4-nitrobenzoyl)piperazin-2-one (LXI) (0.1 gm, 0.4 mmol) in anhydrous DMF was cooled to 0° C. and added sodium hydride (0.02 gm, 0.48 mmol) under nitrogen atmosphere. The mixture was then stirred at room temperature for 30 min. Then the mixture was added appropriate alkyl bromide (R¹-L-Br) (0.4 mmol) at 0° C. and stirred at room temperature for 24 h. After completion of reaction, the reaction mixture was quenched by the addition of water (10 mL), diluted with diethyl ether (100 mL), washed with water (2×25 mL), brine (25 mL), dried over anhydrous sodium sulfate and concentrated in vacuo. The crude product was purified by column chromatography (Silica gel, 60:120; ethyl acetate:hexane, 3:7) to afford product LXII in 65-72% yield.

Synthesis of intermediate LXIII.

To a solution of compound LXII (0.77 mmol) in 15 mL of methanol, iron powder (0.215 gm, 3.85 mmol) and concentrated hydrochloric acid (0.2 mL) were added. The mixture was then heated to 60° C. and stirred for 6 h. After completion of reaction, evaporated the solvent, the residue was added 10 mL of saturated sodium bicarbonate solution and extracted with ethyl acetate (3×25 mL). The combined organic layers were washed with water (10 mL), brine (10 mL), dried over anhydrous sodium sulfate and concentrated under reduced pressure to afford amine LXIII in 60-70% yield.

Synthesis of compounds of Formula II.

To a stirred solution of amine LXIII (0.26 mmol) in 5 mL of 1:1 mixture of pyridine and dichloromethane at 0° C. was added 8-quinoline sulfonylchloride (XLIX; 0.066 gm, 0.29 mmol). The mixture was allowed to stir for 6 h at room temperature. After completion of reaction, the mixture was concentrated under reduced pressure, residue dissolved in dichloromethane (50 mL), washed with dilute HCl (10 mL), water (10 mL), brine (10 mL) and concentrated. The crude product was purified by column chromatography (Silica gel, 60-120; 2% MeOH-DCM) to afford pure product as an off-white solid in 55-60% yields.

The following compounds were prepared according to the above methods using the appropriate alkyl bromide.

N-(4-(4-(cyclopropylmethyl)-3-oxopiperazine-1-carbonyl)phenyl)quinoline-8-sulfonamide (Compound 215)

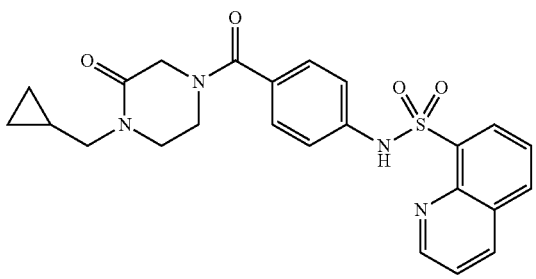 [SMILES: O=C1CN(C(=O)c2ccc(NS(=O)(=O)c3cccc4cccnc34)cc2)CCN1CC1CC1]

$^1$H NMR (400 MHz, DMSO-d$_6$) δ: 0.2-0.4 (m, 2H), 0.45-0.8 (m, 2H), 1.0 (m, 1H), 2.6-2.8 (s, 2H), 3.2-3.4 (m, 2H), 3.5-4.0 (m, 4H), 7.2-7.4 (m, 4H), 7.4-7.6 (m, 2H), 8.0-8.4 (m, 3H), 8.79-8.8 (m, 1H), 10.5 (s, 1H); HPLC Purity: 94.48%; Mass (M+1): 465.2.

N-(4-(4-(3,5-difluorobenzyl)-3-oxopiperazine-1-carbonyl)phenyl)quinoline-8-sulfonamide (Compound 216)

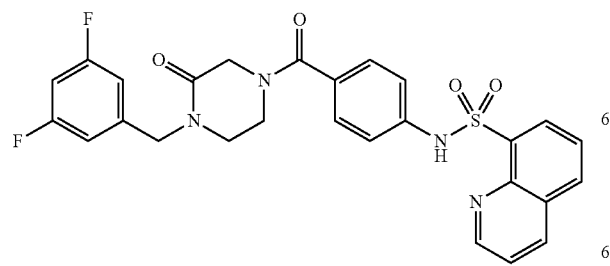

$^1$H NMR (400 MHz, DMSO-d$_6$) δ: 3.2-4.0 (m, 6H), 4.5 (s, 2H), 7.0-7.4 (m, 7H), 7.4-7.6 (m, 2H), 8.0-8.4 (m, 3H), 8.79-8.8 (m, 1H), 10.5 (s, 1H); HPLC Purity: 97.06%; Mass (M+1): 537.45.

Example 11

Preparation of a Compound of Formula Im

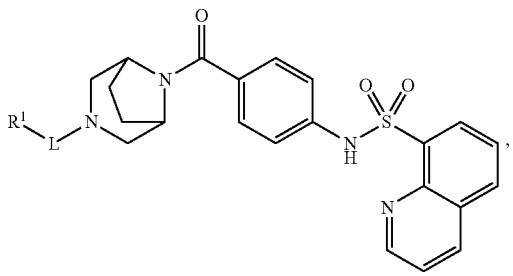

wherein R$^1$ is aryl or carbocyclyl; and L is —(CR$^c$R$^c$)$_m$—.

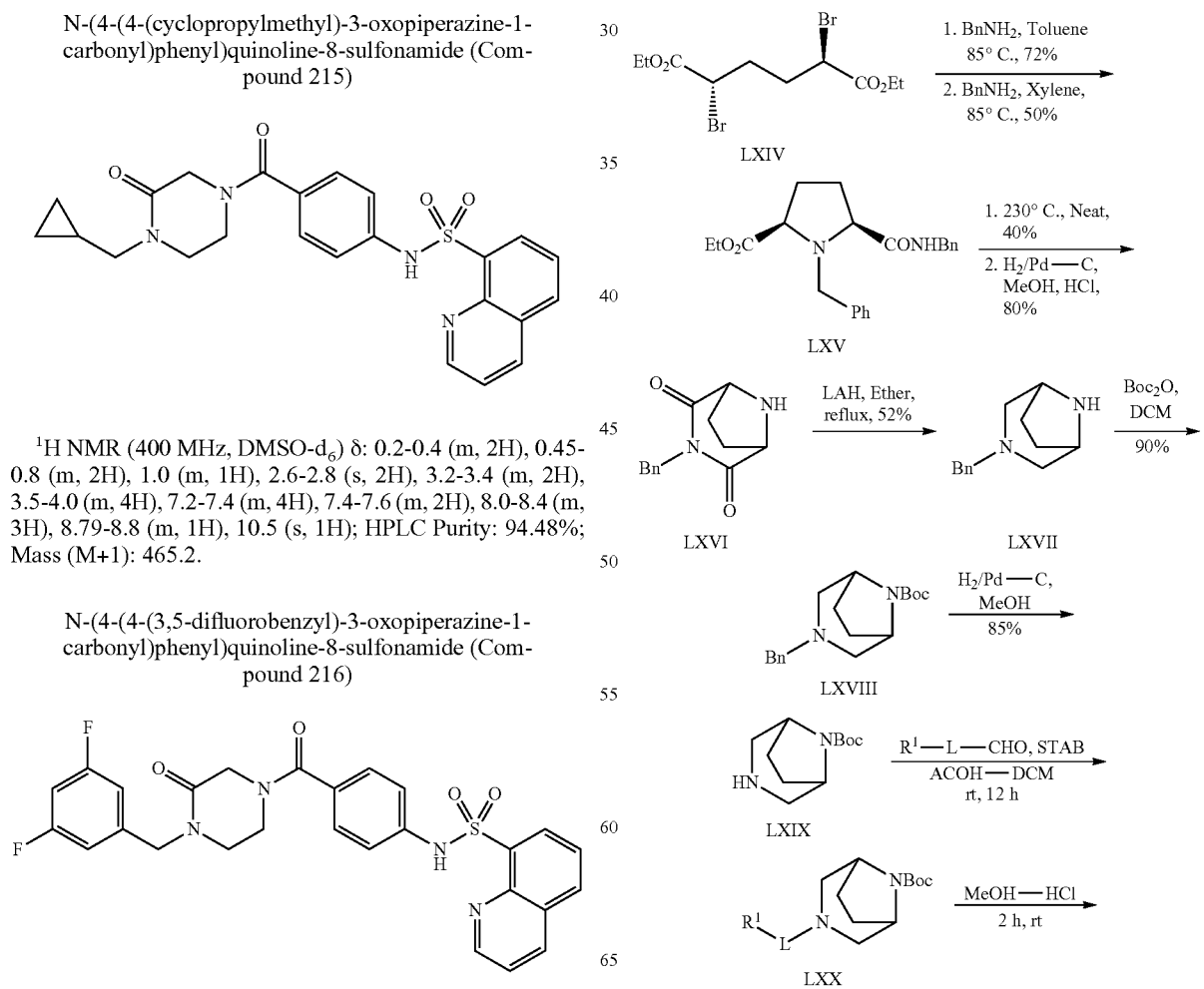

-continued

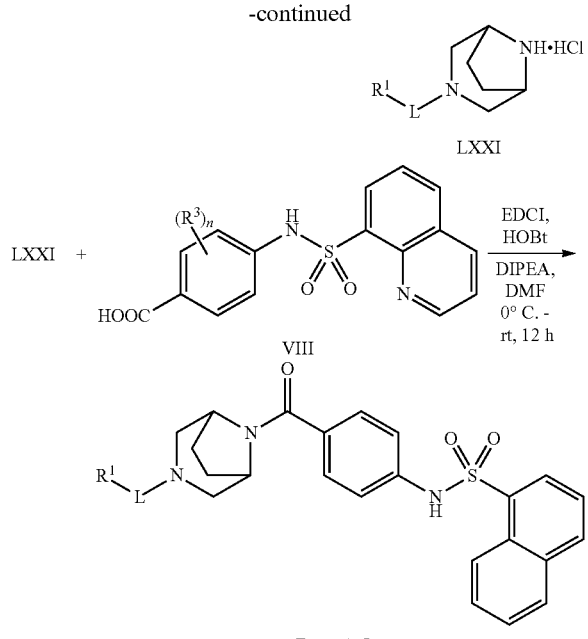

R¹ = aryl, carbocyclyl
L = —(CR^cR^c)_m—

Synthesis of (2R,5S)-ethyl 1-benzyl-5-(benzylcarbamoyl)pyrrolidine-2-carboxylate (LXV)

To a stirred solution of Diethyl meso-2,5-dibromoadipate (LXIV, 0.00069 mol, 250 mg) in toluene (5 mL) was added benzylamine (0.0021 mol, 0.234 mL) and the reaction mixture was heated at 85° C. for 16 h. After completion of the reaction (checked by TLC), the reaction mixture was cooled and the formed solid was filtered. The filtrate was concentrated under reduced pressure to leave the product as pale yellow liquid. The residue was purified by column chromatography (silica gel, 60-120 mesh; EA-Hexane, 2:8) to afford Diethyl pyrrolidine-2,5-carboxylate in 72% yield.

To a stirred solution of Diethyl pyrrolidine-2,5-carboxylate (0.000327 mol, 100 mg) in xylene (5 mL) was added benzylamine (0.000327 mol, 0.035 mL) under nitrogen atmosphere and heated under reflux for 18 h. After completion of the reaction (checked by TLC), the reaction mixture was cooled and concentrated under reduced pressure to leave the product as yellow liquid. The residue was purified by column chromatography (silica gel, 60-120 mesh; EA-Hexane, 4:6) to afford the product LXV in 50% yield.

Synthesis of 3-benzyl-3,8-diazabicyclo[3 2.1]octane-2,4-dione (LXVI).

Ethyl 1-benzyl-5-(benzylcarbamoyl)pyrrolidine-2-carboxylate (LXV, 0.00122 mol, 450 mg) was heated under stirring at 210-220° C. for 3 h under atmospheric pressure and the formed ethyl alcohol was collected. After completion of the reaction (checked by TLC), the reaction mixture was cooled at room temperature and the residue was purified by column chromatography (silica gel, 60-120 mesh; EA-Hexane, 2:8) to afford the 3,8-dibenzyl-3,8-diazabicyclo[3.2.1]octane-2,4-dione in 40-45% yield.

To a stirred solution of 3,8-dibenzyl-3,8-diazabicyclo[3.2.1]octane-2,4-dione (0.00025 mol, 80 mg) in MeOH (2 mL) containing few drops of HCl was hydrogenated with 10% Pd—C (8 mg) for 4 h at room temperature. After completion of the reaction (checked by TLC), the reaction mixture was filtered through celite and the filtrate was concentrated under reduced pressure. The crude residue was purified by column chromatography (silica gel, 60-120 mesh; EA-Hexane, 6:4) to afford the 3-benzyl-3,8-diazabicyclo[3.2.1]octane-2,4-dione (LXVI) in 80% yield.

Synthesis of 3-benzyl-3,8-diazabicyclo[3.2.1]octane (LXVII)

A solution of 3-benzyl-3,8-diazabicyclo[3.2.1]octane-2,4-dione LXVI (0.00108 mol, 250 mg) in dry ether (2 mL) was added to a stirred suspension of LiAlH₄ (122 mg, 0.00315 mol) in dry ether (8 mL) at 0° C. under nitrogen atmosphere. The reaction bath was allowed to return at room temperature and stirring was continued for 30 h. After completion of the reaction (checked by TLC), the reaction mixture was quenched with chilled water and then stirred for 1 h. The reaction mixture was diluted with ether (20 mL) and the organic layer was washed with water, dried over Na₂SO₄, concentrated under reduced pressure. The crude residue was purified by column chromatography (silica gel, 60-120 mesh; EA-Hexane, 1:1) to afford the product LXVII in 52% yield.

Synthesis of tert-butyl 3-benzyl-3,8-diazabicyclo[3.2.1]octane-8-carboxylate (LXVIII)

To a stirred solution of compound LXVII (0.00108 mol, 220 mg) in DCM (10 mL) was added Boc₂O (0.00108 mol, 237 mg) and the reaction mixture was stirred for 16 h at room temperature. The progress of the reaction was monitored by TLC. The reaction mixture was diluted with DCM (30 mL) and washed with water. The organic layer was dried over Na₂SO₄ and concentrated under reduced pressure to give the crude product LXVII which was used for the next step without further purification.

Synthesis of tert-butyl 3,8-diazabicyclo[3.2.1]octane-8-carboxylate (LXIX)

To a stirred solution of compound LXVIII (0.00028 mol, 85 mg) in MeOH (5 mL) was hydrogenated with 10% Pd—C (15 mg) for 4 h at room temperature. After completion of the reaction (checked by TLC), the reaction mixture was filtered through celite and the filtrate was concentrated under reduced pressure. The crude residue was purified by column chromatography (silica gel, 60-120 mesh; MeOH-DCM, 1:9) to afford Compound LXIX in 85% yield.

Synthesis of Intermediate LXX.

To a solution of amine LXIX (0.00023 mol) and appropriate aldehyde (0.00023 mol) in DCM (5 mL), acetic acid (0.1 mL) was added at room temperature and the resulting mixture was allowed to stir for 30 min. Then STAB (0.100 gm, 0.00047 mol) was added to reaction mixture and the resulting mixture was allowed to stir at room temperature for 16 h. After completion of reaction, the crude mixture was diluted with DCM washed with water, dried over Na₂SO₄ and concentrated under reduced pressure. The residue was purified by column chromatography (silica gel, 60-120 mesh; EtOAc-Hexane, 2:8) to afford product LXX in 70-75% yield.

Synthesis of Intermediate LXXI.

To a solution of MeOH.HCl (5 mL), Boc protected amine LX (1.03 mmol) was added and the resulting mixture was stirred for 1 hr. After completion of reaction, solvent was removed under reduced pressure, washed with water followed by addition of NaHCO₃ and extracted with DCM. The organic layer was dried over Na₂SO₄ and evaporated under reduced pressure to afford product LXXI as free base (94.30% yield).

Synthesis of Compounds of Formula Im.

To a stirred solution of acid VIII (0.00021 mol, 1 eq) in DMF (5 mL), EDCI (0.048 g, 0.00024 mol, 1.1 eq), HOBt (0.038 g, 0.00024 mol, 1.1 eq) and DIPEA (0.15 mL, 0.00078 mol, 2.5 eq) were added at 0° C. and stirred for 15 minutes. A solution of amine LXXI (0.00021 mol, 1 eq) was then added at 0° C. and then the resulting mixture was allowed to stir at room temperature for overnight. After completion of the reaction, water (20 mL) was added and extracted with ethyl acetate (2×30 mL). The combined organic layer was dried over anhydrous Na₂SO₄ and concentrated under reduced pressure. The crude product was purified by column chromatography (silica gel, 60-120 mess, 70% ethyl acetate in hexane) to give compound in 49-55% yield.

The above-described method was used to prepare the following compounds using the appropriate aldehyde (R¹-L-CHO) and the appropriate acid VIII.

(2R,5S)-ethyl 1-benzyl-5-(benzylcarbamoyl)pyrrolidine-2-carboxylate (Compound 213)

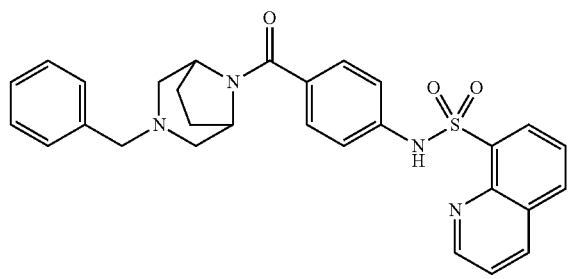 [SMILES: O=C(c1ccc(NS(=O)(=O)c2cccc3cccnc23)cc1)N1C2CCC1CN(Cc1ccccc1)C2]

¹H NMR (400 MHz, CDCl₃) δ: 1.6-1.9 (m, 4H), 2.2-2.4 (m, 2H), 2.6-2.8 (m, 2H), 3.5-3.6 (m, 2H), 3.9 (s, 1H), 4.6 (s, 1H), 7.0 (d, 1H), 7.2-7.3 (m, 6H), 7.5-7.6 (m, 2H), 8.0 (d, 1H), 8.2-8.5 (m, 3H), 9.1 (d, 1H); HPLC Purity: 91.41%; Mass (M+1): 513.33.

N-(4-(3-(4-fluorobenzyl)-3,8-diazabicyclo[3.2.1] octane-8-carbonyl)phenyl)quinoline-8-sulfonamide (Compound 226)

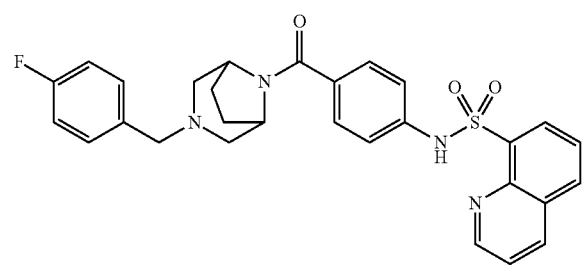 [SMILES: O=C(c1ccc(NS(=O)(=O)c2cccc3cccnc23)cc1)N1C2CCC1CN(Cc1ccc(F)cc1)C2]

¹H NMR (400 MHz, CDCl₃) δ: 1.6-1.9 (m, 4H), 2.2-2.4 (m, 2H), 2.6-2.8 (m, 2H), 3.5-3.6 (m, 2H), 3.9 (s, 1H), 4.7 (s, 1H), 6.9-7.1 (m, 4H), 7.2-7.3 (m, 3H), 7.5-7.6 (m, 2H), 8.0 (d, 1H), 8.2-8.5 (m, 3H), 9.1 (d, 1H); HPLC Purity: 96.11%; Mass (M+1): 531.25.

N-(4-(3-(3,5-difluorobenzyl)-3,8-diazabicyclo[3.2.1] octane-8-carbonyl)phenyl)quinoline-8-sulfonamide (Compound 227)

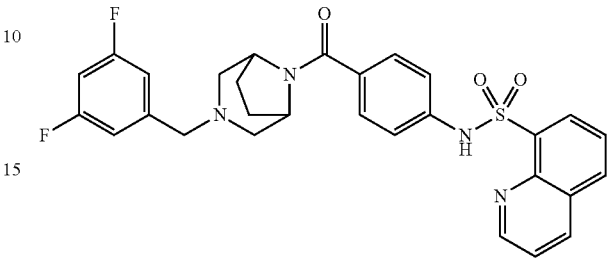

¹H NMR (400 MHz, CDCl₃) δ: 1.6-1.9 (m, 4H), 2.2-2.4 (m, 2H), 2.6-2.8 (m, 2H), 3.5-3.6 (m, 2H), 3.9 (s, 1H), 4.7 (s, 1H), 6.6 (m, 1H), 6.8 (d, 2H), 6.9-7.1 (m, 2H), 7.2-7.3 (m, 1H), 7.5-7.6 (m, 2H), 8.0 (d, 1H), 8.2-8.5 (m, 3H), 9.1 (d, 1H); HPLC Purity: 94.31%; Mass (M+1): 549.23.

N-(4-(3-(cyclopropylmethyl)-3,8-diazabicyclo[3.2.1] octane-8-carbonyl)phenyl)quinoline-8-sulfonamide (Compound 228)

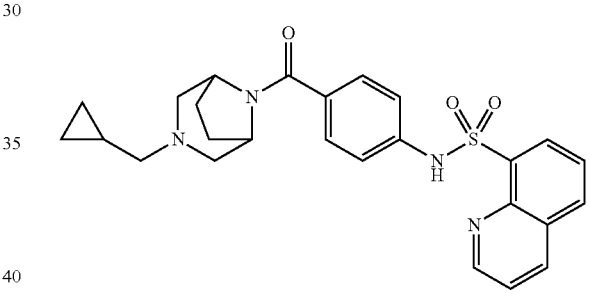

¹H NMR (400 MHz, CDCl₃) δ: 0.2-0.3 (m, 2H), 0.4-0.5 (m, 2H), 0.8-0.9 (m, 1H), 1.6-1.9 (m, 4H), 2.1-2.4 (m, 4H), 2.6-2.8 (m, 2H), 3.9 (s, 1H), 4.7 (s, 1H), 7.0-7.1 (m, 2H), 7.2-7.3 (m, 1H), 7.6-7.7 (m, 1H), 8.0 (d, 1H), 8.2-8.6 (m, 3H), 9.1 (d, 1H); HPLC Purity: 99.28%; Mass (M+1): 477.41.

Example 12

Preparation of Compounds of Formula In

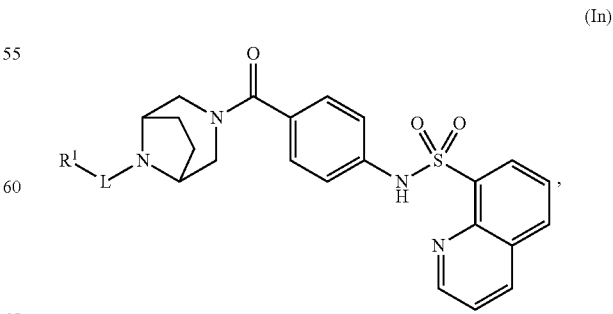

(In)

wherein R¹ is aryl or carbocyclyl; and L is —(CR$^c$R$^c$)$_m$—.

Scheme 12

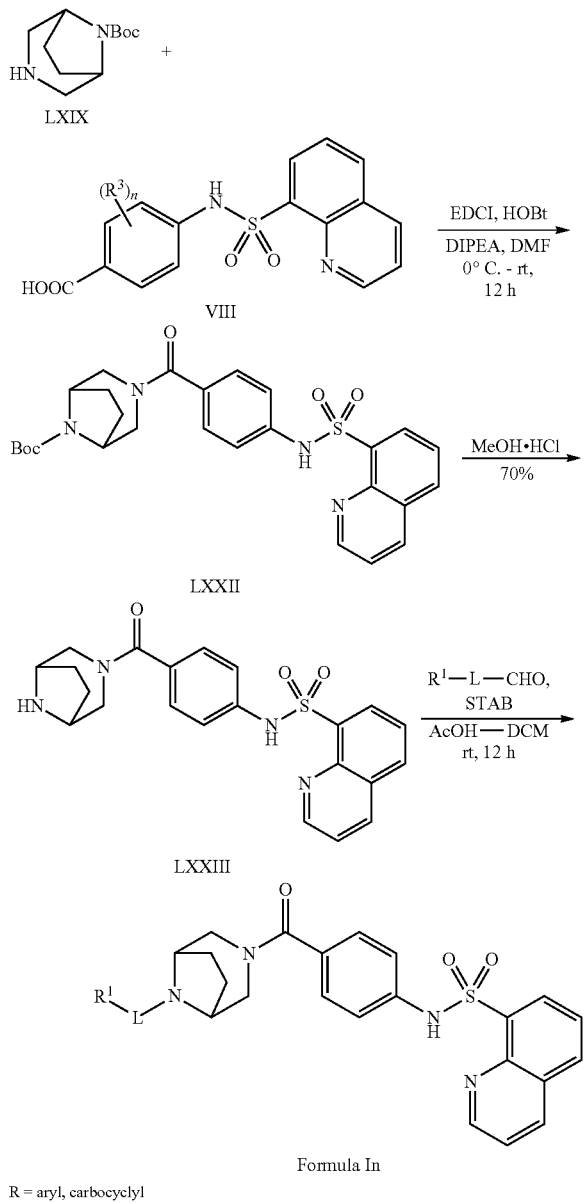

Formula In

R = aryl, carbocyclyl
L = —(CR³R³)ₘ—

Synthesis of tert-butyl 3-(4-(quinoline-8-sulfonamido)benzoyl)-3,8-diazabicyclo[3.2.1]octane-8-carboxylate (LXXII)

To a stirred solution of acid VIII (0.001179 mol, 1 eq) in DMF (5 mL), EDCI (0.248 g, 0.00129 mol, 1.1 eq), HOBt (0.198 g, 0.00129 mol, 1.1 eq) and DIPEA (0.30 g, 0.00235 mol, 2 eq) were added at 0° C. and stirred for 15 minutes. A solution of amine LXIX from Example 11 (0.00117 mol, 1 eq) was then added at 0° C. and then the resulting mixture was allowed to stir at room temperature for overnight. After completion of the reaction, water (20 mL) was added and extracted with ethyl acetate (2×30 mL). The combined organic layer was dried over anhydrous Na₂SO₄ and concentrated under reduced pressure. The crude product was purified by column chromatography (silica gel, 60-120 mess, 70% ethyl acetate in hexane) to give LXXII in 57% yield.

Synthesis of N-(4-(3,8-diazabicyclo[3.2.1]octane-3-carbonyl)phenyl)quinoline-8-sulfonamide (LXXIII)

To a solution of MeOH.HCl (5 mL), Boc protected amine LXXII (1 mmol) was added and the resulting mixture was stirred for 2 hr. After completion of reaction, solvent was removed under reduced pressure, washed with water followed by addition of NaHCO₃ and extracted with DCM. The organic layer was dried over Na₂SO₄ and evaporated under reduced pressure to afford product LXXIII as free base (92% yield).

Synthesis of Compounds of Formula In.

To a solution of amine LXXIII (0.118 mmol) and appropriate aldehyde (0.118 mmol) in DCM (5 mL), acetic acid (0.1 mL) was added at room temperature and the resulting mixture was allowed to stir for 30 min. Then STAB (0.050 gm, 0.236 mol) was added to reaction mixture and the resulting mixture was allowed to stir at room temperature for 16 h. After completion of reaction, the crude mixture was diluted with DCM washed with water, dried over Na₂SO₄ and concentrated under reduced pressure. The residue was purified by column chromatography (silica gel, 60-120 mesh; EtOAc-Hexane, 2:1) to afford product in 25-45% yield.

The following compounds were made by the above-described method using the appropriate aldehyde (R¹-L-CHO) and the appropriate acid VIII.

N-(4-(3-(4-fluorobenzyl)-3,8-diazabicyclo[3.2.1]octane-8-carbonyl)phenyl)quinoline-8-sulfonamide (Compound 220)

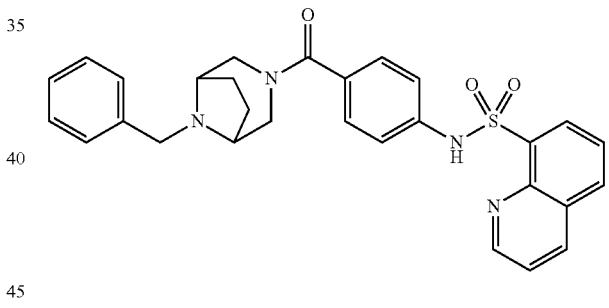

¹H NMR (400 MHz, CDCl₃) δ: 1.7 (br s, 1H), 1.9 (br s, 2H), 3.0 (br s, 2H), 3.2 (br s, 2H), 3.5 (s, 2H), 3.8 (d, 1H), 4.3 (d, 1H), 7.0-7.2 (m, 4H), 7.3-7.4 (m, 4H), 7.6-7.7 (m, 2H), 8.0 (d, 1H), 8.2-8.5 (m, 3H), 9.1 (d, 1H); HPLC Purity: 99.85%; Mass (M+1): 512.62.

N-(4-(8-(4-fluorobenzyl)-3,8-diazabicyclo[3.2.1]octane-3-carbonyl)phenyl)quinoline-8-sulfonamide (Compound 219)

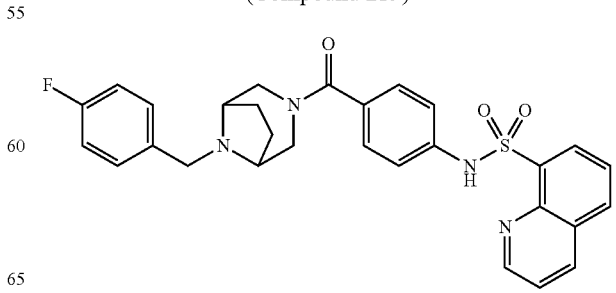

$^1$H NMR (400 MHz, CDCl$_3$) δ: 1.7 (br s, 1H), 1.9 (br s, 2H), 3.0 (br s, 2H), 3.2 (br s, 2H), 3.5 (s, 2H), 3.8 (d, 1H), 4.3 (d, 1H), 6.9-7.2 (m, 5H), 7.2-7.3 (m, 2H), 7.6-7.7 (m, 2H), 8.0 (d, 1H), 8.2-8.5 (m, 3H), 9.1 (d, 1H); HPLC Purity: 99.07%; Mass (M+1): 530.62.

N-(4-(8-(3,5-difluorobenzyl)-3,8-diazabicyclo[3.2.1]
octane-3-carbonyl)phenyl)quinoline-8-sulfonamide
(Compound 218)

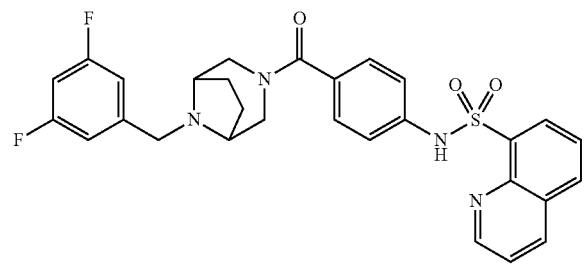 [SMILES: O=C(c1ccc(NS(=O)(=O)c2cccc3cccnc23)cc1)N1CC2CCC(C1)N2Cc1cc(F)cc(F)c1]

$^1$H NMR (400 MHz, CDCl$_3$) δ: 1.7 (br s, 1H), 1.9 (br s, 2H), 3.0 (br s, 2H), 3.2 (br s, 2H), 3.5 (s, 2H), 3.8 (d, 1H), 4.3 (d, 1H), 6.7 (t, 1H), 6.8-6.9 (m, 2H), 7.0-7.2 (m, 3H), 7.5-7.6 (m, 2H), 8.0 (d, 1H), 8.2-8.5 (m, 3H), 9.1 (d, 1H); HPLC Purity: 94.61%; Mass (M+1): 548.60.

N-(4-(8-(cyclopropylmethyl)-3,8-diazabicyclo[3.2.1]
octane-3-carbonyl)phenyl)quinoline-8-sulfonamide
(Compound 221)

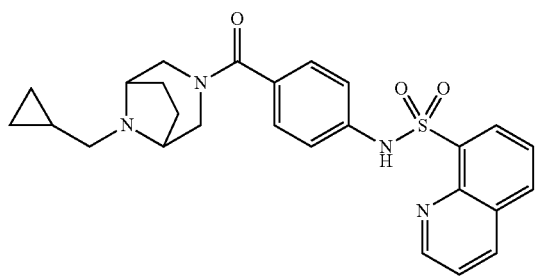 [SMILES: O=C(c1ccc(NS(=O)(=O)c2cccc3cccnc23)cc1)N1CC2CCC(C1)N2CC1CC1]

$^1$H NMR (400 MHz, CDCl$_3$) δ: 0.2-0.3 (m, 2H), 0.4-0.5 (m, 2H), 0.8-0.9 (m, 1H), 1.6-1.9 (m, 4H), 2.1-2.3 (m, 2H), 3.0 (d, 1H), 3.2-3.5 (m, 4H), 4.4 (d, 1H), 7.0-7.2 (m, 3H), 7.5-7.6 (m, 2H), 8.0 (d, 1H), 8.2-8.6 (m, 3H), 9.1 (d, 1H); HPLC Purity: 99.37%; Mass (M+1): 477.59.

Example 13

Preparation of Compounds of Formula Io

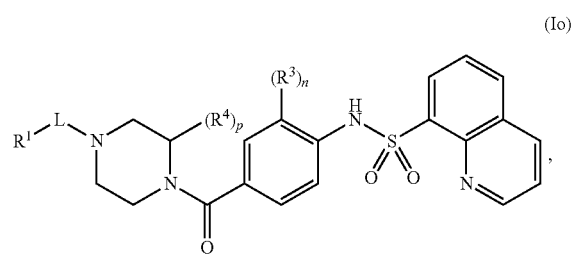
(Io)

wherein R$^1$ is aryl, carbocyclyl, heterocyclyl or heteroaryl; R$^3$ is OCF$_3$ or OCH$_3$; R$^4$ is alkyl; L is —C(O)— or —(CR$^c$R$^c$)—C(O)—; n is 0 or 1; and p is 0 or 1.

Scheme 13:

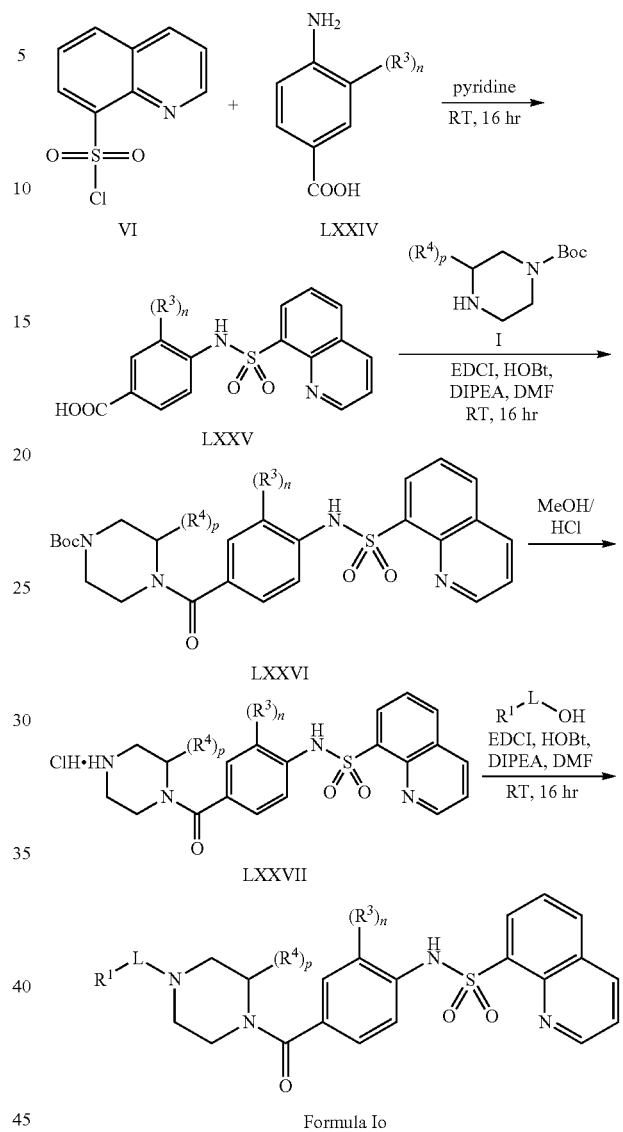

Synthesis of Intermediate LXXV.

To a stirred solution of substituted amine LXXIV (30.3 mmol) under nitrogen atmosphere was added pyridine (50 ml) at 0° C. and stirred for 10 min. Quinoline-8-sulfonyl chloride VI (8.94 gm, 39.4 mmol) was then added to the reaction mixture at the same temperature. The resulting mixture was stirred for 16 h at room temperature. After completion of the reaction, the solvent was removed under reduced pressure. The traces of pyridine were removed by co-distillation with toluene. Diethylether was added to the resulting residue, and the solid product was filtered out and air-dried. The resulting crude product (74%) was taken to the next step without further purification.

Synthesis of Intermediate LXXVI.

To a stirred solution of acid LXXV (0.000315 moles) in DMF (5 ml), were added EDCI (0.066 g, 0.000346 moles), HOBt (0.047 g, 0.000346 moles) and DIPEA (0.13 ml, 0.00078 moles) at 0° C. and stirred for 15 minutes. A solution of amine I (0.000315 moles) was then added at 0° C. and then the resulting mixture was allowed to stir at room temperature overnight. After completion of the reaction, water (20 mL) was added and extracted with ethyl acetate (2×30 ml). The combined organic layer was dried over anhydrous Na₂SO₄ and concentrated under reduced pressure. The crude product was purified by column chromatography (silica gel, 60-120 mess, 70% ethyl acetate in hexane) to give LXXVI in 65-70% yield.

Synthesis of Intermediate LXXVII.

To a solution of MeOH.HCl (10 ml), Boc protected amine LXXVI (4.03 mmol) was added and the resulting mixture was stirred for 2 hr. After completion of reaction, solvent was removed under reduced pressure, washed with water followed by addition of NaHCO₃ and extracted with DCM. The organic layer was dried over Na₂SO₄ and evaporated under reduced pressure to afford product LXXVII in 92% yield.

General procedure for Syntheses of Compounds of Formula Io.

To a stirred solution of aryl/heteroaryl acid (0.000315 moles) in DMF (5 ml), were added EDCI (0.066 g, 0.000346 moles), HOBt (0.047 g, 0.000346 moles) and DIPEA (0.13 ml, 0.00078 moles) at 0° C. and stirred for 15 minutes. A solution of amine LXXVII (0.000315 moles) was then added at 0° C. and then the resulting mixture was allowed to stir at room temperature overnight. After completion of the reaction, water (20 mL) was added and extracted with ethyl acetate (2×30 ml). The combined organic layer was dried over anhydrous Na₂SO₄ and concentrated under reduced pressure. The crude product was purified by column chromatography (silica gel, 60-120 mess, MeOH-DCM, 2:8) to give a compound of Formula Io in 35-50% yield.

The following compounds of Formula Io were made by the above-described method using the appropriate acid (R¹—C(O)OH) and the appropriate Boc-protected amine I.

N-(4-(4-(1,2,3-thiadiazole-5-carbonyl)piperazine-1-carbonyl)phenyl)quinoline-8-sulfonamide (VI-1) Compound 313

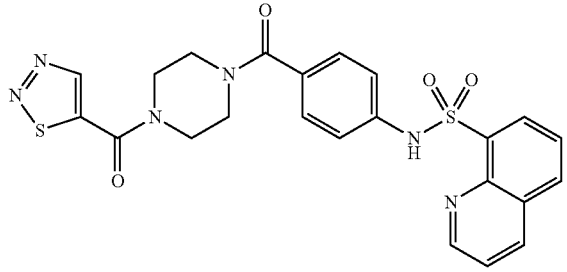 [SMILES: O=C(c1ccc(NS(=O)(=O)c2cccc3cccnc23)cc1)N1CCN(C(=O)c2cnns2)CC1]

¹H NMR (400 MHz, CDCl₃) δ: 3.2-3.5 (m, 8H), 7.2 (m, 4H), 7.6 (m, 2H), 8.3 (m, 2H), 8.8 (m, 2H), 9.1 (m, 1H), 10.0 (bs, 1H); HPLC Purity: 99.55%; Mass (M+1): 509.2.

N-(4-(4-(3-fluoroisonicotinoyl)piperazine-1-carbonyl)phenyl)quinoline-8-sulfonamide (Compound 317)

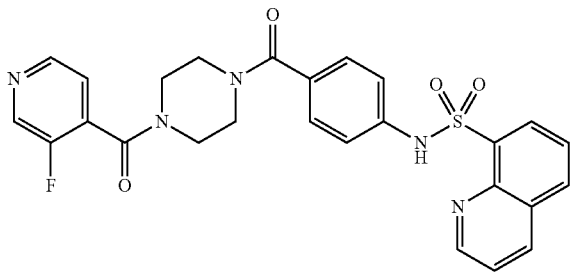 [SMILES: O=C(c1ccc(NS(=O)(=O)c2cccc3cccnc23)cc1)N1CCN(C(=O)c2ccncc2F)CC1]

¹H NMR (400 MHz, CDCl₃) δ: 3.2-3.8 (m, 8H), 7.0 (m, 4H), 7.3 (m, 1H), 7.6 (m, 2H), 8.1 (m, 1H), 8.3 (m, 2H), 8.6 (m, 3H), 9.1 (m, 1H); HPLC Purity: 98.06%; Mass (M+1): 520.30.

N-(4-(4-(3,5-difluorobenzyl)piperazine-1-carbonyl)phenyl)quinoline-8-sulfonamide-(D) (Compound 342)

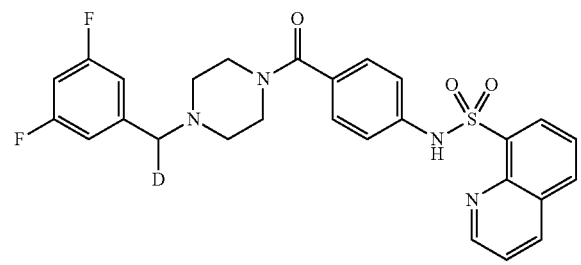

¹H NMR (400 MHz, CDCl₃) δ: 3.0-3.8 (m, 8H), 6.9-7.3 (m, 6H), 7.6 (m, 2H), 7.7-7.9 (m, 2H), 8.0 (m, 1H), 8.3 (m, 1H), 8.6 (m, 1H), 9.0 (m, 1H); HPLC Purity: 99.30%; Mass (M+1): 525.20.

N-(4-(4-(5-methylpyrazine-2-carbonyl)piperazine-1-carbonyl)phenyl)quinoline-8-sulfonamide (Compound 346)

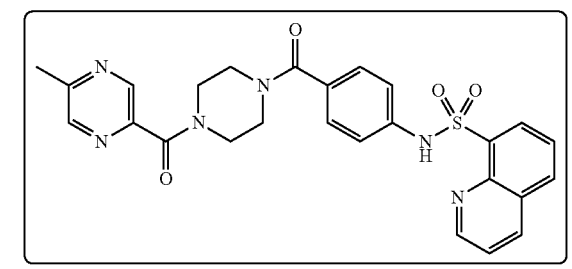 [SMILES: Cc1cnc(C(=O)N2CCN(C(=O)c3ccc(NS(=O)(=O)c4cccc5cccnc45)cc3)CC2)cn1]

¹H NMR (400 MHz, CDCl₃) δ: 2.6 (s, 3H), 3.2-3.9 (m, 8H), 7.0-7.2 (m, 4H), 7.6 (m, 2H), 8.0 (m, 1H), 8.3 (m, 3H), 8.6 (s, 1H), 8.9 (m, 1H), 9.0 (m, 1H); HPLC Purity: 99.74%; Mass (M+1): 517.2.

N-(4-(4-(oxazole-4-carbonyl)piperazine-1-carbonyl)phenyl)quinoline-8-sulfonamide (Compound 347)

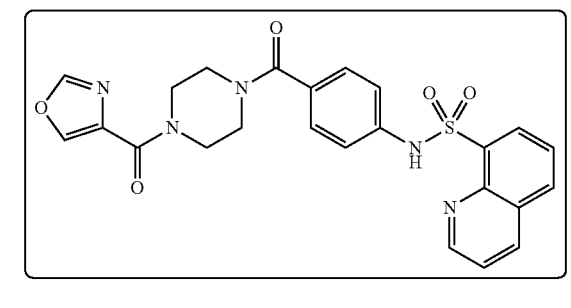 [SMILES: O=C(c1ccc(NS(=O)(=O)c2cccc3cccnc23)cc1)N1CCN(C(=O)c2cocn2)CC1]

¹H NMR (400 MHz, CDCl₃) δ: 3.2-3.9 (m, 8H), 7.0-7.2 (m, 4H), 7.6 (m, 2H), 8.3-8.5 (m, 4H), 9.0 (m, 1H), 10.5 (s, 1H); HPLC Purity: 95.63%; Mass (M+1): 492.15.

N-(4-(4-(thiazole-5-carbonyl)piperazine-1-carbonyl)phenyl)quinoline-8-sulfonamide (Compound 348)

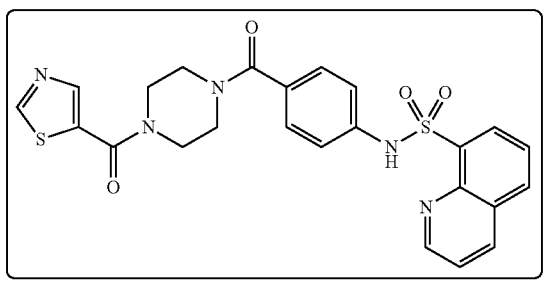 [SMILES: O=C(c1ccc(NS(=O)(=O)c2cccc3cccnc23)cc1)N1CCN(C(=O)c2cncs2)CC1]

¹H NMR (400 MHz, CDCl₃) δ: 3.2-3.9 (m, 8H), 7.0-7.2 (m, 4H), 7.6 (m, 2H), 8.0 (m, 2H), 8.3 (m, 2H), 8.6 (s, 1H), 9.0 (m, 1H), 10.5 (s, 1H); HPLC Purity: 97.14%; Mass (M+1): 508.2.

N-(4-(4-(1H-imidazole-4-carbonyl)piperazine-1-carbonyl)phenyl)quinoline-8-sulfonamide (Compound 349)

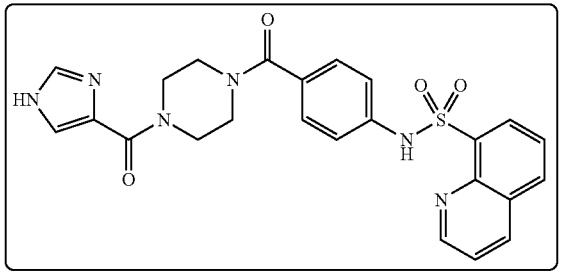 [SMILES: O=C(c1ccc(NS(=O)(=O)c2cccc3cccnc23)cc1)N1CCN(C(=O)c2c[nH]cn2)CC1]

¹H NMR (400 MHz, CDCl₃) δ: 3.2-3.9 (m, 8H), 7.0-7.2 (m, 4H), 7.6 (m, 4H), 8.0 (m, 1H), 8.3 (m, 2H), 8.6 (s, 1H), 9.0 (m, 1H); HPLC Purity: 99.40%; Mass (M+1): 491.2.

N-(4-(4-(1H-imidazole-2-carbonyl)piperazine-1-carbonyl)phenyl)quinoline-8-sulfonamide (Compound 354)

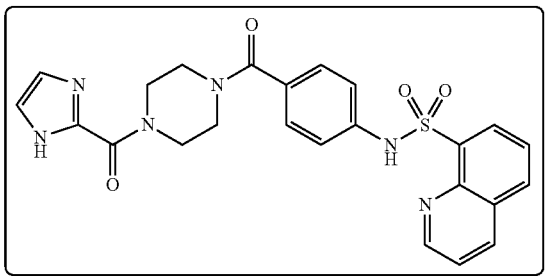 [SMILES: O=C(c1ccc(NS(=O)(=O)c2cccc3cccnc23)cc1)N1CCN(C(=O)c2ncc[nH]2)CC1]

¹H NMR (400 MHz, CDCl₃) δ: 3.2-3.7 (m, 6H), 4.3-4.8 (m, 2H), 7.0-7.1 (m, 5H), 7.6 (m, 2H), 8.0 (m, 1H), 8.2-8.4 (m, 2H), 8.6 (m, 1H), 9.0 (m, 2H) 10.3 (s, 1H); HPLC Purity: 99.22%; Mass (M+1): 491.2.

N-(4-(4-(isoxazole-5-carbonyl)piperazine-1-carbonyl)phenyl)quinoline-8-sulfonamide (Compound 365)

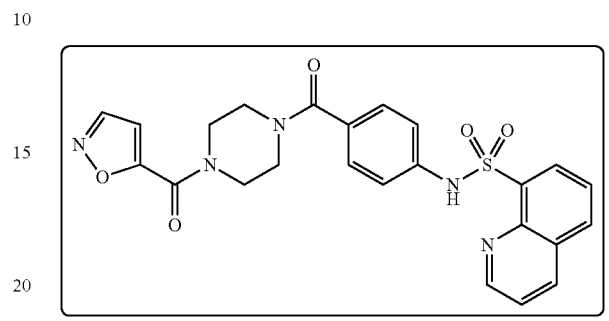

¹H NMR (400 MHz, CDCl₃) δ: 3.2-3.8 (m, 8H), 6.8-7.3 (m, 5H), 7.6 (m, 2H), 8.0 (m, 1H), 8.3-8.4 (m, 3H), 9.0 (m, 1H), 10.4 (m, 1H); HPLC Purity: 99.30%; Mass (M+1): 492.2.

N-(4-(4-(1H-pyrazole-3-carbonyl)piperazine-1-carbonyl)phenyl)quinoline-8-sulfonamide (Compound 350)

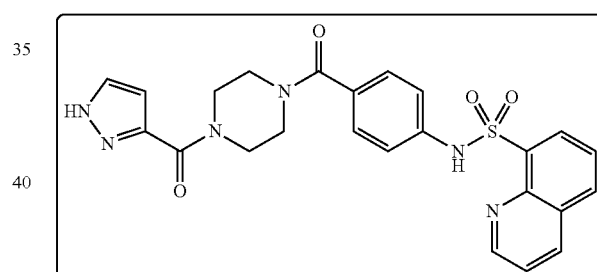

¹H NMR (400 MHz, CDCl₃) δ: 3.2-3.9 (m, 8H), 7.0-7.2 (m, 4H), 7.6 (m, 3H), 8.0 (m, 1H), 8.3 (m, 2H), 8.6 (s, 1H), 9.0 (m, 1H); HPLC Purity: 99.97%; Mass (M+1): 491.2.

N-(4-(4-(thiazole-2-carbonyl)piperazine-1-carbonyl)phenyl)quinoline-8-sulfonamide (Compound 371)

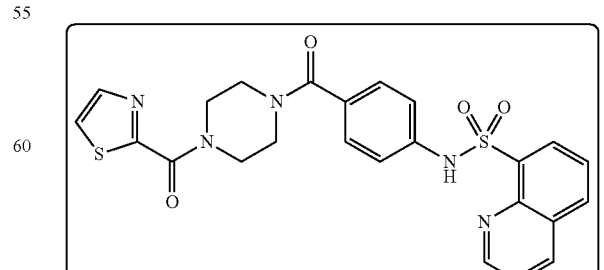

¹H NMR (400 MHz, CDCl₃) δ: 3.4-3.8 (m, 8H), 7.1-7.2 (m, 4H), 7.6 (m, 2H), 8.1-8.4 (m, 4H), 8.6 (m, 1H), 8.9 (m, 1H), 9.0 (m, 1H); HPLC Purity: 97.89%; Mass (M+1): 508.30.

N-(4-(4-(tetrahydro-2H-pyran-4-carbonyl)piperazine-1-carbonyl)phenyl)quinoline-8-sulfonamide (Compound 417)

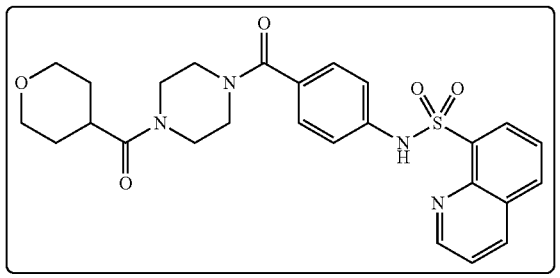 [SMILES: O=C(c1ccc(NS(=O)(=O)c2cccc3cccnc23)cc1)N1CCN(C(=O)C2CCOCC2)CC1]

¹H NMR (400 MHz, DMSOd₆) δ: 1.2-1.6 (m, 8H), 2.8-3.0 (m, 2H), 3.4-3.7 (m, 4H), 3.75-3.8 (m, 2H), 7.0-7.2 (m, 4H), 7.56-7.8 (m, 2H), 8.2-8.4 (m, 3H), 9.0-9.2 (m, 1H), 10.45 (s, 1H); HPLC Purity: 96.68%; Mass (M+Na): 531.2.

N-(4-(4-(tetrahydrofuran-3-carbonyl)piperazine-1-carbonyl)phenyl)quinoline-8-sulfonamide (Compound 418)

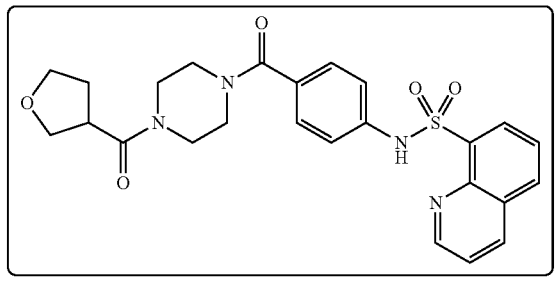 [SMILES: O=C(c1ccc(NS(=O)(=O)c2cccc3cccnc23)cc1)N1CCN(C(=O)C2CCOC2)CC1]

¹H NMR (400 MHz, CDCl₃) δ: 1.95-2.2 (m, 2H), 3.2-3.6 (m, 8H), 3.65-3.8 (m, 5H), 7.0-7.5 (m, 4H), 7.56-7.8 (m, 2H), 8.2-8.4 (m, 3H), 9.1-9.2 (m, 1H), 10.5 (m, 1H); HPLC Purity: 99.65%; Mass (M+1): 495.2.

N-(4-(4-(cyclobutylmethyl)piperazine-1-carbonyl)phenyl)quinoline-8-sulfonamide (Compound 419)

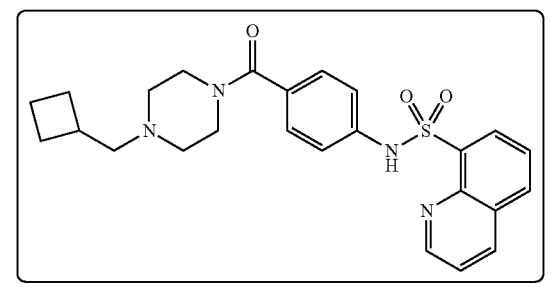 [SMILES: O=C(c1ccc(NS(=O)(=O)c2cccc3cccnc23)cc1)N1CCN(CC2CCC2)CC1]

¹H NMR (400 MHz, CDCl₃) δ: 1.6-2.1 (m, 6H), 2.2-2.8 (m, 7H), 3.2-3.8 (m, 4H), 7.0-7.3 (m, 4H), 7.5-7.7 (m, 2H), 8.2-8.4 (m, 3H), 9.1-9.2 (m, 1H); HPLC Purity: 95.52%; Mass (M+1): 465.2.

N-(4-(4-(tetrahydro-2H-pyran-2-carbonyl)piperazine-1-carbonyl)phenyl)quinoline-8-sulfonamide (Compound 430)

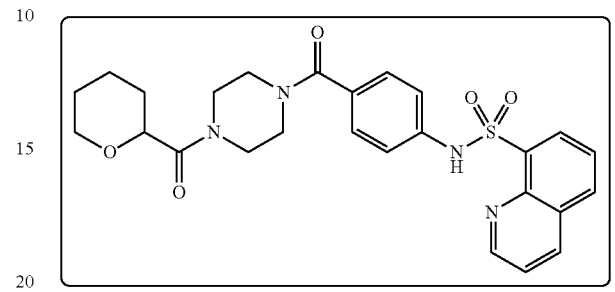

¹H NMR (400 MHz, CDCl₃) δ: 1.2-1.6 (m, 5H), 1.6-1.8 (m, 1H), 3.0-3.2 (m, 3H), 3.4-3.6 (m, 6H), 3.8-4.2 (m, 2H), 7.0-7.4 (m, 4H), 7.6-7.8 (m, 2H), 8.0-8.6 (m, 3H), 9.1-9.2 (m, 1H), 10.5 (s, 1H); HPLC Purity: 97.96%; Mass (M+1): 509.2.

N-(4-(4-(tetrahydrofuran-2-carbonyl)piperazine-1-carbonyl)phenyl)quinoline-8-sulfonamide (Compound 443)

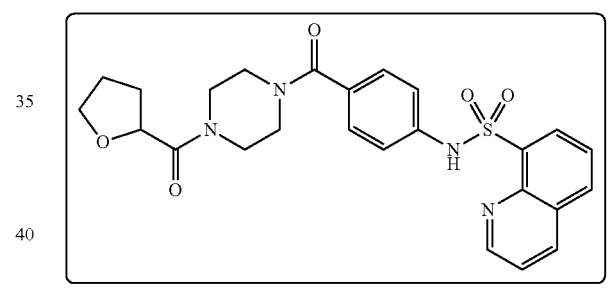

¹H NMR (400 MHz, DMSOd₆) δ: 1.2-1.4 (m, 3H), 1.6-2.1 (m, 4H), 2.9-3.3 (m, 6H), 3.4-3.6 (m, 2H), 7.0-7.25 (m, 4H), 7.6-7.8 (m, 2H), 8.2-8.6 (m, 3H), 9.1-9.2 (m, 1H) 10.5 (bs, 1H); HPLC Purity: 97.44%; Mass (M+1): 484.25.

(R)—N-(4-(4-(cyclobutylmethyl)-2-methylpiperazine-1-carbonyl)phenyl)quinoline-8-sulfonamide (Compound 206)

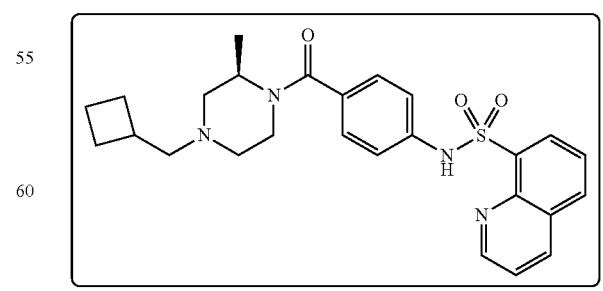

¹H NMR (400 MHz, CDCl₃) δ: 1.2 (d, 3H), 1.6-2.1 (m, 8H), 2.2-2.8 (m, 5H), 4.0-4.1 (m, 3H), 7.0-7.2 (m, 4H), 7.5-

7.7 (m, 2H), 8.2-8.4 (m, 3H), 9.1-9.2 (m, 1H), 10.4 (s, 1H); HPLC Purity: 96.13%; Mass (M+1): 479.15.

N-(4-(4-(2,3-difluorobenzoyl)piperazine-1-carbonyl)-2-methoxyphenyl)quinoline-8-sulfonamide (Compound 318)

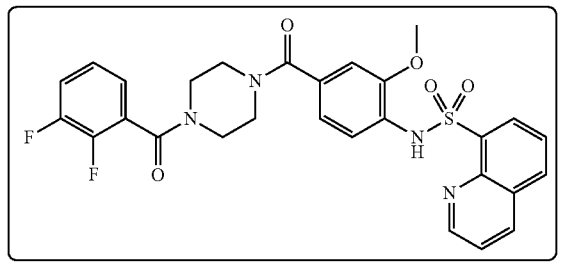 [SMILES: COc1cc(C(=O)N2CCN(C(=O)c3cccc(F)c3F)CC2)ccc1NS(=O)(=O)c1cccc2cccnc12]

¹H NMR (400 MHz, CDCl₃) δ: 3.3 (s, 3H), 3.2-3.8 (m, 8H), 6.8 (m, 2H), 7.2 (m, 2H), 7.6 (m, 3H), 8.0 (m, 1H), 8.2-8.4 (m, 2H), 9.1 (m, 1H); HPLC Purity: 96.96%; Mass (M+1): 567.30.

N-(4-(4-(3,4-difluorobenzoyl)piperazine-1-carbonyl)-2-methoxyphenyl)quinoline-8-sulfonamide (Compound 319)

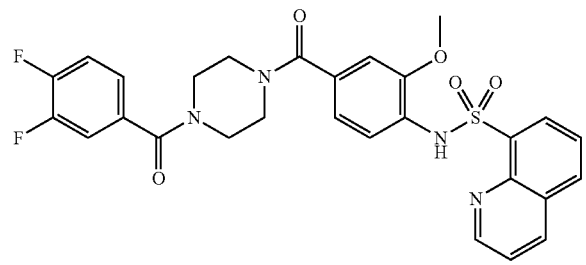 [SMILES: COc1cc(C(=O)N2CCN(C(=O)c3ccc(F)c(F)c3)CC2)ccc1NS(=O)(=O)c1cccc2cccnc12]

¹H NMR (400 MHz, CDCl₃) δ: 3.4 (s, 3H), 3.5-3.8 (m, 8H), 6.8 (m, 2H), 7.2 (m, 2H), 7.6 (m, 3H), 8.0 (m, 1H), 8.2-8.4 (m, 2H), 8.8 (m, 1H), 9.1 (m, 1H); HPLC Purity: 95.87%; Mass (M+1): 567.30.

N-(4-(4-(2-fluoro-3-methoxybenzoyl)piperazine-1-carbonyl)-2-methoxyphenyl)quinoline-8-sulfonamide (Compound 320)

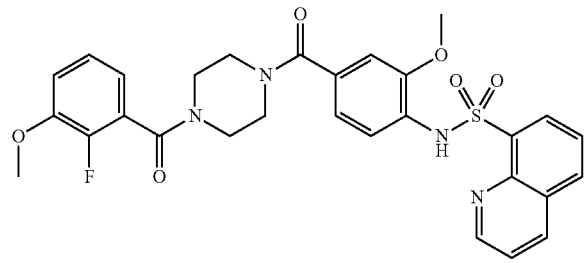 [SMILES: COc1cc(C(=O)N2CCN(C(=O)c3cccc(OC)c3F)CC2)ccc1NS(=O)(=O)c1cccc2cccnc12]

¹H NMR (400 MHz, CDCl₃) δ: 3.2 (s, 3H), 3.4 (s, 3H), 3.6-3.8 (m, 8H), 6.8-7.0 (m, 5H), 7.6 (m, 3H), 8.0 (m, 1H), 8.2-8.4 (m, 2H), 8.8 (m, 1H), 9.1 (m, 1H); HPLC Purity: 95.65%; Mass (M+1): 579.40.

N-(4-(4-(1,2,3-thiadiazole-4-carbonyl)piperazine-1-carbonyl)-2-methoxyphenyl)quinoline-8-sulfonamide (Compound 321)

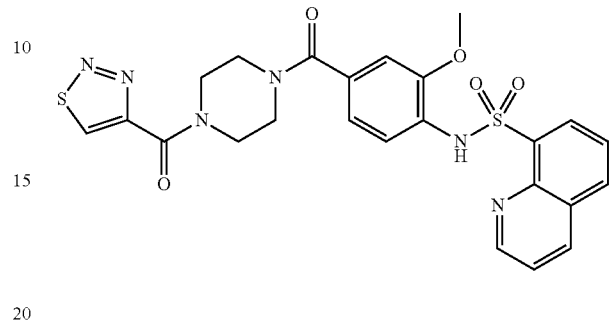

¹H NMR (400 MHz, CDCl₃) δ: 3.4 (s, 3H), 3.6-3.8 (m, 8H), 6.8 (m, 2H), 7.6 (m, 3H), 8.0 (m, 1H), 8.2 (m, 1H), 8.4 (m, 1H), 8.9 (s, 1H), 9.1 (m, 1H), 9.2 (m, 1H); HPLC Purity: 98.30%; Mass (M+1): 539.25.

N-(2-methoxy-4-(4-(thiazole-4-carbonyl)piperazine-1-carbonyl)phenyl)quinoline-8-sulfonamide (Compound 322)

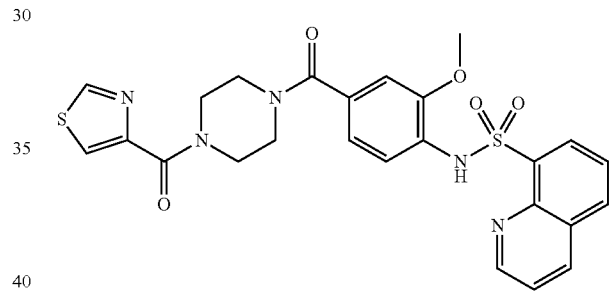

¹H NMR (400 MHz, CDCl₃) δ: 3.4 (s, 3H), 3.6-3.8 (m, 8H), 6.8 (m, 2H), 7.6 (m, 4H), 8.0 (m, 2H), 8.2 (m, 1H), 8.4 (m, 1H), 8.7 (m, 1H), 8.9 (s, 1H), 9.1 (m, 1H); HPLC Purity: 96.49%; Mass (M+1): 538.10.

N-(4-(4-nicotinoylpiperazine-1-carbonyl)-2-(trifluoromethoxy)phenyl)quinoline-8-sulfonamide (Compound 323)

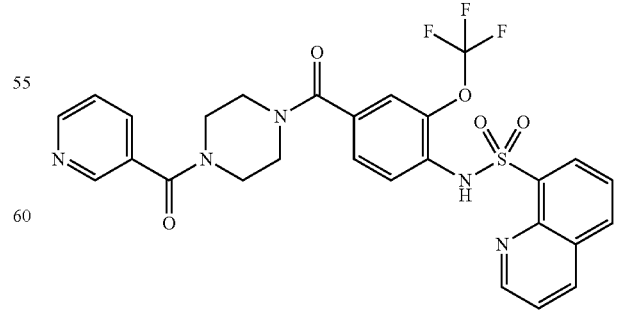

¹H NMR (400 MHz, CDCl₃) δ: 3.4-3.8 (m, 8H), 7.2 (m, 2H), 7.4 (m, 1H), 7.6 (m, 2H), 7.8 (m, 1H), 8.0 (m, 1H), 8.1

(m, 1H), 8.2 (m, 1H), 8.4 (m, 2H), 8.6 (m, 1H), 9.1 (m, 1H); HPLC Purity: 99.38%; Mass (M+1): 586.27.

N-(4-(4-(thiazole-4-carbonyl)piperazine-1-carbonyl)-2-(trifluoromethoxy)phenyl)quinoline-8-sulfonamide (Compound 324)

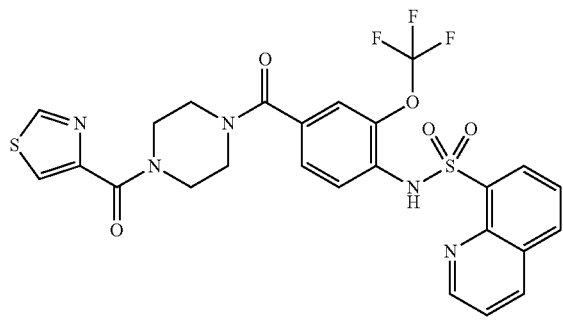 [SMILES: O=C(c1ccc(NS(=O)(=O)c2cccc3cccnc23)c(OC(F)(F)F)c1)N1CCN(C(=O)c2cscn2)CC1]

$^1$H NMR (400 MHz, CDCl$_3$) δ: 3.4-3.8 (m, 8H), 7.2 (m, 2H), 7.5 (m, 2H), 8.0 (m, 3H), 8.4 (m, 2H), 8.8 (m, 1H), 9.1 (m, 1H); HPLC Purity: 99.30%; Mass (M+1): 592.15.

N-(4-(4-(5-methylpyrazine-2-carbonyl)piperazine-1-carbonyl)-2-trifluoromethoxy)phenyl)quinoline-8-sulfonamide (Compound 325)

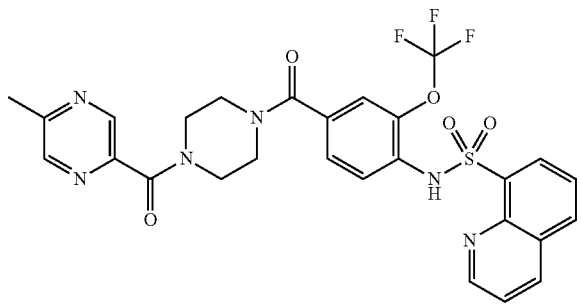 [SMILES: Cc1cnc(C(=O)N2CCN(C(=O)c3ccc(NS(=O)(=O)c4cccc5cccnc45)c(OC(F)(F)F)c3)CC2)cn1]

$^1$H NMR (400 MHz, CDCl$_3$) δ: 2.6 (s, 3H), 3.5-3.8 (m, 3H), 7.2 (m, 2H), 7.6 (m, 2H), 8.0 (m, 2H), 8.4 (m, 3H), 8.9 (m, 1H), 9.1 (m, 1H); HPLC Purity: 97.67%; Mass (M+1): 601.30.

N-(4-(4-(3,5-difluorobenzoyl)piperazine-1-carbonyl)-2-(trifluoromethoxy)phenyl)quinoline-8-sulfonamide (Compound 326)

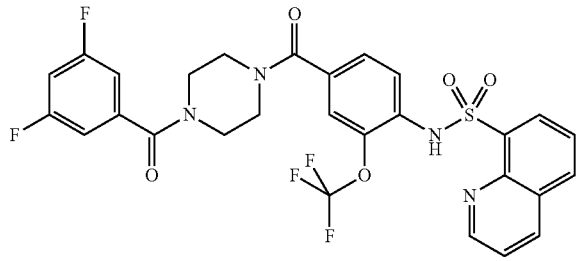 [SMILES: O=C(c1cc(F)cc(F)c1)N1CCN(C(=O)c2ccc(NS(=O)(=O)c3cccc4cccnc34)c(OC(F)(F)F)c2)CC1]

$^1$H NMR (400 MHz, CDCl$_3$) δ: 3.3-3.8 (m, 8H), 6.9 (m, 3H), 7.2 (m, 2H), 7.6 (m, 2H), 8.0 (m, 2H), 8.4 (m, 2H), 9.1 (m, 1H); HPLC Purity: 99.48%; Mass (M+1): 621.25

N-(4-(4-(3,5-dimethylbenzoyl)piperazine-1-carbonyl)-2-(trifluoromethoxy)phenyl)quinoline-8-sulfonamide (Compound 327)

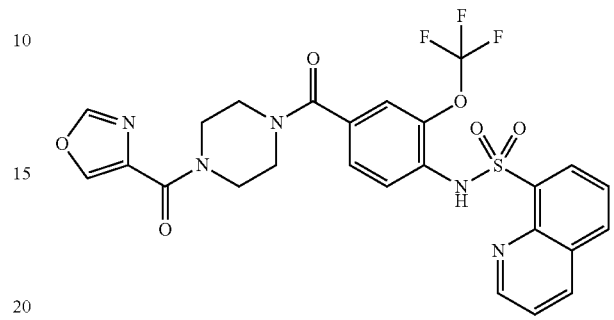

$^1$H NMR (400 MHz, CDCl$_3$) δ: 3.5-4.2 (m, 8H), 7.2 (m, 3H), 7.6 (m, 2H), 7.9 (m, 1H), 8.1 (m, 1H), 8.3 (m, 1H), 8.4 (m, 1H), 9.1 (m, 2H); HPLC Purity: 96.80%; Mass (M+1): 576.25.

Example 14

Preparation of Compounds of Formula Ip

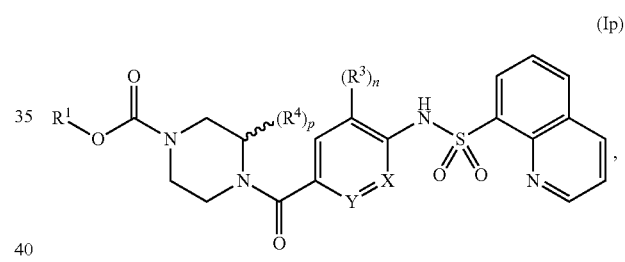

wherein R$^1$ is alkyl, cycloalkyl, aryl, or heteroaryl; R$^3$ is OCH$_3$, or OCF$_3$; R$^4$ is alkyl; X and Y are independently selected from CH and N; p is 0 or 1; and n is 0 or 1.

Scheme 14

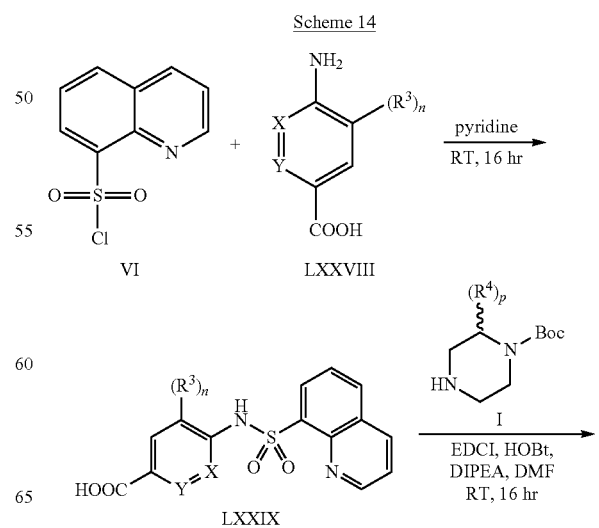

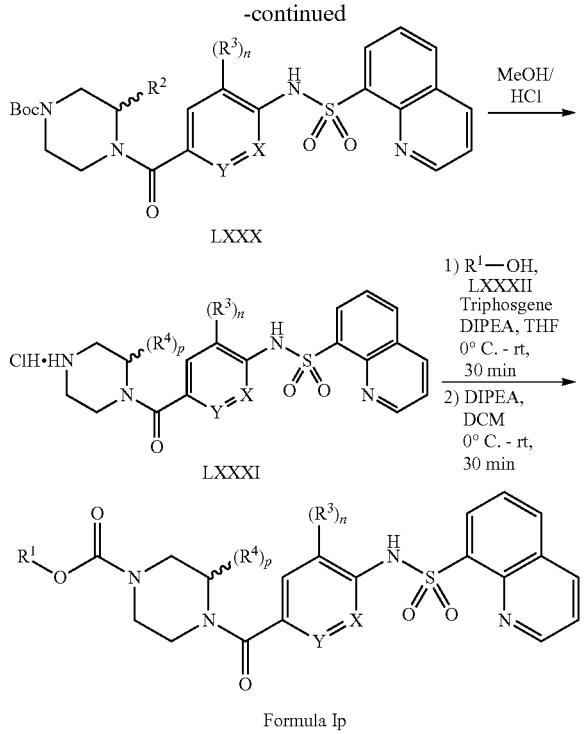

Formula Ip

Synthesis of Intermediate LXXIX.

To a stirred solution of appropriately substituted amine LXXVIII (30.3 mmol) under nitrogen atmosphere was added pyridine (50 ml) at 0° C. and stirred for 10 min Quinoline-8-sulfonyl chloride VI (8.94 gm, 39.4 mmol) was then added to the reaction mixture at the same temperature. The resulting mixture was stirred for 16 h at room temperature. After completion of the reaction, the solvent was removed under reduced pressure. The traces of pyridine were removed by co-distillation with toluene. Diethyl ether was added to the resulting residue, and the solid product was filtered out and air-dried. The resulting crude product LXXIX (74%) was taken to the next step without further purification.

Synthesis of Intermediate LXXX.

To a stirred solution of acid LXXIX (0.000315 moles) in DMF (5 ml), were added EDCI (0.066 g, 0.000346 moles), HOBt (0.047 g, 0.000346 moles) and DIPEA (0.13 ml, 0.00078 moles) at 0° C. and stirred for 15 minutes. A solution of amine I (0.000315 moles) was then added at 0° C. and the resulting mixture was allowed to stir at room temperature overnight. After completion of the reaction, water (20 mL) was added and extracted with ethyl acetate (2×30 ml). The combined organic layer was dried over anhydrous Na$_2$SO$_4$ and concentrated under reduced pressure. The crude product was purified by column chromatography (silica gel, 60-120 mess, 70% ethyl acetate in hexane) to give LXXX in 45-55% yield.

Synthesis of Intermediate LXXXI.

To a solution of MeOH.HCl (12 ml), Boc protected amine LXXX (4.03 mmol) was added and the resulting mixture was stirred for 2 h. After completion of reaction, solvent was removed under reduced pressure, washed with water followed by addition of NaHCO$_3$ and extracted with DCM. The organic layer was dried over Na$_2$SO$_4$ and evaporated under reduced pressure to afford product LXXXI in 94% yield.

General procedure for Syntheses of Compounds of Formula Ip.

To a stirred solution of Triphosgene (1.7 g, 57 mmol) in dry THF (15 ml) was added alcohol LXXXII (39 mmol) at 0° C. under nitrogen atmosphere and reaction mixture was stirred further for 15 minutes at room temperature. DIPEA (2.5 ml, 0.014 moles) was added slowly to the reaction mixture and stirred for further 30 minutes. The reaction mixture was filtered and filtrate was concentrated under reduced pressure to leave the crude chloroformate which was used for the next step.

To a stirred solution of amine IX (24.3 mmol) in dry DCM (10 ml) was added DIPEA (0.1 ml, 0.007 moles) at 0° C. under nitrogen atmosphere. The crude chloroformate (29.2 mmol) was added to the reaction mixture and stirred further for 30 minutes at room temperature. After completion of the reaction, water (10 mL) was added and extracted with DCM (2×30 ml). The combined organic layer was dried over anhydrous Na$_2$SO$_4$ and concentrated under reduced pressure. The crude product was purified by column chromatography (silica gel, 60-120 mess, MeOH-DCM, 1:9) to give a compound of Formula Ip in 50-60% yield.

The following compounds of Formula Ip were made by the above-described method using the appropriate acid LXXVIII, the appropriate alcohol LXXXII and the appropriate Boc-protected amine I.

Pyridin-2-yl 4-(3-methoxy-4-(quinoline-8-sulfonamido)benzoyl)piperazine-1-carboxylate (XI-3) (Compound 315)

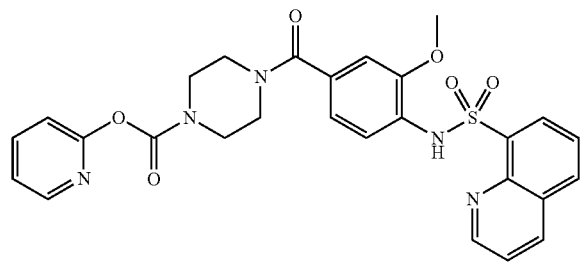 [SMILES: COc1cc(C(=O)N2CCN(C(=O)Oc3ccccn3)CC2)ccc1NS(=O)(=O)c1cccc2cccnc12]

$^1$H NMR (400 MHz, CDCl$_3$) δ: 3.4-3.7 (m, 8H), 6.9 (m, 2H), 7.2 (m, 2H), 7.6 (m, 3H), 7.9 (m, 1H), 8.1 (m, 1H), 8.3 (m, 1H), 8.5 (m, 1H), 9.1 (m, 1H); HPLC Purity: 97.17%; Mass (M+1): 548.20.

(S)-Tetrahydrofuran-3-yl-4-(4-(quinoline-8-sulfonamido)-3-(trifluoromethoxy)benzoyl)piperazine-1-carboxylate (Compound 343)

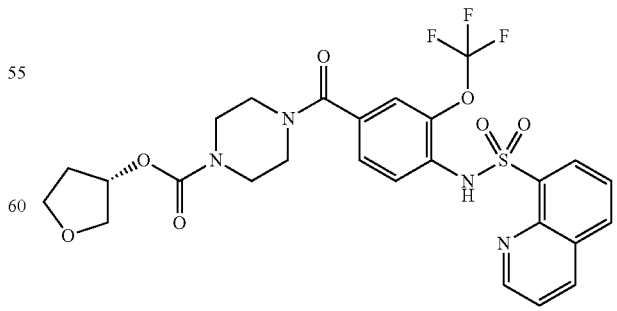

$^1$H NMR (400 MHz, DMSO-d$_6$) δ: 2.2 (m, 2H), 3.2-3.7 (m, 4H), 3.9 (m, 2H), 5.1 (m, 1H), 7.2 (m, 2H), 7.6 (m, 2H), 7.8

(m, 1H), 8.1 (m, 1H), 8.4 (m, 2H), 9.1 (m, 1H), 10.0 (bs, 1H); HPLC Purity: 98.45%; Mass (M+1): 595.3.

2-cyclopentylethyl-4-(4-(quinoline-8-sulfonamido)-3-(trifluoromethoxy)benzoyl)piperazine-1-carboxylate (Compound 312)

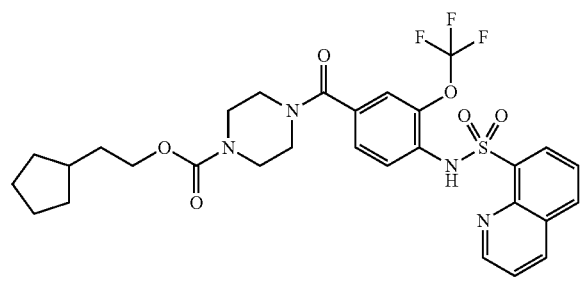 [SMILES: O=C(OCCC1CCCC1)N1CCN(C(=O)c2ccc(NS(=O)(=O)c3cccc4cccnc34)c(OC(F)(F)F)c2)CC1]

¹H NMR (400 MHz, CDCl₃) δ: 1.2 (m, 6H), 1.7 (m, 6H), 3.2-3.5 (m, 8H), 4.6 (m, 1H), 7.2 (m, 2H), 7.6 (m, 2H), 8.1 (m, 2H), 8.4 (m, 2H), 9.1 (m, 1H), 10.0 (bs, 1H); HPLC Purity: 99.18%; Mass (M+1): 621.4.

tetrahydro-2H-pyran-4-yl-4-(4-(quinoline-8-sulfonamido)-3-(trifluoromethoxy)benzoyl)piperazine-1-carboxylate (Compound 314)

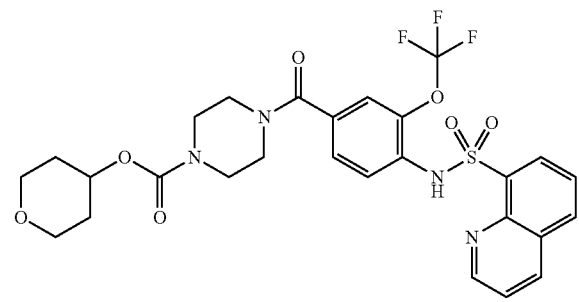 [SMILES: O=C(OC1CCOCC1)N1CCN(C(=O)c2ccc(NS(=O)(=O)c3cccc4cccnc34)c(OC(F)(F)F)c2)CC1]

¹H NMR (400 MHz, CDCl₃) δ: 1.6 (m, 3H), 2.1 (m, 1H), 3.3-3.6 (m, 10H), 3.9 (m, 2H), 4.8 (m, 1H), 7.2 (m, 2H), 7.6 (m, 2H), 7.9 (m, 1H), 8.1 (m, 1H), 8.4 (m, 2H), 9.1 (m, 1H); HPLC Purity: 99.45%; Mass (M+1): 609.4.

(tetrahydrofuran-2-yl)methyl-4-(4-(quinoline-8-sulfonamido)-3-(trifluoromethoxy)benzoyl)piperazine-1-carboxylate (Compound 316)

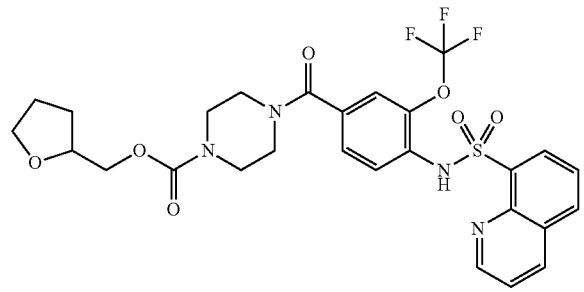 [SMILES: O=C(OCC1CCCO1)N1CCN(C(=O)c2ccc(NS(=O)(=O)c3cccc4cccnc34)c(OC(F)(F)F)c2)CC1]

¹H NMR (400 MHz, CDCl₃) δ: 1.6 (m, 1H), 1.9-2.0 (m, 3H), 3.4-3.7 (m, 8H), 3.8 (m, 2H), 4.2 (m, 3H), 6.9 (m, 2H), 7.2 (m, 2H), 7.6 (m, 3H), 7.9 (m, 1H), 8.1 (m, 1H), 8.3 (m, 1H), 8.5 (m, 1H), 9.1 (m, 1H); HPLC Purity: 96%; Mass (M+1): 609.30.

(R)-tetrahydrofuran-3-yl4-(4-(quinoline-8-sulfonamido)-3-(trifluoromethoxy)benzoyppiperazine-1-carboxylate (Compound 311)

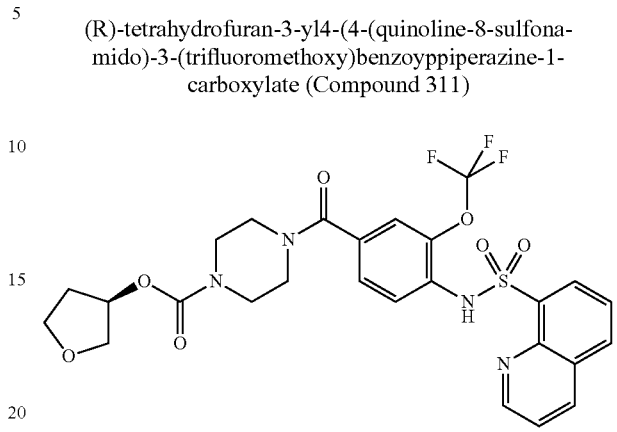

¹H NMR (400 MHz, DMSOd₆) δ: 2.2 (m, 2H), 3.2-3.7 (m, 8H), 4.0 (m, 4H), 5.2 (m, 1H), 7.2 (m, 2), 7.8 (m, 2H), 8.0 (m, 2H), 8.4 (m, 2H), 9.0 (m, 1H); HPLC Purity: 99.63%; Mass (M+1): 595.35.

Pyridin-2-yl4-(4-(quinoline-8-sulfonamido)-3-(trifluoromethoxy)benzoyl)piperazine-1-carboxylate (Compound 344)

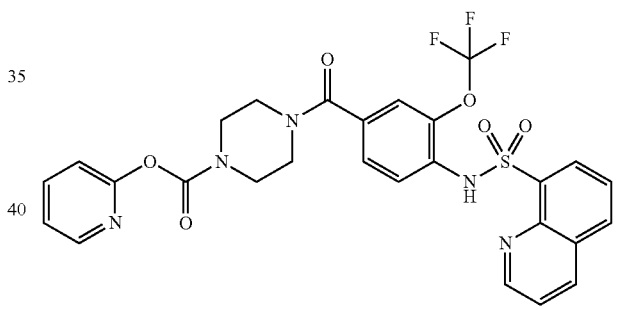

¹H NMR (400 MHz, CDCl₃) δ: 3.0-3.8 (m, 8H), 7.0 (m, 6H), 7.6 (m, 2H), 7.7-7.9 (m, 2H), 8.0 (m, 1H), 8.4 (m, 3H), 9.0 (m, 1H); HPLC Purity: 94.84%; Mass (M+1): 601.0.

(S)-Ethyl 3-methyl-4-(4-(quinoline-8-sulfonamido)benzoyl)piperazine-1-carboxylate (Compound 107)

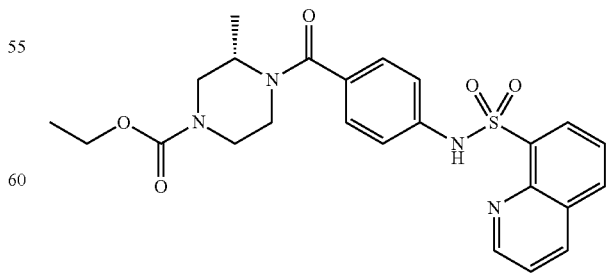

¹H NMR (400 MHz, CDCl₃) δ: 1.2 (t, 3H), 1.6 (q, 2H), 3.0-3.4 (m, 3H), 3.8-4.2 (m, 4H), 5.0 (m, 1H), 7.0-7.3 (m,

4H), 7.6 (m, 2H), 8.0 (m, 1H), 8.2-8.4 (m, 2H), 8.6 (s, 1H), 9.0 (m, 1H); HPLC Purity: 99.05%; Mass (M+1): 483.2.

(S)-isopropyl 3-methyl-4-(4-(quinoline-8-sulfonamido)benzoyl)piperazine-1-carboxylate (Compound 108)

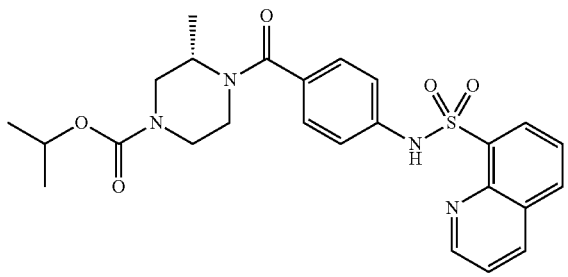 [SMILES: CC(C)OC(=O)N1CCN(C(=O)c2ccc(NS(=O)(=O)c3cccc4cccnc34)cc2)[C@@H](C)C1]

¹H NMR (400 MHz, CDCl₃) δ: 1.2 (d, 6H), 1.4 (m, 1H), 2.8-3.2 (m, 2H), 3.8-4.2 (m, 4H), 5.0 (m, 1H), 7.0-7.2 (m, 4H), 7.6 (m, 2H), 8.0 (m, 1H), 8.2-8.4 (m, 2H), 8.6 (s, 1H), 9.0 (m, 1H); HPLC Purity: 99.77%; Mass (M+1): 497.3.

(R)-Ethyl 3-methyl-4-(4-(quinoline-8-sulfonamido)benzoyl)piperazine-1-carboxylate (Compound 109)

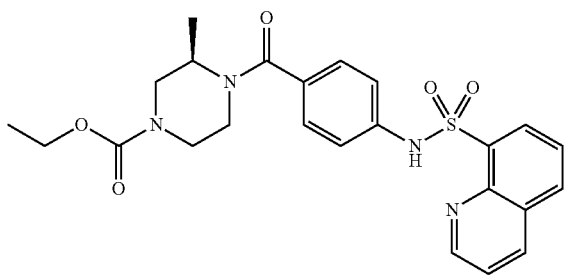 [SMILES: CCOC(=O)N1CCN(C(=O)c2ccc(NS(=O)(=O)c3cccc4cccnc34)cc2)[C@H](C)C1]

¹H NMR (400 MHz, CDCl₃) δ: 1.2 (t, 2H), 1.4 (q, 2H), 2.2 (d, 3H), 3.4-3.8 (m, 7H), 7.0-7.2 (m, 4H), 7.6 (m, 2H), 8.1 (m, 1H), 8.2-8.4 (m, 2H), 8.6 (m, 1H), 9.0 (m, 1H); HPLC Purity: 99.23%; Mass (M+1): 483.20.

(R)-Isopropyl 3-methyl-4-(4-(quinoline-8-sulfonamido)benzoyl)piperazine-1-carboxylate (Compound 110)

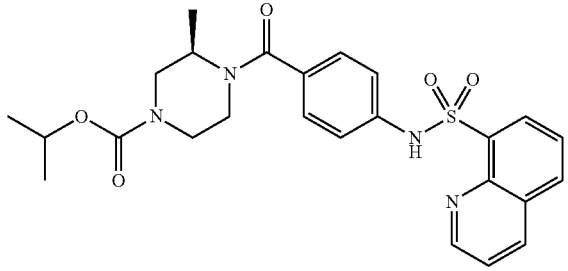 [SMILES: CC(C)OC(=O)N1CCN(C(=O)c2ccc(NS(=O)(=O)c3cccc4cccnc34)cc2)[C@H](C)C1]

¹H NMR (400 MHz, DMSO-d₆) δ: 1.2 (d, 9H), 1.25 (m, 1H), 2.8-3.2 (m, 4H), 3.8-4.2 (m, 2H), 4.9 (m, 1H), 7.0-7.2 (m, 4H), 7.55-7.6 (m, 2H), 8.0 (d, 1H), 8.38 (d, 2H), 8.5 (s, 1H), 9.0 (m, 1H); HPLC Purity: 99.23%; Mass (M+1): 497.40.

(S)-Cyclopropylmethyl 3-methyl-4-(4-(quinoline-8-sulfonamido)benzoyl)piperazine-1-carboxylate (Compound 111)

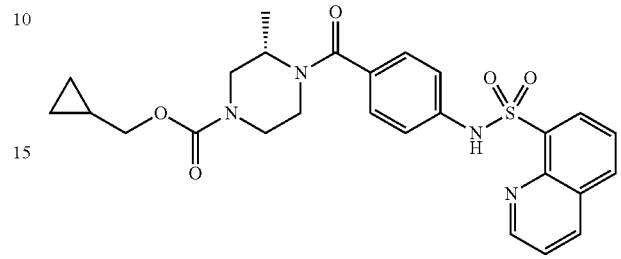

¹H NMR (400 MHz, CDCl₃) δ: 0.1 (m, 1H), 0.2 (m, 2H), 0.5 (m, 2H), 1.2 (s, 3H), 2.6-3.2 (m, 4H), 2.8-3.0 (m, 3H), 3.8-4.2 (m, 6H), 7.0-7.2 (m, 4H), 7.55-7.6 (m, 2H), 8.0 (d, 1H), 8.2-8.4 (d, 2H), 8.5 (s, 1H), 9.0 (m, 1H); HPLC Purity: 99.02%; Mass (M+1): 509.3.

(R)-Cyclopropylmethyl 3-methyl-4-(4-(quinoline-8-sulfonamido)benzoyl)piperazine-1-carboxylate (Compound 112)

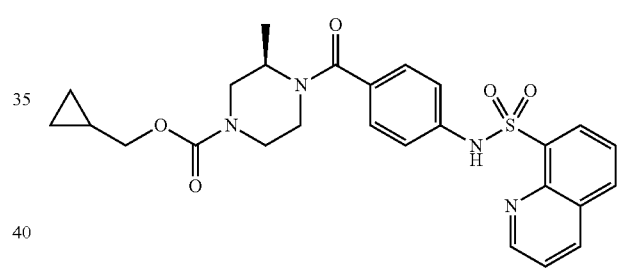

¹H NMR (400 MHz, CDCl₃) δ: 0.3 (m, 2H), 0.5 (m, 2H), 1.2 (d, 3H), 1.3 (m, 1H), 2.8-3.2 (m, 4H), 3.8-4.2 (m, 5H), 7.0-7.2 (m, 4H), 7.55-7.6 (m, 1H), 8.0 (d, 1H), 8.2-8.4 (d, 2H), 8.57 (s, 1H), 9.0 (m, 1H); HPLC Purity: 92.31%; Mass (M+1): 509.3.

(R)-2-Cyclohexylethyl 3-methyl-4-(4-(quinoline-8-sulfonamido)benzoyl)piperazine-1-carboxylate (Compound 121)

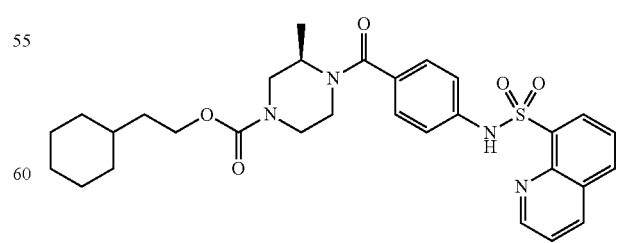

¹H NMR (400 MHz, CDCl₃) δ: 0.85 (m, 2H), 1.15-1.2 (m, 10H), 1.4-1.56 (m, 2H), 1.59-1.67 (m, 1H), 1.8 (d, 3H), 2.7-3.2 (m, 4H), 3.8-4.2 (m, 2H), 7.19-7.3 (m, 4H), 7.5-7.6 (m, 2), 8.0 (d, 1H), 8.2-8.4 (m, 2H), 9.1 (m, 1H); HPLC Purity: 97.73%; Mass (M+1): 565.25.

(R)-2-Cyclopentylethyl-3-methyl-4-(4-(quinoline-8-sulfonamido)benzoyl)piperazine-1-carboxylate (Compound 122)

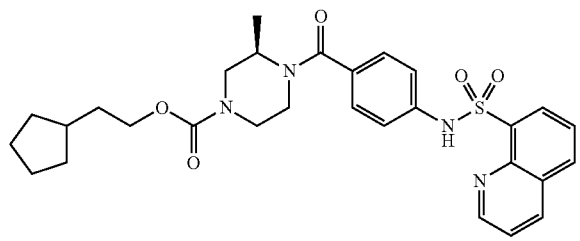 [SMILES: C[C@@H]1CN(C(=O)OCCC2CCCC2)CCN1C(=O)c1ccc(NS(=O)(=O)c2cccc3cccnc23)cc1]

¹H NMR (400 MHz, CDCl₃) δ: 1.2-1.4 (m, 10H), 1.4-1.56 (m, 5H), 2.0 (m, 1H), 2.7-3.2 (m, 3H), 3.8-4.2 (m, 2H), 7.0-7.2 (m, 4H), 7.5-7.6 (m, 2), 8.0 (d, 1H), 8.2-8.4 (m, 2H), 9.1 (m, 1H); HPLC Purity: 99.96%; Mass (M+1): 551.23.

(R)-Cyclohexyl 3-methyl-4-(4-(quinoline-8-sulfonamido)benzoyl)piperazine-1-carboxylate (Compound 123)

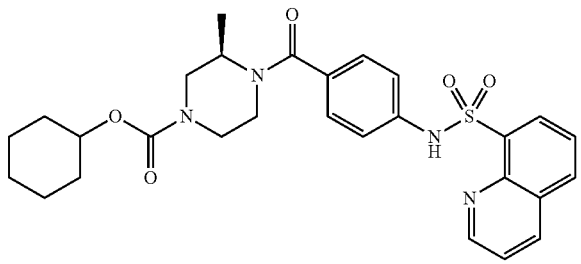 [SMILES: C[C@@H]1CN(C(=O)OC2CCCCC2)CCN1C(=O)c1ccc(NS(=O)(=O)c2cccc3cccnc23)cc1]

¹H NMR (400 MHz, CDCl₃) δ: 1.2 (d, 3H), 1.23-1.4 (m, 8H), 1.5 (m, 1H), 1.6 (m, 2H), 1.89 (m, 2H), 2.7-3.2 (m, 3H), 3.8-4.2 (m, 3H), 7.0-7.2 (m, 4H), 7.5-7.6 (m, 2), 8.0 (d, 1H), 8.2-8.4 (m, 2H), 9.1 (m, 1H); HPLC Purity: 99.72%; Mass (M+1): 537.50.

(R)-Tetrahydro-2H-pyran-4-yl-3-methyl-4-(4-(quinoline-8-sulfonamido)benzoyl)piperazine-1-carboxylate (Compound 124)

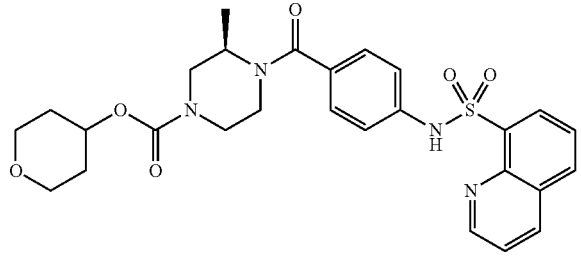 [SMILES: C[C@@H]1CN(C(=O)OC2CCOCC2)CCN1C(=O)c1ccc(NS(=O)(=O)c2cccc3cccnc23)cc1]

¹H NMR (400 MHz, CDCl₃) δ: 1.2 (d, 3H), 1.23 (m, 1H), 1.5 (m, 1H), 1.6-1.7 (m, 2H), 1.89-2.0 (m, 2H), 2.7-3.2 (m,

4H), 3.8-4.85 (m, 6H), 7.0-7.2 (m, 4H), 7.5-7.6 (m, 2H), 8.0 (d, 1H), 8.2-8.4 (m, 2H), 9.1 (m, 1H); HPLC Purity: 98.83%; Mass (M+1): 539.30.

(R)—((R)-tetrahydrofuran-3-yl)-3-methyl-4-(4-(quinoline-8-sulfonamido)benzoyl)piperazine-1-carboxylate (Compound 126)

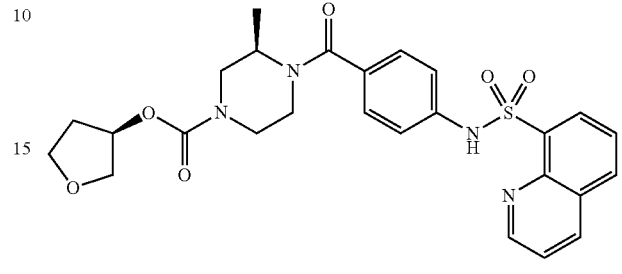

¹H NMR (400 MHz, DMSO-d₆) δ: 1.0 (d, 3H), 1.23 (m, 1H), 1.8-2.2 (m, 2H), 2.7-3.2 (m, 3H), 3.6-4.0 (m, 6H), 5.17 (m, 1H), 7.0-7.2 (m, 3H), 7.6-7.8 (m, 2H), 8.0 (d, 1H), 8.2-8.4 (m, 2H), 9.1 (m, 1H), 10.45 (s, 1H); HPLC Purity: 99.52%; Mass (M+1): 525.45.

(R)—((R)-tetrahydro-21'-pyran-3-yl)-3-methyl-4-(4-(quinoline-8-sulfonamido)benzoyl)piperazine-1-carboxylate (Compound 127)(R)

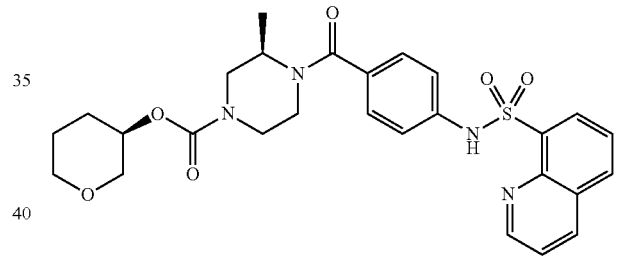

¹H NMR (400 MHz, DMSO-d₆) δ: 1.0 (d, 3H), 1.23 (m, 1H), 1.75-1.78 (m, 3H), 2.85-2.9 (m, 3H), 3.41-3.79 (m, 6H), 3.89-3.9 (m, 1H), 4.44 (m, 1H), 7.0-7.2 (m, 4H), 7.6-7.8 (m, 2H), 8.23 (d, 1H), 8.4 (d, 1H), 8.5 (d, 1H), 9.1 (m, 1H), 10.45 (s, 1H); HPLC Purity: 99.67%; Mass (M+1): 539.1.

(3R)-(Tetrahydrofuran-2-yl)methyl3-methyl-4-(4-(quinoline-8-sulfonamido)benzoyl)piperazine-1-carboxylate (Compound 128)

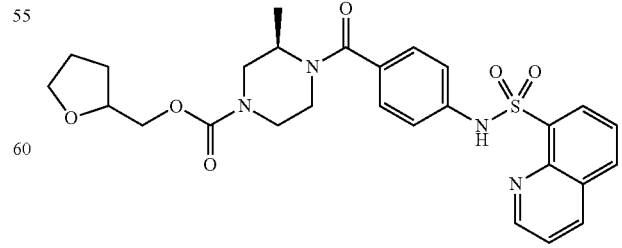

¹H NMR (400 MHz, DMSO-d₆) δ: 1.0 (d, 3H), 1.53 (m, 1H), 1.57-2.0 (m, 3H), 2.8-3.1 (m, 3H), 3.6-4.1 (m, 9H), 7.0-7.2 (m, 4H), 7.6-7.8 (m, 2H), 8.23 (d, 1H), 8.4-8.5 (m, 2H), 9.1 (m, 1H), 10.45 (s, 1H); HPLC Purity: 99.80%; Mass (M+1): 539.1.

(R)-Cyclopentyl 3-methyl-4-(4-(quinoline-8-sulfonamido)benzoyl)piperazine-1-carboxylate (Compound 129)

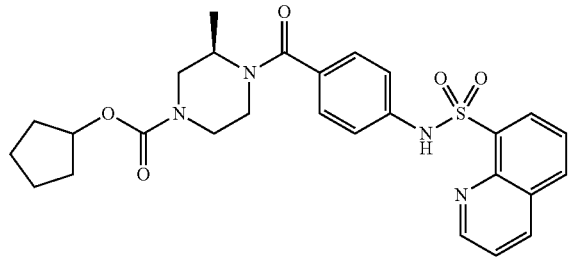 [SMILES: C[C@@H]1CN(C(=O)OC2CCCC2)CCN1C(=O)c1ccc(NS(=O)(=O)c2cccc3cccnc23)cc1]

$^1$H NMR (400 MHz, DMSO-d$_6$) δ: 1.0 (d, 3H), 1.38 (m, 1H), 1.39-1.8 (m, 8H), 2.6-3.0 (m, 3H), 3.5-3.8 (m, 3H), 4.95 (m, 1H), 7.0-7.2 (m, 4H), 7.6-7.8 (m, 2H), 8.23 (d, 1H), 8.4-8.5 (m, 2H), 9.1 (m, 1H); HPLC Purity: 99.68%; Mass (M+1): 523.50.

(R)—((S)-tetrahydrofuran-3-yl) 3-methyl-4-(4-(quinoline-8-sulfonamido)benzoyl)piperazine-1-carboxylate (Compound 129)(S)

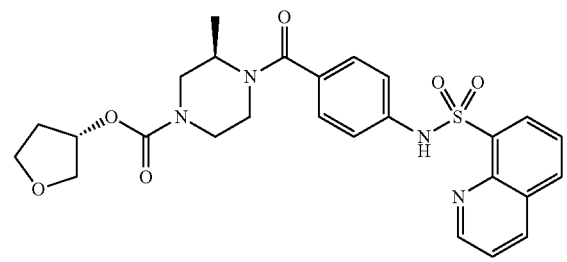 [SMILES: C[C@@H]1CN(C(=O)O[C@H]2CCOC2)CCN1C(=O)c1ccc(NS(=O)(=O)c2cccc3cccnc23)cc1]

$^1$H NMR (400 MHz, DMSO-d$_6$) δ: 1.0 (d, 3H), 1.8 (m, 1H), 2.0-2.2 (m, 1H), 2.8-3.3 (m, 3H), 4.0-4.2 (m, 8H), 7.0-7.2 (m, 4H), 7.6-7.7 (m, 2H), 8.0 (d, 1H), 8.3-8.6 (m, 2H), 9.1 (m, 1H), 10.4 (s, 1H); HPLC Purity: 96.16%; Mass (M+1): 525.45.

Ethyl 4-(5-(quinoline-8-sulfonamido)picolinoyl)piperazine-1-carboxylate (Compound 447)

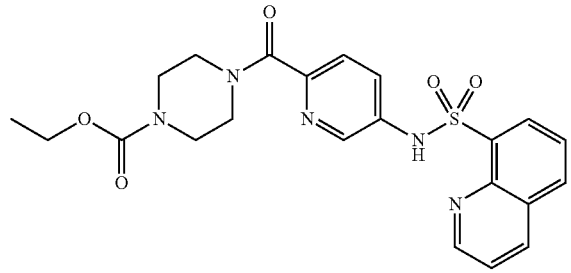 [SMILES: CCOC(=O)N1CCN(C(=O)c2ccc(NS(=O)(=O)c3cccc4cccnc34)cn2)CC1]

$^1$H NMR (400 MHz, CDCl$_3$) δ: 1.2 (t, 3H), 3.2-3.6 (m, 8H), 4.0-4.2 (q, 2H), 7.4-7.8 (m, 4H), 8.0-8.6 (m, 4H), 9.1-9.2 (m, 1H); HPLC Purity: 97.7%; Mass (M+1): 470.2.

Ethyl 4-(6-(quinoline-8-sulfonamido)nicotinoyl)piperazine-1-carboxylate (Compound 446)

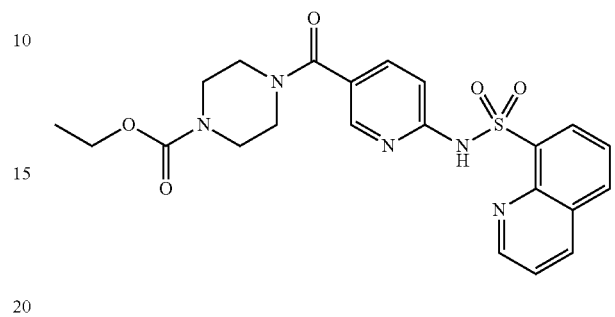

$^1$H NMR (400 MHz, DMSO-d$_6$) δ: 1.0-1.2 (t, 3H), 2.2-2.4 (m, 2H), 3.2-3.35 (q, 2H), 3.4-3.6 (m, 4H), 3.99-4.0 (m, 2H), 7.5-7.7 (m, 4H), 8.3-8.5 (m, 4H), 9.1 (m, 1H); HPLC Purity: 99.89%; Mass (M+1): 470.4.

Example 15

Preparation of Compound 104 (Racemic)

Scheme 15:

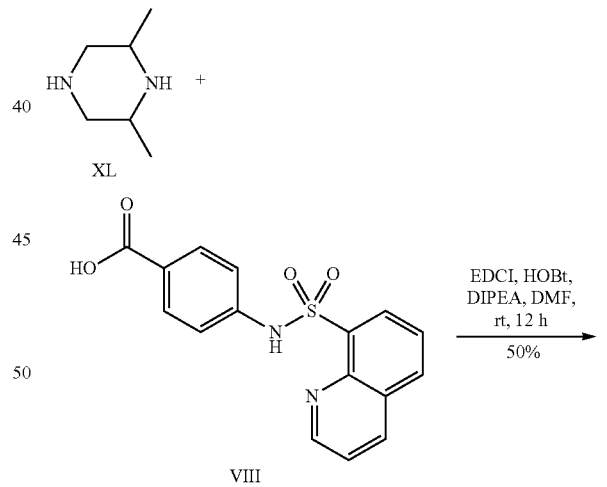

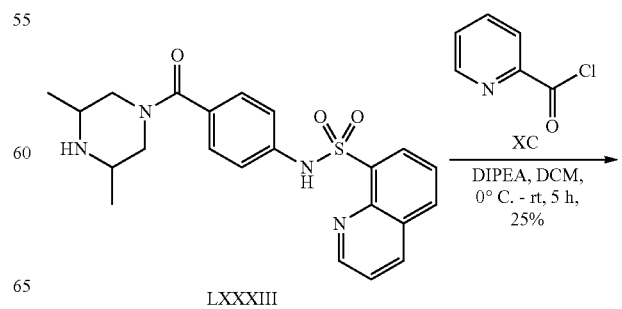

139

-continued

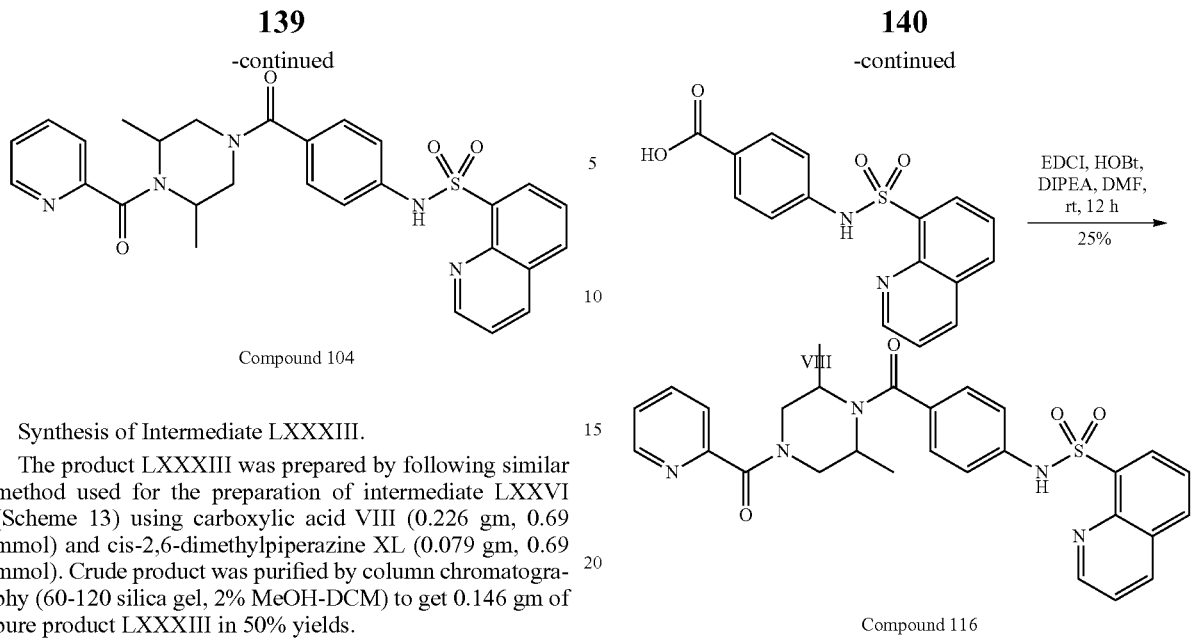

Compound 104

Synthesis of Intermediate LXXXIII.

The product LXXXIII was prepared by following similar method used for the preparation of intermediate LXXVI (Scheme 13) using carboxylic acid VIII (0.226 gm, 0.69 mmol) and cis-2,6-dimethylpiperazine XL (0.079 gm, 0.69 mmol). Crude product was purified by column chromatography (60-120 silica gel, 2% MeOH-DCM) to get 0.146 gm of pure product LXXXIII in 50% yields.

Synthesis of N-(4-(3,5-dimethylpiperazine-1-carbonyl)phenyl)quinoline-8-sulfonamide (Compound 104) (racemic)

To a solution of amine LXXXIII (0.125 gm, 0.29 mmol) and ethyldiisopropylamine in dichloromethane was added picolyl chloride (XC, 0.045 gm, 0.32 mmol) at 0° C. The reaction mixture was allowed to warm to room temperature and stirred for 5 h. After completion of reaction, the mixture was diluted with dichloromethane, washed with water (2×10 ml), brine (10 ml), dried over anhydrous $Na_2SO_4$ and concentrated. The crude material was then purified by column chromatography (60-120 silica gel, 2% MeOH-DCM) to get 0.039 gm of pure Compound 104 (racemic) in 25% yield.

$^1$H NMR (400 MHz, $CDCl_3$) δ: 1.2 (s, 6H), 3.0 (m, 1H), 3.6 (m, 2H), 4.3 (m, 2H), 7.0 (m, 4H), 7.4-7.6 (m, 4H), 8.0 (m, 1H), 8.2 (m, 1H), 8.4 (m, 3H), 9.0 (m, 1H); HPLC Purity: 98.75%; Mass (M+1): 530.3.

Example 16

Preparation of Compound 116 (Racemic)

Scheme 16:

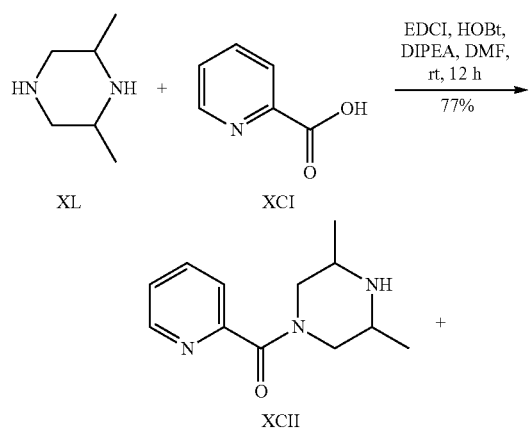

140

-continued

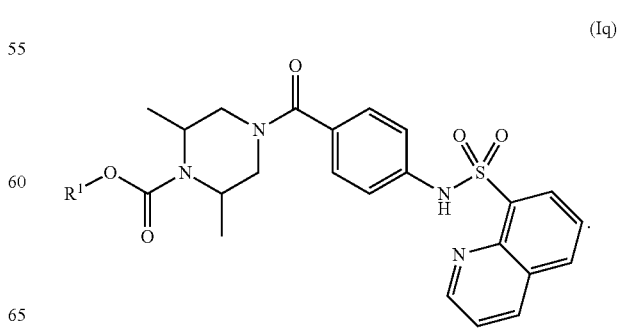

Compound 116

Synthesis of Intermediate XCII.

The product XCII was prepared by following similar method used for the preparation of intermediate LXXVI (Scheme 13) using picolinic acid XCI (0.092 gm, 0.75 mmol) and cis-2,6-dimethylpiperazine XL (0.086 gm, 0.75 mmol). The crude material was purified by column chromatography (60-120 silica gel, 2% MeOH-DCM) to get 0.126 gm of pure product XCII in 77% yield.

Synthesis of Compound 116 (racemic).

Compound 116 was prepared by following similar method used for the preparation of a compound of Formula Io (Scheme 13) using carboxylic acid VIII (0.164 gm, 0.50 mmol) and amine XCII (0.110 gm, 0.50 mmol). Crude product was purified by column chromatography (60-120 silica gel, 2% MeOH-DCM) to get 0.066 gm of pure Compound 116 (racemic) in 25% yields.

$^1$H NMR (400 MHz, $CDCl_3$) δ: 2.8-3.0 (s, 6H), 3.35-3.4 (m, 2H), 4.0 (m, 2H), 4.5-4.66 (m, 1H), 7.0-7.2 (m, 4H), 7.3-7.8 (m, 6H), 8.0-8.1 (m, 1H), 8.2-8.6 (m, 4H), 9.0 (m, 1H); HPLC Purity: 93.09%; Mass (M+1): 530.45.

Example 17

Preparation of a Compound of Formula Iq (Iq)

Scheme 17:

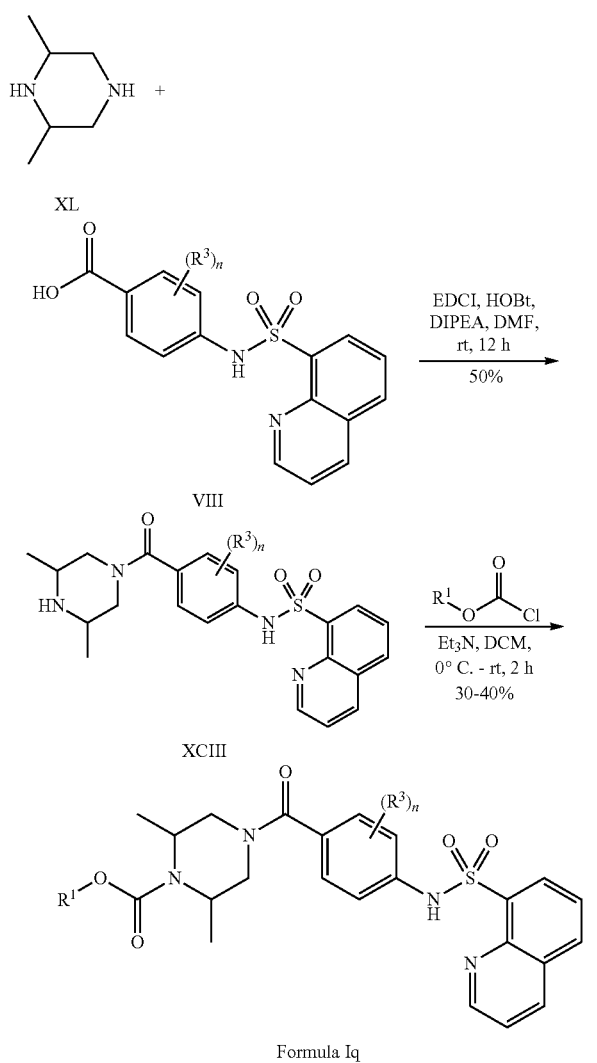

Formula Iq

Synthesis of Intermediate XCII.

EDCI (0.09 gm, 0.46 mmol) and HOBt (0.062 gm, 0.46 mmol) were added to a stirred solution of the carboxylic acid (VIII, 0.151 gm, 0.46 mmol) in anhydrous DMF. The temperature of the mixture was reduced to 0° C., at which time DIPEA (0.24 mL, 1.38 mmol) was added under nitrogen atmosphere and the resultant solution (or suspension) was stirred at room temperature for 30 min Amine XL (VI, 0.46 mmol) was then added at 0° C. The reaction mixture was then brought to room temperature and stirred for 12 h. After completion of the reaction, the reaction mixture was diluted with water and extracted with ethyl acetate (2×25 ml). The organic layer was washed with water (2×10 ml), dried over anhydrous sodium sulfate, filtered and concentrated under vacuum to get the crude product. The obtained crude product was purified by column chromatography (60-120 silica gel, 2% MeOH-DCM) to get pure product XCIII as an off-white solid in 40-50% yields.

Synthesis of Compounds of Formula Iq.

To a solution of amine XI (0.102 gm, 0.24 mmol) and triethyl amine (0.66 mmol) in 5 mL of dichloromethane, appropriate chloroformate (0.26 mmol) was added at 0° C. and allowed to stir at room temperature for 1-2 h. After completion of reaction, the mixture was diluted with dichloromethane (25 mL), washed with water (2×10 mL), brine (10 mL), dried over anhydrous $Na_2SO_4$ and concentrated. The crude product was purified by column chromatography (60-120 silica gel, 2% MeOH-DCM) to afford a Compound of Formula Iq as an off-white solid in 30-40% yields.

The following compounds were made according to the above procedure using the appropriate chloroformate.

(2S,6R)-ethyl 2,6-dimethyl-4-(4-(quinoline-8-sulfonamido)benzoyl)piperazine-1-carboxylate (XXIV-1) (Compound 117)

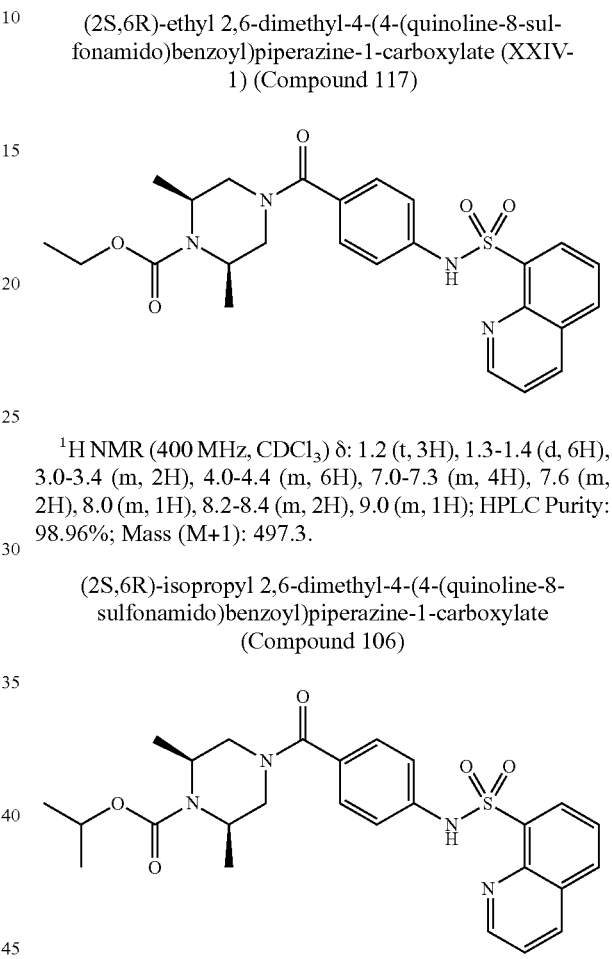

$^1$H NMR (400 MHz, CDCl$_3$) δ: 1.2 (t, 3H), 1.3-1.4 (d, 6H), 3.0-3.4 (m, 2H), 4.0-4.4 (m, 6H), 7.0-7.3 (m, 4H), 7.6 (m, 2H), 8.0 (m, 1H), 8.2-8.4 (m, 2H), 9.0 (m, 1H); HPLC Purity: 98.96%; Mass (M+1): 497.3.

(2S,6R)-isopropyl 2,6-dimethyl-4-(4-(quinoline-8-sulfonamido)benzoyl)piperazine-1-carboxylate (Compound 106)

$^1$H NMR (400 MHz, CDCl$_3$) δ: 1.2 (s, 6H), 3.0-3.4 (m, 3H), 4.0-4.4 (m, 3H), 4.9 (m, 1H), 7.0-7.3 (m, 4H), 7.6 (m, 2H), 8.0 (m, 1H), 8.2-8.4 (m, 2H), 9.0 (m, 1H); HPLC Purity: 99.96%; Mass (M+1): 511.4.

(2S,6R)-isobutyl-2,6-dimethyl-4-(4-(quinoline-8-sulfonamido)benzoyl)piperazine-1-carboxylate (Compound 105)

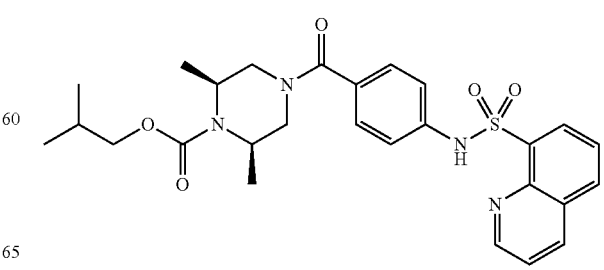

¹H NMR (400 MHz, CDCl₃) δ: 3.2-3.8 (m, 8H), 6.8-7.3 (m, 5H), 7.6 (m, 2H), 8.0 (m, 1H), 8.3-8.4 (m, 3H), 9.0 (m, 1H), 10.4 (m, 1H); HPLC Purity: 99.45%; Mass (M+1): 492.2.

Example 18

PKM2 Assay

Procedure:
PKM2 stock enzyme solution was diluted in Reaction Buffer
2 μL of compound was added into each well first, and then 180 μL of the Reaction Mix was added.
Reaction mixture with compound (without ADP) was incubated for 30 minutes at 4° C.
Plates were re-equilibrated to room temperature prior to adding 20 μL ADP to initiate the reaction.
Reaction progress was measured as changes in absorbance at 340 nm wavelength at room temperature (25° C.)
Reaction Mix: PKM2 (50 ng/well), ADP (0.7 mM), PEP (0.15 mM), NADH (180 μM), LDH (2 units) in Reaction Buffer
Reaction Buffer: 100 mM KCl, 50 mM Tris pH 7.5, 5 mM MgCl2, 1 mM DTT, 0.03% BSA.

Representative compounds of the invention were tested for their ability to activate PKM2 using the above assay. For simplicity, the activation activity of these compounds is represented as an $AC_{50}$ in Tables 4 and 5 and throughout the application. As shown in Tables 4 and 5, "A" refers to an activator of PKM2 with an $EC_{50}$<100 nM. "B" refers to an activator of PKM2 with an $EC_{50}$ between 100 nM and 500 nM. "C" refers to an activator of PKM2 with an $EC_{50}$ between 500 nM and 1000 nM. "D" refers to an activator of PKM2 with an $EC_{50}$ between 1 μM and 20 μM. "E" refers a compound whose activation of PKM2 was not measurable. "N/C" refers to $AC_{50}$ data not available.

TABLE 4

| Compound # | $AC_{50}$ |
| --- | --- |
| 131 | A |
| 119 | A |
| 118 | A |
| 150 | A |
| 149 | A |
| 206 | A |
| 151 | A |
| 132 | A |
| 112 | A |
| 213 | A |
| 129 | A |
| 148 | A |
| 125 | A |
| 133 | A |
| 135 | A |
| 223 | A |
| 120 | A |
| 114 | A |
| 113 | A |
| 110 | A |
| 216 | A |
| 217 | A |
| 226 | A |
| 183 | A |
| 161 | A |
| 143 | A |
| 145 | A |
| 147 | A |
| 167 | A |
| 196 | A |

TABLE 4-continued

| Compound # | $AC_{50}$ |
| --- | --- |
| 163 | A |
| 152 | A |
| 137 | A |
| 189 | A |
| 194 | A |
| 140 | A |
| 222 | A |
| 122 | A |
| 142 | A |
| 130 | A |
| 200 | A |
| 220 | A |
| 144 | A |
| 203 | A |
| 199 | A |
| 186 | A |
| 190 | A |
| 123 | A |
| 111 | A |
| 221 | A |
| 212 | A |
| 155 | A |
| 165 | A |
| 108 | A |
| 160 | A |
| 211 | A |
| 128 | A |
| 227 | B |
| 228 | B |
| 202 | B |
| 124 | B |
| 109 | B |
| 136 | B |
| 218 | B |
| 164 | B |
| 207 | B |
| 134 | B |
| 102 | B |
| 195 | B |
| 191 | B |
| 141 | B |
| 157 | B |
| 219 | B |
| 201 | B |
| 115 | B |
| 138 | B |
| 153 | B |
| 126 | B |
| 103 | B |
| 168 | B |
| 154 | B |
| 178 | B |
| 127 | B |
| 121 | B |
| 192 | B |
| 173 | B |
| 106 | B |
| 181 | B |
| 170 | B |
| 166 | B |
| 159 | B |
| 171 | B |
| 100 | B |
| 187 | B |
| 198 | B |
| 105 | B |
| 180 | B |
| 197 | B |
| 169 | B |
| 172 | B |
| 174 | B |
| 179 | B |
| 184 | B |
| 209 | B |
| 210 | B |
| 182 | B |
| 104 | B |
| 162 | B |

TABLE 4-continued

| Compound # | AC$_{50}$ |
|---|---|
| 139 | B |
| 158 | B |
| 214 | B |
| 215 | B |
| 101 | B |
| 107 | C |
| 188 | C |
| 204 | C |
| 156 | C |
| 185 | C |
| 177 | D |
| 146 | D |
| 175 | D |
| 116 | D |
| 176 | D |
| 117 | E |
| 224 | N/C |
| 225 | N/C |

TABLE 5

| Cmpd # | AC$_{50}$ |
|---|---|
| 442 | A |
| 449 | A |
| 394 | A |
| 419 | A |
| 438 | A |
| 420 | A |
| 408 | A |
| 388 | A |
| 421 | A |
| 450 | A |
| 313 | A |
| 385 | A |
| 448 | A |
| 341 | A |
| 342 | A |
| 407 | A |
| 332 | A |
| 445 | A |
| 404 | A |
| 405 | A |
| 396 | A |
| 357 | A |
| 403 | A |
| 356 | A |
| 384 | A |
| 387 | A |
| 433 | A |
| 395 | A |
| 371 | A |
| 364 | A |
| 431 | A |
| 355 | A |
| 348 | A |
| 358 | A |
| 370 | A |
| 372 | A |
| 399 | A |
| 423 | A |
| 406 | A |
| 393 | A |
| 410 | A |
| 434 | A |
| 351 | A |
| 400 | A |
| 354 | A |
| 330 | A |
| 365 | A |
| 397 | A |
| 430 | A |
| 331 | A |
| 401 | A |
| 425 | A |
| 426 | A |
| 436 | A |
| 427 | A |
| 317 | A |
| 444 | A |
| 437 | A |
| 424 | B |
| 345 | B |
| 318 | B |
| 319 | B |
| 422 | B |
| 432 | B |
| 321 | B |
| 435 | B |
| 386 | B |
| 440 | B |
| 409 | B |
| 320 | B |
| 350 | B |
| 412 | B |
| 352 | B |
| 428 | B |
| 322 | B |
| 439 | B |
| 347 | B |
| 414 | B |
| 429 | B |
| 416 | B |
| 307 | B |
| 382 | B |
| 377 | B |
| 413 | B |
| 383 | B |
| 379 | B |
| 375 | B |
| 359 | B |
| 334 | B |
| 417 | B |
| 418 | B |
| 367 | B |
| 368 | B |
| 362 | B |
| 376 | B |
| 339 | B |
| 366 | B |
| 300 | B |
| 349 | B |
| 338 | B |
| 378 | B |
| 310 | B |
| 391 | B |
| 335 | B |
| 380 | B |
| 415 | B |
| 324 | B |
| 373 | B |
| 304 | B |
| 315 | B |
| 303 | B |
| 301 | B |
| 402 | B |
| 381 | B |
| 360 | B |
| 326 | B |
| 340 | B |
| 305 | B |
| 363 | B |
| 390 | C |
| 308 | C |
| 361 | C |
| 302 | C |
| 392 | C |
| 312 | C |
| 336 | C |
| 327 | C |
| 389 | C |
| 333 | C |
| 306 | C |

TABLE 5-continued

| Cmpd # | AC$_{50}$ |
|---|---|
| 374 | C |
| 346 | C |
| 353 | C |
| 323 | C |
| 443 | C |
| 369 | C |
| 344 | C |
| 411 | D |
| 337 | D |
| 441 | D |
| 309 | D |
| 343 | D |
| 398 | D |
| 316 | D |
| 311 | D |
| 328 | D |
| 314 | D |
| 329 | D |
| 452 | D |
| 325 | D |
| 447 | D |
| 446 | D |
| 451 | E |

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of formula (Ia) or (Ib) or a pharmaceutically acceptable salt thereof, wherein:

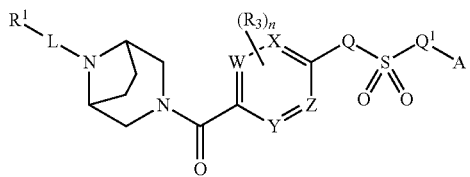
(Ia)

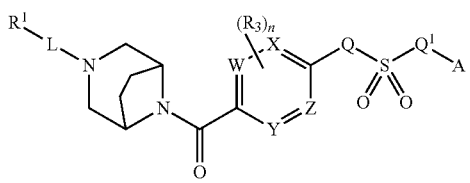
(Ib)

W, X, Y and Z are each CH;
Q is NR$^b$;
Q$^1$ is a bond;
A is optionally substituted bicyclic aryl or optionally substituted bicyclic heteroaryl;
L is a bond, —C(O)—, —(CR$^c$R$^c$)$_m$—, —OC(O)—, —(CR$^c$R$^c$)$_m$—OC(O)—, —(CR$^c$R$^c$)$_m$—C(O)—, —NR$^b$C(S)—, or —NR$^b$C(O)— (wherein the point of the attachment to R$^1$ is on the left-hand side);
R$^1$ is selected from alkyl, carbocycle, aryl, heteroaryl, and heterocyclyl; each of which is substituted with 0-5 occurrences of R$^d$;
each R$^3$ is independently selected from halo, haloalkyl, alkyl, hydroxyl and —OR$^a$, or two adjacent R$^3$ taken together with the carbon atoms to which they are attached form an optionally substituted heterocyclyl;
each R$^a$ is independently selected from alkyl, acyl, hydroxyalkyl and haloalkyl;
each R$^b$ is independently selected from hydrogen and alkyl;
each R$^c$ is independently selected from hydrogen, halo, alkyl, alkoxy and halo alkoxy, or two R$^c$ taken together with the carbon atoms to which they are attached form an optionally substituted cycloalkyl;
each R$^d$ is independently selected from halo, haloalkyl, haloalkoxy, alkyl, alkynyl, nitro, cyano, hydroxyl, —C(O)R$^a$, —OC(O)R$^a$, —C(O)OR$^a$, —SR$^a$, —NR$^a$R$^b$ and —OR$^a$, or two R$^d$ taken together with the carbon atoms to which they are attached form an optionally substituted heterocyclyl;
n is 0, 1, or 2; and
m is 1, 2 or 3.

2. A compound of formula (I) or a pharmaceutically acceptable salt thereof, wherein:

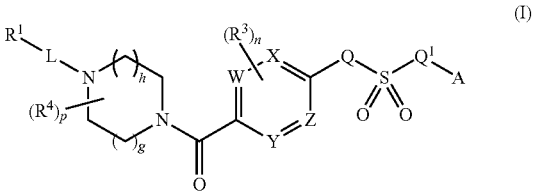
(I)

W, X, Y and Z are each CH;
Q is NR$^b$;
Q$^1$ is a bond;
A is optionally substituted bicyclic aryl or optionally substituted bicyclic heteroaryl;
L is a bond, —C(O)—, —(CR$^c$R$^c$)$_m$—, —OC(O)—, —(CR$^c$R$^c$)$_m$—C(O)—, —(CR$^c$R$^c$)$_m$—C(O)—, —NR$^b$C(S)—, or —NR$^b$C(O)— (wherein the point of the attachment to R$^1$ is on the left-hand side);
R$^1$ is selected from alkyl, carbocycle, aryl, heteroaryl, and heterocyclyl; each of which is substituted with 0-5 occurrences of R$^d$;
each R$^3$ is independently selected from halo, haloalkyl, alkyl, hydroxyl and —OR$^a$, or two adjacent R$^3$ taken together with the carbon atoms to which they are attached form an optionally substituted heterocyclyl;
each R$^4$ is independently selected from alkyl, phenyl, (S)-alkyl, (R)-alkyl, (S)-phenyl, and (R)-phenyl;
each R$^a$ is independently selected from alkyl, acyl, hydroxyalkyl and haloalkyl;
each R$^b$ is independently selected from hydrogen and alkyl;
each R$^c$ is independently selected from hydrogen, halo, alkyl, alkoxy and halo alkoxy, or two R$^c$ taken together with the carbon atoms to which they are attached form an optionally substituted cycloalkyl;
each R$^d$ is independently selected from halo, haloalkyl, haloalkoxy, alkyl, alkynyl, nitro, cyano, hydroxyl, —C(O)R$^a$, —OC(O)R$^a$, —C(O)OR$^a$, —SR$^a$, —NR$^a$R$^b$ and —OR$^a$, or two R$^d$ taken together with the carbon atoms to which they are attached form an optionally substituted heterocyclyl;

n is 0, 1, or 2;

m is 1, 2 or 3;

h is 0, 1, 2;

g is 0, 1 or 2;

the sum of g+h is equal to or greater than 2; and p is 1 or 2.

3. The compound of claim 2, wherein:

g is 1;

h is 1; and each R$^4$ is independently selected from methyl, (S)-methyl, (R)-methyl, ethyl, (S)-ethyl, (R)-ethyl, isopropyl, (S)-isopropyl, (R)-isopropyl, phenyl, (S)-phenyl, and (R)-phenyl.

4. The compound of claim 1 or 2, wherein A is

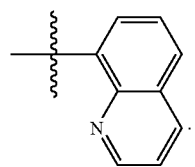

5. The compound of claim 4, wherein:

n is 1; and

R$^3$ is selected from fluoro, chloro, methyl, ethyl, CF$_3$, methoxy, and OCF$_3$.

6. The compound of claim 1 or 2, wherein:

Q is NH.

7. The compound of claim 1 or 2, wherein L is selected from a bond, —C(O)—, —OC(O)—, —CH$_2$—OC(O)—, —(CH$_2$)$_2$—OC(O)—, —C(CH$_3$)$_2$—C(O)—, —CH$_2$—, —(CH$_2$)$_2$—, —(CH$_2$)$_3$—, —CH(CH$_3$)—, —CH(CF$_3$)—, —C(CH$_3$)$_2$—, —CHD-, —CD$_2$-,

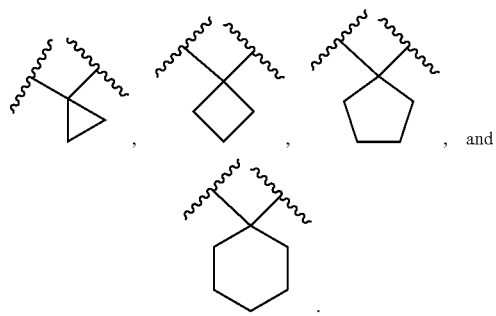

, and

8. The compound of claim 7, wherein R$^1$ is selected from methyl, ethyl, isopropyl, cyclopropyl, cyclobutyl, cyclopentyl, cyclohexyl, phenyl, pyridin-2-yl, pyridin-3-yl, pyridin-4-yl, 1,2,3-thiadiazol-5-yl, 1,2,3-thiadiazol-4-yl, thiazol-4-yl, thiazol-5-yl, 1H-imidazol-4-yl, 1H-imidazol-2-yl, 1H-pyrazol-3-yl, 1H-pyrazol-4-yl, 1H-pyrazol-5-yl, pyrazin-2-yl, oxazol-4-yl, isoxazol-5-yl, tetrahydrofuran-2-yl, tetrahydrofuran-3-yl, tetrahydro-2H-pyran-4-yl, tetrahydro-2H-pyran-3-yl, and tetrahydro-2H-pyran-2-yl.

9. The compound of claim 1 or 2, wherein the compound is selected from:

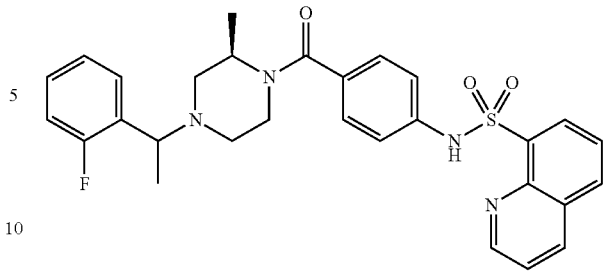

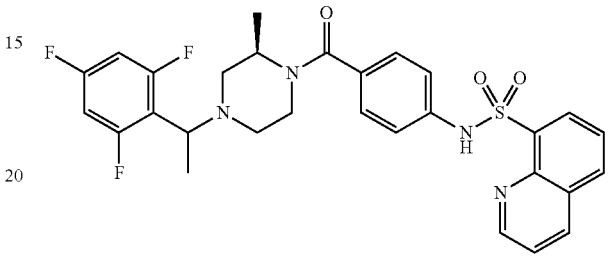

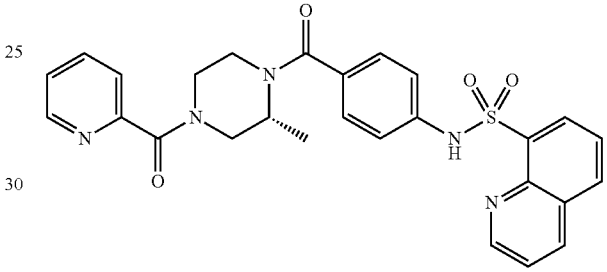

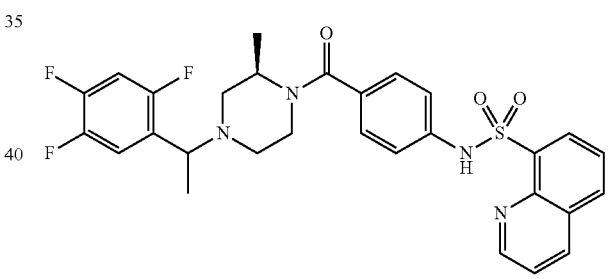

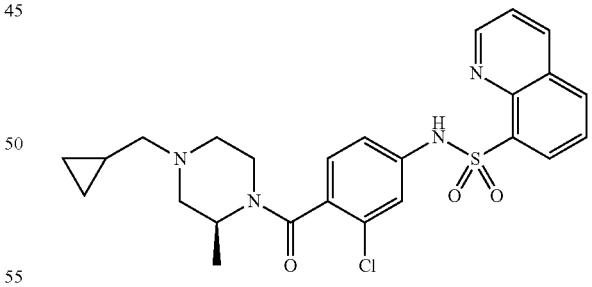

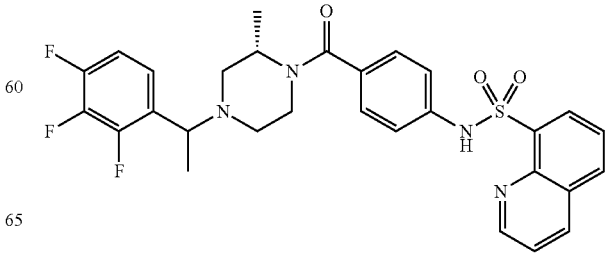

151
-continued
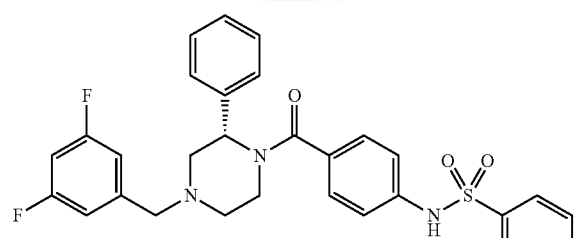
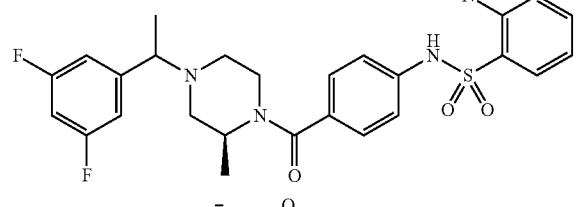
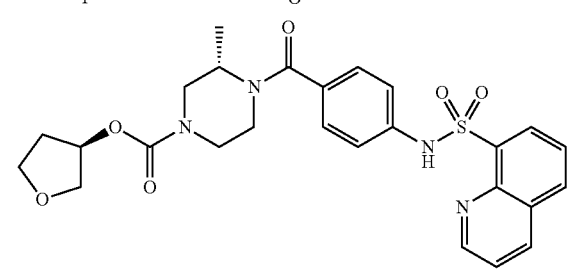
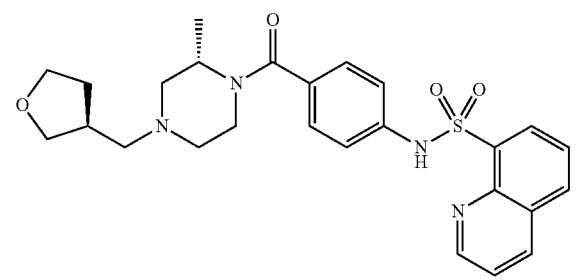
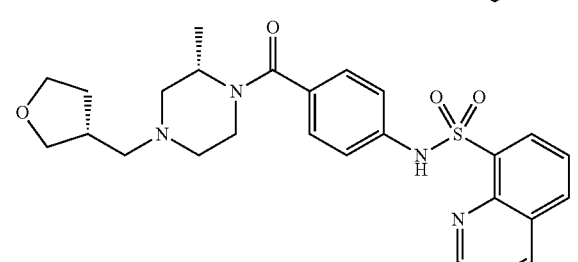
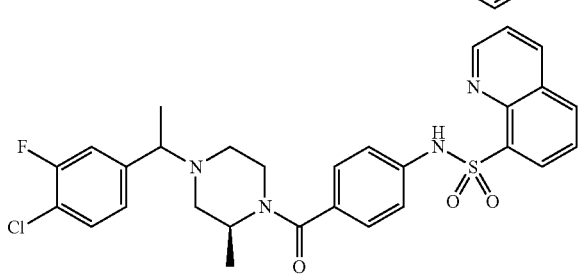
152
-continued
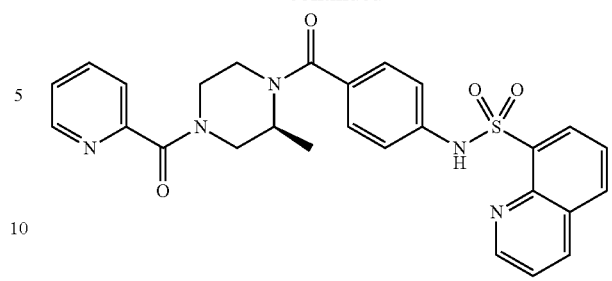
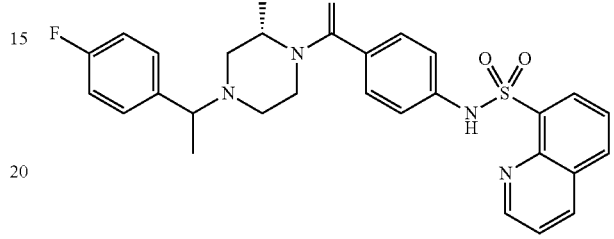
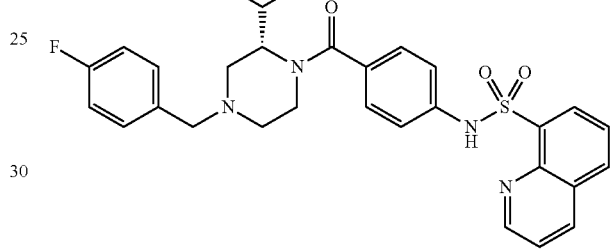
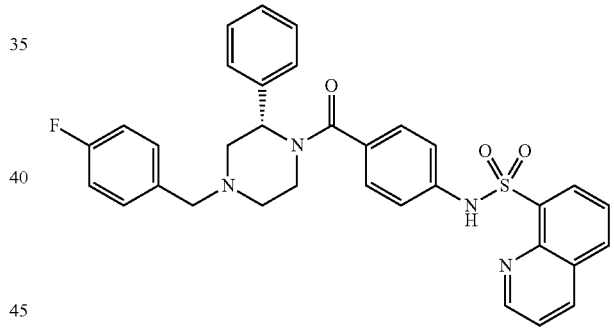
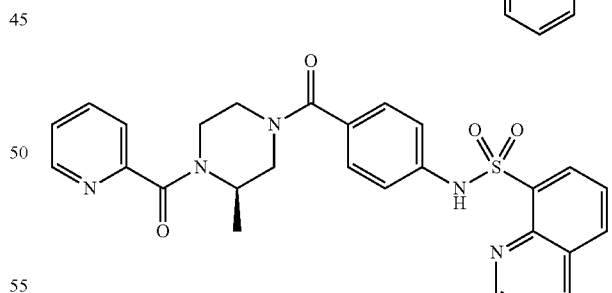
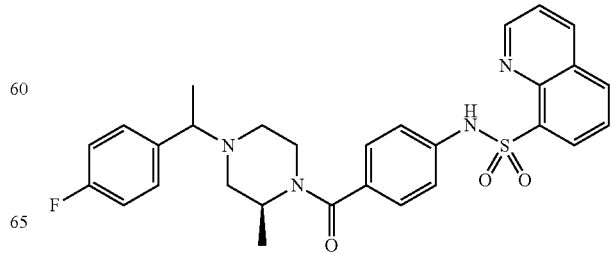

153
-continued
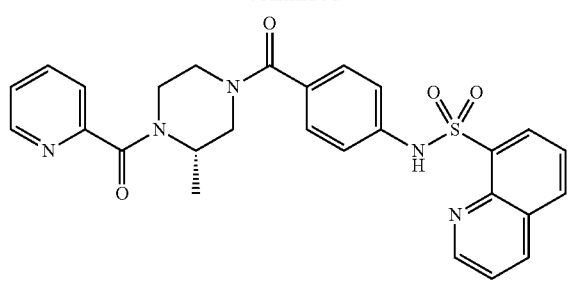
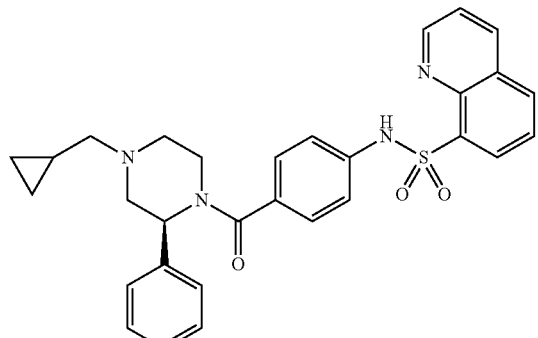
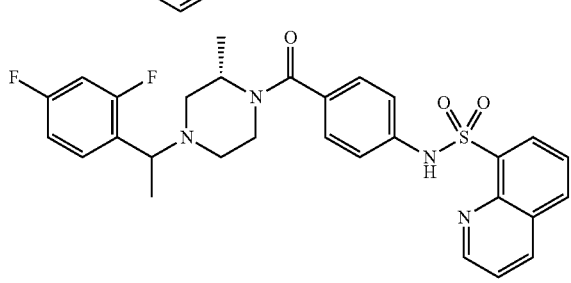
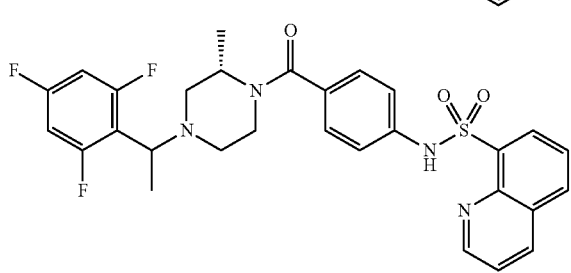
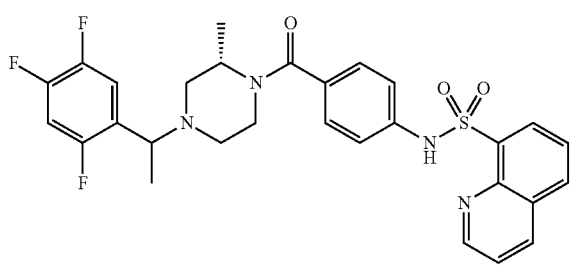
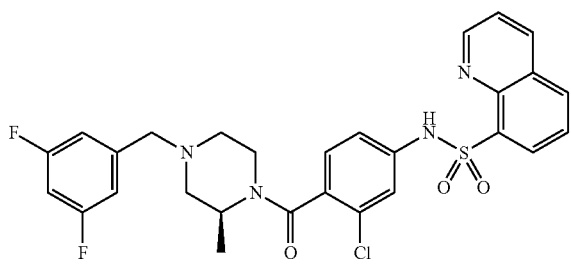
154
-continued
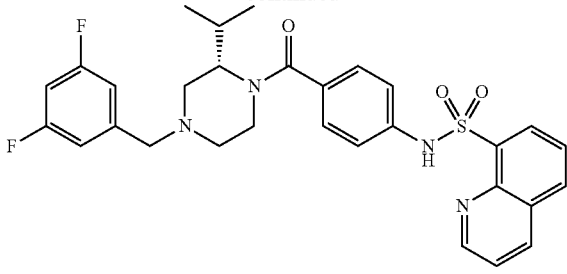
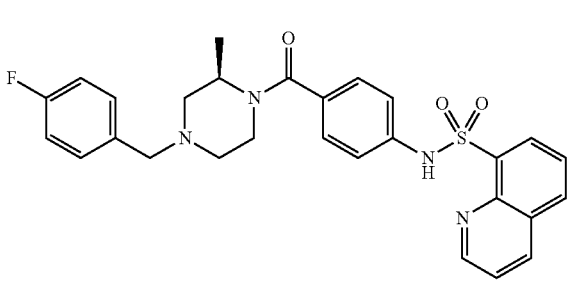
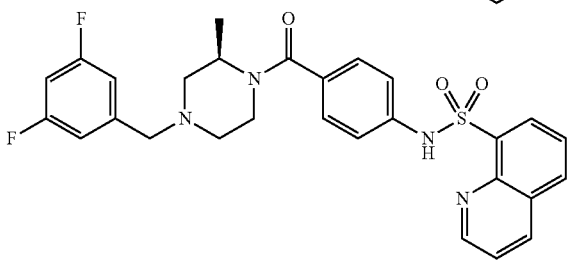
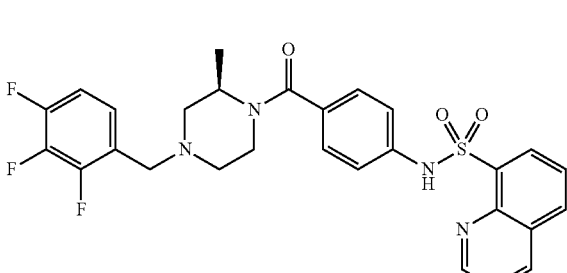
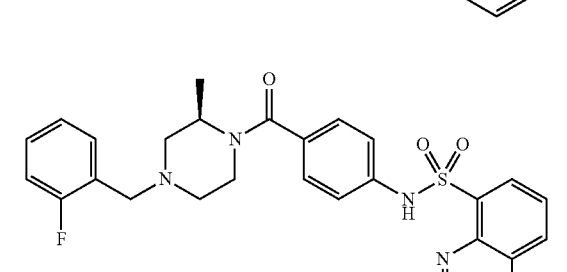
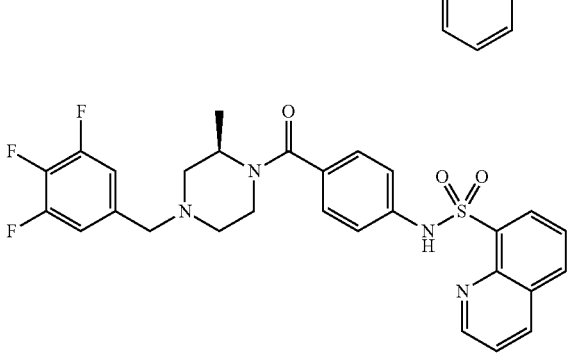

155
-continued
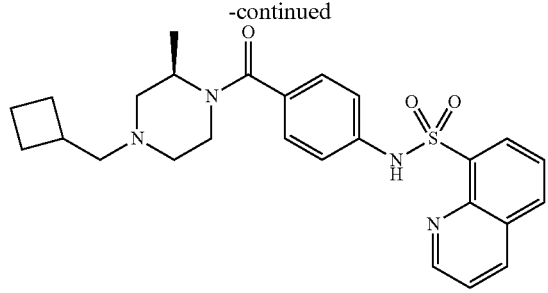
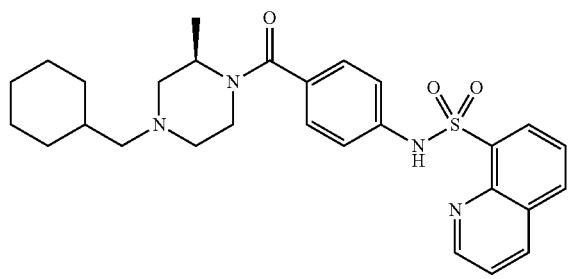
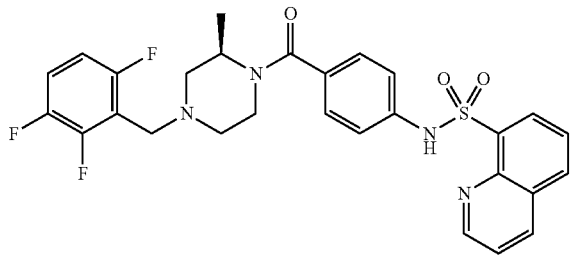
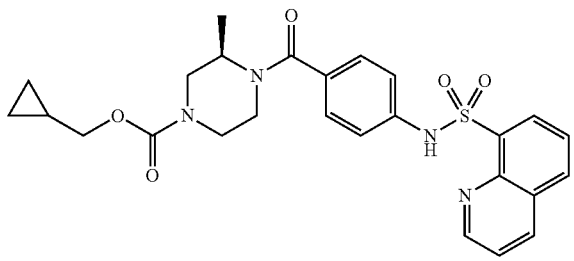
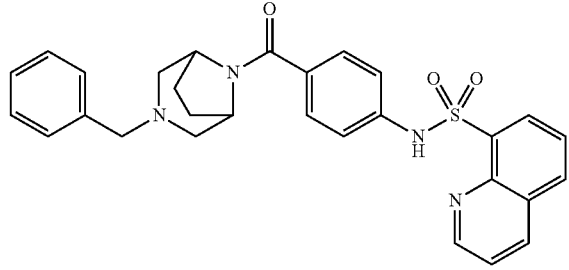
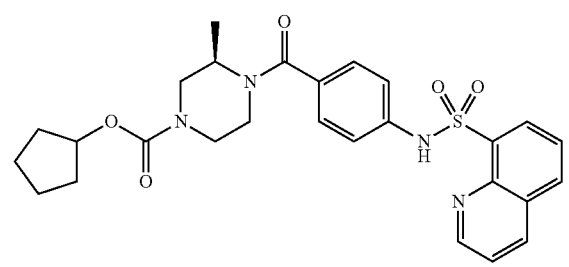
156
-continued
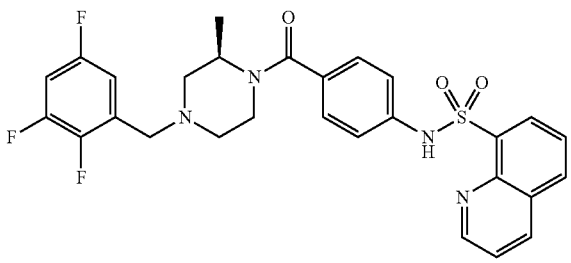
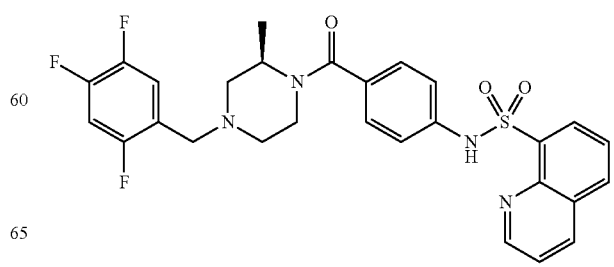

157
-continued
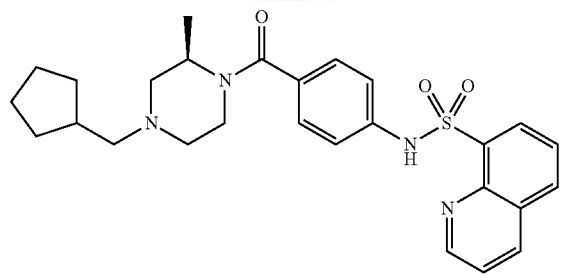
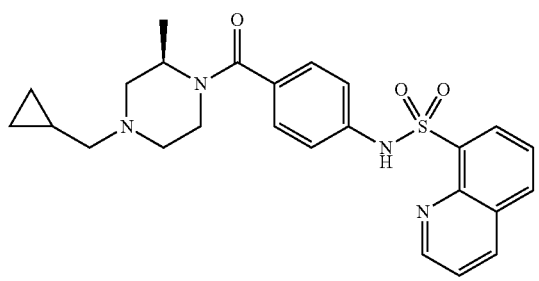
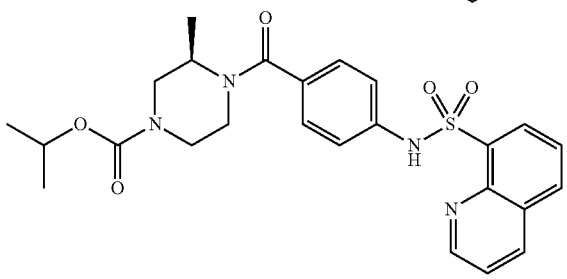
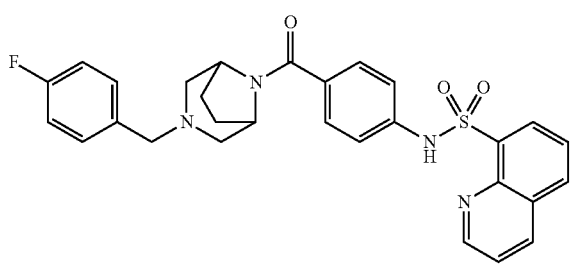
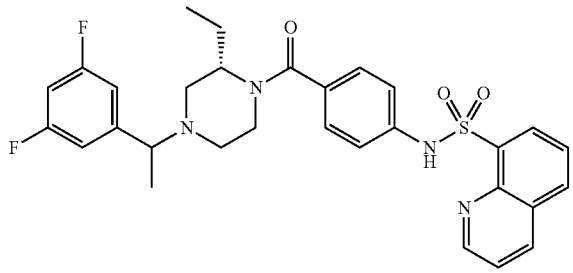
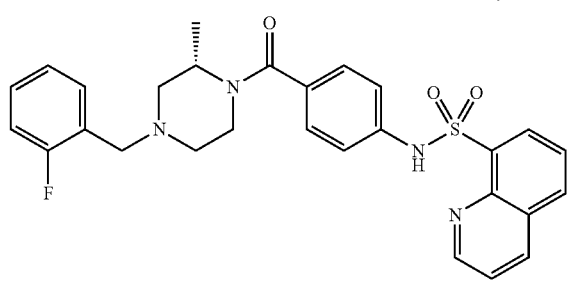
158
-continued
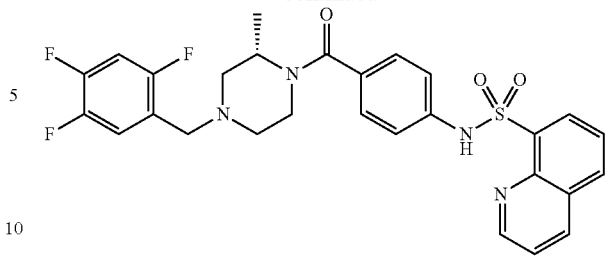
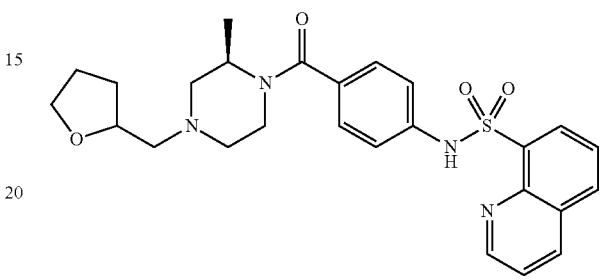
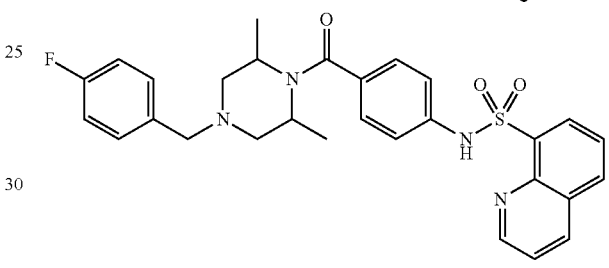
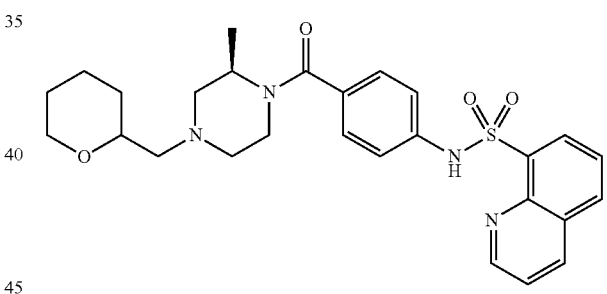
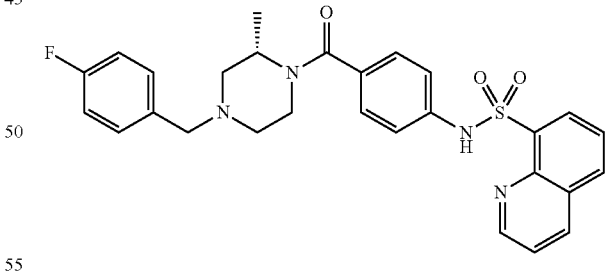
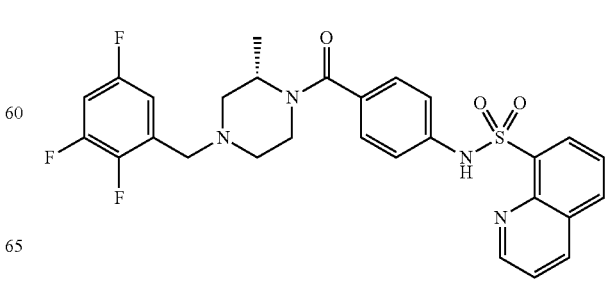

159
-continued
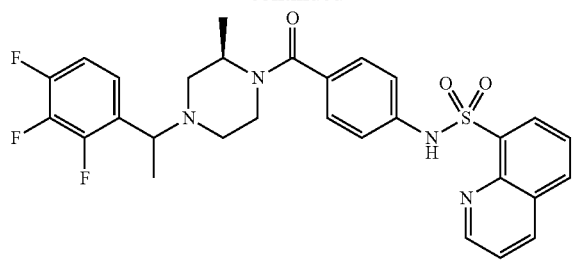
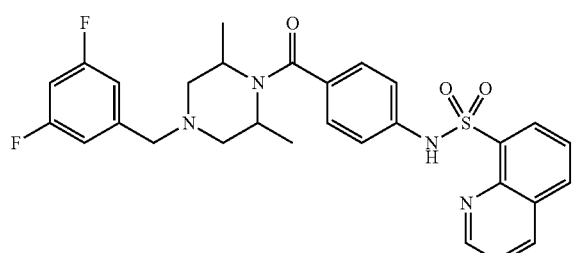
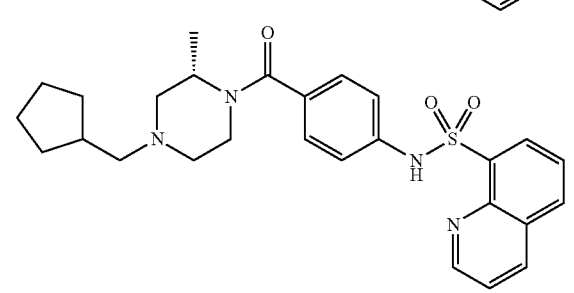
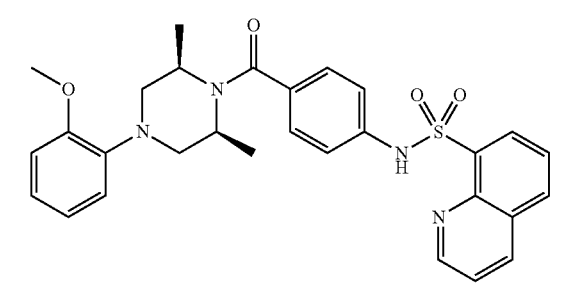
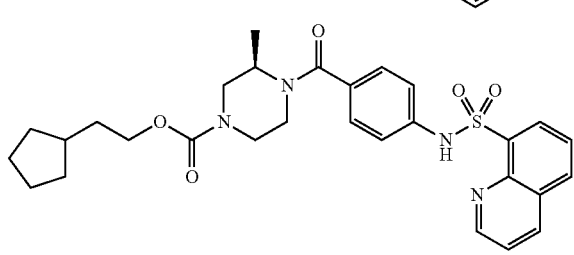
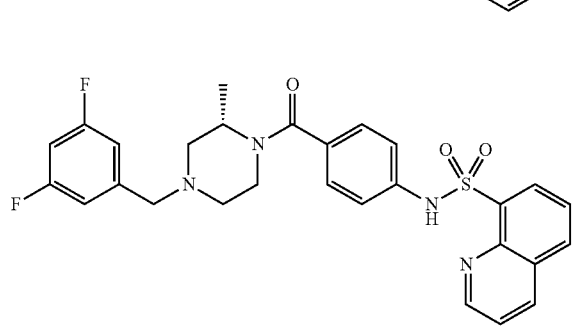
160
-continued
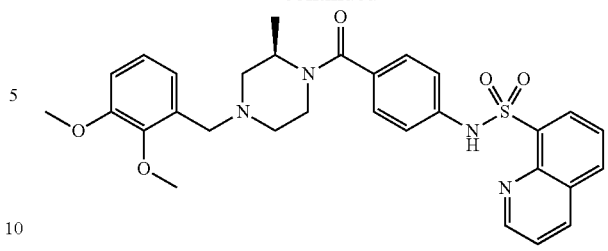
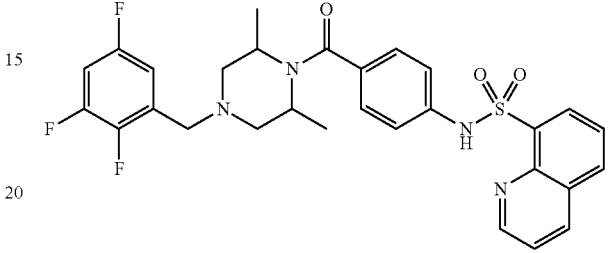
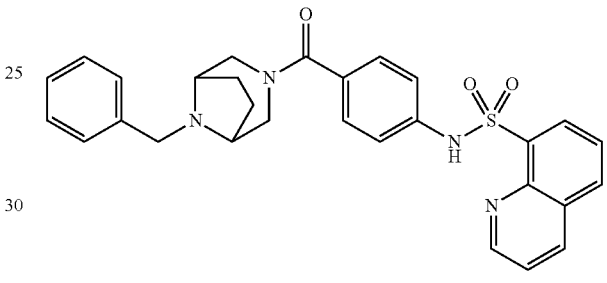
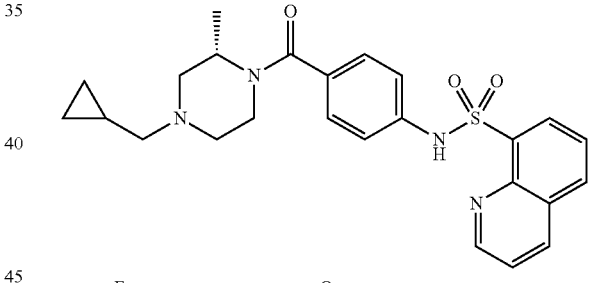
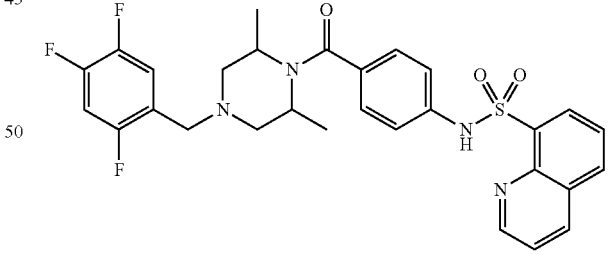
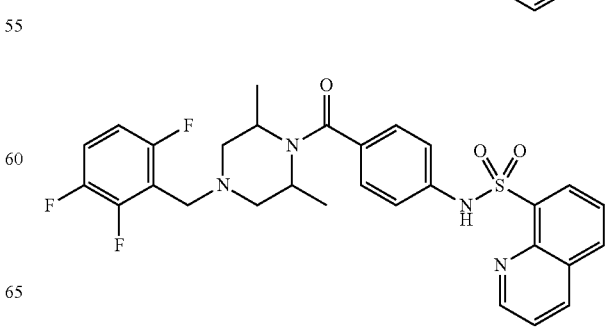

161
-continued
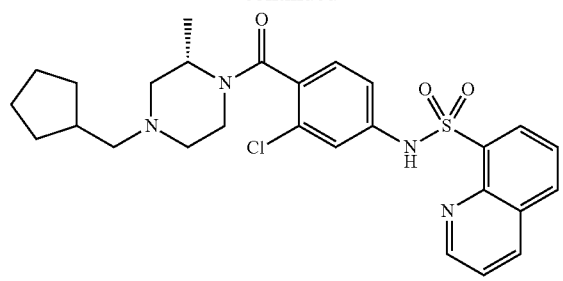
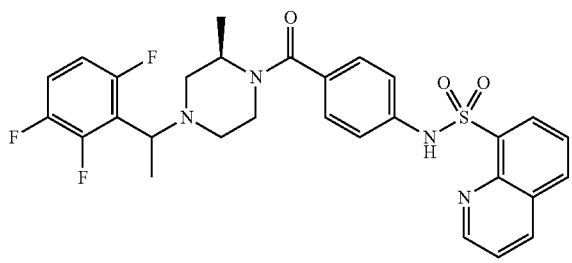
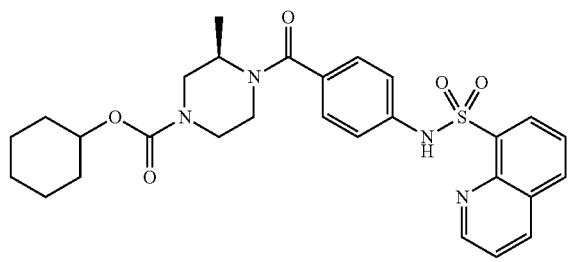
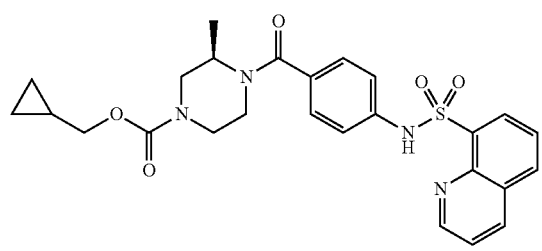
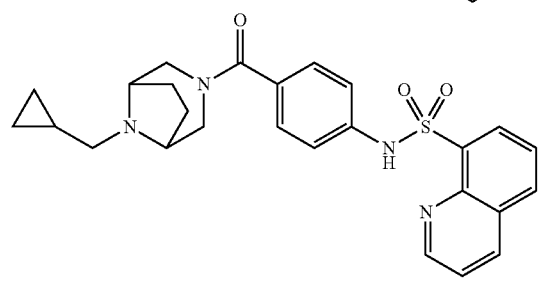
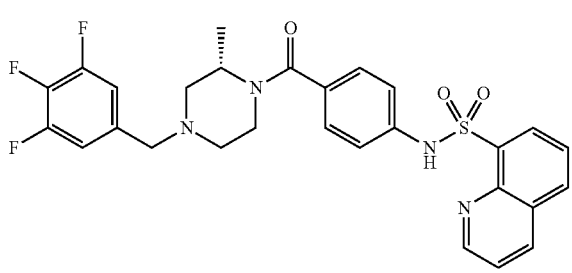
162
-continued
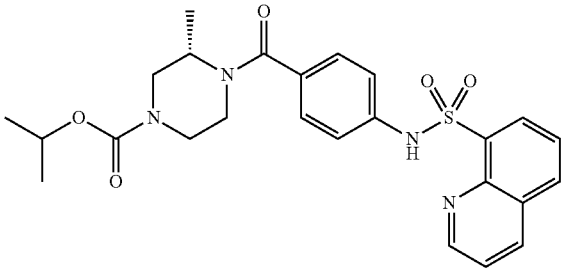
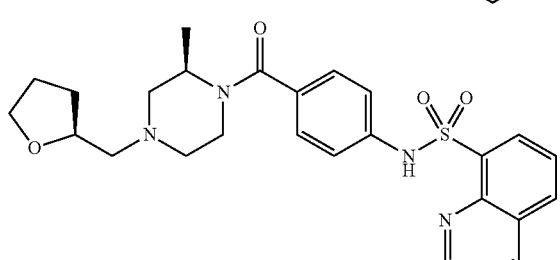
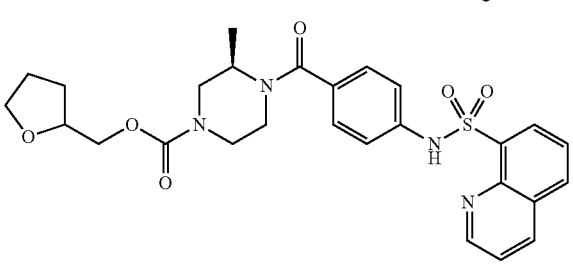
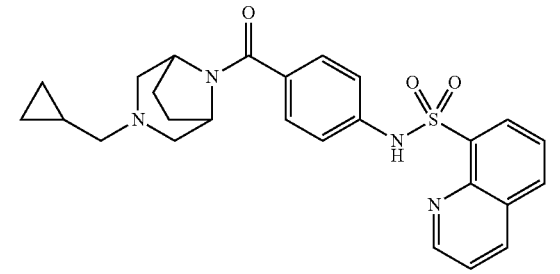

163
-continued
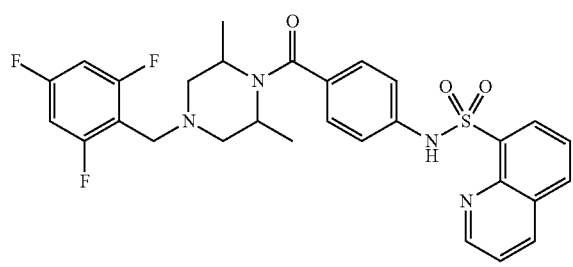
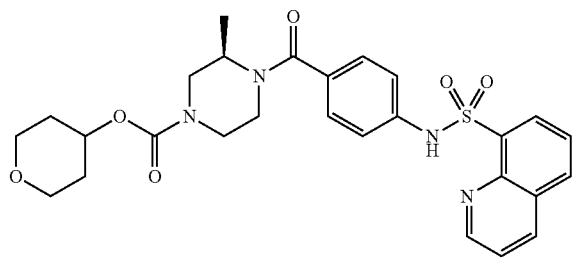
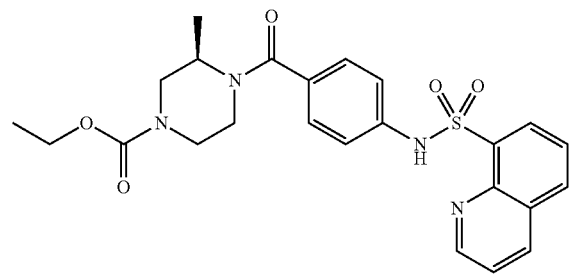
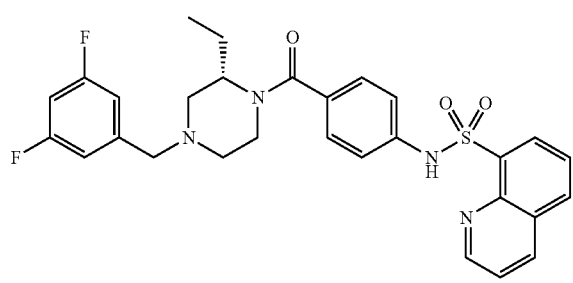
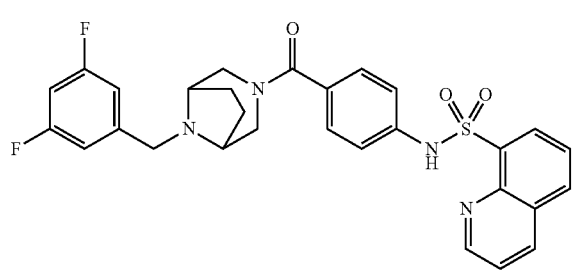
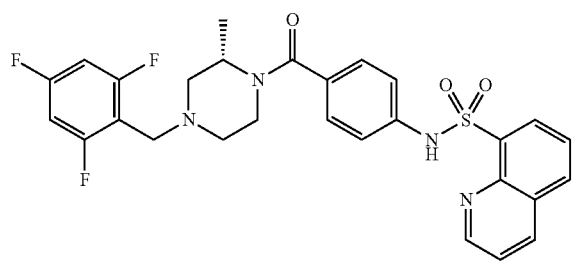
164
-continued
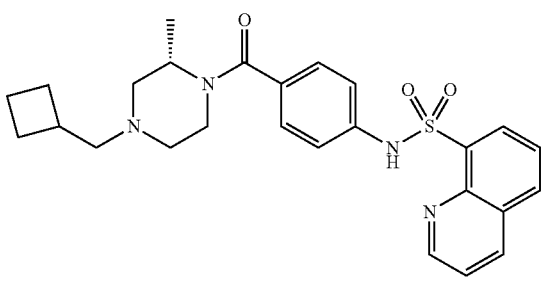
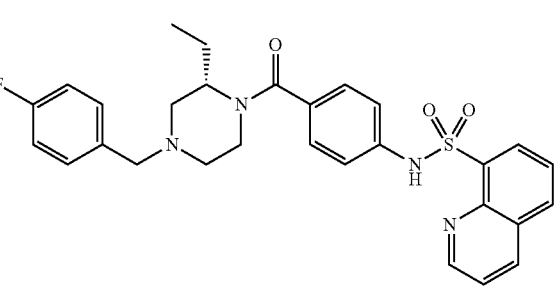
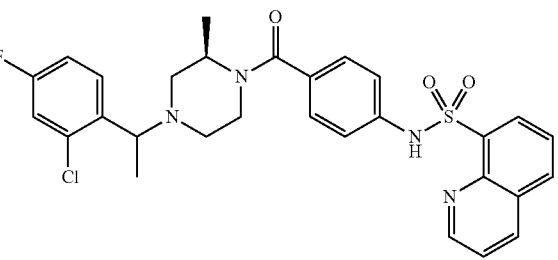
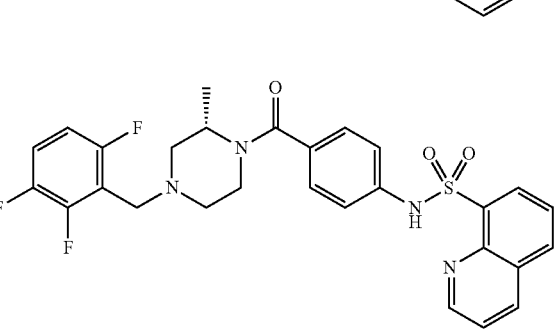
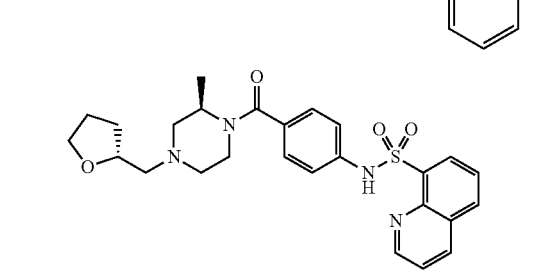

165
-continued
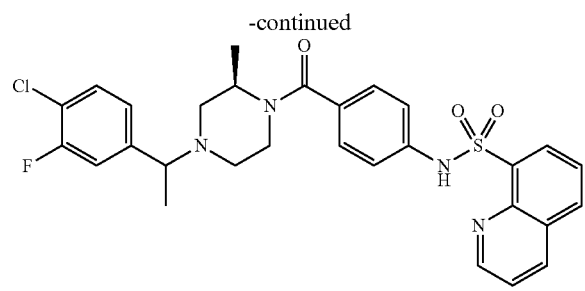
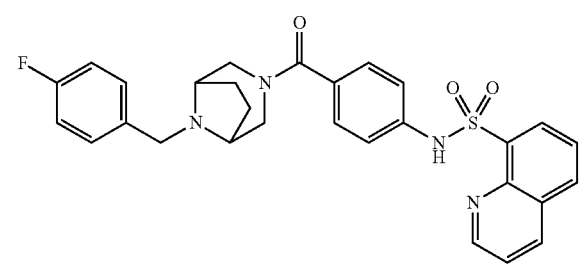
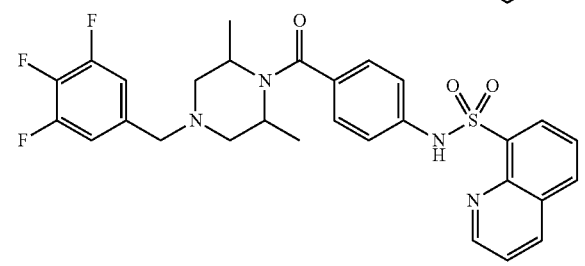
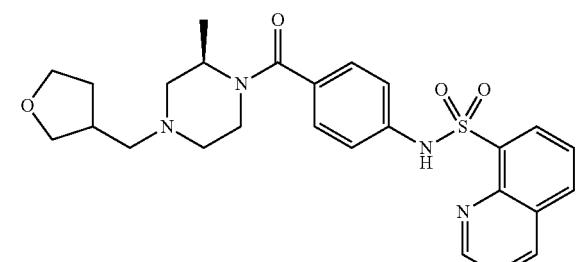
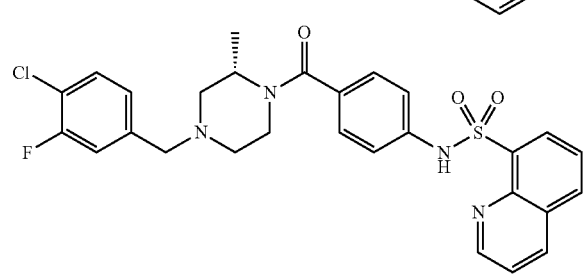
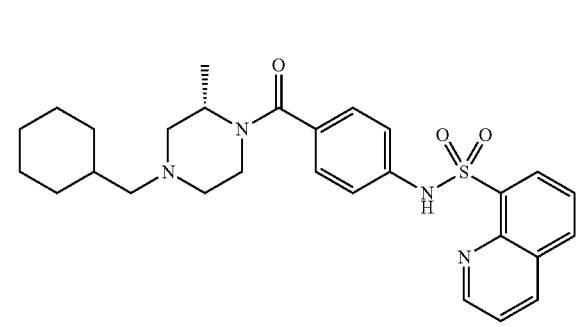
166
-continued
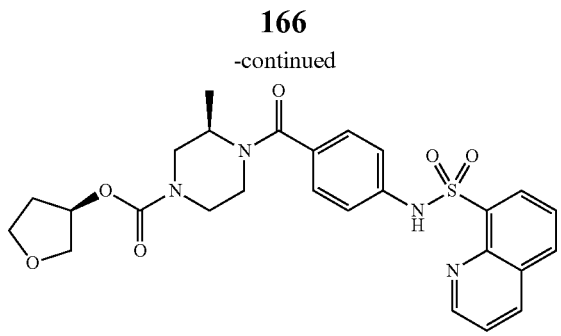
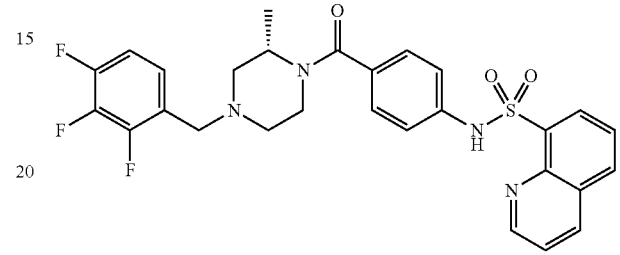
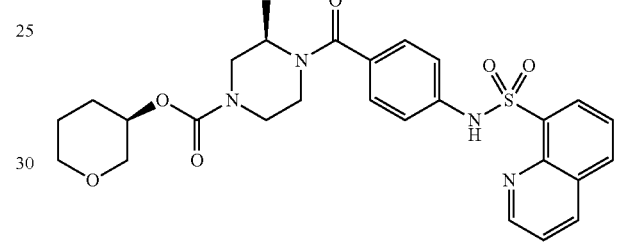
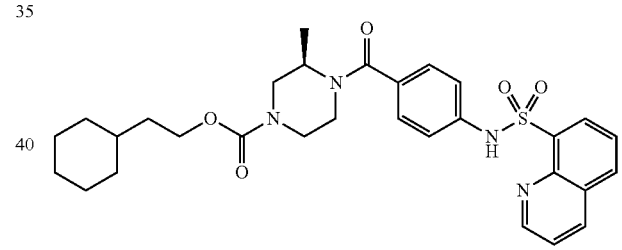
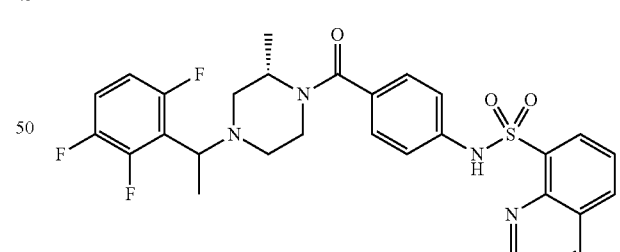
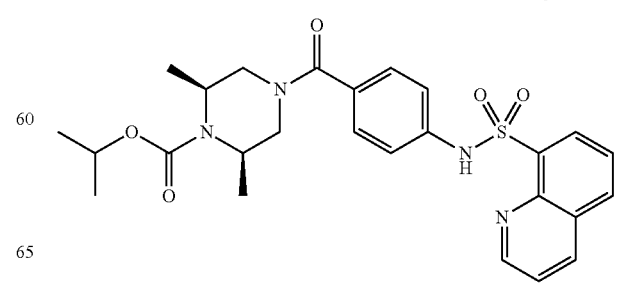

167
-continued
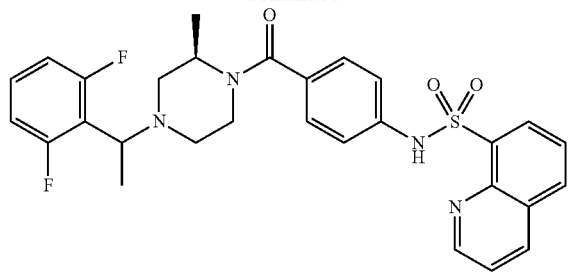
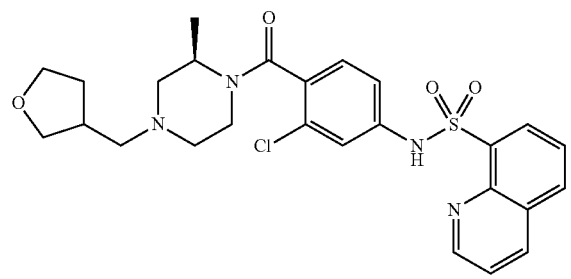
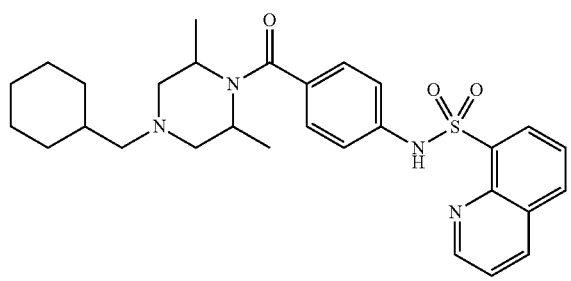
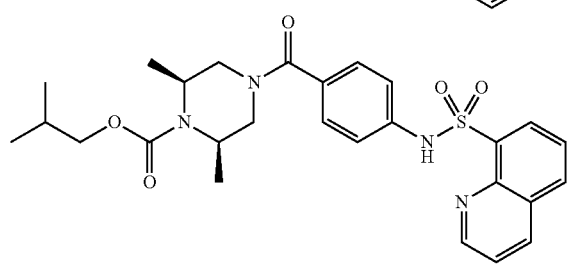
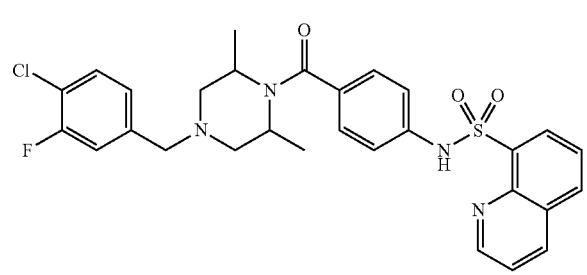
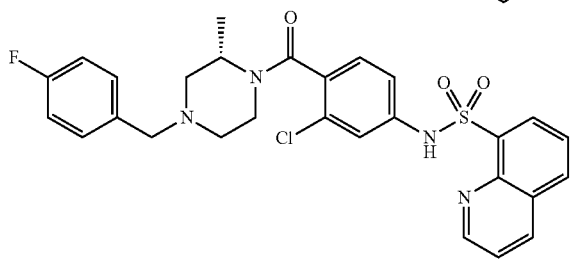
168
-continued
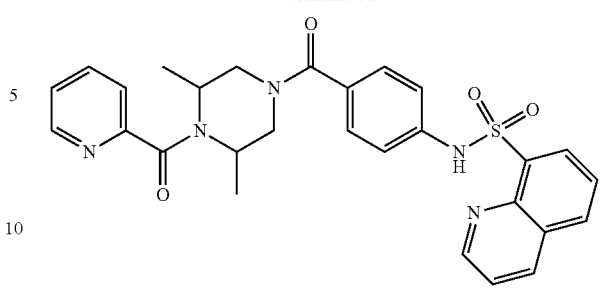
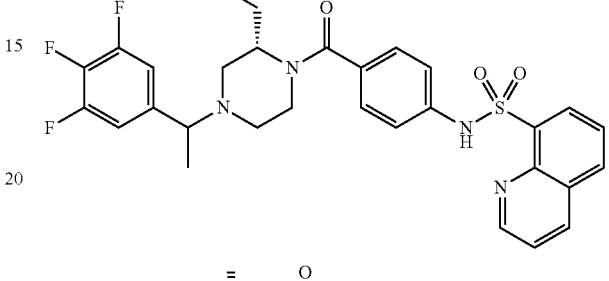
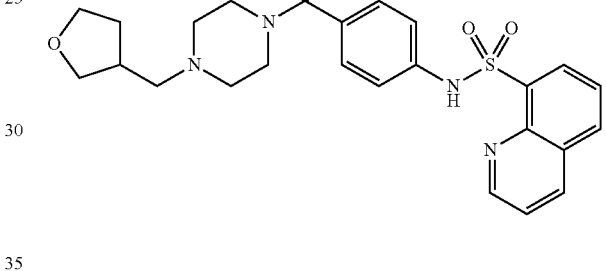
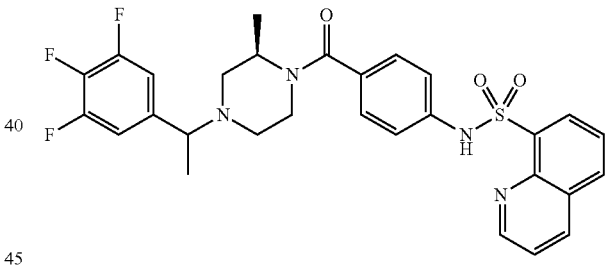
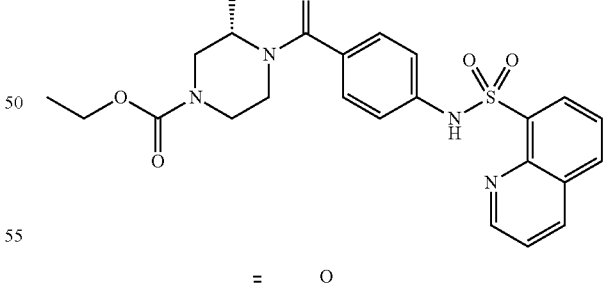
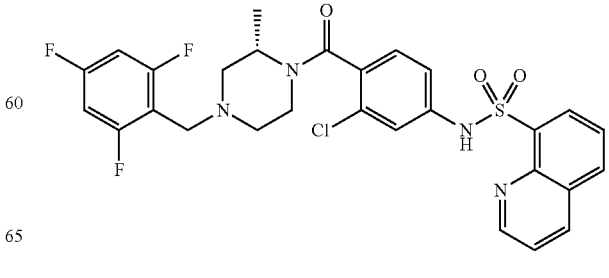

169
-continued
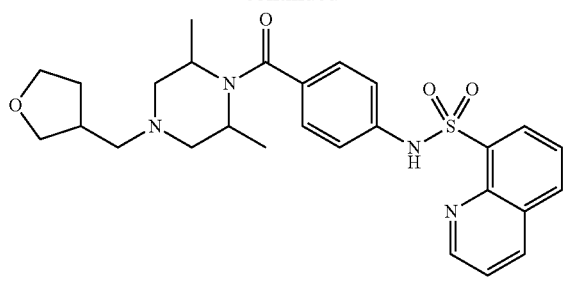
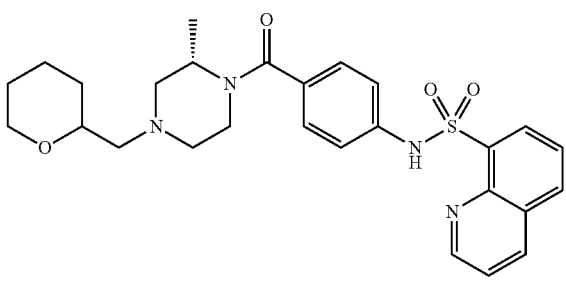
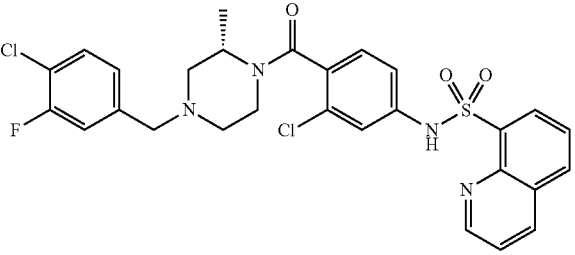
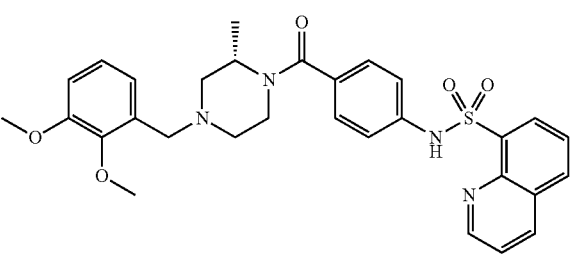
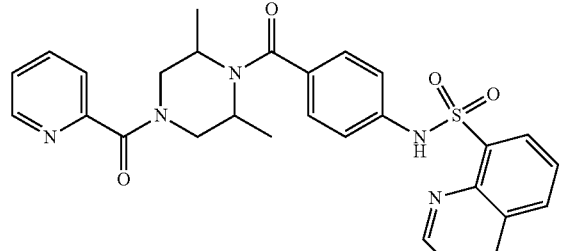
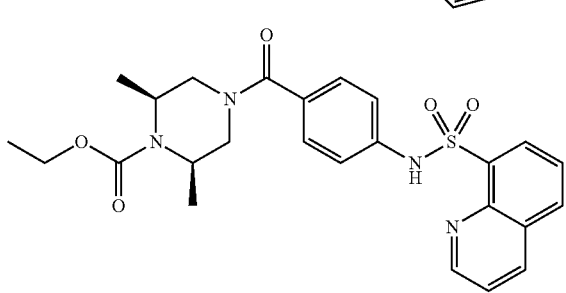
170
-continued
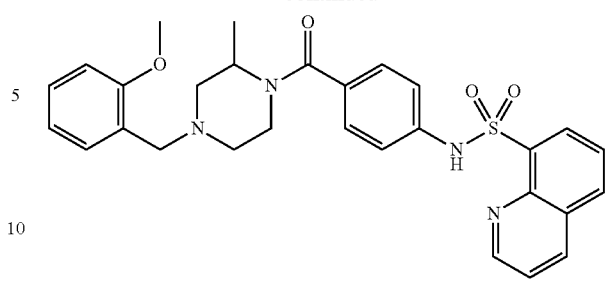
and
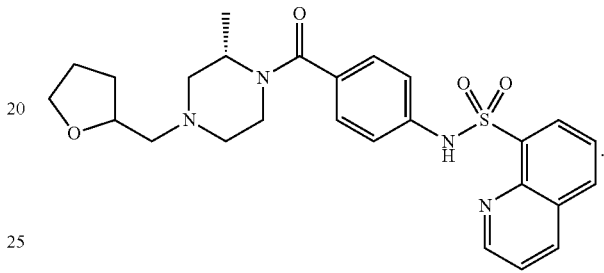
10. The compound of claim 9, wherein the compound is selected from:
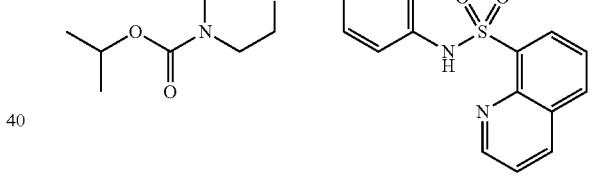
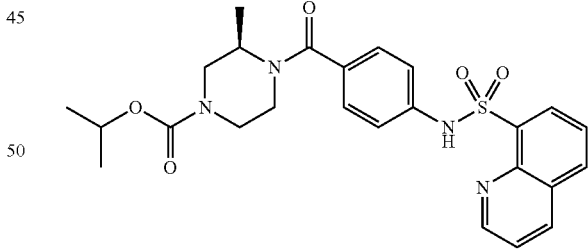
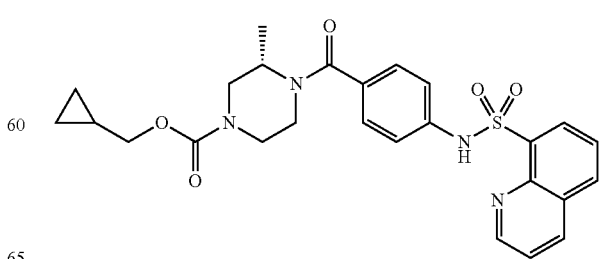

171
-continued
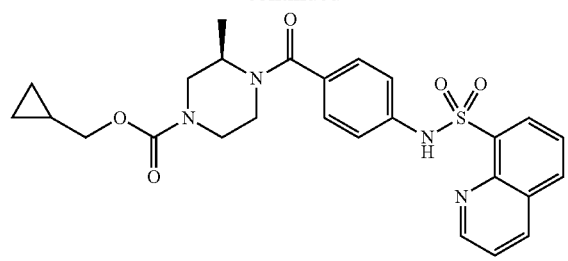
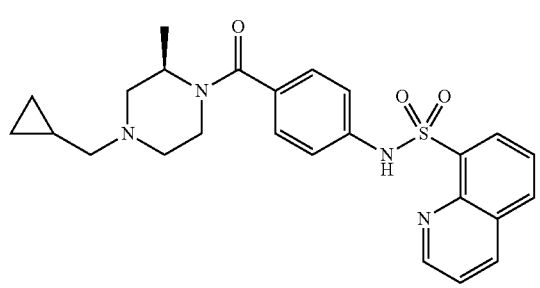
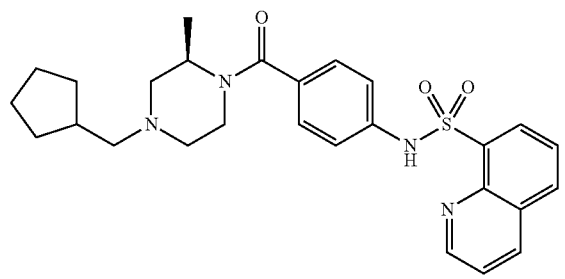
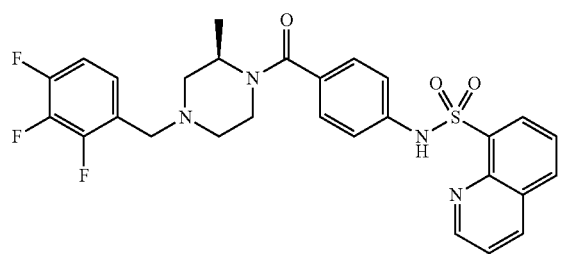
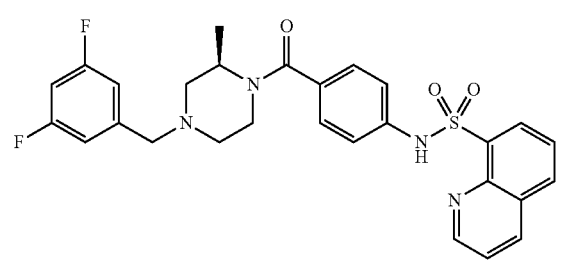
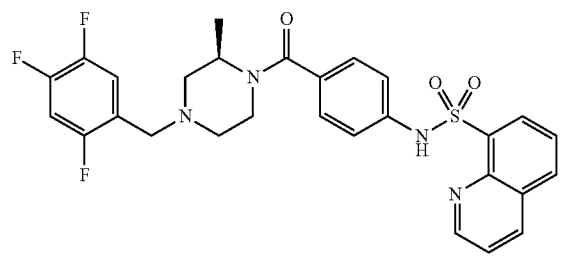
172
-continued
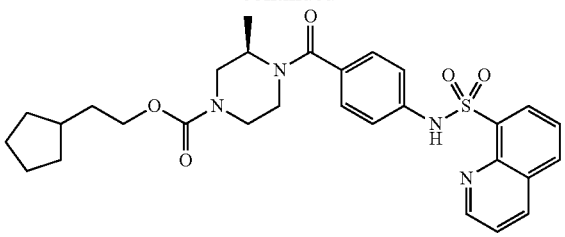
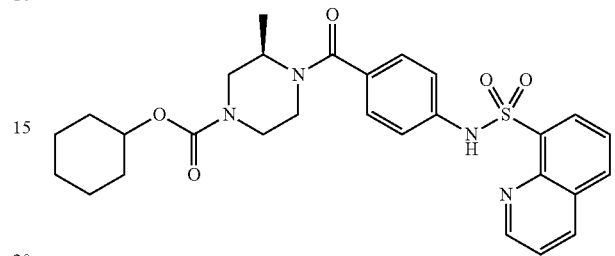
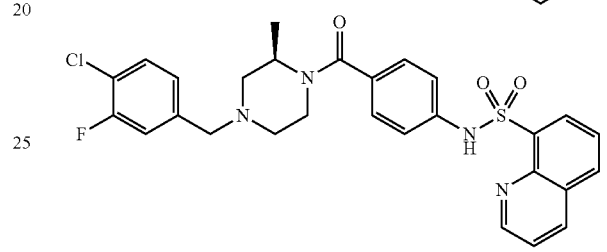
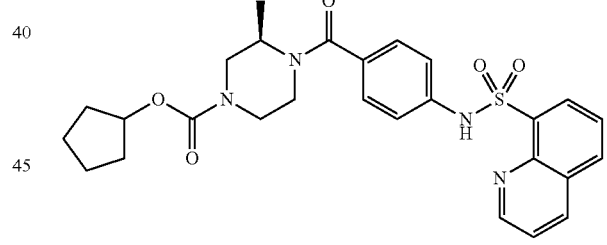
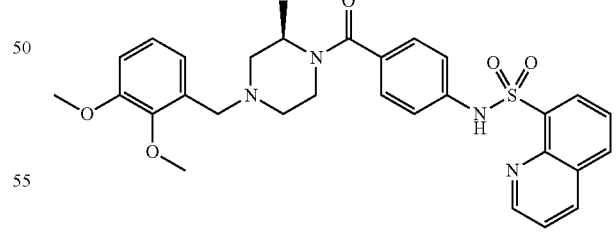
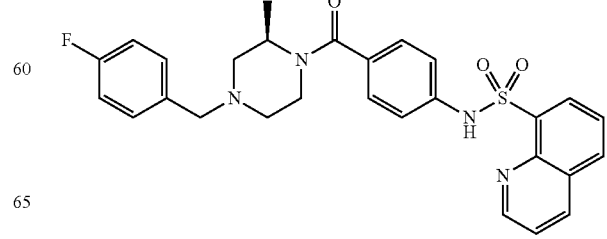

173
-continued
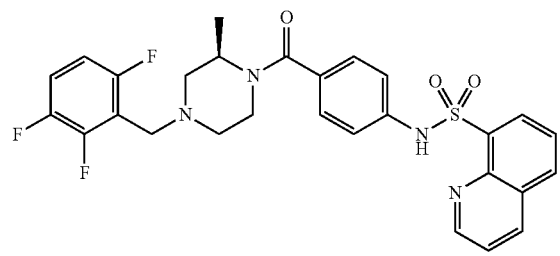
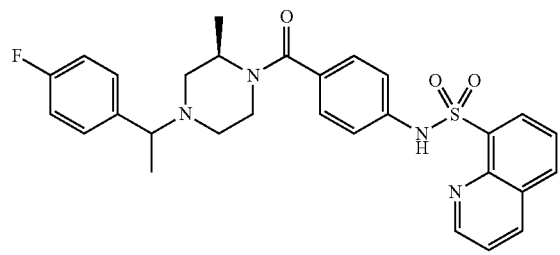
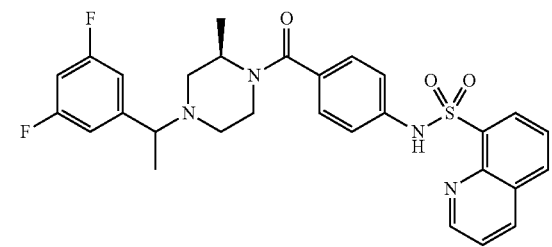
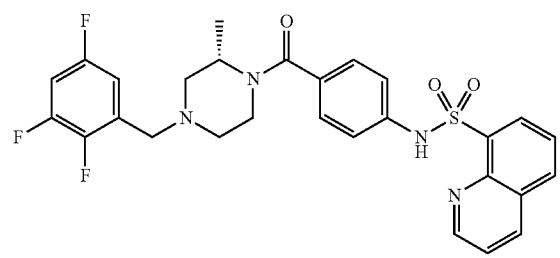
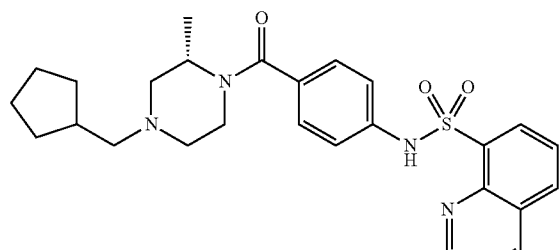
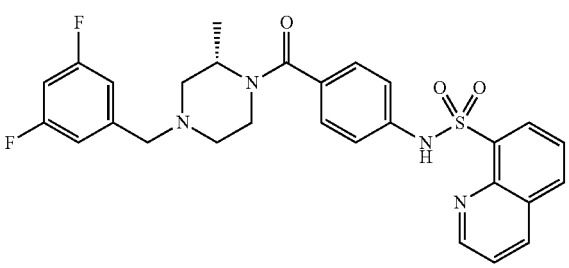
174
-continued
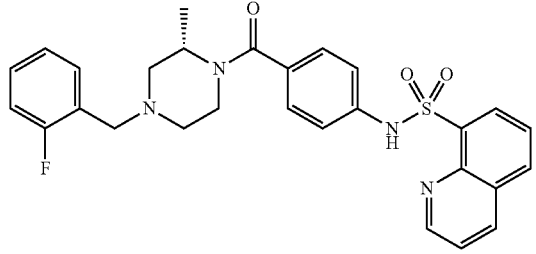
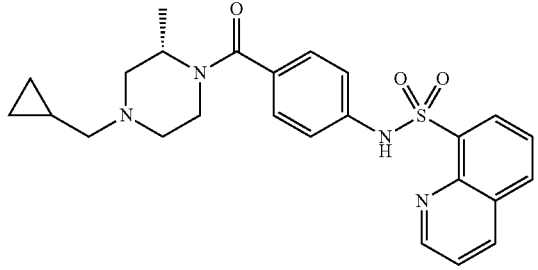
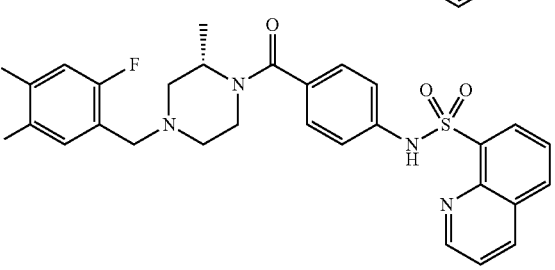
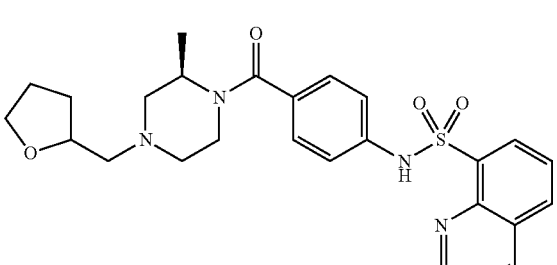
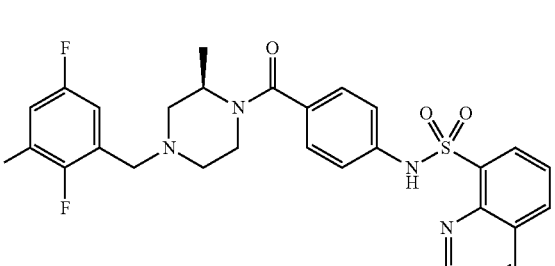
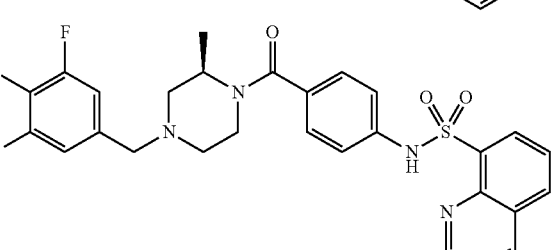

175
-continued
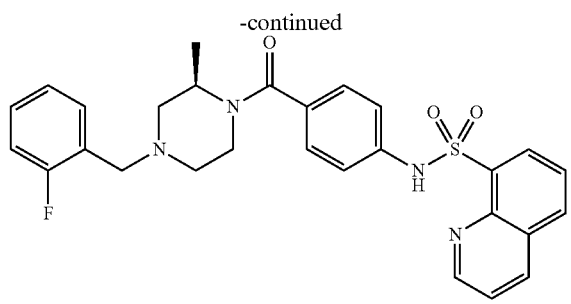
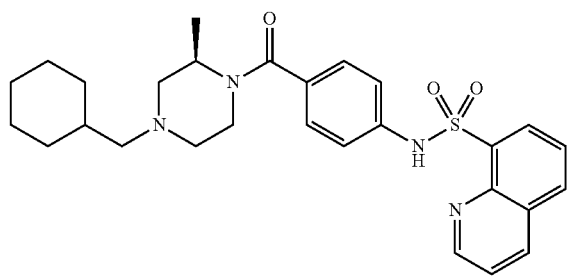
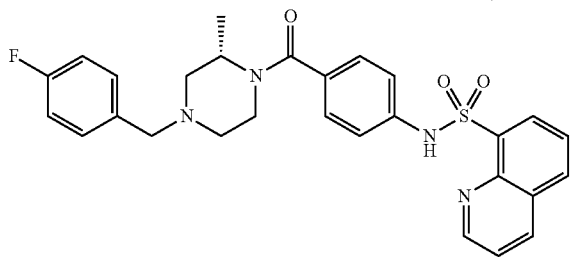
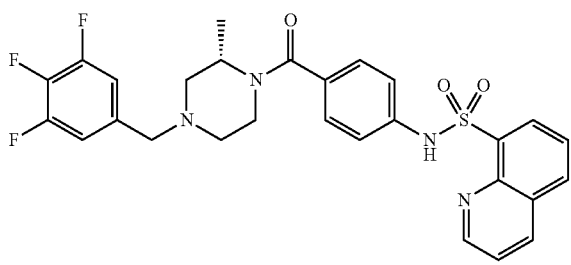
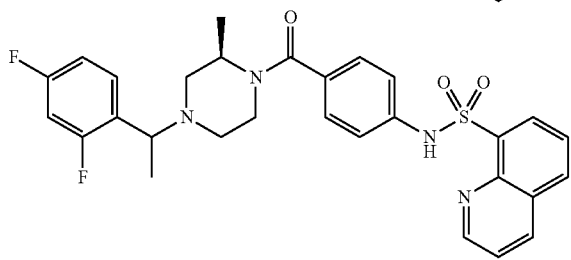
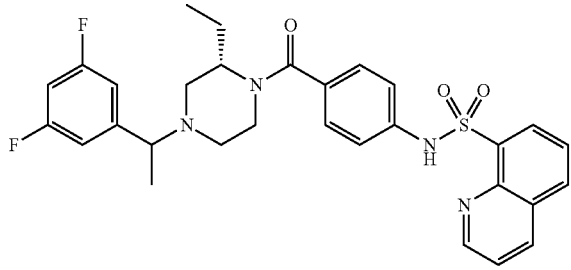
176
-continued
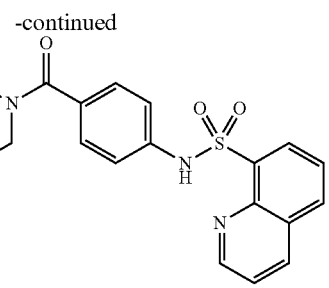
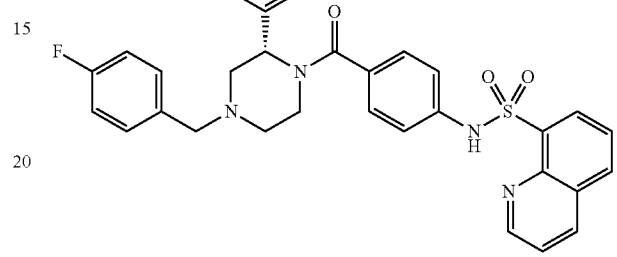
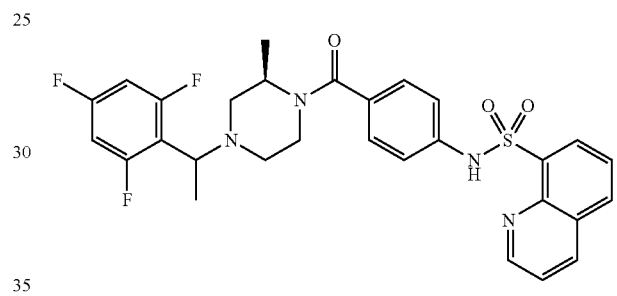
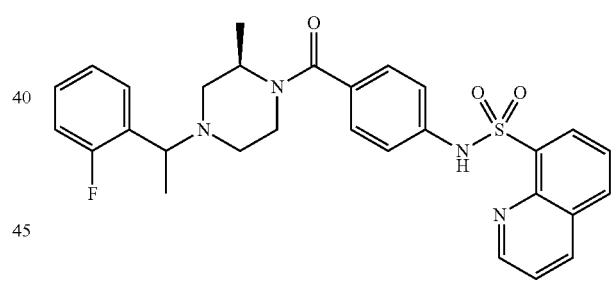
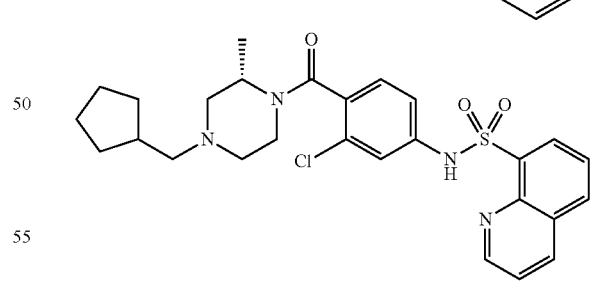
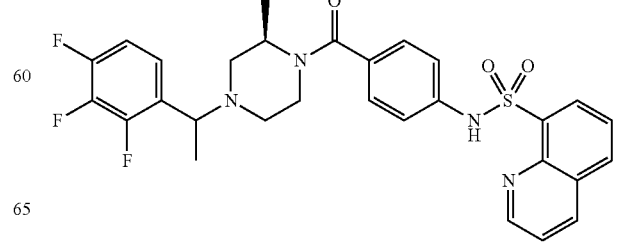

-continued
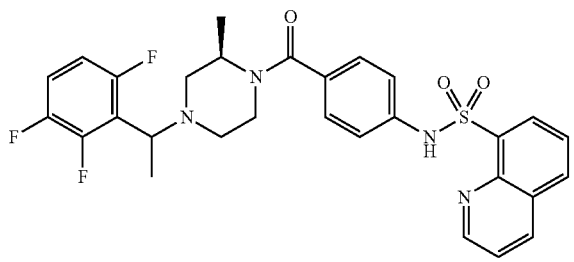
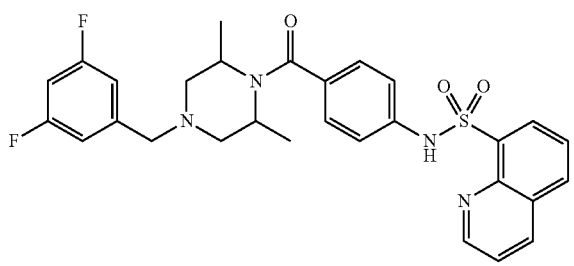
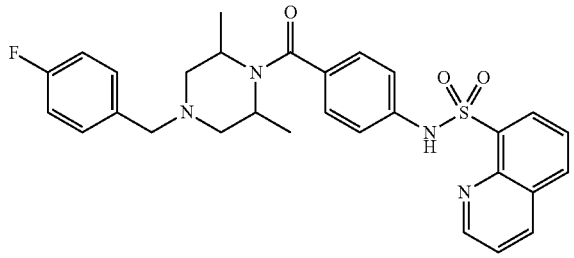
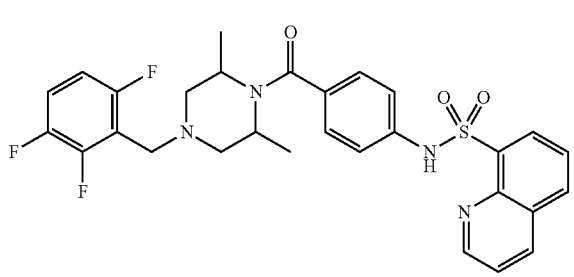
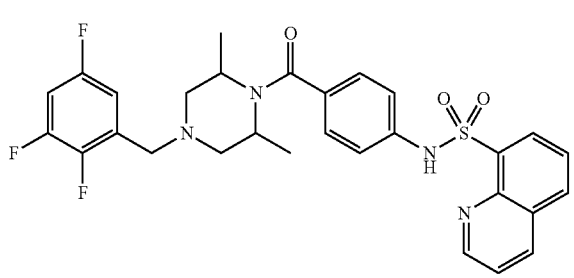
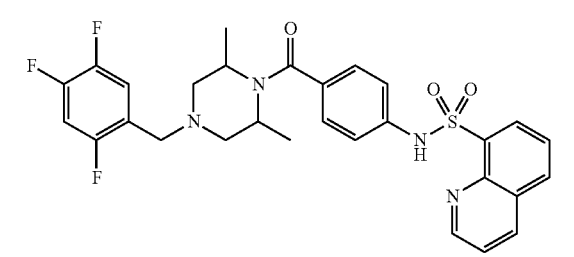
-continued
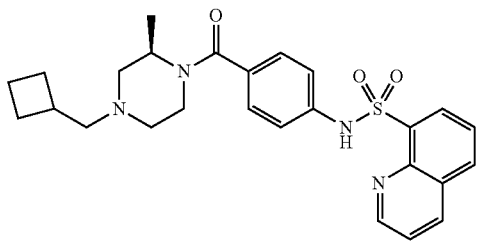
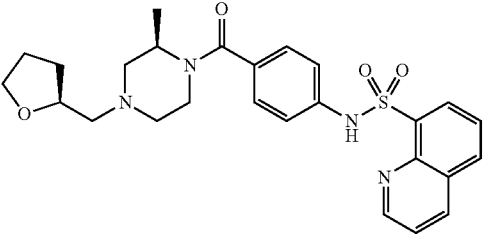
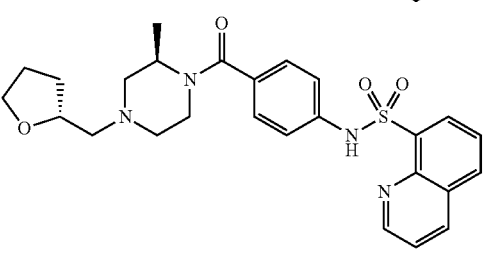
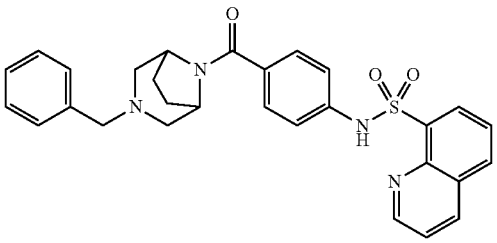
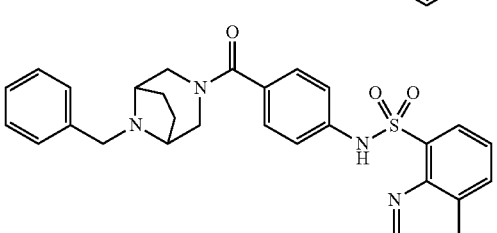
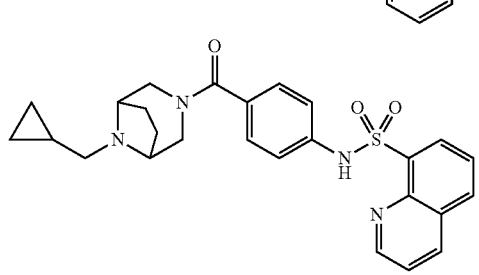
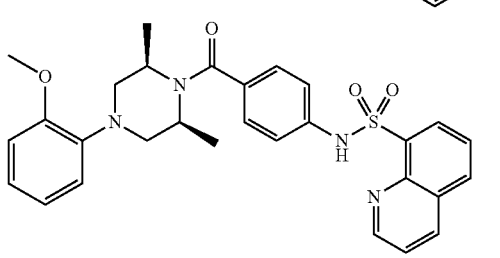
and -continued
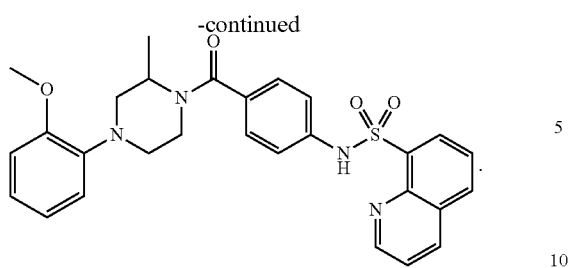
11. A pharmaceutical composition comprising a compound of claim 1 or 2, and a pharmaceutically acceptable carrier.
* * * * *